US012171178B2

(12) United States Patent
Karlson

(10) Patent No.: US 12,171,178 B2
(45) Date of Patent: Dec. 24, 2024

(54) MUSTARD GREEN PLANTS NAMED 'PWRG-1', 'PWRG-2,' AND 'PWSGC'

(71) Applicant: Pairwise Plants Services, Inc., Durham, NC (US)

(72) Inventor: Dale Karlson, Cary, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 0 days.

(21) Appl. No.: 18/355,489

(22) Filed: Jul. 20, 2023

(65) Prior Publication Data

US 2024/0016108 A1 Jan. 18, 2024

Related U.S. Application Data

(63) Continuation of application No. PCT/US2023/070367, filed on Jul. 18, 2023.

(60) Provisional application No. 63/368,717, filed on Jul. 18, 2022.

(51) Int. Cl.
*A01H 6/20* (2018.01)
*A01H 5/10* (2018.01)
*A01H 5/12* (2018.01)

(52) U.S. Cl.
CPC ............... *A01H 6/201* (2018.05); *A01H 5/10* (2013.01)

(58) Field of Classification Search
None
See application file for complete search history.

(56) References Cited

U.S. PATENT DOCUMENTS

2005/0055744 A1 3/2005 Quiros et al.
2010/0317518 A1 12/2010 Stevens et al.
2014/0335063 A1 11/2014 Cannon et al.
2015/0067922 A1 3/2015 Yang et al.
2019/0225955 A1 7/2019 Liu et al.
2019/0225977 A1 7/2019 Ulmasov et al.
2022/0377995 A1 12/2022 Karlson et al.

FOREIGN PATENT DOCUMENTS

WO 2019143926 A1 7/2019
WO WO-2021030738 A1 * 2/2021 ............. A01H 1/101

OTHER PUBLICATIONS

Gasic et al 2007 (Plant Molecular Biology 64: p. 361-369) (Year: 2007).*

International Search Report and the Written Opinion of the International Searching Authority corresponding to International Patent Application No. PCT/US2020/046483 (26 pages) (mailed Dec. 17, 2020).

Augustine, Rehna, et al., "Biotic elicitors and mechanical damage modulate glucosinolate accumulation by co-ordinated interplay of glucosinolate biosynthesis regulators in polyploid Brassica juncea", Phytochemistry 117, pp. 43-50 (2015).

Augustine, Rehna, et al., "Targeted silencing of BjMYB28 transcription factor gene directs development of low glucosinolate lines in oilseed *Brassica juncea*", Plant Biotechnology Journal. vol. 11(7), pp. 855-866 (2013).

Barth, Carina, et al., "*Arabidopsis myrosinases* TGG1 and TGG2 have redundant function in glucosinolate breakdown and insect defense", The Plant Journal. vol. 46(4), pp. 549-562 (2006).

Bellostas, Natalia, et al., "Qualitative and quantitative evaluation of glucosinolates in cruciferous plants during their life cycles", Agroindustria. vol. 3, No. 3, pp. 5-10 (2004).

Burow, Meike, et al., "The Glucosinolate Biosynthetic Gene AOP2 Mediates Feed-back Regulation of Jasmonic Acid Signaling in *Arabidopsis*", Molecular Plant. vol. 8, pp. 1201-1212 (2015).

Chen, Ya-Zhou, et al., "Proteomics and Metabolomics of *Arabidopsis* Responses to Perturbation of Glucosinolate Biosynthesis", Molecular Plant. vol. 5, No. 5, pp. 1138-1150 (Apr. 2012).

Dosz, Edward B., et al., "Total Myrosinase Activity Estimates in Brassica Vegetable Produce", J. Agric. Food Chem. vol. 62(32), pp. 8094-8100 (2014).

Fahey, Jed W., et al., "The chemical diversity and distribution of glucosinolates and isothiocyanates among plants", Phytochemistry 56, pp. 5-51 (2001).

Golicz, Agnieszka A., et al., "The pangenome of an agronomically important crop plant *Brassica oleracea*", Nature Communications. 7:13390 (2016).

Halkier, Barbara Ann, et al., "Biology and Biochemistry of Glucosinolates", Annu. Rev. Plant Biol. vol. 57(1), pp. 303-333 (2006).

Harper, Andrea L., et al., "Associative transcriptomics of traits in the polyploid crop species *Brassica napus*", Nature Biotechnology. vol. 30, No. 8, pp. 798-802 (2012).

Karlson, Dale, et al., "Targeted Mutagenesis of the Multicopy Myrosinase Gene Family in Allotetraploid *Brassica juncea* Reduces Pungency in Fresh Leaves across Environments", Plants, 11, 2494, 2022.

Neal, Calida S., et al., "The characterisation of AOP2: a gene associated with the biosynthesis of aliphatic alkenyl glucosinolates in *Arabidopsis thaliana*", BMC Plant Biology. 10:170 (2010).

Rask, Lars, et al., "Myrosinase: gene family evolution and herbivore defense in Brassicaceae", Plant Molecular Biology. vol. 42, pp. 93-113 (2000).

(Continued)

*Primary Examiner* — Matthew R Keogh
(74) *Attorney, Agent, or Firm* — Myers Bigel, P.A.

(57) ABSTRACT

The present invention relates to a novel *Brassica juncea* varieties designated PWRG-1, PWRG-2, and PWSGC, which have a reduced pungent flavor and/or odor traits. The invention provides seeds of the varieties PWRG-1, PWRG-2, and PWSGC, plants and parts thereof of the varieties, a tissue culture derived from the varieties, hybrids produced from varieties, and lines derived from varieties, as well as genetically modified forms of the foregoing plants and tissue culture. Also provided are methods of producing PWRG-1, PWRG-2, and PWSGC plants, hybrid plants, and lines derived from varieties PWRG-1, PWRG-2, and PWSGC. In addition, products produced from the plants of the present invention are provided.

23 Claims, 1 Drawing Sheet

Specification includes a Sequence Listing.

(56) References Cited

OTHER PUBLICATIONS

Reintanz, Birgit, et al., "bus, a Bushy *Arabidopsis* CYP79F1 Knockout Mutant with Abolished Synthesis of Short-Chain Aliphatic Glucosinolates", The Plant Cell. vol. 13, pp. 351-367 (Feb. 2001).
Sharma, Manisha, et al., "BjuB.CYP79F1 Regulates Synthesis of Propyl Fraction of Aliphatic Glucosinolates in Oilseed Mustard *Brassica juncea*: Functional Validation through Genetic and Transgenic Approaches", PLoS One. 11(2): e0150060, pp. 1-17 (2016).
Sønderby, Ida E., et al., "Biosynthesis of glucosinolates—gene discovery and beyond", Trends in Plant Science. vol. 15, No. 5, pp. 283-290(2010).
Thangstad, Ole Petter, et al., "The myrosinase (thioglucoside glucohydrolase) gene family in Brassicaceae", Plant Molecular Biology. vol. 23, pp. 511-524 (1993).
Xu, Zhiwei, et al., "Functional genomic analysis of *Arabidopsis thaliana* glycoside hydrolase family 1", Plant Molecular Biology. vol. 55, pp. 343-367 (2004).
Xue, Jiaping, et al., "The glucosinolate-degrading enzyme myrosinase in Brassicaceae is encoded by a gene family", Plant Molecular Biology. vol. 18, pp. 387-398 (1992).
Zhang, Jifang, et al., "Three genes encoding AOP2, a protein involved in aliphatic glucosinolate biosynthesis, are differentially expressed in *Brassica rapa*", Journal of Experimental Botany. vol. 66, No. 20, pp. 6205-6218 (2015).
International Search Report and Written Opinion corresponding to International Patent Application No. PCT/US2023/070367; mailed Nov. 8, 2023 (15 pages).
Bell, Luke, et al., "Taste and Flavor Perceptions of Glucosinolates, Isothiocyanates, and Related Compounds", Molecular Nutrition & Food Research. 62(18): 1700990, 2018.
Tantikanjana, Titima, et al., "Functional Analysis of the Tandem-Duplicated P450 Genes SPS/BUS/CYP79F1 and CYP79F2 in Glucosinolate Biosynthesis and Plant Development by Ds Transposition-Generated Double Mutants", Plant Physiology. 135: 840-848, 2004.
Wieczorek, Martyna N., et al., "Bitter taste of *Brassica* vegetables: The role of genetic factors, receptors, isothiocyanates, glucosinolates, and flavor context", Critical Reviews in Food Science and Nutrition. DOI: 10.1080/10408398.2017.1353478, 2017 (11 pages).

* cited by examiner

SEQUENCE LISTING

```
Sequence total quantity: 61
SEQ ID NO: 1            moltype = DNA  length = 3078
FEATURE                 Location/Qualifiers
source                  1..3078
                        mol_type = other DNA
                        organism = synthetic construct
SEQUENCE: 1
tggccacaag gatccacaca acacaacaca tacatcaaca gattaaacat gaagcttctt  60
cgtcgactcg ctttagtttt tctattagct gctgcgagtt gcaaggctga tgaagaaatt  120
acttgcgaag agaacaatcc atttacttgt agtaacactg atattttaag cagcaagaac  180
ttcggaaaag atttcatctt tggtgttgcg tcttctgctt accaggcatg tagcaaatgt  240
tgtcacaccc taattttgaa ataaaattca aagcaccaat atccaatttt gcatagttgt  300
ttcttttcat ttcagattga aggagggaga ggtcgtggtg ttaatgtttg ggatggtttc  360
agtcaccggt acccaggtat gtcgttcgca cggtgacatc taaactaata atgttggtta  420
catatacaca tattaatgta tttgtaatta atattatcag agaaagctgg gtcagatttg  480
aagaatggag acactacttg tgagtcatat acgagatggc aggttaattt ctgagtacac  540
tgattctcat gactgaatta tatatgtata agaactccct aaaaactata cgtgtggatt  600
gacatgaaat ttaaattaat tgtaaactgc agaaagatgt agacgtgatg ggcgaaatca  660
atgctactgg ctacagattc tcctttgcat ggtcaagaat cattccaagt atgtacatat  720
taacgatcaa tgtatatata tctttgtatt ttaattggga taatttagtt ggaaaggtac  780
taattaatgt acgatatata tctacccgag cagaaggaaa ggtgagtagg ggagtgaacc  840
aaggaggtct tgattattac caccaactca tagatgcact cctcgaaaag aatataacgc  900
ctttcgtaac cctctttcac tgggaccttc ctcaaacact ccaagatgag tatgaaggtt  960
tcttggaccg ccagatcatg taggtgccat gcttcttaat tatatttgag gagagtaaat  1020
attattagta atagaagaag aagatttagt cttaattaca tgtttactga aatgattcta  1080
tactaatatg aacagccagg atttcaaaga ttacgcggat ctatgtttca aagaatttgg  1140
tggaaaggta aagcattgga tcacgatcaa ccagctatac acagttccta caagaggcta  1200
tgcagtcgga acagatgcac ccggtcgatg ttctcctatg gttggtgtta cggcggaaat  1260
tcttcaacag atgtaggcga gtagtctcca tatttaatac gatggtgtga tcttaatcca  1320
tctgattctg atctagtcat atatatcatg tgaccaacag gaccaacaag ggaagattgg  1380
acctgtgatg ataacaagat ggtttcttcc atatgatgag tctgatcccg cttgcgtaga  1440
agcagctgag aggatgaacc aattcttcca tggatggtat atcttttttg tttgacatca  1500
aacaattatt cttttttttg tttgtttaca ttaaatggtt attttattat ttaaaactaa  1560
aggtggtctg tataactaga atgattatat tgtatgtata atgaaaaaaa tatacaccga  1620
tcaggcacat ggagccgcta acaaagggta gatacccaga catcatgagg cagattgtgg  1680
gtagtaggct tcccaacttt accgaggaag aagccgcact cgttgccggt tcatatgatt  1740
ttcttggtct caactattat gttactcagt acgcccagcc acaacctaac ccatatcctt  1800
cagagacaca cactgccatg atggacgctg gagtaaagct cacatgtacc actctgtttc  1860
cactttgtta caacctcctt tctatatata tattcctttt tgttataaaa catacttaat  1920
ttgtgagtga ccataagtta tttcttcctt gtgtttacag ataataactc acgtggtgaa  1980
tatcttggtc cactggtaat tatgcatgat ccatcctcat gatatctctc tcattgatat  2040
gtatattttg ttctgattga tatgtatttt ttgtttgctt ccctttccca gttcgctgaa  2100
gacaaaatag ccggcaacag ctattactac ccaaaaggaa tatattacgt aatggacttc  2160
ttcaaaacca attacagcaa ccctttaatc tatatcaccg agaacggtga gttctacata  2220
ctacttacta ctcatctatt ctacataaat taattagtgt atttttatat attagtcgag  2280
gaaactgatt ttcaaatatt gtggaatgtt ttcacggttt aattaggaat aagttcgccc  2340
ggtacagaaa accgttgcga agctattgcc gattccaagc gcattgatta tctctgcagt  2400
catctatgtt ttctccgtaa ggtcatcaag taagtggatg ctactgtaca tgcttttctt  2460
ccaatatttt atcatctttt tcttcttctt tttaagtata catatatatg attgatttat  2520
tgtttccagg gagaggggtg tcaacgtgag aggatacttt gcatgggctc ttggggataa  2580
ttatgaattc tgtaaaggct ttaccgtcag atttggtctc agttacgtta attgggatga  2640
tctcgacgac agaaacctca aagaatctgg caaatggtac cagagattca ttaacggaac  2700
cgtcaaaaac cctgcggaac aagatttcct ccgctcaagc ctttcctctc agagtcagaa  2760
gaagaggctt gcttgctgat gcatgaaaca cttttccacc tgtcaagatc atctctatgt  2820
ctctcacact tcctagttgc tccatagata aggagcttct tctactacag tgtactaaat  2880
aaaaattctc aacaaaaaga tgatcaagaa taaaaataat ttacctacaa ctacattatg  2940
tcaagtcaag gggggtgagg gggacaataa cgcaatttaa attgtaaaag gctcacacac  3000
atacaaaata aaaacccaaa ccgcaaacta gtttagtgtt acaaaaatat taatgggccg  3060
ataagcgtac aattcact                                                3078

SEQ ID NO: 2            moltype = DNA  length = 2667
FEATURE                 Location/Qualifiers
source                  1..2667
                        mol_type = other DNA
                        organism = synthetic construct
SEQUENCE: 2
ttggcacaag gttccataca acacaacaca aacatcaaca tatattaacc atgaagattc  60
ttcatggact cgctttagtt tttctattag ctattgcgag ttgcaaagct tatgaagaaa  120
ttacttgcga acagaacgaa ccattcacat gtggtaacac tgatatctta agcagtaaaa  180
acttcggaga agacttcatc ttcggtgttg catcttctgc gtaccaggca tgcaacaaat  240
gctgccatac catatttttg acgtatagaa aataatattc aaaaatgcta acatcaaact  300
ttgcgtggtt gtttccattt cagatcgaag gagggagagg tcgtggtgtt aacgtttggg  360
atggtttcag tcaccgatac ccaggtatgt cacggtggca tatatataca tataagatga  420
atgtcgttta tatctacaca cattaatgta tttgtaatta ctatcagaga aatcagggtc  480
agatttgctg aatggagaca cttcttgtga gtcatatacg agatggaagg ttagttcctc  540
agtacatata cactcatatg actaaactac gtataaaatt tacgtgtgaa ctgaattccg  600
tttaaaatgc agaaagatgt agagattatg ggagaactca atgctactgg ctacagattc  660
tccttagcgt ggtcaagaat cattccaagt acgaacataa atttgtattt ttattgggat  720
```

-continued

```
cctttagctg gaagagtata ctaattaatg tatgatataa atgagcagaa ggaaaggtga  780
gtaggggagt gaaccaagga ggtcttgatt actaccacca actcatagac gccctcctcg  840
aaaagaatat aactcctttc gttaccctct ttcactggga ccttcctcaa acactccaag  900
atgagtatga aggtttttg gatcgccaga tcatgtatgt gccatgcttc ttaattatat  960
acaaattatt aataaaaaca agaagaagaa gaagaaggtt ttgtcttaat tacatgcttt  1020
actgaaagaa tgattatata ttaatatgca cagacaagat ttcaaagact atgcggatct  1080
atgtttcaaa gaatttggtg gaaaggtaaa ggatcacgat caaccagcta ttcacagtgc  1140
ctacgagagg ctatgcactc ggaacagatg caccccggtag atgttctcct atgagaggtg  1200
ttacggcgga aactcttcaa cagaacccta tatcgttgca cataacgagc ttcttgctca  1260
tgctgcggta gtggatcttt acaggaagaa ctatgcggtg agtagtcttc atatgtgaaa  1320
aggtggtgaa aatctaacat atttgatcct aatttactca tatatgatgt gactaacagg  1380
accaaaaagg gaagattgga cctgtgatga ttacaagatg gtttcttcca tatgatgagg  1440
ctgatccttc ttgtagagaa gcagctgaca ggatgaacca attcttccat ggatggtata  1500
tcttttttt gacatcaaac ggttattcta ttactcaaaa ttaaagatgg tctaggtaat  1560
tagattgatt atattgtatg tacatataat gaaacaaaat ataaatggat caggtacatg  1620
gagccgctaa caaagggtaa atacccagac atcatgagga agattgtggg aagtcggctt  1680
cccaacttca ccgaagctga agccaaactt gttgctggtt catatgattt tcttggtctc  1740
aactattacg tcactcagta cgcccagcca aaagctaacc cattgctctc agagaaacac  1800
actgccatga tggacgctgg cgtaggactc acatgtacgc atcactcgat ctgctttgtt  1860
acaacttaca acctccttta tatatgtata tataagatgt tcaatatata tatatatata  1920
tatatatata tatatatata tatattcctt tttgttacaa catacttatt tgtgattgac  1980
catcagttat ttcttccttg tgtttacaga tgataactca cgtggtgaat ttattggtcc  2040
actggtatat atgcatgatc caccccttatg attttcttt cattatttta tcttctttc  2100
ctaactgtag tgtacttgga acacccacaa taacttctta ttttctttg attgatatgt  2160
atattttgtt tgcttccctt tctcagttca ttgaagacaa aatagccggc aacagctatt  2220
attacccaaa aggaatttac tacgtcatgg aatacttcaa aacccaatac aacgaccctt  2280
taatctatgt caccgagaat ggtaagttct acatattact agtaatctat ttttatttat  2340
gctacatatc atcagataat tagtgtactt tgatactgag tccaaagaaa ctgactttca  2400
aatactgtgg aatattttta tgtgatggcg attcaattag gatttagtac gcccagctca  2460
gaaaaccgtt gcgaagctat tgccgattac aagcgaattg attatctctg cagtcatcta  2520
tgttttctcc gtaaggtcat caagtaagtc ctactataca tgcttttctt ccaatattta  2580
tcttcttttt aagtaatata tatatatgta tatgattgtt attgtttcca gggatagggg  2640
tgtcaacgtg agaggatact ttgcatg                                       2667
```

```
SEQ ID NO: 3            moltype = DNA  length = 6445
FEATURE                 Location/Qualifiers
source                  1..6445
                        mol_type = other DNA
                        organism = synthetic construct
SEQUENCE: 3
attgaagtgg agtaacctat gatttatgtt ttcgatgatc aagagaaaca gagatccgaa  60
agaagaggaa gaataagagg aagagaaaga aaaaaaaata gaaagagatc acacggttga  120
tttcaaaggt attttgatat atatgataga aaatatgttg aatatactgt caactttttt  180
tggttagata actaattata atttgtttat tgtataatga gtgcaatttc ccttgaaact  240
tcttctcctt gttcttgaat ggtacataca ctaaaaaatc tagtgatggg aatttgactc  300
aaaaccatgg gtttcttgat ccgccttggg tgaatgcatg tcagttattt tttgaagtgg  360
gatagatgtg gattatatat ttaaatacga atggatgtaa atttattata tttaaaattg  420
gggatataat tcagtccatc agatttataa ataaaaaatt aaatattatt acttatttaa  480
attttaatta taataattag ataatatata aaaaaatact aaataaaaat tatttaaaat  540
cattttaata tgtatttatt tttataatat aaaatttata ctattaaaat taactaaaag  600
atatgaaata tcggttttta atttattaat gatttatgga ttttgtggat ttcgattaac  660
ttagactaat acaaatgcgg ttataataaa tttatttgcg gtctttgtaa ataaataaaa  720
atagacaaaa aaaaaactct gatctgctgc gaatggatca aatcaaagga acggagaaaa  780
ctatcccaaa cattgtgaaa ttataaacga aaacttaaat tcaaatatat ttaactttta  840
atattaacgt accctagttt aaataaaact aatataaaca ttgtacgagc tccgaatatt  900
ttccatcatc attcacgaca tcacaccatt gcaccttacc cgaaatctct ttttctattc  960
aggtttctaa agcaatctcc gcacaccaaa tcttctcgtt gtcctgaaga aaaagaacca  1020
atttctcacc ccaacgcact gtatacgtac cccatgaacc attcgtctta gacaacaatt  1080
cttccacacc tttcaccaca ctccggcacc tctgctttgg tccttaattt ggatcatgcg  1140
ctctcaactt gttcttgtag acatcgtaat agtaaaatac attgtcaaca acacaacctt  1200
gctcccattt cctccaattc ccatttactt tccttaggtt cataagagta gctataatag  1260
tcatctctca cgtaaatttt atgtgagtga taaaatttca tatgtaaaat cccattaagt  1320
ttcagttgag gatgatagac ctttggttta gttacttttg acttttgagt ttgcattagt  1380
tttggttatt gtttcttgaa tacacatttt attatataag ttaactagtt tgggatttct  1440
gagtgttttc tatttaaatt gtgttatttc cctctttcct catcctcttg acttggcata  1500
atgtagttgt agataaatta tttttactca ttagtaattg atcatctttt tattgagatt  1560
atttatttag tatattgtag atagaagaag ctccttaact atggagcaag taggaagagt  1620
gagagatata gagatgatcc gatggtggaa agtgtttcat gcatcagcaa gcctcttctt  1680
ctgactctgg gaggaaagac ttgagcggag gaaatcttgt ttcgcaggat tcttggcggt  1740
cccgttaatg aacctctggt accatttacc agattctttg aggtttctat cgtcgagatc  1800
gtcccaatta acataactga gtccaaatct gacggtaaaa cctttacaga attcataatt  1860
atctccaaga gcccatgcaa agtatcctct cacgttgaca ccccttctccc tgaaaacaag  1920
aacaatcata tatatataga tgttacccga aaagaagaag aaaataacat atgaagaaaa  1980
tcatttataa tagcatccac tcacttgatg accttgcgga gaaaacatag atgactgcac  2040
agataatcaa ttcgcttgta atcggcaata gcttgctcac ggttttctga actgggggta  2100
ctaaatccta attaaccgcc ataacatgaa aaagtataca atatttgaaa atcagtttct  2160
tggatttatt tcgaaataca ctaattacga tatgttatat atgaaaatat gagtagtgga  2220
agtatgtaga actcgccatt ctcggtgaca tagattaatg ggtcgccgta tttggttttg  2280
aagtagtcca ttacgtaata aatccctttt gggtagtaat agctgttgcc gttgactttg  2340
```

```
tcttcaacga actgagaaag gaagcaaaca tatatataca tattaacaag gagaaagtgg  2400
tgttatattg caaatagaaa aaaaaattga aagagaaatc aaaggggtgg atgatcattt  2460
atatatacca gtggaccaag aaattcacca cgtgaattat catctgtaaa cacaaggatg  2520
aaataattga tggtcactca gaaagtatgt tgtaacaaaa aggagatagc acatatatat  2580
atgtatatag aaagcttgta actaagtggt aatgttgtag tacatgtgag ctttacgcca  2640
gcgtccatca tggcagtgtg tgtctctgaa ggatatgggt tcggttttgg ctgggcgtac  2700
tgagtgacgt aatagttgag accaagaaaa tcatatgaac cagcaacgag ttccgcttct  2760
tcctcggtga agttgggaag ccgactaccc acaatctgcc tcatgatgtc tgggtatcta  2820
ccctttgtta acggctccat atacctgatc caagtatatt tttgtttcat tataaataca  2880
aaaatacaaa ctgatacatt tttggtaata tataaaatta tatataccat ccatggaaga  2940
attggttcat cctctcagct gcttctatgg aggcaggatc agattcatca tatggaagaa  3000
accatctagt tatcatcaca ggtccaatct tccctttttg gaactgttca tcacgtgata  3060
tatatatgac tatacattag aatcggatat gttagattta gaccaccttt tcacatatgg  3120
aggccactca ccttatattt ggtcctgtaa agatcgatgc atgagcaaga agctggttat  3180
gtgcaacgat gtagggttct gttgaagaat ttccgccgta acacctgaat caaccatagg  3240
agaacatcga ccgggtgcat ctgttccgat cgcatagcct cttgtaggca ctgtgtatag  3300
ctggttgatc gtgatccaat gctttacctt tccaccaaat tctttgaaac atagatccgc  3360
gtaatctttg aaatcttggc tgtgcatatt agtatagaat catttcagta atacatgtaa  3420
attaaaccaa atattcttct tctatcacta attatattta ctctcttcag atataattaa  3480
gaaggatggc acatacatga tctggcggtc caagaaacct tcatactcat cttggagtgt  3540
ttgaggaaga tcccagtgaa agagggtaac gaaaggcgtt atattttttt cgaggagtgc  3600
atctatgagt ttgtggtagt aatcaaggcc tccttggttc actcccctac tcacctttcc  3660
ttctgctcat gtatatatac atcgtacttt aattagtact cttccaacta aatcatccca  3720
attaaaaaaa ataatatata tttatatata tatatatata tataattgat cgataatatg  3780
tacatacttg gaatgattct tgaccacgca aaggagaatc tgtagccagt agcattgagt  3840
tcgcccatca cgtctacatc tttctgcagt ttacatatta attttaatct catgtcaatc  3900
cacacgtata gtttttatac atactatagt tcagtcatga gtatcaatgt actgagaaat  3960
taacctgcca tctcgtatat gactcacaag tagtgtctcc attcttcaaa tctgacccag  4020
ctttctctga tattaaatta caaatacatt aatatgtgta tatgtaacca acattcctct  4080
cacatataaa atagatgtca ccgtgcaaac gacatacctg ggtatcggtg actgaagcca  4140
tcccaaacgt taacaccacg acctctccct ccttcgatct gaaatgaaaa gaggcaacca  4200
tgcaaagttg cattttagtg ttttaaattt tatttcaaaa ttagggtgtg acaacatttg  4260
ctacatgcct ggtaagcaga agatgcaaca ccgaagatga aatcttttcc gaagttctta  4320
ctgcttaaaa tatcagtgtt actacaagtg aatggattgt tctcttcgca agtaatttct  4380
tcatcagctt tgcaactcgc agcagctaat agaaaaacta aagcgagtcc atgaagaagc  4440
ttcatgttta atctgttgat gtatgtgttg tgttgtgtgg aaccttgtgc tcatctaggg  4500
tttatatagc ctttccgaaa gaagagtgac atatgtattt tcttgtctta gtatcttgat  4560
agtttgggag aggtgtaggt gggatcatgt gtcccgtggg ttcactgact tttgctcagt  4620
gttcaccgat ttttgtaata tttctgattg ttatgtttcc actttttagt ctttcattat  4680
ctattgcaaa aaaaaattgt tagatagcac aagttgtgtt ccttaaccga aacacgaatt  4740
gacacatctt caaattgatc cgtcaacagt catgcaatga tgcaatgcag catgtaagat  4800
ttgcgccaaa actagaacta cacttaacgt caagattcgt tattgaaaat ttatatcgaa  4860
attttatcaa gtgttgaatc tagagtaaca ctggtgtaaa gccgcactta tcagttatca  4920
cgagctctac cgtcacaaaa tcacatcata tcatattggt tttgatcgct ctatttctgc  4980
tttatcacat gagaccggtg cctccgaaag actaaagaaa acgaaaacca accacagttt  5040
ttgctttttt tggtatcgtt tttaaatgat tgaaaaggtt ggaacggata cgtatccgtg  5100
acttccagat aaatagattg atacttgtgt attaacctat agtttgttcc atagtttttt  5160
actctataaa gttacaattc atactgttta cgtgccacca acttgagttt gaaatcaatt  5220
atttacgtag cacatataca taagttaact tgtatttaat aatatcgcaa taggtgattc  5280
tcctgtactc ttccacgagt ataactgtta tgaactaaat atatatagta gtaactaatt  5340
aatgttttct tttcaatttc aaataatttt ataacttatt ctaagagaaa ttgttttaaa  5400
aaccttaaat tagccatggc ttttcaaaaa tagactcaat caaaaatatc ttaaaataaa  5460
ctgtttatat tttaagaaaa aacaagatga aatagttcaa atatgaatta agataagctg  5520
ttcgtatttt aagaataaaa cacttaaatt tatgtgcttt aggccttcgt tatctttaag  5580
taacatttac tttgcgaact tatactggat ttttgtttag gttaacatgt tctttctgca  5640
aagtgtaaac tgccatgaaa aaaaaaagct actagttacg gacaacaatc atgttgacgg  5700
aacaacaaac agacgtcatc tttgaaacat gtgcacactt ctatgtatta tccaaataga  5760
taaacacaag tgttatttgt ttgtcacttg ttagatcacc tacaatgaag gtgttgaatc  5820
ttgtattcaa ctgttgaact tcttccagta agggtgttga agttttagaa caatcctatg  5880
tggtatcaac agctgaaact tttattttat gggccagctt cgccacacgg cgcatttgga  5940
ttggaagaaa ttgttggata gatttttaag ttttatttc acccaataac tgaaaatcat  6000
ttattttata atagaaattt ttaattatat caaaaaattt atgatttttt actatctata  6060
aataaaaact actctcattt catttggaca caagaaaaaa aaacaccatt ttttcattag  6120
aatcaattat tttagtgttt taaacatttt ttgttaaata aatcctaatt gttttaacaa  6180
tattgatttt agtattattt tttaaaatgt aaggtatgta cataaataaa ataaaattta  6240
aaaaattatg ttattttaat ttttaaataa attataatca aagatatcat taatatacgt  6300
acttgttata ctgtaaaaga taaagtatga attaagtggt ggggtagagt gttaaatttt  6360
taagcaaacc attataaatg ttgtagatgt ttaaaatgaa atgaatgtta aataaattat  6420
gtggaagaga gaggatgatg tggaa                                         6445
```

```
SEQ ID NO: 4           moltype = DNA  length = 6631
FEATURE                Location/Qualifiers
source                 1..6631
                       mol_type = other DNA
                       organism = synthetic construct
SEQUENCE: 4
ttttgcgaag aggtatacaa tcactcaaat atatacttta aacttgatta atattattac  60
taatattttc ctatattatt ttgtattaaa aatacggaca ataggattgg gatcaatcaa  120
cgattttccc agggtaacct cttcctatgt tcgttgaggt gatgttccgg ctcaactctg  180
```

```
aacggagttg acagatgctc ataacaagat ttcatcaatg aggattgatt gatccatatg  240
tttgtaaacc atatgttttt cggcatacat gtggagagac ttgacagcta ctcgagcttt  300
agagattaca cgtaaaaata ttaatatcat cataccaact ttggaggagc aagctgaccg  360
ggaattaata atggataaag cggtttgaga gactagggtc gagtttttca acgatgttga  420
ttagaaatag tttctgtatt tttattttgt tttataattt ctataaaaac tagtttaaaa  480
ttttataaaa tattcattaa ttttattgat gttctggtgt attaaatagt taattcattt  540
aaacataaac tagataccaa atgtttctat tctttaaatc caacatttgc atcaataaaa  600
taacttcgaa aatattatga tgttgtcgat aaaaatacaa aaggactttc cttttttttat  660
ttgctaatat gatcatcttt agcacattgt ctattttcac aaattcaatg tccgattaag  720
aaggcaacta caaaacgtgg aaatgaattt atacaaaata tttaaaagga cgatccagaa  780
catttttgga gttatcatat aaattcagat gttttttttag atttgtgcag acttagacat  840
ctttaagaaa tacaagatgg attttggttg aagaaatgct tgccacattt tttttcattg  900
ttggccagta agagatatat tctccctcga gatgtattca agagatcaag tttggaaaca  960
attcagagtt taataaaagg gtgttaaaca gtattggcca agtttgtagg ctaaaccagg  1020
aactgcattg cctttacaaa catgagaaac aaaagatttt attcctactt taaagtatgt  1080
aaaaattgtc ttatctattt gtttattttt atccgttaac agtttcattt atattttcag  1140
gattgtattg gagctattga tggaacatat ttctgctatt gtagtaataa ttaaataaaa  1200
ctgttagtta tcaaaacaga aatagagttt tatctatgaa tgtcctagtt gcgtgcaatt  1260
ttgatttgca gttcaaatat gttacaactg gttgggaagg ttcagctcat gatgcaaaag  1320
tgttaaatga tgcattaatg agaagtagca ataaatttga aacccccaag gtaattgcat  1380
tactcaatag aaatatatag tatgtgttta agatcggtta attaattata agttcttgat  1440
ttttcatgta ggagatttgg tagataacca tctgaaatct gaaaacttgg tagccgagtt  1500
tgtaggctaa accaggaact gcattgcatc caaataaatt tagctaaatt ccatcaaatc  1560
taaaatcctt taaaaatttc aaatccctaa tcaaataagc cctttaatat atttgaaggt  1620
atatttaagt accaaatggt tatatatttt aaaaaatcca acagttaatt caacaaaata  1680
aactttacat aattttttat ccctttcgta atttgttaaa atatgataat ctacttacaa  1740
ggttgtcatt ttattcagat aatagtccct tgttatttac aaaataaact ttacaaaaaa  1800
ataacgacca atcacaatga tgatactgat tcagctaaag taactgagcc cacggaattc  1860
accccaccaa acctctccca aaatatcaag atattgaaga aaagaaaatg tatacgtgac  1920
actactttac aaaggctata taaaccctag actagcacaa ggttccatcc aacacaaaca  1980
catacatcta cttattaacc atgaagcttc atggactagc cttgataggt tttctaattg  2040
ccgtggtgag ttgcaaagct attgaggaat gccgagagaa cgagccattc acatgtggaa  2100
acgctgatca gttaagcagt aaaagttttc caaaagactt catattcggt gttgcttctg  2160
ctgcttacca ggcatgttac aaatcaacaa tttttgacgt agaaaaccat ttaaaatatt  2220
aaatccaacg ttgcatggtt gtttcttatt attgtaggtg gaagggggca gaggacgtgg  2280
tcttaacgtt tgggatggct tcactcaccg atacccaggt atatcatcta catggtacat  2340
atatatacat atgtacaact cttatcattc ttagtataaa atgtatctgt ttactatcag  2400
agaagggagg atccgatcat gggaatggag acactacttg tgagtcatat acgagatggc  2460
aggttagttc ctcactgagt catataccag atggcaggtt aatttctcat ttcttcacta  2520
tatataatga tatccgagtg cgtgtgtaaa ctgaagaaag atatagacat catagacgaa  2580
ctcaatgcta ctggctacag attctcattt gcctggtcaa gaatcattcc aagtatgaac  2640
acataaacaa tctatttata caaaagaatt ctcgtaattt gattgtgatt gttgggaaga  2700
ttaaatatat gatatgtata catgagcaga aggaaaggtg agtaggggag tgaacaaagg  2760
aggtatcgaa tactaccaca aacttctaga tggcctcatc gctaagaata taaccccttt  2820
tgttaccctc tatcactggg accttcctca aacactgcaa gatgagtatg aaggtttctt  2880
gaaccgcacc gtcatgtatg tcatttgggc cgcgttctta gcaaggaata taagaagaaa  2940
aacatatata cataagtgat ctcatgttaa tgatttgatt ctatgctatg cacagagatg  3000
actttagaga ctatgcggat ctatgtttca aggaatttgg tggaaaggtg gatcacgatc  3060
aaccagctgt acacagtgcc tacgagaggc tatgcaatcg gaacagatgc acccggtcga  3120
tgttctccgg cggttgatga gagatgttac ggcgggaatt cttcaacaga accatatata  3180
gttgcacata accagcttct tgctcatgct gcggcggtcg atgtttacag gagaaaatat  3240
aaggtgagag tacgtgggtt tgtgaatagg tgtagtcttt acgtatatga ctatatctaa  3300
tcatatcatt atcgtatgcc gtgaccaaca gttccaaaaa gggaagatcg gaccagtgat  3360
gataaccaga tggtttcttc catttgatga gactgatgcc agcagagatg cagctgagag  3420
gatgaaagaa ttcttcttgg gatggtaacg tatatgtatg tatatatcaa caaaaatgaa  3480
atgattttct tatacgtatg tacgtcgacc aggttcatgg agccgctaac aaagggtaga  3540
tacccagaca tcatgaggga aattgtgggt agtcggcttc ccaatttcac ggaagcagaa  3600
gcggaactcg ttgcgggttc atatgatttt cttggtctca actactacac cactcagtac  3660
gcccaggcaa aacctaaccc agttacatgg gcaaatcaca ctgccatgat ggacccaggc  3720
gcaaagctca catgtaccat tctgtttcct cttatagtta caacctttct atatatagat  3780
atctcctttt aattataaca tatatgtaca ttgtgagtga ccatcaatta tttcatcctt  3840
gggtttacag ataacaattc acgtggtgaa aatcttggtc cactggtacg tgcatgatcc  3900
acccctgtta cttctcaata ttttttttc tttcttgttt atgggtataa tatgtacgct  3960
tccttttctc agttcgttaa agacgaaaaa aacgggaatg cctattacta cccaaaaggc  4020
atctattacg ttatggacta cttcaaaacc aaatacagta accctttgat ctatatcact  4080
gagaacggtg actactactc atctcttttt tgcatattaa ttaagtaaat gtgtgtttca  4140
aataatgtat agttgttgat gtaccatgat ggtctaatta ggatttagta ctcccggtga  4200
agaaaaccgt gacaaagcta ttgctgattc caagcggatc gattatctct gcagtcatct  4260
atgttttctc cgcaaggtca tcaggtgagg ggagctact ttattttttt ctcttttgaa  4320
tttgatgtat ggtcatcatc atgcataggc tttgaattat gatttttcct gtttccaggg  4380
agaagggtgt caacataaaa ggatactttg catgggctct tggagataat tatgaattct  4440
gcaaaggttt taccgttaga ttcggactta gttacgttaa ctggacagac ctcaatgata  4500
gaaatctcaa agactctggc aaatggtacc aaagctttat taacggtacc aataagaacc  4560
ctgccaaaca atatttccgc cgcccaaacc tctccttcca gaaccagaag aagaagctcg  4620
cagatgcatg aaacacttta tcccaccatc atgatcatct tcatatctct actacttgct  4680
tcatagataa ggagcttgtt gtactaaata aatattctaa taaaagatga tcatttacta  4740
atgaatattt tcgtttgagt tcaatccctt cttaccgctt cagttacgtt ttactttgga  4800
tgattaggtt aggttttaca aattataaaa cttggcatgt cagctattca tgtgagattt  4860
gtagatttag ataagagaga gtctatgtgt aaatgcgaga actagcaaga atagtaacac  4920
```

```
aaagtacaca agagaatatc tctacaaaaa atatatgtat ttactagtat ttttaaagta  4980
aatttactga tatcaacctt agattctgtc agcacttgct tccaaaaaac cctagattct  5040
tcaatcgcga cctcctctga gctgagtctg aattctgata ccaatttgtt caacttaacg  5100
ctcagattac gacctagatc tactcgattg cttgaatata aaaaaaacat gcaagaagac  5160
acggtttgtt cacccgtgtt ggctctccct acaaaatgtt gtagatcaaa tgtcagtaaa  5220
cccgcatgaa gcaaaattat tggctctccc ttgccgtttg cgatctatga tgaatgtgaa  5280
ggagaaggaa atagtttggc agtacaaaca gagacagaga gacttattga aatttctact  5340
gaacctgtgt cagtcagtca aaacgtggag gaagaaatcc aaacggagaa acacgaggag  5400
agacagctta gatcatctct tcatcaaaat gtaaaaaaaa aagattgacg aaagaataga  5460
cttatgggct gacatccgga actactatga ttcttctatc atttggaaaa atctgtagat  5520
ggttgtagga gattttaatg agactttgaa cattgataaa cactcttcaa atgctgtgag  5580
ctctaatgag ggagtttcaa gatgtggtgc aatattgttc tcttctcgat tctacctcac  5640
atggaacaat agaagagcat aaggccatat agcgaagagg ttaataaata atcacgtgtt  5700
acaactattt ccgcagtctt atagtgtatt ggaaggagga ggttgctagg atcacttgag  5760
atgcagaatt aagttactat cagagctttg tcgaccaaag atgcctctta aatttgttaa  5820
cgttgtgcca gagatggaac aattcaaggt cgatattttt gggaggaata cttatgaaat  5880
atccaaaatg gtaaccggag cagaggccaa ccagacacac cactcaacca accaaagaat  5940
cgacatgacg tatgtgcatt ctaaacacca tatctcacaa agcatgaggt cttttgccaa  6000
tatgtaaaat atatttaata tatatttatt atttgacaat atgtaaaata atgtaaaata  6060
cataaatatt aatttatata tagaatgatc attccgcgca agctgcagat cttaacctag  6120
ttatgtattg gtttaaaatt cagtgtatca caaaaaaaat aagaagtaat gaattaatta  6180
tttttaata ttgaaaagag gagtaatgtt gtacgttgat atcaaatgag agataacaga  6240
agttgttcat ccataagcaa agtgaccctt gtatcattag tgagggataa aaatttgttt  6300
gtaaagataa gcattttaag taatacttaa cctataagtt catgctgata tttttttttc  6360
attttataaa tgtatagttt tgatattatc ataaacgttt gaaatatatg atttacattt  6420
tagtgttata tattgtgtaa ctttttaatt ttttgtttaa gttttttat tcaacatgat  6480
taataatata gagtgatttt tttatatatt ttaatttgtt tttaatattt attacatttt  6540
caagcagggt agaataaatt cataatctga aataatcaaa tagagaatct tattcaaaat  6600
atatattttt gatattatca taaacgtttt a                                6631

SEQ ID NO: 5            moltype = DNA  length = 6614
FEATURE                 Location/Qualifiers
source                  1..6614
                        mol_type = other DNA
                        organism = synthetic construct
SEQUENCE: 5
tatacataat atataaatga atacaaataa ataataatag ataaaaatag ttttatatat  60
aacattcatc ctgcgcaatt gcccgggtct taagctagtt cattgttaac ttaacaacaa  120
attaacattg actgtcgcag ttaatttatt gctaatttaa caacaataat aaacatccac  180
gatttaaagt cttatattgt aagtcaaagt tacgaagata gtttcagcgc aaaatttata  240
tctagtttac gatgaatata tttacgacaa aataacgacg tatcatggac cttgcaactt  300
aagtctgtac gacgatcttt caataactat gtgcacttaa cgatgaagtt acattccttg  360
ttatttagtt gtagaccaga tgtctttttt agatttgtac agacttagac agagtttaat  420
aaaatattaa gggtgttaaa cagtattggc caagtttgta ggctaaacca ggaactgcat  480
tgcctttaaa aatatgagaa aacaaaagat tttgttcttg ctttaaggta tgtgaaaaat  540
tgtcttatct ttttgtttaa ttatccgtta acagttcaat ttatattctc aagattatat  600
tggagctatt gactgcatta ctcaatatat atatatatat gtattatata tgtttaatta  660
agataggtta cttaattata agtttgagtt ttatttatat ttcacattaa aaatatttca  720
tgaaaatttt atctcgcaaa ctgtgggtac ataaacaaga taaattttag agctctattt  780
cgtagtacac ataatcatat gaaataattt actggagaag gcattgatcg aagaaataaa  840
taagaattat tcaaccatcg tcattcttgt ttgagaaata tcatcgaaag gatttgggt  900
attttcaaat caagatttct tatattcaaa ttcgctccta gtttttcata aatgacacaa  960
gcagagcaag tgcttgtatc tgctgcattg cataactttt tccgtcagaa atgtcggcca  1020
gatgagtttc ttccagaaga aacatctgat gaacaaaatg ttactcaatt aagtagtaat  1080
ggttatcaat ttcttggcga acaagaacaa caaagagaac atgctactga atagagaaca  1140
accaatgctt caaatatgtg gaatgatggt actagtggat ctcaacggtg aaatatgcct  1200
gagtaagtta acatttttat gtgtttaatt ttatagttga caataatagt gaaatctcac  1260
aatgtatttt taggtgtgag atgatttatg gcattgttgg catgatatta aaaacacaca  1320
ttcgtctgtc acaataaagt caaaattgca gtcaagtatt tgtaattttt tttcatgctt  1380
ttttcgaaat tgattacact tttttgcgtg gtttcgataa attgttgtga gaaaatgttt  1440
tttaatgatc ttaggaaatc aatttttatt ttctttaaaa ttctaccaaa ttaatctcct  1500
atcaaaagct ctatcaaatt ccttaaaatc caaacaaatt tagctaaatt ccatcaaatc  1560
tgaaatcctt aaaaaaattc aaatccctaa tcaaataagc cctttaatat atttgaacct  1620
atacttaagt accaaatggt tatatattta aaaagatcca acagttaatt caacaaaata  1680
aactttacat aaatttttat ccctttcgta atttgttaaa atatgataat ctacttacaa  1740
ggttgtcatt ttattcagat aatagtccat agttatttac aaaataaact ttacaaaaaa  1800
ataacgacca atcacaatgc tgatactgat tcagctaaag taactgagcc cacggaattc  1860
accccaccaa acctctccca aaatatcaag atattgaaga aaagaaaatg tatacgtgac  1920
actactttac aaaggctata taaccctag actagcacaa ggttccatcc aacacaaaca  1980
catacatctc cttattaacc atgaagcttc atggactagc cttgataggt tttctaattg  2040
ccgtggtgag ttgcaaagct attgaggaat gccgagagaa cgagccattc acatgtggaa  2100
acactgatca gttaagcagt aaaagtttcc caaaagactt catattcggt gttgcttctg  2160
ctgcttacca ggcatgttac aaatcaacaa tttttgacgt agaaaaccat ttaaaatatt  2220
aaatccaacg ttgcatggtt gtttcttatt attgtaggtg gaagggggca gaggacgtgg  2280
tcttaacgtt tgggatggct tcactcaccg atacccaggt atatcatcta catggtacat  2340
atatatacat atgtacaact cttatcattc ttagtataaa atgtatctgt ttactatcag  2400
agaagggagg atccgatcat gggaatggag acactacttg tgagtcatat acgagatggc  2460
aggttagttc ctcactgagt catataccag atggcaggtt aatttctgat ttcctcacta  2520
tatataatga tatccgagtg cgtgtgtaaa ctgcagaaag atatagacat catagacgaa  2580
```

```
ctcaatgcta ctggctacag attctcattt gcctggtcaa gaatcattcc aagtatgaac  2640
acataaacaa tctatttata caaaagaatt ctcgtaattt gattgtgatt gttgggaaga  2700
ttaaatatat gatatgtata catgagcaga aggaaaggtg agtaggggag tgaacaaagg  2760
aggtatcgaa tactaccaca aacttctaga tggcctcatc gctaagaata taacccccttt  2820
tgttaccctc tatcactggg accttcctca aacactgcaa gatgagtatg aaggtttctt  2880
gaaccgcacc gtcatgtatg tcatttgggc cgcgttctta gcaaggaata taagaagaaa  2940
aacatatata cataagtgat ctcatgttaa tgatttgatt ctatgctatg cacagagatg  3000
actttagaga ctatgcggat ctatgtttca aggaatttgg tggaaaggtg gatcacgatc  3060
aaccagctgt acacagtgcc tacgagaggc tatgcaatcg gaacagatgc acccggtcga  3120
tgttctccgg cggagagatg ttacggcggg aattcttcaa cagaaccata tatagttgca  3180
cataaccagc ttcttgctca tgctgcggcg gtcgatgttt acaggagaaa atataaggtg  3240
agagtacgtg ggtttgtgaa taggtgtagt ctttacgtat atgactatat ctaatcatat  3300
cattatcgta tgccgtgacc aacagttcca aaaagggaag atcggaccag tgatgataac  3360
cagatggttt cttccatttg atgagactga tgccagcaga gatgcagctg agaggatgaa  3420
agaattcttc ttgggatggt aacgtatatg tatgtatata tcaacaaaaa tgaaatgatt  3480
ttcttatacg tatgtacgtc gaccaggttc atggagccgc taacaaaggg tagataccca  3540
gacatcatga gggaaattgt gggtagtcgg cttcccaatt tcacggaagc agaagcggaa  3600
ctcgttgcgg gttcatatga ttttcttggt ctcaactact acaccactca gtacgcccag  3660
gcaaaaccta acccagttac atgggcaaat cacactgcca tgatggaccc aggcgcaaag  3720
ctcacatgta ccattctgtt tcctcttata gttacaacct ttctatatat agatatctcc  3780
ttttaattat aacatatatg tacattgtga gtgaccatca attatttcat ccttgggttt  3840
acagataaca attcacgtgg tgaaaatctt ggtccactgg tacgtgcatg atccacccct  3900
gttacttctc aatatttttt tttctttctt gtttatgggt ataatatgta cgcttccttt  3960
tctcagttcg ttaaagacga aaaaaacggg aatgcctatt actacccaaa aggcatctat  4020
tacgttatgg actacttcaa aaccaaatac agtaaccctt tgatctatat cactgagaac  4080
ggtgactact actcatctct tttttgcata ttaattaagt aaatgtgtgt ttcaaataat  4140
gtatagttgt tgatgtacca tgatggtcta attaggattt agtactcccg gtgaagaaaa  4200
ccgtgacaaa gctattgctg attccaagcg gatcgattat ctctgcagtc atctatgttt  4260
tctccgcaag gtcatcaggt gaggggaagc tactttattt ttttctcttg tatggtcatc  4320
atcatgcata ggctttgaat tatgattttt cctgtttcca gggagaaggg tgtcaacata  4380
aaaggatact ttgcatgggc tcttggagat aattatgaat tctgcaaagg ttttaccgtt  4440
agattcggac ttagttacgt taactggaca gacctcaatg atagaaatct caaagactct  4500
ggcaaatggt accaaagctt tattaacggt accaataaga accctgccaa acaatatttc  4560
cgccgcccaa acctctcctt ccagaaccag aagaagaagc tcgcagatgc atgaaacact  4620
ttatcccacc atcatgatca tcttcatatc tctactactt gcttcataga taaggagctt  4680
gttgtactaa ataaatattc taataaaaga tgatcattta ctaatgaata ttttcgtttg  4740
agttcaatcc cttcttaccg cttcagttac gttttacttt ggatgattag gttaggtttt  4800
acaaattata aaacttggca tgtcagctat tcatgtgaga tttgtagatt tagataagag  4860
agagtctatg tgtaaatgcg agaactagca agaatagtaa cacaaagtac acaagagaat  4920
atctctacaa aaaatatatg tatttactag tatttttaaa gtaaatttac tgatatcaac  4980
cttagattct gtcagcactt gcttccaaaa aaccctagat tcttcaatcg cgacctcctc  5040
tgagctgagt ctgaattctg ataccaattt gttcaactta acgctcagat tacgacctag  5100
atctactcga ttgcttgaat ataaaaaaaa catgcaagaa gacacggttt gttcacccgt  5160
gttggctctc cctacaaaat gttgtagatc aaatgtcagt aaacccgcat gaagcaaaat  5220
tattggctct cccttgccgt ttgcgatcta tgatgaatgt gaaggagaag gaaatagttt  5280
ggcagtacaa acagagacag agagacttat tgaaatttct actgaacctg tgtcagtcag  5340
tcaaaacgtg gaggaagaaa tccaaacgga gaaacacgag gagagacagc ttagatcatc  5400
tcttcatcaa aatgtaaaaa aaaaagattg acgaaagaat agacttatgg gctgacatcc  5460
ggaactacta tgattcttct atcatttgga aaaatctgta gatggttgta ggagatttta  5520
atgagacttt gaacattgat aaacactctt caaatgctgt gagctctaat gagggagttt  5580
caagatgtgg tgcaatattg ttctcttctc gattctacct cacatggaac aatagaagag  5640
cataaggcca tatagcgaag aggttaataa ataatcacgt gttacaacta tttccgcagt  5700
cttatagtgt attggaagga ggaggttgct aggatcactt gagatgcaga attaagttac  5760
tatcagagct ttgtcgacca aagatgcctc ttaaatttgt taacgttgtg ccagagatgg  5820
aacaattcaa ggtcgatatt tttgggagga atacttatga aatatccaaa atggtaaccg  5880
gagcagaggc caaccagaca caccactcaa ccaaccaaag aatcgacatg acgtatgtgc  5940
attctaaaca ccatatctca caaagcatga ggtcttttgc caatatgtaa aatatattta  6000
atatatattt attatttgac aatatgtaaa ataatgtaaa atacataaat attaatttat  6060
atatagaatg atcattccgc tcaagctgca gatcttaacc tagttatgta ttggtttaaa  6120
attcagtgta tcacaaaaaa aataagaagt aatgaattaa ttattttttta atattgaaaa  6180
gaggagtaat gttgtacgtt gatatcaaat gagagataac agaagttgtt catccataag  6240
caaagtgacc attgtatcat tagtgaggaa taaaattttg tttataaaga taagcatttt  6300
aagtaatact taacctataa gtttatgctg atattttttt ttcattttat aaatgtatag  6360
ttttgatatt atcataaacg tttgaaatat atgatttaca ttttagtgtt atatattgtg  6420
taactcttta atttttttgt ttaagttttt ttattcaaca tgattaataa tatagagtgg  6480
ttttttatat attttaattt gtttttaata tttattacat tttcgagcag ggtagaataa  6540
attcataatc tgaaataatc aaatagagaa tcttattcaa aatatatatt tttgatatta  6600
tcataaacgt gtta                                                    6614
```

```
SEQ ID NO: 6           moltype = DNA  length = 5885
FEATURE                Location/Qualifiers
source                 1..5885
                       mol_type = other DNA
                       organism = synthetic construct
SEQUENCE: 6
tgttatttag tcatagaccc gatgtctttt ttagattttt aaagacttag acaactttag  60
gaaatacgag atggattttg gttgaagaaa ttcttgccac attttttctc attgttggcc  120
agtgtacgag atattattct tcctcgagat gtattcaaga gatcaagttt tgaaataatt  180
cagagtttaa taaaatatta agggtgttaa acagtattgg ccaagtttgt aggctaaacc  240
```

-continued aggaactgca ttgcatttaa aaatatgaga aaacaaaagt ttttgttctt gctttaaggt 300
atgtgaaaat tgtcttatct ttttgtttaa ttatccgtta acagttcaat ttatattctc 360
aggattatat tggagctttt gatagaacat atattcctga tatggtagta gtaaataaaa 420
ctgttagcta tcgaaaccga aatggagttt tatctcagaa tgctctagct gcatgcaatt 480
tttatttgca gttcaaatat gttattactg gttgggaagg ttcagcacat gatgcaaaag 540
tgtaaaatga tgccttaacg agaagtagca aaaaatttga accccccccc cccccgaggt 600
aactgcatta ctcaatatat atatctatgt gttatatgtg tttaattaag ataggttact 660
taattataag tttgattttt atttatattt cacattaaaa atatttaagg aaaaatttat 720
ctcgcaaact gtggatacat aaacaagata aatttaaaag ctctatttcg tagtacacat 780
agttatatga aagaatttac tggaggaggc atttatctaa gaaataaata agaattattc 840
aaccattgtc attcttgctt gagatatgtc atcgaaagga ttttgggtat tttcaaatca 900
agatttctta tattcaaatt cgctcctagg ttttcataaa tgacacaagc agagcaagtg 960
cttgtatctg ctgcattgca taactttttc cgtcagaagt gtcggccaga tgagtttctt 1020
ccagaagaaa catctgatga acaaaatgtt actcaaagta gtgatggtta tcaatttctt 1080
ggcgaacaag aacaacaaag agaacatgct actgaataga gaacaaccaa tgcttcaaat 1140
acgtggaatg atgctactag tggatctcaa cggtgaaata tgcctgagta agttaacatt 1200
tttatgtgtt ctttaatttt tataattgac aataatagtg aaatctccca acgtattttt 1260
gattgatagg tgtgagatga tttatggcat tgttggcatg atattagaaa cacacattcg 1320
tctgtcacaa taaagtcaaa attacagtca agtatttgta attttttcat gctttttccg 1380
aaattgatta cactttttttg cgtggtttcg ataaattgtt gtgagaaaat gttttttaat 1440
gatcttagga aatctatttt tattttcttt aaaattctac caaattaatc tcctatcaaa 1500
agctctatca aattccttaa accccaaata aatttagcta aattccatca aatctgaaat 1560
ccttaaaaat tttcaaatcc ctaatcaaat aagcccttta atatatttga acgtatactt 1620
aagtaccaaa tggttctata tttaaaaaaa catccaacag ttaattcaag aaaacaacac 1680
tttaaatcac tttttatccc tttcgtaatt tgctaaaata tgataatcta cttacaaggt 1740
tgtcattttt ttcagatata aatagtccct tgttatttac aaaattaact ttacaaaaaa 1800
attaacgacc aatcacaatg ctgatactga ttcagctaaa gtaactgagc ccacggaatt 1860
caccccacca aacctctccc aaaatatcaa gatattaaag aaaagaaaat gtatacgtga 1920
ctctttttac aaaggctata taaaccctag tctggcacaa ggttccatac aacacaaaca 1980
aatacattta cttattaacc atgaagcttc atggactagc cttgataggt tttctaattg 2040
ccgtggtgag ttgcaaagct attgaggaat gccgagagaa cgagccattc acatgtggaa 2100
acactgatca gttaagcagt aaaagtttcc caaaagactt catattcggt gttgcttctg 2160
ctgcttacca ggcatgttac aaatcaacaa tttttgacgt agaaaaccat ttaaaatatt 2220
aaatccaacg ttgcatggtt gtttcttatt attgtaggtg gaagggggca gaggacgtgg 2280
tcttaacgtt tgggatggct tcactcaccg atacccaggt atatcatcta catggtacat 2340
atatatacat atgtacaact cttatcattc ttagtataaa atgtatctgt ttactatcag 2400
agaagggagg atccgatcat gggaatggag acactacttg tgagtcatat acgagatggc 2460
aggttagttc ctcactgagt catataccag atggcaggtt aatttctcat ttcctcacta 2520
tatataatga tatccgagtg cgtgtgtaaa ctgcagaaag atatagacat catagacgaa 2580
ctcaatgcta ctggctacag attctcattt gcctggtcaa gaatcattcc aagtatgaac 2640
acataaacaa tctatttata caaaagaatt ctcgtaattt gattgtgatt gttgggaaga 2700
ttaaatatat gatatgtata catgagcaga aggaaaggtg agtaggggag tgaacaaagg 2760
aggtatcgaa tactaccaca aacttctaga tggcctcatc gctaagaata taaccccttt 2820
tgttaccctc tatcactggg accttcctca aacactgcaa gatgaggtgt agtctttacg 2880
tatatgacta tatctaatca tatcattatc gtatgccgtg accaacagtt ccaaaaaggg 2940
aagatcggac cagtgatgat aaccagatgg tttcttccat ttgatgagac tgatgccagc 3000
agagatgcag ctgagaggat gaaagaattc ttcttgggat ggtaacgtat atgtatgtat 3060
atatcaacaa aaatgaaatg attttcttat acgtatgtac gtcgaccagg ttcatggagc 3120
cgctaacaaa gggtagatac ccagacatca tgagggaaat tgtgggtagt cggcttccca 3180
atttcacgga agcagaagcg gaactcgttg cgggttcata tgattttctt ggtctcaact 3240
actacaccac tcagtacgcc caggcaaaac ctaacccagt tacatgggca aatcacactg 3300
ccatgatgga cccaggcgca aagctcacat gtaccattct gtttcctctt atagttacaa 3360
cctttctata tatagatatc tccttttaat tataacatat atgtacattg tgagtgacca 3420
tcaattattt catccttggg tttacagata acaattcacg tggtgaaaat cttggtccac 3480
tggtacgtgc atgatccacc cctgttactt ctcaatattt tttttttcttt cttgtttatg 3540
ggtataatat gtacgcttcc ttttctcagt tcgttaaaga cgaaaaaaac gggaatgcct 3600
attactaccc aaaaggcatc tattacgtta tggactactt caaaaccaaa tacagtaacc 3660
ctttgatcta tatcactgag aacggtgact actactcatc tcttttttgc atattaatta 3720
agtaaatgtg tgtttcaaat aatgtatagt tgttgatgta ccatgatggt ctaattagga 3780
tttagtactc ccggtgaaga aaaccgtgac aaagctattg ctgattccaa gcggatcgat 3840
tatctctgca gtcatctatg ttttctccgc aaggtcatca ggtgagggga agctacttta 3900
tttttttctc ttttgaattt gatgtatggt catcatcatg cataggcttt gaattatgat 3960
ttttcctgtt tccagggaga agggtgtcaa cataaaagga tactttgcat gggctcttgg 4020
agataattat gaattctgca aaggttttac cgttagattc ggacttagtt acgttaactg 4080
gacagacctc aatgatagaa atctcaaaga ctctggcaaa tggtaccaaa gctttattaa 4140
cggtaccaat aagaaccctg ccaaacaata tttccgccgc ccaaacctct ccttccagaa 4200
ccagaagaag aagctcgcag atgcatgaaa cactttatcc caccatcatg atcatcttca 4260
tatctctact acttgcttca tagataagga gcttgttgta ctaaataaat attctaataa 4320
aagatgatca tttactaatg aatattttcg tttgagttca atcccttctt accgcttcag 4380
ttacgtttta ctttggatga ttaggttagg ttttacaaat tataaaactt ggcatgtcag 4440
ctattcatgt gagatttgta ggtttagata agagagagtc tatgtgtaaa tgcgagaact 4500
agcaagaata gtaacacaaa gtacacaaga gaatatctct acaaaaaata tgtgtattta 4560
ctagtatttt taaagtaaat ttactgatat cgaccttaga ttctgtcagc acttgcctcc 4620
aagaaaaccc tagattcttc aatcgcgacc tcctctgagc tgagcctgag ttctgatatc 4680
aatttgttca acttaacgct cagattacga cctagatctt ctcgattgct tgaatataaa 4740
aaaacatgca agaagacacg gtttgttcac ccggtgtcca actccttttt cgatgtaagt 4800
aagagatatt ctcacctggt ctggttagac cagcaataca ctatctcagc tcaaactcga 4860
gcccggatca acaaccgatc acaatcttct tctccgatct tatctctctc tctctcttat 4920
cagctagaga tataaagtga gttttaacgt cgttttacaa cactcatctc ccccccaacg 4980

```
tgctaacaca cgtgcaactt gaacaagcta taaccggctt aaatcacttc taatttaacc  5040
cgtcaatcaa accagtttgc atacactcgg attcctgtca tcctgagtag acccactcag  5100
cttcgtatct tgcgaactta gaaactcagt tctcagtcac cctgagaaaa gtcaattctt  5160
ccctcatctt gccaactggt aaaaccttgg taatatattt gcgggattgt actgcgaagc  5220
aatcttcaca acattgatga tcttctcact taccaactca cgaacaaagt tgtacttcac  5280
gtccacatga tttgtcctct tctgaagcac tgtgtttctt gatagtgcaa tatcactttg  5340
agaatcacaa aacacctcca cttgggttgg tcttaagcaa aacccaactc gttcataaaa  5400
cccctgagcc atactgcttc ccgagctgct tcactcaatg caatgtacct ggttgttgat  5460
agtgccacta ctttctgtaa actcgacctc cagctcacta aattctctcc aaatgtgaat  5520
accattcctg tgattgacct ctttttatcc aagtctgctc catattcttc atcacagtac  5580
ccctttataa taaaatgtca ttgcttcttg tgttaaagca tcaccttgat attatttcct  5640
ttctctttct cttcttattc tttcagatct ctgattttct tgatatcgac gaaaacataa  5700
atcacaggtt actccagtta agttacctcc acttatacaa ccagcatcac catttaccac  5760
tgcattagtt tctgctgctg tcgtcatccg tcattcaatt gatatcattt catattatct  5820
tccatgtaga tcgtactgtc caatctggtt tggaggaaac gctagacgag gttctgtcat  5880
tgccg                                                               5885

SEQ ID NO: 7           moltype = DNA  length = 6791
FEATURE                Location/Qualifiers
source                 1..6791
                       mol_type = other DNA
                       organism = synthetic construct
SEQUENCE: 7
tccaacaaag atggaaacct agatttctaa tcaaggcgca acacaaggac gtctctctcc  60
actcatcatt actctttgaa ttgccattct ctacggcaca tggggcaatg agcttgactc  120
gtctgtgaat tgacccattt caaaatacaa tggagatgaa acgaatggtt gcaagctccc  180
caaactgctc gataaccata taacgatcca ggtttaagaa tacaaataag atataacgat  240
ccaggtttaa gaatacaaat aaggggtttt agttttgaaa caatcacagt gtgtagaaag  300
agacatgaaa agagaggaga cacgtactta gagggcaatc atctccaggg agtttgcagt  360
ctggacaaca accgtcgaat ggcatacgac atatcccaca tgtctcatcc tgagcatccc  420
atgtccatga cgcaaccgca tgccacctta cagtttattt tttcacaatg taagagttca  480
cgtattggaa ttgagaatgt atgtaacaca tgtagtggga caaagaaact tactctgttt  540
ttttttttaa aaagtcagta gacattgtag cactgagagt caaggaagaa acagttcttt  600
ggaaacaaaa tcctaaatta aagaaccttt gagataatct tcgcctacct tatatgaact  660
agttgggagc tgataaccaa aatcttcacc gaaaaaaaac tattagaacg tcatctacat  720
cagtattcaa aactgaaatt catgaaaaga gaacaacttt atgaaatcat gaaacctaag  780
ctgcatcttt taaaaaaatc atgttttaaa catcaaagaa actatgtact ggaaaacatc  840
aagcattgac gtgaacattt ggatgcatga ttgacatgca gagaagatga agtagaagga  900
tacgcaagat cttgactttc atgtcttcct cctaaatgaa acataaaaat aatcttatat  960
cagttaaaca aactaaaaaa aaatagaaaa cacaaactca agaaagcaca atcctttttt  1020
actatactat aaatctaata ctactaaggc ttcatcgtct gaaaacttag acgagataaa  1080
ttcatgtttt tgacgcattc gtacactagc atgcagcaga tggcgtttcc ttagctgata  1140
gagtgatatc aacagaacgg agcaaaccca tcagaaaatt caaaaactca ccggagtttg  1200
acggagaagc gaactgcgac agagaagaag cggcgagatg tgaatagaag acacgaatta  1260
gttaagatat gggcttttat ttaaactggg ctttatttaa aattgatctc agggcccata  1320
cgtgtgctct tcttaacaag attatatatt atttataaac gacaccaata aaacgtggtt  1380
tgttttcgtt ttcttttgtc tttccgagcc tctagtttca tgtgataaaa gcaaatagag  1440
aggtcaaaag aatcaacacc aatacgatat gctgtgattt tttttttaa atatgttgta  1500
attgttagcg gtgaggctcg tgaagagtgt ggcattggtt cagctttact ttagtttcaa  1560
cactcgataa tatttcgata aaaatcttca ataactttat ggcgctatga ccaagctttg  1620
aacattattt actacagtga atcttaatga tgcgtatcat tcttgttaac cttcgatata  1680
tatatgctgc attgcaccac cgtcgacgga acaatttgaa gatgtgacgc aactcgtgtt  1740
caagtcgtac gtgttcccgt aaaggaacat aaatatttgc aatagatcat gaaagactaa  1800
acgtggaaac aagcaagaaa tttggagtaa actcggtgaa tattgagcta aagtaaccca  1860
cgggactcat cccacctaaa cctctcccaa agtatcagga caagaaatac ttacgtcact  1920
attctttagc aatggctata tataccctag atcggtacaa ggtttcatac aacaccaaca  1980
catacaacaa cagattaacc atgaagcttc ttcatggact cgctttagtt tttctattag  2040
ctgctgcgag ttgcaaagct gatgaagaaa ttacttgcga agagaacaat ccattcacat  2100
gtagtaacac tgatatttta agcagtaaaa acttcggaaa agacttcatc ttcggtgttg  2160
catcgtctgc gtaccaggca tgcaacaaat gctgccatac tatatttttg acgtatacaa  2220
aataatattc aaaaatgcta aaatatccaa ctttgcatgg ttgtttcttt tcatttcaga  2280
tcgaaggagg gagaggtcgt ggtgttaacg tttgggatgg cttcagtcac cgatacccag  2340
gtatgtcact gtggcatata catatatata tatatttaaa tgagataaat gacggttata  2400
tgtatacata ttaatgtatt tgtaaattac tatcagagaa atcagggtca gatttgaaga  2460
atggagacac tacttgtgag tcatatacta gatggaaggt gaattcctca gtacatatat  2520
actcatatga ctaaactacg tataaaaagt aactgtggac tgaattgcgt ttaaaatatg  2580
taaactgcag aaagatgtag aaattatggg agaactcaat gctacaggct acagattctc  2640
cttagcgtgg tcaagaatca ttccaagtat gaacaaatta ttcattcgtt tgtattttag  2700
ttaggatcat gtagctggaa gagtactaat tgatatacaa tatacatgag cagaaggaaa  2760
ggtgagtagg ggagtgaacc aaggaggtct tgattactac cacagcctca tagatgcact  2820
cctcgaaaag aatataacgc ctttcgttac cctctttcac tgggaccttc ctcaaacact  2880
ccaagatgag tatgaaggtt ttttggaccg ccagatcatg tatgtgccat gcttcttaat  2940
catatacaaa tttttaataa gaacaagaag aagaagattt tgtcttaatt acatgcttta  3000
ctgaaagaat gattatatat taatatgcac agacaagatt tcaaagacta tgcggatcta  3060
tgtttcaaag aatttggtgg aaaggtgaag ctattcacag tgcctacgag aggctatgca  3120
ctcggaacag atgcacccgg tcggtgttct cctatggttg atagcaagca caggtgttat  3180
ggcggaaact cttcaacaga accctatatc gttgcacata accagcttct tgctcatgcc  3240
gcggtagtgg atctttacag gaagaactat gcggtgagta gtcttcatat gtgaaaaggt  3300
ggtgaaaatc taatgtattt gatcctaatt tactcatata tgatgtgacc aacaggacca  3360
```

```
acaagggaag attggacctg tgatgattac aagatggttt cttccatatg atgaggctga  3420
tccttcttgt atagaagcag ctgacaggat gaaccaattc ttccatggat ggtatatctt  3480
ctttttttga catcaaacgg ttactctatt attcaaaatt aaagatggtc taggtaatta  3540
gattgattat atatattgta tgtacatata atgaaacaaa atataaatgg atcaggtaca  3600
tggagccgct aacaaatggt aaatacccag atatcatgag gaagattgtg ggaagtcggc  3660
ttcccaactt caccgaagct gaagccgaac ttgttgctgg ttcatatgat tttcttggtc  3720
tcaactatta cgtcactcag tacgcccagc cgaaagctaa tccattgctc tcagagaaac  3780
acactgccat gatggacgct ggcgtaggac tcacatgtac gcattactct ccttttttgtt 3840
acaacatact tatttgtgat tgaccttcag taatttcttt cttgtgttta cagatgataa  3900
ctcacgtggt gaatttcttg gcccactggt atatatgcat gatccactct tatgattttt  3960
ctttcattat tttatcttct tttcctaact gcagtgtact tggaacaccc acaataactt  4020
tttttctga ttgatatgta tattttgttt gcttcccttt ctcagtttat tgaagacaaa  4080
aaagccggca acagctatta ttacccaaaa ggaatttatt acgtcatgga atacttcaaa  4140
acccaataca acaacccttt aatctatgtc actgagaacg gtaagttcta catattacta  4200
gtaatctatt tttatttatg ctacatatca tcagataatt agtgtatttt gatactgagt  4260
ccaaagaaac tgactttcaa atactgtgga atatttttat gtgatggcga tttaattagg  4320
atttagtacg cccagctcag aaaaccgttg cgaagctatt gccgattaca agcgaattga  4380
ttatctctgc agtcatctat gttttctccg taaggtcatc aagtaagtgc tactatacat  4440
gcttttcttc caatatttat cttctttttc ttcttctttt taagtaatat atatatatat  4500
atatatatgt atatgattgt tattgtttcc agggagagga atgtgaacgt gagaggatac  4560
tttgcatggg ctcttgggga taattatgaa ttctgtaaag gctttaccgt cagatttgga  4620
ctcagttacg ttaattggga taatcttgac gacagaaacc tcaaagaatc tggcaaatgg  4680
taccagagat tcattaacag gacttccaag aaccctgcga aacaagattt cctccgctca  4740
agcctctcct ctctcaaagc cagaagaaga ggcttgcttg ctgatgcatg aaacactttt  4800
ccccttcaa gatcatctcc acgtctctga tcactctttt ttgttgctcc atagataagg  4860
agcttctaca agtaaaaaga tgatcaacta ctaatgaata aaataaattt atctacaagt  4920
acattatgtc aagtcaaaga ggtgaggata acgcatttta aacagtaaac atcacttaga  4980
cgcacataca aaataaaaac tcaaaccgcc aactagttta gtgtattaaa aatactaagg  5040
aaatgattag cctaaattca gtaattatct aatacaaatc taaaactaac taaacgaaag  5100
tataacaata atttaacaat ccatcaaggg tcggtcgtat taaattcgga acaacaatcc  5160
aacacatctt tagaaatgaa aaccaatgct agatatctaa tcaaagcaca gcacaaaggg  5220
tttctctctc tccactcatc gttactcttt gaattgccgt tctctacggc acatggggca  5280
atgagcttga ctcgtctgtg agttgaccca tttcaatata caatggaggt tgtcattcta  5340
gacaaaatcg ttatatctaa acaattttaa tgatgtctgc ttactttaat atttgaaaac  5400
tttttatttt tctgtttcta aaagaaaaac gaaaaaaaat attttaataa cacccattaa  5460
gacttttgtt tgatcgtgaa ttattttat cataaatatt tgtacgtcaa tgtatcttct  5520
aggttccaat cttaaccaaa tgtataaatc tatttttta gaatctataa tattaaaaca  5580
tatgtacgaa ttgaaaacta actttgttct tatgtattac aaaatatatc catttaata  5640
atcatatata ttattttgta aaaataatta aaaactaaat tttaacgtaa attaaaatat  5700
tatatcaaac caaaaaccga actctataaa ataaattata tacgtcaaaa attattaact  5760
atatatattt agtttaaaat tatcaaatag tctaaaaata ctatttaaac atcgaactat  5820
ccaaaaatcg tattatccta ttacttttta cttgaaatat tttaaattat cctaatttta  5880
gaactgaacc atccaatatt ttttatctga aatattaaat atctgaatta tcaatatttt  5940
gtaaaaatat atttaaaatc aattttatcc gaattattca aaattatcca aaagatgaga  6000
ccaaacctaa accaaattga actcaaaatt ttataagatt cctaacattg ttatctaaaa  6060
caagccaaaa atcaaaattg ccaaaccaaa accaaaggta aacttataaa taaccaaata  6120
gtgtttatat ctcttggact aaaataccaa aaaaccaata ccacaaatga accggaaccc  6180
aatcaaaaca taaaataatt gaaattcaac aaaaatcaaa catccatacc taaacatatt  6240
agtaaaaaac agatgaattc ataaattatc aacacaaaat atagttcatg tttaaaggcg  6300
taactttttt gtaacagaaa aaaaaagaat atctaatttt gggaaatata actaaaaatg  6360
tattaattct aacataaaat gtagagctaa actattaaat aaactatagg ttaatacaaa  6420
aggtattttt taccatatat gtgaatatct atctatacta ttaaacagaa aaattttga  6480
gaccctttga tttttatagt atttacaaca gtgctattat cttttaaatt aaattctata  6540
ttattataaa ttattattaa acagaaaaat tgcagggaat taactgccta catacccgat  6600
tttccttaat taattatagc taccataaag tggtttcttt aaaaaatagg gattatttgt  6660
aaattactct attaatagtt tgaaatttga aaactacact tctattttat tttttgaaag  6720
ccacacttta ttcaatgtga attgacattt ttatccagat tagatatttt aataattaaa  6780
atataaaatc g                                                        6791
```

```
SEQ ID NO: 8            moltype = DNA  length = 7046
FEATURE                 Location/Qualifiers
source                  1..7046
                        mol_type = other DNA
                        organism = synthetic construct
SEQUENCE: 8
taaaatgtca gaccagaata actaaggggg ttattggtaa ggaattctca ccaattttga  60
aaattttaag aatccattgt tattggttct tggatttcaa aaatcttagt agaaactatt  120
gttattggtt taagaatttt caaaatccat aaatctcttg ttattaagtt tagttattac  180
tgattctcta attctaacta aatctagtat tattggaaga tgaattatat tcatttttac  240
tcataagact taacttttaa aatatcatat gtattcatgt gattttcaaa atctttgtga  300
taaaaaacat agaaaacaaa agaattattc ttaccaaata tctattgcac ctaaatccaa  360
attatatgtt caaaactata attcattaca tttatatact tttacatttt tgaataatta  420
ttttaaaaaa tataatatat taaaaaaatt atagttttac attacattta caaatcttaa  480
taattttgaa atattttttt ttaaatagtt tcaaaaacat tttcgaattt caaaaaaaaa  540
tcgaaaaata taaaaattat aaaaaatttt gaatttgaaa acatataatt tgaaattata  600
taaaaacaat ttttaatttt ttaatttttt attacttata catctatata gcaaggggta  660
aaataatctt ttaccttttt aatgaaattt ctttgggtca ttttttaatg ctctttttgt  720
gataaaatct tttaaaatgg ctatttaaga aaattgctca attttgtatg tatcagtatt  780
attttctttt taatttgaat gcaaaaaata aataatcatg ctatatgatt tagaaaataa  840
```

-continued

```
atagattata tatttatttt acaaaaaaat gatagaaaaa aggtaataca aattcatgaa  900
aatataaatc aatctaaaaa agtcataatc aaatttaata agcaatatat ataaattttt  960
actatccact taacttttta aaatctatca actctcaaaa ttcacaaact ctacataaat  1020
tcatctccca ataacttctc ctaaatttaa aattaaaagt aaaatattaa ttacttatta  1080
taatatttag ttcataaata gttatattca tgcaagagca cggaaaattt acctaaagca  1140
atattaaata caagttaacg tatatatgtg ctacgtaaat aatttatttc aaaaacttga  1200
tggcacgtaa acggtaatga tgttatctat agaaactaaa taatatgtaa tatggctatt  1260
tataacaaaa cgtatgtatt ctaactttat agagttaaaa actatggaac aaactatagg  1320
tcaatcttat ctatctggaa gtcggatccg tatccgttcc aacccttcca aacatttaaa  1380
acgatgccaa aaaggcaaaa aatgggttgg ttttcgtttt ctttagtctt tcggaggcac  1440
cggtctcatg tgataaagca gaaatagacc gatcaaaacc aataagatat gatgtgagat  1500
cttgtgagcg gtaaggctcg tgataagtgt ggctttgcac cagtgttaat ctagattcaa  1560
cacttgataa tatttcgata tacgtttcca gtaacgaatc ttgacgttgc gtgtcgttct  1620
agttttgcgc aaatcttaca tgctgcattg catcattgca tgactgttga cggatcaatt  1680
tgaagatgtg tcaattcgtg ttccggttaa ggaacacaaa tatatatatg tgctatctaa  1740
caaaagaata atatttgcaa tagaaaatga aagactataa agtgggaaca taacaatcac  1800
aaatattaca aaaatcggtg aacactgagc taaagtaatt aagtgaaccc acgggactca  1860
tgatcccacc tgcacctccc caaaatatca agatactaag acaaaaaaat agtggtgtca  1920
ctcttctttt ggaaaggcta tataaaccct aatgggcaca aggttccaca caacacaaca  1980
catacatcaa cagattaaac atgaagcttc ttcatggact cgctttagtt tttctattag  2040
ctgctgcgag ttgcaaagct gatgaagaaa ttacttgcga agagaacaac ccattcacat  2100
gtagtaacac tgatatttta agcagtaaga acttcggaaa agatttcatc ttcggtgttg  2160
catcttctgc ttaccaggca tgtagcaaat gttgtcacac cataattttg aaataaaatt  2220
taaaacacta aaatgcaact ttgcatggtt gtttctattc atttcagatt gaaggaggga  2280
gaggtcgtgg tgttaacgtt tgggatggct tcagtcaccg atacccaggt atgtcatttg  2340
cacagcgaca tctatattta tatgtgagag gaatgttggt tacatatact catatagtca  2400
tattaatgta tttgtaatta atatcagaga aagctgggtc agacttgaag aatggagaca  2460
ctacttgtga gtcatatacg agatggcagg ttaatttctc agtacattga tactcatgac  2520
tgaactatat atgtataaaa ctacagtgtg gattgacatg agattaaaat taatatgtaa  2580
aatgcagaaa gatgtagacg tgatgggcga tctcaatgct actggctaca ggttctcctt  2640
tgcgtggtca agaatcattc caagtatgta catgttatcg attcgtttgt attttaattg  2700
ggatcattta gttgaaaaag tactaattaa tgtacgacat atatatacat gagcagaagg  2760
aaaggtgagt aggggagtga accaaggagg tcttgattac taccacaaac tcatagatgc  2820
actcctcgaa aagaatataa cgcctttcgt taccctcttt cactgggacc ttcctcaaac  2880
actccaagat gagtatgaag gtttcttgga ccaaatacaa ggtgagttgt ctcaatatgt  2940
gtaaagatgg tgtaatgtaa tctaagatat ctgattctaa cttagtcaaa tatcacgtga  3000
ccaacagttc caaaaaggga agattggacc tgtaatgatt acaagatggt ttcttccatt  3060
tgatgagtct gatcctgcct ccatagaagc agctgagagg atgaaccaat tcttccatgg  3120
atggtatata tatatattta tattaccaaa aatgtatcag tataaattgt atatatgtat  3180
aatgaaaaga tatacatgga tcaggtacat ggagccgcta acaaagggta gatacccaga  3240
catcatgagg cagattgtgg gtagtaggct tcccaacttc accgaggaag aagcagaact  3300
cgttgctggt tcatatgatt ttcttggtct aaactattac gtcacccaat acgcccagcc  3360
aaaacctaac ccatatcctt cagagacaca cactgccatg atggacgctg gcgtaaagct  3420
cacatgtact tttctattac cacttagtta caaccttttg atatatataa atgttttatc  3480
tcctttttgt gagtgaccat cagttatttc attcttgtgg ttacagatga taattcacgt  3540
ggtgaatttc ttggtccact ggtataatat gaatgatcca cccctatgat ttctaattca  3600
ttttattttt tcaatttcca atataagcac cactaattag gttttcttga ttgatatgta  3660
tacgcttaac tcccgtttct cagtttgttg aagacaaagt aaacggcaac agctattact  3720
acccaaaagg catttattac gttatggact acttcaaaac caaatacggc gacccctttaa  3780
tctatgtcac cgaaaatggt gagttctaca tgcatatatt ttcatctata acatctacta  3840
taatttgtgt atttcgaaat aattccaaga aactgacttt caaatattgt gtactttttc  3900
atgttatgtc ggtttaatta ggatttagta cccccagttc agaaaaccgt gagcaagcta  3960
ttgccgacta caagcgaatc gattatctat gcagccatct atgttttctc cgcaaggtga  4020
tcaagtgagt ggatgctact ataaatgatt ttctacagat gttacttctt tcttggtaac  4080
atttatatat atgattcttc ttgttttcag ggagaagggt gtcaacgtga gaggatactt  4140
tgcatgggct cttggagata attatgaatt ctgtaaaggt ttcaccgtca gatttggact  4200
cagttacgtt aattgggaag atcttgacga tagaaacctc aaagaatctg gcaaatggta  4260
ccagagattc atcaacggga ccgttaagaa cgctgtgaaa caagatttcc tccgctcaag  4320
cctctcttcc cagagtcaga agaagaggtt cgctgatgca tgaaacactt ttccccccgg  4380
tcaagatcat ctccatgtct ctcactcttt ctagttgctc caaagataag gagcttcttc  4440
tacctacaat aatgtactaa ataaatattc tcaataaaaa gatgatcagt tactaatgaa  4500
taaaaaaatt gtctacaact acattttgtc aagatgatcg agagagagag agagtgaaat  4560
aacacaattt aaaccaaaaa cgtcacttag acacacatag aaaataaata aataattacc  4620
ccaaaccgca aactagtttt gtgtaataaa tatataaaca tcaaaccgat cagcttaaat  4680
taacttaata agttcaactt tatatactag aatagatttt caacataata aacaatgacc  4740
aaaccttata caaactcaaa tctagctaca ccaaagttct atcatcctca actgaaactt  4800
aatagtattt tacatatgat tttcctatca ttcaaatgat tttattttat tttggttctt  4860
atacaatcaa gaaaaccaaa agaaggtaaa cctcagtact ttatgtttta tgaatgcttc  4920
ctcaaagaat ctggcaaatg gtaccagaga ttcattaacg ggactgtcaa gaattctgcg  4980
aaacaagatt tcctccgctc aagcctctct tcccagagtc agaagaagag gctcgctgat  5040
gcatgaaaca ctttccacca tcaagatcat ctctatatct ctcactcttc ctacttaccc  5100
catagataag gaggttcttc tatctacaat gtactaaata aacaatctca ataaaaagat  5160
gatcagttat taaatgaata aaaataattt gtctacagct acattatgac aagtgaagat  5220
gacgaggaaa gagggaaaat aacaaaattt aaaacataga acactcagaa atctcaaact  5280
agtctagtgt taaaaaatat taacggacgg attagcctaa attcactaat tagtttaata  5340
agtgcaactt atataataaa aggtatcttc aacataataa ataacaacca aacctaatac  5400
aaactcaaag tttctaaacc aaagttctat aatcctcaac taaaacttta tgagatctta  5460
catatgatct tttatcattc atataatttt atttgatttt gttacttttt tttttgaaca  5520
aactaccttt catccaataa aatcgaaata cactccatcg tgagtagcga aggaattttg  5580
```

```
ttacttatat aattaataaa cccagaagaa gctaaacccc aatcctttgt ttttatttct  5640
ttgtatttca acattgtgaa caagaagagg gtcagtagtc tctgccgttg caggtccttc  5700
tccttccgct gagacggccc tctttttgt ttgttcaccg cggcacgaaa tcatgaagaa  5760
gctggaataa ctcagaaaga gagtggcacc tagccgttga gagcgtctat tatctgagaa  5820
cagagctccc atcacaacag aatgcacgca tgaagccgcc atccgtccca acgtattctg  5880
ctcttgaatg atggaaaaat aatatcaaga attgaagtat cagaagtttc tgaaagaaca  5940
tgtcatttcc ggtttcctat attctttaag actttttgcg gatttcccaa aacaaaatta  6000
aagacgtggt tagccatttc tggtttctta taaagattcg atttatcttg tactccttcc  6060
gtttttttaat ataagtcgtt tttgaattgt ctacgtagat taaaaaatca ttaatttttt  6120
atattttcta aacaaaaaca tcattaatta tttacataac cacaaatcaa ccaataaaaa  6180
aatagaaggt atattatcac tggtcatata acattaagtg ttaataaatt ttacatagaa  6240
aaccgaaaac gtcatttaat ttggaacata aatttttctt ctaaaacgac ttatattaaa  6300
aaaaatagag ggagtattac acaagctata ataatttagt gagtctcaaa tttataattt  6360
tggtttaaat aatataataa gtttttttc tttaattcag aaaataagca tgtttagtag  6420
tattattaga attgtatgaa ttttcctttg gatatatctc tgtaatttta gtcctactat  6480
ctacgcagca ttagctggca acattttctt ctaaatttgc attgaagttt actgtttttt  6540
attggttggt ttaattgctt caactaaggg aaacatatct tgagttatac aaataatatc  6600
taaaattaca tgattattat ctgccttatc caatgatttc ccgacaactg ttaatgaata  6660
tatatattct ttttgtaact attataatta tatttactgc aatttagcat taatgatcca  6720
aaagaaagtg ataagatctg catacgtaat accagcctca ttacactata taaacaagag  6780
cattatcaag tgccaacata tctctatcat tcaccaacac aaaataatgc caaagggaag  6840
gataaaaata gagcccatga ctaatagcgc tgcaatgaac caaactttca ggaagaggaa  6900
gaaaggttta ctcaaaaaag ccaacgagct gtcgactctc tacggtgtca aagtttgtgc  6960
ggttatcaac agctgcgaca gtacggagcc gccggagttt tggccgtcaa aggaaggcgc  7020
tgaagcagtg cactcagcgt ttatgg                                  7046

SEQ ID NO: 9           moltype = DNA  length = 5320
FEATURE                Location/Qualifiers
source                 1..5320
                       mol_type = other DNA
                       organism = synthetic construct
SEQUENCE: 9
ccagtctaag aatcgacagg ccaaatttct catcttctct acttcagtta tggttctcta  60
cgtgaaaccc atccaactaa ttcactgatt caaatttgta tcttttagat atgtaaggcc  120
acttggccta ctgagttcaa tctctacaaa acattttcgg tctcttgcat ttaaaggcct  180
gttcgtttgt acatctggaa gatgcatcca gatggtccat ctagatgtct tatccagatg  240
atccatctgg gtgttgttcg tttcttcatt tcgtccatgc atccagatga aatcatctaa  300
atgcaactat gttcgttttt ttcatttttt aacttccata tgcatccaga tggacttatt  360
aataaaatga cttaaatata ttttttacgt ttcgacggaa aaatagcatt tttacggttt  420
tggctgaaaa tatttttgcg gtttttgagg aaatatgtgt ttttcgcaaa aaagtgtatt  480
ttatggtttt ggcggaaaaa tacgttttat gggtttggcg gaaaaaatacg tttttgtggt  540
ctggacggaa aaagtgtgtt ttgaagtttt ggcgggaaaa gcattttcgc gatttttggcg  600
agaaaagcat ttttgcggtt ttggcgggaa aatacatttt tctggttttg gcggaaaaat  660
acattttctg gtttttggcg ggaaaatgcg ttttttccag ttttgagggg aaaatgcatt  720
tttccagttt tagcgaaaaa atgcgttttt ccggttttgg tggaaaattt tcattttcca  780
attttggcgg taaaattgac tttttcagtt ttggcggaaa aatacgtttt tccggttttg  840
gcggtaaaat tgtgttttc agttttggcg ggaaaatgcg tttttccgga tttagcggga  900
aaattgtgtt ttccggtttt ggcgggaaaa ttgtgttttc tggttttggc gagaaaatgc  960
gttttccggt tttggcggaa aaattacgtt ttcccggttt tggcgagaaa atgtttttttg  1020
cggttttggc gagaaaatgc tttttggagt tttggcggga aaatgcgttt ttttttgttt  1080
tggtcgaaaa gtgcggtttt actggtttgg ccaaaaaaatg tgttttatga aaatttgtgt  1140
tttatgtttt tttttgcgga aaaacgcatt ttgcggtttt ggcgggaagt gtgtttttttc  1200
agtttttgcg agaaaatgca ttttttggtt atagcggaaa aatgtatatg caaaaaaaaa  1260
ttgaatttac ggtttaaaaa taatattttg attttaaaaa gtcattttttg tcttttatca  1320
ttttggacta aactagatgc atctggataa tgcaccatca agactcactt tcatttgggt  1380
gagaatttga gatgagtttt taaaaattca gctggatgat ctatgtggat gtagcattat  1440
aatgcacaaa acgaatatca atttgcatct tcacccagat gaatcacctg ggtgaccaaa  1500
cgaagagggc caaatagtaa aatcttttttc aaaaaaaaagt aactatcttg tttattcaga  1560
agtcacggtt ttttattctc tattataata tgtattatta tatttagtga aaagattttt  1620
attattcgct tcgatcaatc ataaacgcgc gtacgggtct gattatctag aaacgataga  1680
aaaaaatgca aaaaatgtgg ttggttttgg ttttctttgg tctttcgtag actccggtct  1740
catgtgataa aagtatatat agagaggtaa aaagactcaa aaccaataag atatgctgtg  1800
attatgagcg gtgaggctcg tgataagtgt ggccttggat cagtgttaca ggaccaaata  1860
caaggtgagt tgtctcaata cgtgataaag atggtgtagt gtaatctaag atatctgatt  1920
ctaacttagt catatatcac gtaaccaaca gttccaaaaa gggaagattg gacctgtaat  1980
gattacaaga tggtttcttc catttgatga gtctgatcct gcctccatag aagcagctga  2040
gaggatgaac caattcttcc atggatggta tatatatata tatatattac agaacaatgt  2100
aacagtatat agtgtatgta tgtataatta aaagatatac atggatcagg tacatggagc  2160
cgctaacaaa gggtagatac ccagacatca tgaggcagat tgtgggtagt aggcttccca  2220
actttaccga ggaagaagcc gcactcgttg ccggttcata tgattttctt ggtctcaact  2280
attacgtcac tcagtacgcc cagccaaaac ctaacccata tccttcagag acacacactg  2340
ccatgatgga cgctggcgta aagctcacat gtactagtct attaccacta attagataca  2400
gcctttctat acatataaat attcttttat ctccttttttg ttgcaacata ctttatgagt  2460
gaccatctgt tatttcatcc ttgtgttaca gatgataact cacgtggtga atttcttggt  2520
ccactggtat atatcaatga tccaccccct aagatttgtt tttctttcat tttttcagtt  2580
ttcagtataa caaccctaat tatgtttttt aattgatgtg tatatttatt tacttccatt  2640
ttcacagttc gttgaagaca aggtaaacgg caacagctat tactacccaa aaggcattta  2700
ctacgtaatg gactacttca aaaccaaata cggagaccct ttaatctatg tcaccgagaa  2760
cggtgagttt tacgaactct ttttatttat accacataat aattattgta ttttgatatt  2820
```

```
agtcgaagaa actgacttta ttgtggaata tttttaatgt ggcggtttat ttaggattta  2880
gtacccccag tgaagaaaac cgtgagcagg ctattgccga ttacaagcga attgattatc  2940
tctgcagtca tttatgtttt ctccgcaagg tcatcaagtg agtggatact actataaatg  3000
attttcttct tatgttattt cttcttcttt tttgctaaca tttatatatg attgttcttg  3060
ttttcaggga gaagggtgtc aacgtgagag gatacttcgc atgggctctt ggagacaatt  3120
atgaattctg taaaggcttt accgtcagat ttggactcag ttacgttaat tgggaagatc  3180
ttgacgatag aaacctcaaa gaatctggca aatggtacca gagattcatc aacgggaccg  3240
tcaagaacgc tgtgaaacaa gatttcctcc gctcaagcct ctcttcccag agtcagaaga  3300
agaggttcgc tgatgcatga acacttttttc ccccggtcaa gatcatctcc atgtctctca  3360
ctctttctag ttgctccaaa gataaggagc ttcttctacc tataataatg tactaaataa  3420
atattctcaa taaaaagatg atcagttact aatgaattaa aaaattgtct acatctacat  3480
tttgtcaaga tgatcgagag agagagtgaa ataacacaat ttaaaccaaa aacgtcactt  3540
agacacacat agaaaataaa taaataatta ccccaaacta gttttgtgta ataaatatat  3600
aaacatcaaa ccgatcagct taaatcaact taataagttc aactttatat actagaatag  3660
attttcaaca taataaacaa tgaccaaacc ttatacaaac tcaaatctag ctacaccaaa  3720
gttctatcat cctcaactga aatttaatag tattttacat atgattttcc tatcattcaa  3780
atgattttat tttattttgg ttcttatata atcaagaaaa ccaaaagaag gtaaacctca  3840
gtactttatg ttttatgaat gcttccccat tctcatatta agatctcgac gacagaaacc  3900
tcaaagaatc tggcaaatgg taccagagat tcattaacgg gactgtcaag aattctgcga  3960
aacaagattt cctccgctca agcctatctt cccagagtca gaagaagagg ctttctgatg  4020
catgaaacac tttttcccct caagatcatc tctatgcatg tctctcactc tttctacttg  4080
ctccatacat aaggagcttt ttccatctat aatgtactaa gtaaacaatc tcaataaaaa  4140
gatgatcaat tattaatgaa taaaataatt tatctacagc tacattatga caagtcaaga  4200
ggacgaggaa agagggaaaa taacacaatt taaaacagaa aacactcaga aatctcaaac  4260
tactctagtg taaaaaaata tatattgacg ggacggatta gcctaaattc actaattagt  4320
ttaatgagtg caacttatat aataaaaggt atcttcaaca taataaataa caaccaaacc  4380
taatacaaac tcaaaagttt ctaaccaaag ttctataatc caataaaagg gaaatacact  4440
ccatcctggg aggagaggtt agagtagcga aggaatattg ttacttatat aatcaataaa  4500
cccaaaagaa tctaaaccgc aatcctttgt ttttatttgt ttgtatttca acattgtatt  4560
ctactcttta atgatggaaa aataatatca agaattgaag tatcagaagt ttctgaaaga  4620
acatatcatt tccggtttcc tatattctgt aagacttttt gcggatttcc caaacctaaa  4680
ataaagacgt gattagccat ttccggtttc ttataaagat tcgatttatc ttgtgttaca  4740
caagctatag taatttaatg agtcaaaaat ttataatttt ggtttaacta atataataag  4800
tttttttctt taattcagaa aataagcatg tttagtagta ttactaggga ttaacccggg  4860
ctacgcccgg gattttattt tttttctaat ttaagttgtt aaattattta tatttaggtt  4920
atgatatata tttatataaa tattaagatg catgtcataa ttaaaattta tttttaaatt  4980
ttaacacgtt aaattaacat attttttac tatttaaata attttttttg taattttgtt  5040
ggctatctag ttatcatatt tagtaaaact atctgttgag tattagaata aaagtttag  5100
atatttaatt aaactgcaga gtattttcgg atcgaccaca tgctcaacaa tcgatcgatc  5160
cgtaaaaaga tggtcgattt ccttggccag gtaagtacaa ttttagcaaa aatatcttag  5220
attttcaaat attaagtata taactattat tttgaataat atttttttga attgtatttt  5280
ttgattaaat tattgtatta taatgtttat gtaaatattt                        5320
```

```
SEQ ID NO: 10          moltype = DNA  length = 6347
FEATURE                Location/Qualifiers
source                 1..6347
                       mol_type = other DNA
                       organism = synthetic construct
SEQUENCE: 10
aataatagta tagataaaca aagtttggat gttaaaataa gcacaagttt taaaagtttg  60
tgttttaaaa tgagcaaaat aattagttgg ggtattaaac taggtagtga aaaaatttgt  120
gtattaaaaa gcttaacaaa atttagttga aatattatat ggaattttcc caaatattat  180
caatagataa tatcagtcta tttttattat gttttgaaac cgcaatccat attccgtggg  240
atttttttc aaaactgtgt tttggccgat tataattcat gcagagaata aactgaattt  300
gtcagtctga gtgaatttat gaattttcaa cgaataggat atattcatat atcgaaaata  360
gttaagtaat tcaataaata aagtttatca gaaattcttt atattttttt gaaaatttgt  420
cagaaattga aatttgtccg gaaaaaagaa tcacctaaac ttttgtgaag caccaaatta  480
aaaaatttct aatggattgc aaacttgatt cgtcaaaata ttttaacata agaaccaaat  540
agtttttcttt ttcttcttca tttcaactct ccctctctcg aaaaacagat gtgaatcctt  600
ccctacaact cttattaaat catgttagtc atatgttatc ctcttaataa tcatatatgt  660
taatttgtat atgtgtttgg ttattagagt tgatagattt tagggattga aatgttagaa  720
atgaattagg ttggttgatt taggatttat atgttatatt tgtgttagaa ttgtttgttt  780
taggatttca cattttagat ttaggatttg aaaacttatt ttatattttt gatgttttat  840
tatttatgtt gttttaaaat gttcttacgg ttttataaaa cgtaagattt tataaaacat  900
ttttatgttc tgtaatttat aaaaagtttt tatgtttctg gaatttatag aaaacatttt  960
tttcactttc taaaaatgtt tctgtttata atatttttac tattttataa tttatacaac  1020
ttttttcac ttttcgaaaa acgctttcaa tttataaaac gtttaatggt ttttctagaa  1080
tttataaaaa agtttttcac tttttaaaaa gcgttttttt ttaattttaa tagttattat  1140
atttatatat aagattaaaa attattataa acaattttta tctagatatg taaatttagt  1200
ttgttaaatt gttaattaat ttaaatatat cttttaataa tttacaaagg ttttgacaaa  1260
tattgtccaa tttctgatgg atgatattcg ttgaaaatat tgccgaattc ttgataatgt  1320
ctttcggcta tttttgtcag tatctcgtcg ggaatgcata tgtcggaatc tgctggaaat  1380
tcgtcgaatt gtccaaaaaa gttttatcga atttttaac gaaataaaac caaacgaaaa  1440
aatttcgttg gaaattgctt cttttttcc gatgaatttc cgacaaaatt atccatacaa  1500
aacattttgt tttcttgcag tgtccactta tcccaaatcc atatcttctt ttattgagat  1560
tttttattta gtatacagtg gtaggtagat gaagctcctt atctatggag caagtagaaa  1620
gagggaacat gagatgatct tgatgaggta aatatagtgg actggatctt tcatgcatct  1680
gcgaacttct tcttctcaaa ggtgaggctg gagcgcagaa aatttggctt tgcaaggttc  1740
ttggttgcaa tgaacttctt ataccatttg ccagactctt tgagatctct atcagtgaca  1800
```

```
ttgttccagt caatgtaagt gagtccgaat ctgacggtaa atcctagccc gaattcataa  1860
ttatccccaa gagaccacgc acagtatcct ttcaccttga cacctgtctc cctaaaagca  1920
ggaacaataa atcattagac gccatacgta catacaagta tatacataaa acacaagaag  1980
caaaagagag aagcatcaac tcacttgatg actttactga ggaaacagag atgactgcag  2040
agataatcaa tccgcctgta atcaaactta gcctcctcac gggtttcatc accggaggta  2100
ctgaatccta gttaaccgtc ataacatgaa caatttcaac aaatttcaaa ttacatttaa  2160
catgtaaaga tgaatttaga gatgagtagt agaacccacc gttctcggtt atatagatta  2220
cagggtcatt gtaattggtt ttgaagtgat ccatcacata ataaatgcct tttgggtagt  2280
aataggtgtt tttggtctcg tcatctttgt gttcagtgaa cttagaaagg gaagcaaatt  2340
agtatcagaa aactgaattt tgcttagaaa aaaaatgaaa gaatagggat ggttgatgca  2400
tatatatacc actgggccaa tggcatgatt acttgcatta cgatctgtta acacaaatta  2460
ttgtaattaa caaaaggcgt taggtagata taaattaagg ttgtaactaa gtcgaaatat  2520
atagatggat acatgtgagc cttgtgccag cgtccatcat ggcagtgtga ccatccgaat  2580
caacatgatt aggacttggc tggacatact gagtgaagta atagttgaga ccaagaaaat  2640
catatgaacc ctttacgagt ttggattcct ctggagtgaa cgatggaagc cgctcaccca  2700
cagtgtctat catgatttga gggtatgtac catttgttag cggcccccatg tacctggtgt  2760
acatataaat acatattttt cgtcagttca tatatacagc atatattcat gttaagaata  2820
tcatttcatt ttataaaaca tataccatcc caagaagaat tctttcatcc tctcggttgc  2880
agctatggag tctggatcag tgtcattata tggaagaaac catctagtta tcatcacagg  2940
tccaatctta cctccttgat gctgtggtca cgcagatata tatacccaac gataagatta  3000
atttagaatc agataataca cctttcataa aatggagaac ctgccttata ttttgtcctg  3060
taaagatcga ccaccgtggc atgagcaagg agctggttat gtgcaacaat atagggttcc  3120
gttgaagaat ttccggcgta acatgtagaa tcaacctttg gagaacatcg accagtgatc  3180
ctaatccata gcctctcgta ggcactgagt agagctggtt gattgtgaac cagtgcttta  3240
ctttatcacc atattcttca aaacatagat ccgcgaaatc tctgaaatca tctctgcgaa  3300
tattatagtc atttcattaa tcccagaaca aatctttata tattgtcgtc cttcttaata  3360
agcagcatgg cataaatata acatacatga tctgagggtc caagaaacct tcatagtcat  3420
cttgtagtac ttgaggaagg tcccagtgaa agagcgtaac taaaggcgtt ataccccttgt  3480
cgatgaggcc atttatgagt ccgtggtagt agttaatacc tccttggtgt actcccctgc  3540
tcctctttcc tcctgctcat atgtatccta tatttaatct ttcgaaagaa tcataatcga  3600
atattaccat atatgattta tatatataca tggatcaata acgttcacat acttggaatg  3660
attcttgacc aggcaatgga gaatctgtag ccagtagctt tgagttcatc cattacctct  3720
atatctttct gcagttcaca tataatcgca tgtcaatcca cactaggttg gtagttgata  3780
aataattcag tgagtaatat taatatgcac acacatatat attgaggaat ttaattacct  3840
cccagtacga atatgagtta caagtagtgt ctccatttcc atgatcgggt cctgctttat  3900
ctgatagtaa ataaatacat aactataaat gcatggagac atataaccga cataatatgt  3960
atatgtgatg agtaaccatg caaaaaaacaa acgtgggaat cggtgagtga agccatccca  4020
aacgttaact ccacgattta tgctaccttc gatctgaaat gaaaagaaac aaccatgcaa  4080
cgttagattt taatgtttat atatgatgtt ttatacgtaa aatatgacgt ctggcaacat  4140
aatactaatg gttgatatat atatgttaca tgcctggtaa gcagaagatg caagaccgaa  4200
gatgaagtct ttctcgaaac tgctactgtt gaaacgatca gtttgaccac atgtgaatgg  4260
caggttctct tcgcaagtaa tttcttcatc agctttgcaa gtcgccaaag ccaatagaaa  4320
agctaatgtg agccaaagat gcttcatggt taatttgtag atgtgtttct tatgttgtat  4380
ggaaccttct gccaatctag ggtttatata gccattgcaa cggagggtga tctatgcatt  4440
ttttttttgc aacttggtga tctatgcatt ttcttctcta ataagtgtct tgatcaatat  4500
tttgggagag ggttaggtga catgaaaccc gtggcgtttt acagtggctt gctcttcaat  4560
tgatcatttc attaagaaaa cttttgacta tttcttttat ctcaattgtg attgctagat  4620
tactatcatt tttcgaagtt aatctgtaaa taacgatggg gtagatttat ttgtagaacg  4680
acaaacgtac tttttgagtt tcttaaccat tgaggtttct ctaatactct tttcttatca  4740
aagagacagt tttttttttt accaaaaaaa gagagagttt ttagatccta gtcctaaaaa  4800
tgcatggcat gtaatttgca aaaaagaaaa aacacttaac atacaaagaa ctattcgtta  4860
attgatcggt caacagtgat acgatgcagc atgtgacaaa ggtatgcgca aaagcaggcc  4920
cggcttaatt tttgagtgga ccttgtgcaa gttctaactt tcagaaacaa taaaagtaat  4980
ttgcaaaaaa aggtcctaaa ttctataaaa ttagatctta aattctaact aaattttatt  5040
tattttttgg ggaccctgtg caaatgtgcc ttgtgcacag ggtaagagcc ggcactgcgc  5100
aaaagtaaaa ggacatgtct caagattccc tatagtaaag ttccaaaaaa cgattccttg  5160
tagtagatga tgctcaatgg ctcttacgtt tgacttggag ttagaactga cgccctaagt  5220
tattgaaaaa gtctccagta atattatcaa gtagtctgga gtaacaatga ctaagaaaaa  5280
aaaacaatta tcatgtcatc caaaaagcca cactcatcac gagcctcgcc gctcaccatc  5340
accgcatatc tttttgattt tcgttgctcc ctgctttatc atacgaaaaa ggtggacacg  5400
tatcgaatat acgagatttt taagatattt atgattttat acatttcgtt tgaataatca  5460
gttattcgat tcgatttcca ttcacttgaa tatccagaaa ttttaaattt ttaactggat  5520
atccaatttg aacaatacaa aaaaaattaa aattaaaata taaataaaaa taaaaatcca  5580
aaaaataata ataatctcat tacaaaaatt attttatttt taaattataa taactagtat  5640
aatatattta atacataaat attataaaaa tgtataaaat ataacattta tacaagttat  5700
atatataatc ctttaagcat ggctatatat attataatac ttctttttgt tctctctagg  5760
aagattgtct aaacaacata ttttatatta aagaagattc catttatcat taggcggtaa  5820
aaatcacttg acctgaaagc ctgaacccgg aggccggagg tcagaagtcg gaaccaagat  5880
attggcgcca tgttctaacc cgcaagctct tattgtggat aaattatccc catcaatata  5940
tatatattta attgttttca ttaaaataat agttattttt taaatattga caaactagta  6000
gaaagttata catggacaaa tttattttaa atatgacata ttttgccagt ttcctcaaac  6060
ctctcattta ggatctaact ggtttatatg ctatcactcg caaacacatc ttttgcggct  6120
gatatcagtt gttggtgttt cacaacaatc acaaaaaaca atacaaaccg ctttacaccg  6180
ttctaaactt cactaaatca aaagctggtt acagctagcg tttgtggtta tgggtggttg  6240
tggtatggta attttttatt tattgtaaaa ttataaaaat ataaaaacaa ataattttaa  6300
atattttttt aaatgagata atataaatac taatatatat atatatt              6347
```

```
SEQ ID NO: 11          moltype = DNA  length = 6937
FEATURE                Location/Qualifiers
```

```
source                  1..6937
                        mol_type = other DNA
                        organism = synthetic construct
SEQUENCE: 11
tatcgaatga aacaaaagta caatcacagt tcatatagaa aggagataag attggatcaa  60
acaatacctt tgtttcaact ttggaggtgc gaaggagagc ttggaggtgc aaaggaaagc  120
caattgaaca aacaatacgt ttgtttcaac cttggaggtg cgtaggagag aacgacagcc  180
atcgtcgtct tgcgtcttgc ggagacaacg agggaagcgg cggagaagcc gagagaaacc  240
aaagaaaaga aaaagagaaa agaaaaatag aaaaatatat gctttgcctt tcgttagctg  300
acacgtggag gaaaaacccc tttagttatc gatcacaaaa atcctttctt aaggatcgat  360
aactcccctt ttatttagtt ttcatttaat taaataccca attaacttta aaaccccact  420
taaaatcccc cgttaaagat gctcttaggt cttatttaca aaattttccc aaatcgattc  480
aaaactacta cttgtaagaa ataaaacaat tgaaatgatt attgtgaaaa aatgaaatca  540
tatgtatatg tctcgataat ttttatttta ttgaatgaaa aataagagta ttacagtcta  600
tgttattgat aattcatggt gcatggatag tttttatttt attgaatgaa cattaagaga  660
attccatagt agttctcaaa aacaaaccaa aaagttattt aaactgaaac tattatttag  720
gtgatgattg tttacatggt ttttggattt tagtttttat tttttagatt tggtttttac  780
attttagttt ctgatttttg aattttgatt ttgctatata ttttaatttt tcaaaaaaac  840
ttgaatggtg attctagatt ttgctttttg gtttttaatt aattttttta aaatatattg  900
gaatctaaag tttgataact aattatttaa ttttaaagtt atttttttatt tttaagaact  960
tcactcataa gttaatttc ttttaaacaa acttaaaatt actaaaataa atatcatttt  1020
aaataagtaa taccaataga actcttaaca aatatgcaaa atttacataa actaattaac  1080
caaattttaa atttatttta tccaaatgcc taaagcacag aaatttaata aaatgtttta  1140
ttcttgaaat aatacgaaca gtttatttta attcatgttt gaactttgaa aacatagctt  1200
tgtactgtca tagaagaatt ttttcaaaaa taatatctaa ttataaaaaa tatatataac  1260
taaagtttat gaattcttac ataagtgtta aactataggt taatacacaa gattcttgca  1320
tttcaaccct tccaatcata tctagaaacg ttaccaaaaa aagcaaaaaa tgttgttggt  1380
tttcgttttc gttttctttt gtctttcgga tactgtggtc tcatgtgata aagcatatat  1440
agagaggtca aaagaatcaa aacaaataag atatgctatg attgtttttt cttgataatg  1500
ttgattatta gcggtgatct catgaaaagt gtggccttgg atcagtgtta ctctagattt  1560
agcacttgat aatatttcga taaaagtctt caataacttt atggcgttat gacgacgctt  1620
tgaacattat ttactgcagc taatcttgat atataattcg tcttttctag ttcgcgcacg  1680
ccttccatat atacatgctg catcgcacca ctggtcgacg gatcaatttg aagatgtgac  1740
acaattcgtc ttccaagtcg tacgtcttcc aagtcgtacg tgttccaagt cgtacgtgtt  1800
cccgtaattt gaagatggaa cacaactatg tgctatgtaa caaaaaaaaa ttatttgcaa  1860
tagataatga aaaactaaaa agtggaagca aacaagaaat ttaagcaaaa tcggtgaaca  1920
ctgagctaaa gtaagtgaac ccacgggact catgatccca cctaaacctc cccaaaatgt  1980
cgagatacta agacaagaaa atgtatgtgt cactcttctt taggaagggc tatataaacc  2040
gtagatggac acaaggttcc atacaacaca acacatacat caacatatta actatgaagc  2100
ttcttgggct cgctttagtt tttctgttag cttctgcgag ttgcaaagct gacgaagaaa  2160
ttacttgtga agagaacaat ccattcacat gtagtaacac tgatatttta agcagtaaga  2220
acttcggaaa agacttcatc ttcggtgttg catcttctgc ttaccaggca tgtaacaaat  2280
gttgacatac catacttttt gacgtataga aaacactatt caaaaatgat aatatctaac  2340
tttgcatggt tgtttctttt catttcagat cgaaggaggg agaggtcgtg gtgttaacat  2400
ttgggatggc ttcagtcacc gatacccagg tatgtcgttt gcacggtgac atctatatat  2460
atatcatata tgacaggaat gttggttata agtactcata ttaatgtatt tgtaattact  2520
atcagagaaa tcagggtcag atttgaagaa tggagacact acttgtgagt catatacgag  2580
atggcaggtt aattcttcag tacatttgta gatactcatg actgaactat gtatacaaac  2640
tacgtgccga ttgagatgca atcaaaatat gaaactgcag aaagatgtag acgttatggg  2700
cgaactaaat gctactggct acagattttc ctttgcgtgg tcgagaatca ttccaagtac  2760
gtacagatta tcgatcagta catgtatata tatagttgga cgtgttttaa atgtacgatt  2820
tatatataca tgagcagaag gaaaggtgag taggggagtg aaccaaggag gtcttgatta  2880
ctaccacaaa ctcatagacg ccctcctcga aaagaatata actcctttcg ttaccctctt  2940
tcactgggac cttcctcaaa cactccaaga tgagtacgaa ggtttcttgg accgccagat  3000
catgtatgtt tatatttgtg acatgcttct tatattatta ataagagaag aaaaagatgg  3060
ttaattttag ttacatgcat tactgaaatg attctatatt aatatgcaca gacaagattt  3120
caaagattat gccgatctat gtttcaaaga atttggtgga aaggtggatc acgatcaacc  3180
agctatacac agtccctacg agaggctatg cagtcggaac agatgcaccc ggtcgatgtt  3240
ctcctatggt tggtgttacg gcggaaattc ttcaacagaa ccctatatcg ttgcacataa  3300
ccagcttctt gctcatgcca cggtcatctt tacaggacca aatataaggt gaatgctgtc  3360
tccatatgtg aaaattaagg tggtgtctaa catatctgat tctaatgtaa atatcacgtg  3420
accaacagtt ccaaaaaggg aagattggac ctgtgatgat aacaagatgg tttcttccat  3480
ttgatgagtc tgatccggcc tccatagaag cagctgagag gatgaaccaa ttcttccatg  3540
gatggtatat atatatatta ccaaaaatgt aacagtatct actgtatttg tatgtatgta  3600
taatggaaaa atatacatgg atcaggtaca tggagccgct aacaaagggt agatacccag  3660
acatcatgag gcagattgtg ggtagtaggc ttcccaactt taccgaggaa gaagcccaac  3720
tcgttgccgg ttcatatgat tttcttggtc tcaactatta cgtcactcag tacgcccagc  3780
cgaaacctaa cccatatcct tcagagacac acactgccat gatggacgct ggtgtaaagc  3840
tcacatgtaa gtaccacaca atattactac ttagttacga cctttctata tatttttttt  3900
cttctttttg ttaacatact ttgtgagagt atcaattatt tcatccttgt gtttacagat  3960
gataattcgc gtggtgaatt tcttggtcca ctggtatata tgaatgaacc acccctatga  4020
tatctctttc atttttttatt ctatttgcaa tatatagaac accactgatt atgttctcgt  4080
gattgatatg tatatttgtt tgcttccctt gctcagttcg ttgaagacaa agataacgga  4140
aacagctatt actatccaaa aggaatttat tacgtgatgg actacttcaa aaccaactac  4200
ggcaaccctt taatctatgt caccgagaac ggtgagttct acatactact actcctctat  4260
tttcatttat accacgcata atattatgta accacaaaag tagaccgata ttcaatctac  4320
cgcagggtga atagtaatga aaataattgt aaaagttatt ttacaattat tgtattttcg  4380
aaattggtcc aagaaactaa cttacaaata ttgtgtaata tttttcatgc aatggcggct  4440
taattaggat ttagtacgcc cagttcagaa aaccgtgagc aggctattgc ggattacaag  4500
```

```
cgaattgatt atctctgcag tcatctatgt tttctccgta aggtcatcaa gtaagtaatg  4560
ctactatatg gatgcttttc ttccaatgtt tatcaacttc ttctcttttt ggtaatatat  4620
atatatatat atatatatat atatatatat atatatatat atatatgatt gttcttgttt  4680
tcagggagaa gggtgtcaac gtgagaggtt attttgcatg ggctcttgga gacaattacg  4740
aattctgtaa aggctttacc gtcagatttg gactcagtta cgttaattgg gacgatctcg  4800
atgatagaaa cctcaaagaa tctggcaaat ggtaccagag attcattaac gggacagtca  4860
agaaccttgc caaacaagat ttcctccgct caagcctctc ttcccagagt cagaagaaga  4920
ggctgtctga tgcatgaaac acttcccccc cttcaagatc atctccatgt ctctcactct  4980
ttatacttgc tcaaccgata aagagcttct tctacctata gtaatgtact aaataaatat  5040
tctcaataaa aagatgatca gttactaatg aataaaaaat ttatctacca ctacattatg  5100
tcaagtcaag aagatcgaga gagggagaca gagggaaata acacaattta aaccaaaaac  5160
gtcacccata caaaataaaa aaaaaaatac acggtttatg cgagaaactt aagagcaacc  5220
ttatggttga tactaaattt agatatctca aaccaaaaat attgttagtt taatctgttt  5280
ttacctaaag ttcaatttta ttttttattt tttaagtcaa tctaattggt gaaagacaat  5340
atgcggccat atgagatttg ttaaaaactt aaaatcgtgt taaaagttct cgcatgcgaa  5400
cctgcttctc ttctctttcg tgttttttgt atttttgaat ttttttaatc taagatactc  5460
tatctaaaac gtatccattt tgtttatcaa tgttatcaag gtcttatttt tttcgagatt  5520
ccacattgat atgtaagacc atccactaca agaaaacacg ccgaattccg acggagattc  5580
cgacggacgt cacaggcgtc ggacaattta gacgaaattc tgaccgattt ccgacgaaaa  5640
caaaaaatct gaagtcgtcg gaattccgtc ggctaattcc gacgaacttc cgagaaaaca  5700
agggtcgtcg gaatattccg acgacttttc gacgacatcc gataaacaat ataaccgttg  5760
tagtcgtcga aaagtcgtcg gaatatccga cgattttggc catcagaatc cccctgtttt  5820
cttgtagtga tctcaactct atttatttt tcactttttt gcttcatttt gaaagaactt  5880
ttgttccaat tctacctcat ttcttgcttc aacaaagcaa taaacaatat atcttcaaat  5940
ttaaaaatat atcgttcacg ttttcaattt tataagataa aattttaact ataaattgat  6000
tcttaatttt tagttatttt tattttgtca ccataaatta tataatatta attacccaat  6060
caatttcaaa atttttgact attgttttca tctaatatta attacccaat aaattttgac  6120
tatttagctt gattaagaaa aatcaaagat aaatagtctc atatttttat ttcaaaacac  6180
ttttgttaac tcatagaaaa atattttctt tctaaaatat gatattcttt gtttgtttct  6240
tgtgttatgt aataatttta ttaaatgata atgtttaata tatattaaac tctaattgtg  6300
atagattatt ggtaaaataa taattgagta acatttataa atatgaaaaa gtacaaatgt  6360
aattaataac taataattat tggagataga atatagttag aatattcttt ttacagaaaa  6420
taaaaaaaaa accattgaaa taaatgttat ttcatttttt tttataaaag tgaactctga  6480
aaaataaaaa tgaaaccaat cttaagagat gccctaaatc catgagtctt tttttaataa  6540
gaaaaatata tttcatcaat atgttggaag ctgaagtaat ataaatagta tctcctaacg  6600
agaattgaac tcaaatggtg atatgtctac tagacagatt tttactgcta aaccaacata  6660
tagttggttc catgaatctc ttcaatctta ttttccatat acaaaaagaa aataaataat  6720
tttaaaacta actcatgcac attcgtgaat gtttatttta cgatagatat atagatattt  6780
ctaaacacaa caatttagta gttgcatttg tattacttta gtgtatcgtt gagaccatat  6840
attgtattac tggatcatgt gatatatttt tcttattaga tatgtgttgg atgagttatg  6900
taattataaa tatgattaga tctatgtatt gatatgc                         6937
```

```
SEQ ID NO: 12          moltype = DNA  length = 6016
FEATURE                Location/Qualifiers
source                 1..6016
                       mol_type = other DNA
                       organism = synthetic construct
SEQUENCE: 12
tgtcatgatg cttattattt aactcataca ttgctatata tatatattat atatattata  60
tatattcttt tttagatggt aacgacgacg aatcattatc tctttttata ttgtatcatt  120
gtcaaaccat tttctttttg atttgcaatg ttccttaggt gggacgtgag cgaacaacag  180
tggctcttgg tcaattggac gacttggcta cagtcatttt actttccatg catgcatggc  240
ccgctttctc cacctggttt gggtatcagt gacaacattt gcttgagaaa cttcctcggc  300
tagctgctca aggtacagtt tatttgctat cgcctccaca acaatgttgc ttctagacat  360
gctgcaattt tcaaaatatt agaccggctg atcattgaca ccatcctggg ggataggaat  420
cgaaaagctt tcaggaacca tatgcaacaa tgactgactc tagtctaatc tttgcttctt  480
tcatctttta ctccatatga cttccttgtt tttatttttt ttccaagcat gtctcatgtg  540
ttggaattgt atcctttgat taaataagaa aaagaaacaa aaagaaaata agaataagaa  600
aaatgtggaa gaagcaacaa gtcaagggag ttagtgaaag cttttgtttt ggtatgtaaa  660
agtctctaag tttgcttgct gtattagcca aggctgagtc aaaaagtata ggcaagatat  720
ggagattata ctcctaagtc taggtcaaaa agtgtgggag agagtggaga aaacagagat  780
tgctatcatg ttttcttgta taaatatgtg tgtgcaatgt tgtgtaaaaa catccttgag  840
atgatcaatg taagaaatct agacaaacaa agagttctct cttctatcta taggaacaga  900
acaagcgaca agtgagagta aaaagagtaa gcttgtgtac aaagaaatta acacaagcat  960
aaaaacagag agaacaagag aggcttgcca tgagtgagag gtaaagccaa gagaaaagtt  1020
caacatcgtg atcataactc ttggtaatat ttacaagctt tctcattctc ataatgaaat  1080
tcgcaaacaa aatgcaaaaa caaccaatat ctttattctg taaatcgcca ataaatatag  1140
taagtgattt atcatatctg caaagcatga atcttttgtg gccactgaat tgttctcttt  1200
ttttttctat tgagatcatt aaattaggtt aatttaaaaa ccaaatgaaa aaattattac  1260
tagctacagt tttacagaaa tcaaccaaga aaacctcaag tcaaaaacca gctagaagca  1320
gggaaggagc ctaggctcat gattttcatg aatcagggac ccgaacatga ttaatttagt  1380
tttatcccga cgatcagtta aatacttacc ccttagatag ctgatctgtg ccaagtttta  1440
taacttaaaa atgctaataa tcccaagtaa aagtaattca tcgtgtaagt aggatcgaac  1500
tcaaacgaaa atagtcatca gtaaatgatc atcttttatt ggaatattta tttagtacaa  1560
tattgataga acaagctcct tatctatgaa gcaagtagta gagatatgaa gatgatcatg  1620
atggtgggat aaagtgtttc atgcatctgc gagcttcttc tggttctgga aggagaggtt  1680
tgagcggagg aaatcttgtt tagcagggtt cttagaggta ccgttaataa agctttggta  1740
ccatttgcca gattctttga gatttctatc atcgaggttt gtccagttaa cataactaag  1800
tccgaatcta acggtaaaac ctttgcagaa ttcataatta tctccaagag cccatgcaaa  1860
```

```
gtatccttta atgttgacac gcttctccct ggaaacacga acaatcattc aaagcctaag  1920
cctatgcatg atgatgacca tacatttatg tatgcatgca tcaaattcaa aagagaaaaa  1980
aaaaatatag tagcttccac tcacctgatg accttacgga gaaaacatag atgactgcag  2040
agataatcga tccgcttgga atcagcaata gcttcctcac gggtttcttc accgggagta  2100
ctaaatccta atttaaccat catggtacat aaacaacttg tacattattt taaacataca  2160
tatttgctta atatggaaaa agagatgagt agtagtcacc gttttcagtg atatagatca  2220
aagggttacg gtatttggtt ttgaagtagt ccataacgta ataaatgcct tttgggtagt  2280
aataggagtc gccgtttatt tcgtccttaa cgaactgaga aaaggaagca tacgtataca  2340
catcaactag aaagaaaaaa aataataagt aacaggggtc aggggtggat catgcatata  2400
ccagtggacc aagattttca ccacgtgaat tcgtatctgt aaacccaatg atgaaataat  2460
tagtggtcac tcacaaagta tatatatgct taatttaaaa gacttagaag cctatatata  2520
tatatatata tatagaaagg ttgtaactat aagaggaaac tgagtggtac atgtgagctt  2580
tgcgcctggg tccatcatgg cagtgtgatt ttcccatgta actgggttag gttttggctg  2640
ggcatactga gtggtgtagt agttgagacc aagaaaatca tatgaacccg caactagttc  2700
tgcttctgct tccgtgaaat tgggaagccg actacccaca atttgtctca tgatgtctgg  2760
gtatctaccc tttgttagcg gctccatgaa cctgatcgat gtacatacgt ataaataatc  2820
atatcatttt tgtgtacata tacatacaaa tacgtaccat cccaagaaga attctttcat  2880
cctatcagct gcatataggc tagctttatc agtctcatca aatggaagaa accatctagt  2940
tatcatcact ggtccgatct tccctccttg gaactgtttg tcacggcata cgaaatgaaa  3000
tgatatgatt agaacattga catatatgtt agactacacc tatttacaaa cctatatata  3060
ctcaccttat attttgtcct gtaaacatcg accgcctata taaggtacat acatgatggt  3120
gcggttcaag aaaccttcat actcatcttg cagtgtttga ggtaggtccc agtgatagag  3180
ggtaacaaaa ggtgttatat tctttgcgac gagaccatct atgagtttgt ggtagtattc  3240
gagacctcct ttgttcactc ccctactcac ctttccttct gctcatgtat acatatcata  3300
tatttaatct tctcaacact cacaatcaat ttacgagaat tttttgtata aatagatcgt  3360
ttatgtgttc atacttggaa tgattcttga ccacgcaaaa gagaatctgt agccagtagc  3420
attgagctcg tccatgatgt ctatatcttt ctgcgcagtt tacatacaca ctcggatatc  3480
atttatatat agtgaggaat gtggaattaa cctgccattt tcctatatga ctcagtgagg  3540
aattaacctg ccatcttgta tatgactcac aagtagtgtc tccattcccg agatcggatc  3600
cacccttctc tgatagtaaa catatacatt actacgaatg atatataaga gatgtggaca  3660
ttatatatat atgtaccatg tagatgatat acctgggtat cggtgagtga agccatccca  3720
aacgttaaga ccacgtcctc tgccccccttc cacctacaat aataagaaac aaccatgcaa  3780
cgttggattt aatattttaa atggttttct acgtcaaaaa ttgttgattt gtaacatgcc  3840
tggtaagcag cagaagcaac accgaagatg aagtcttttg ggaaattttt actgcttaac  3900
tgatcagtgt ttccacatgt gaaaggctcg ttctcttggc aattaatgtc ctcaatagct  3960
ttgcaactcg ccgcagcaat tagaaaacct atcaaggcta gtccatgaag cttcatggtt  4020
aataagtaaa tgtatgtgtt tgtgttgatg gaaccttgtg ccattcaagg gtttatatag  4080
cctttgtaaa gaagagtcac gtattttctt ttctttaata tcttgatatt ttgggagagg  4140
tttggttggg tgaattccgt gggctgagtt actttagcta aatcagtatc agaattgtga  4200
ccggtcgtta tttttgtgaa gttaattttg taaataacaa gggactaagt ttatctgaat  4260
aaaatgaatt gtaagtaaat tatcatatac tccctccgtt ttcttttata agtcgtttta  4320
gagaaaaaat tttgttccaa attatatgac gttttcggtt ttctatgtaa aatttcttaa  4380
tagttaatgt tgtatgacca aatgataata tgtcttctat tttttcattg attgatttgt  4440
ggttaggtaa ataattaatg atgtttttgt ttagaaaata taaaaaattt atgtttttttc  4500
ttaatctatg tgcaaggttc taaaacgact tataaaagta aacggaagga gtattagcaa  4560
ataacgaaag ggcataaaaa aatatttaaa gtgttatttt attgaattaa ccgctggatt  4620
tttaaatata tatatatata tatatatata taaccatttg gtactaaata taaatatacg  4680
ttcaaatata ctaaaggagc ttattagatt agggatttgg aaaaaacttt aaggatttca  4740
gattctaaat tatttggatt taatggattt tgatagagat tttgatagga catttgatag  4800
aattttaaaa taaaaataaa aaatagtttt gctaatgttt tcttaaaaac attttctaac  4860
aacataaaat aaacacaatt tagtaaaacc aggcaaaaag tgtaatctgt tttcaaaaat  4920
atcattacaa gtgacaaata cttcacttga tttgcaattt tgactttact gtgagagtcg  4980
atttttttta atacatcatg ttaacaatgc cataaatcat ctcaacacat atcagccaaa  5040
aatacgttgt gatattttac cattcttatc aaccataaaa ttcaaagaac acataaaaat  5100
gataacttac tcatgcatat accaccgttg agatccacta atacaatcat tttacatatt  5160
tgaagcaatt gttgttgttt tttttgttg taacatcaat tgttgtttta attacattat  5220
tagcatgttc tctttgttgt ttctgagagc ctaaaaaatt gatgaccatc ggtacttggt  5280
tgagtaacat tttattcatt agaggtttct tctggaggaa actcatttgg ccgacacttc  5340
tgatggagaa agttatgcac tgcagcacat acaagctcta attctgcttc tgtcttatat  5400
ggaaaacttg aagcagattt ggatatcaca aatcttgatt agaaaatact aaaagacatt  5460
tgacgacatt tctcaaacaa gcatgatgat agttgaataa ttcttcttta tttcctggat  5520
cactgcccct tccagtaaat tctttcagat gataatgggt actttgaaat tgagttagaa  5580
tatttaactc attttcatat ccacaatatg ctatataaaa ttttcatgat ttttttttga  5640
tgtaaaataa atataaaaat cataaaattt atagtaaaat atcctatctt aaacaacaat  5700
aatgtatata tttattaagt aacacattta cccaggagaa tttcaaatat attgctactt  5760
tccgttaatg catcatttaa cacttttgca ttatgaactg atccttccca gctagtttga  5820
aaatatatga gtttcaaatc aaaattgcat gcagctaaca cattctcaga taaaactcta  5880
ttatgttttg atacctaaca atttaatttc ctactaccat agcagaaata tatgtttcat  5940
cgatagttcc aatacaagta ttttcttttc tttaatatct tgatatttta ggagaggttt  6000
ggttgggtga attccg                                                  6016
```

```
SEQ ID NO: 13          moltype = DNA  length = 6278
FEATURE                Location/Qualifiers
source                 1..6278
                       mol_type = other DNA
                       organism = synthetic construct
SEQUENCE: 13
ttcgcgtaat cttttagcag ttaaattgaa attggccttg tgttgaagtg cattgtcgag  60
aaaactgtat ctgtgatgag tttttcttcc aaaatgagac ggtgaagagg ctctcattat  120
```

```
gtcttctctt ctgactctgc gaactggtat tgtcccaacg ggacagtttc cagatttgga  180
ccaaatctgg gacgtgattg gtttagaaga accgttgttt ggaatagtag tcgtctttgc  240
atcaaattct gcactaggtt tcatctgcat ggcatcagtg tatagaattt ataagtattt  300
aggactgaaa attcatgaat aaatctttta taaataattt aaatataata tgagtacgaa  360
aacaaaatgt cattaatatg tagaatatgt ttacctgaat cttatggttt cttaaggcag  420
gatgatcaaa agcatgttgt ttgtagatat ctatgcagtc tattacatct ccatcttcac  480
tctacaaata tattacaatc aattttcgga actcagaaac cgaaacaaat tctacacatg  540
aaatattata ttgcgccttc agatcccata catacttga tcgtctctaa ggctggctta  600
ttaagagtcc tcaatttctt gtcgatatct aatgaaactt ccccatatgt ttcgttgtaa  660
aagccacaca taatcacaaa gattaggatc aatctcattg cggctttatc tatagttttt  720
cctacgatgc aaagaatagt tatagatata ggctttgaat cttgagcctt catacttata  780
aagcttatga gaccaaatgc atttgttctg ttgttaatta atgtgattca ccacgcaaca  840
attgaaaaca ggtccataaa caattgaaaa caatttaaaa gataagcttc tggatccttc  900
tttatggaca aaaattagaa tagagattgg tctgatttca tcgagaggct catgtgtagt  960
gttgtgtcta agcctcatta aaaactttgt ttggaaaacc tagtggaaca aaaccaaacc  1020
aagaaaaaga gtgcaagtca caacacctct cttaatgaat gagctagccg gcttgaatca  1080
caaccagtgt ggttgaatca tcacactcta aagtactgag gtttagcttc ttttggtttt  1140
cttgattata taagaaccaa aataaaataa aatcatttga atgataggaa aatcatatgt  1200
aaaatactat taagtttcag ttgaggatga tagaactttg gtgtagctag atttgagttt  1260
gtataaggtt tggtcattgt ttattatgtt gaaaatctat tctagtatat aaagttgaac  1320
ttattaagtt aattagtgaa tttaagctga tcggtttgat gtttatatat ttattacaca  1380
aaactagttt gcggtttggg gtaattattt atttattttc tatgtgtgtc taagtgacgt  1440
ttttggttta aattgtgtta tttcactctc tctctctctc gatcatcttg acaaaatgta  1500
gctgtagaca atttttttat tcattagtaa ctgatcatct ttttattgag aatatttatt  1560
tagtacatta ttataggtag aagaagctcc ttatttttgg agcaactaga aagagtgaga  1620
gacatggaga tgatcttgac cgggggaaaa agtgtttcat gcatcagcga acctcttctt  1680
ctgactctgg gaagagaggc ttgagcggag gaaatcttgt ttcacagcgt tcttgacggt  1740
cccgttgatg aatctctggt accatttgcc agattctttg aggtttctat cgtcaagatc  1800
ttcccaatta acgtaactga gtccaaatct gacggtaaag cctttacaga attcataatt  1860
gtctccaaga gcccatgcga agtatcctct cacgttgaca cccttctccc tgaaaacaag  1920
aacaatcata tataaaaatg ttacaaagaa agaagaagaa tataacagat gtagaaaatc  1980
atttatatag tagcatccac tcacttgatg accttgcgga gaaaacataa atgactgcag  2040
agataatcaa ttcgcttgta atcggcaata gcctgctcac ggtttcttc actgggggta  2100
ctaaatccta aataaaccgc cacattaaaa atattccaca ataaagtcag tttcttcgac  2160
taatatcaaa atacaataat tattatgtgg tataaatgaa aagagttcgt aaaactcacc  2220
gttctcggtg acatagatta aagggtctcc gtatttggtt ttgaagtagt ccattacgta  2280
gtaaatgcct tttgggtagt aatagctgtt gccgtttacc ttgtcttcaa cgaactgtga  2340
aaatggaagt aaataaatat acacatcaat taaaaaacat aattagggtt gttatactga  2400
aaactgaaaa aatgaaagaa aaacaaatct tagggggtgg atcattgata tataccagtg  2460
gaccaagaaa ttcaccacgt gagttatcat ctgtaaacac aaggatgaaa taacagatgg  2520
tcactcacaa agtatgttgc aacaaaaagg agataaaaga atatttatat gtatagaaag  2580
gctgtatcta attagtggta atagactagt acatgtgagc tttacgccag cgtccatcat  2640
ggcagtgtgt gtctctgaag gatatgggtt aggttttggc tgggcgtact gagtgacgta  2700
atagttgaga ccaagaaaat catatgaacc ggcaacgagt gcggcttctt cctcggtaaa  2760
gttgggaagc ctactaccca caatctgcct catgatgtct gggtatctac cctttgttag  2820
cggctccatg tacctgatcc atgtatatct tttaattata catacataca ctatatactg  2880
ttacattgtt ctgtaatata tatatatacc atccatgaaa gaattggttc atcctctcag  2940
ctgcttctat ggaggcagga tcagactcat caaatggaag aaaccatctt gttatcatca  3000
caggtccaat cttccctttt tgaaactgtt ggtcacgtga tatatatata tatatgacta  3060
tacattagaa tcagatatgt tagatttgca ccaccttaat atggagagac cactcacctt  3120
atatttggtc ctgtaaagaa ccataggaga acatcgaccg ggtgcatctg ttccgaccgc  3180
atagcctctc gtagggactg tgtatagctg gttgatcgtg ctttaccttt ccaccaaatt  3240
ctttgaaaca tagatccgcg tagtctttga aatcttgtct gtgcatatta tacagaatca  3300
tttcattaat gcatgtaact aaaaccaaaa cgttttcttc tcttatttat aatataagaa  3360
gcatggaaca aatataaaca tacatgatct ggcggtctaa gaaaccttca tactcatctt  3420
ggagtgtttg aggaaggtcc cagtgaaaga gggtaacgaa aggcgttata ttcttttcga  3480
gtagtgcatc tatgagtttg tggtagtaat caagacctcc ttggttcact cccctactca  3540
cctttccttc tgctcatgta tatatatgtc gtacattaat tagtactttt ctcaactaaa  3600
tgatcccaat taaaatacaa acgaatcgat aacatgtaca tacttggaat gattcttgac  3660
cacgcaaagg agaacctgta gccagtagca ttgagttcgc ccatcacgtc tacatctttc  3720
tgcggtttac atattttaat cacatgtcaa tccacacgta tagtttttat acatatatag  3780
ttcagtcata tgagtatcaa tgtattaacc tgccatctcg tatatgactc acaagtagtg  3840
tctccattct tcaaatctga ccctgatttc tctgatagta gttacaaata cattaatatg  3900
tgtacatata aaccgacgtt catctcatgt gtgtatatac gctgtgacat acctggatat  3960
cggtgactga agccatccca aatgttaaca ccacgacctc ttcctccttc gatctgaaat  4020
gaaaagaaac aaccatgcga agttgcattt tagtattttt gaattgtatt tatttatacg  4080
tcaaaaaaat ttgttacatg cctggtaagc agaagatgca acaccgaaga tgaagtcttt  4140
tccgaagttt ttactgctta aaatatcagt gttactacat gtgaatggat tgttctcttc  4200
gcaagtaatt tcttcatcag ctttgcaact cgcagcagct aatagaaaaa ctaaagcgag  4260
tccatgaaga agcttcatgg ctaatatgtt gatgtatgtg ttgtgttgta tgaaaccttg  4320
tgccaatcta gggtttatat agccattcct aaagaagagt gacgtttgta ttttcttgtc  4380
ttagtatctt gatattttgg gagaggttta ggtgggatca tgaatcccgt gggttcactt  4440
actttaacct cagtgttcac ccattgttgt tatatttgtt gttttgtttc cactttttag  4500
tctttcattt tctattgctg atttttcttt tgttacatag cacatatctg tgttccttaa  4560
tcggaacaca cgaacatgat ttttgtcaca tattcaaatt gatccgtcga cagtgatgca  4620
gtgcagcatg tatatattga aggaatatgc gcaaaactag aacgacacgc atcgtcaaga  4680
ctcgttactg aaaatgtgta tcgaaatata catttttttg ttatcgaaat attatcaagt  4740
ggtgaatcta tagtaaatct gatccaaagc cacacttatc acgagctcac cgttcacaat  4800
cacatcatat catattggtt tcgttggctc tatatctgct tctttatcac atgagactgg  4860
```

```
tgtctctgaa agacaaaaga aaacgaaaac caactacatt tgttttttttg cctttttttgg 4920
tattgtttta aaatgattgg aagggttggg aaggatacgg aacccttagg gcatccacat 4980
tggttacatc tctaacaaaa gtctcttgat ttattttatt aatatcatta aattttaaac 5040
acaataaaat tgtaaccact cacaacatga ccattgtcat gaattgttaa gagacgtctc 5100
ctttcaagaa tcgtcccttc tattttctct ttctctctta ctcttctctg atttttttaa 5160
ctatttttat cttgaaaaat catgggaggt actctcacta ctcatgctct aagataagat 5220
taattgtaga attatagaat aaatatatta ttgtgttgtg tcttataagt tacaagagat 5280
ttctatatat acacaagact tagatctatc tcaattacga atataactta tcaataaatt 5340
ttcggtttgg atttcataga ctttatgtgc ttcacttcat aatcagattt caacggtcct 5400
cagttggttc gtaagataca tatcttgttt tctaatatat cttcaatact tccctacacg 5460
ataaatgtgg atgcaacaaa caaatctgca attacaaagt aaactacgta tatcgtggac 5520
actatgtcaa taatgtacaa aaatgtcaat aaactttttt gggcaaaaac tcttagatat 5580
ggaaagatga aaacttcagc tcatatttgg tcttgataat gagaatacat tatgtgagct 5640
caactataga cccgtaaata atcttcctta tctctgtcaa tccaaaactt gaattaaaca 5700
aattgaccta aaaaagcaag cgtttcctac aaaaactccc ccataatgga aactataacc 5760
aacaaatctc aaacaatgga aaaacaacac tttgagatat tcatattata aataaatctt 5820
agacaaaatt tgtaacactc taatttctat tatatgtgga aagactgaga attgatttgg 5880
ctacttattt caacaaagtg cgtttatctt ttcgggcaca tgtccgttta gaactctaga 5940
gttaatcata tttgagctgg agtagtagaa agatgagtga cctatcagaa agtgattcgc 6000
gatatcgtgc gaatgaggtc acccaccaaa tagatctcgt gcgtcttgat aacctttatc 6060
ggttcgcgat atcgtgcaaa tgtgatcatc caccacatac ctttctcggc actttgacct 6120
cactcacggg tgcacacgtc aaaggtcagg ggactgacac cattaaatct ctctgaaact 6180
ctttcacaca ccaaagccaa actataaaaa tttcttggaa aataacaaag cacgtagaaa 6240
actattgcat gtaacacaat aaaacccact aaagcttt 6278
```

```
SEQ ID NO: 14          moltype = DNA  length = 6371
FEATURE                Location/Qualifiers
source                 1..6371
                       mol_type = other DNA
                       organism = synthetic construct
SEQUENCE: 14
gttgggtcta aaaacccgag aagggtacat tcgttagaaa ttaaaatttt cccggaaaaa 60
aaaaccgcct aatttttgtg aaacgccaaa tttttttttt aaaaaaccat aaatttccga 120
cgaacttgat caatcgattt tttaacataa gaacatgata gtttcttct tctatttcat 180
ttcaactctt tctttcattt caactctttc tttcatttct ccctcttagt cgaagaacat 240
acgtgactcc ttctctaaaa gttctcttaa atcatgttaa tcatctatta tcctcttaat 300
agttatatat attagtttgt atatttgtgt ggttattata attaatagat tttaggaatt 360
gaaatgttag atatgagtta ggttggttgg tataggattt aatatgttag atttatgtga 420
gaattgttag ttttaggatt tgaaaacttg ttttatgttt ttgatgtttt gttattttta 480
ttttttttaa gcgtttttaa gattttataa aatgttttaa agtttttata aaaatgttct 540
caagttttta taaaacgttt ttatgttttt ttgttgtaat tcataaaacg tttaatgttt 600
cttagaattt ataaaaacgg tattcactta aaaaaaaaac tgttttcaat ttataaaaag 660
ttttagtgtt tttttttaat ttataaaaat gtatttttac ttaaaaatgt aatttataaa 720
aacggatttc actttaaaaa agaactgttt tcaatttata gaacgtttta tgtttttttt 780
tttggaattt acaaaaatat tttcacttaa aaatgtttaa ttgatcaaac gtttaagtgt 840
tatttaaaat ttgtaaaaaa aaaattcact taatttttt tttcaattta taaaatgttt 900
aagttgcttt ttgggaattt aataaaaaaa atcaaataat atattgtaaa aacgtttaag 960
aataattaca taataaaaat gatttcaaat tttaatttta ttatgtatat atataaaata 1020
tttttataga ttatttatca taaacaattt tttcatctaa tatgtaaatt tgtttttaa 1080
atagttaatt aattgtgttt caaaaaagtt aattatctaa ttattaaatt ttaatttttc 1140
taaaaaatgt ttaacaaaat ttcccgctaa aatcatttgt caaaattttt tgatggatga 1200
tacacatcga aaatgttgct gacaaattct agacagtgtt ttacgacggc tgttcttgtt 1260
ggtattttgt tgggaatgtg tcggacggag ttcactggga atgtgtccga cggagtccgt 1320
tggaaatgtg tccatcggaa attctgtgga taattggaaa atacttttag acgaaataga 1380
acagacaaaa aaaaaaaatt ggttggactt tcgttgaaaa tggttttttt tttccaatga 1440
atttctgaca aaatccttcg tatatatata tgaaagagtc tgttttcttg tagtgcccac 1500
atatcccaaa ccccatatct tcttttattg aggtttttta tttagttata cagtggtagg 1560
tagacaaagc tagctcctta tctatggagc aagtagaaag aggggacatg aagatgatct 1620
tgatgaggta aataaagtgg attggatctt tcatgcatct gcgaacttct tcttctcaaa 1680
ggtgaggctg gagcgaagaa aatctttctt cgcaaggttc ttggtggcaa tgaacttctt 1740
aaaccattgg ccagactctt tgagatctct atcagtgaca ttattccagt caatgtaagt 1800
gagtccgaat ctgacggtaa atccttgtcc aaattcataa ttatccccaa gagaccacgc 1860
acagtatcct ttcaccttga cacctgtctc cctaaaagca ggaacaatga atcattagac 1920
gtcatatgat acgtcataca tgtatatata tatatatata tatataaaac gcacaagaag 1980
gaaaagagag aagcatcaac tcacttgatg actttactga gaaaacagag atgactgcag 2040
agataatcaa tccgtctgta atcaaactta gcctcctcac gggtttcatc accggaggta 2100
aggattccta gttaaaccgt cataacatga aatcatttca acaaatttca aattacattt 2160
aacatgtaga gatgaattta gagatagagt agtagaaccc accgttctcg gttatataga 2220
ttaaagggtt attgtacttg gttttgaagt aatccatcac ataataaatg ccttttgggt 2280
agtaatagat gtttctggtc tcgtcttccc tgtgttcagc gaacttagaa agagaagcga 2340
aatagtatca gaaaactgaa ttttgcttag aaaaaaatga aagaataggg atggatgcat 2400
atataccact ggaccaatga gatgattact tgcattacga tctgttaaca caaataattg 2460
atggtcacaa attattgtac ttaacaaaag gcaaattaag gttgtaaata agtcgaaata 2520
tatatagatg gatacatgtg agctttgtgc cagcgtccat catggcaatg tgacgatccc 2580
aatcaacacg attaggactt ggttggacat actgactgaa gtaatagttg agaccaagaa 2640
aatcatatga accctttacg agtttggatt cctctggagt gaaggatgga agccgctcac 2700
ccacagtgtc tatcatgatt tgagggtatg taccatttgt tagaggcccc atgaacctgg 2760
tgtacataaa tacatatttt tcgtcagttc ataaatacaa catatattaa tgttaagaat 2820
ataatttcat tttataagca tttaccatcc caagaagaat tctttcatcc tctcggttgc 2880
```

```
agctatgctg tcttgatcag tgtcattata tggaagaaac catctagtta tcatcacagg  2940
tccaatctta cctccttgat gctgtggtca cgcagataaa tatacacagt gatatgatta  3000
atttagaatc agatatgtta gaatacacct ttcacaaaat ggagaattaa tctaccttat  3060
attttgtcct gtaaagatcg accaccctgg catgagcaag gagctggtta tgtgcaacga  3120
tatagggttc cgttgaagaa tttccggcgt aacatgtagg atcaaccttt ggagaacatc  3180
gaccatgatc ctaatccata gcctctcgta ggcactgagt agagctggtt gattgtgaag  3240
ctttactttg tcaccaaatt cttcgaaaca tagatccgcg taatctctga aatcatctct  3300
gcgagtatta tagaatcatt tcattaatcc aagaacaaat atctatatat tatcgtcttt  3360
cttaataagc agtatgccat aaatataatt aacatacatg atctgggggt ctaagaaacc  3420
ttcataatca tcttgtagta cttgaggaag gtcccagtga aagagcgtaa ctaaaggcgt  3480
tataccettt tcgatgaggc catttatgag tccgtggtag tagttaatac ctccttggtg  3540
tactcccctg ctcctctttc ctcctgctca tatgtatcgt aatatataat ctttccaaag  3600
aatcacaatc gaatattacc atatatgata tatatatata tatacataaa tcaataacgt  3660
tcacatactt ggaatgattc ttgaccaggc aatggagaat ctgtagccag tagctttgag  3720
ttcgtccatc acctctatat ctttctgcag ttcacataca atcgcatgtc aatccacact  3780
aggttggcag ttgatagata attcagtgag taatattagt tagcacacac atattcatat  3840
agaggaattt aattacctcc cagtatgaat atgagttaca agtagtgtct ccatttccat  3900
gatcgggtcc tgctttatct gatagtaaac aaatacagta ctataagtgc gtggagacat  3960
gtaaccgaga taatatgcat atgtgatgag taatgcaaaa aacaaacgtg ggaatcggtg  4020
agtgaagcca tcccaaacgt taagtccacg atttatgcta ccttcgatct gaaatgaaac  4080
gaaacaacca tgcaacgttg gattttaatg ttcgtatatg atgttattta tacgttaaat  4140
taatatgacg tctggcaaca taatactaat ggttgatatg tagcatatgt tacatgcctg  4200
gtaagcagaa gatgcaagac cgaagatgaa gtctttctcg aaactgctac tgttgaaacg  4260
atcagtttga ccacatgtga atggcaggtt ctcttcgcag gtaatttctt catcagcttt  4320
gcaaatcgcc aaagctaata gaaaagctaa tgcgaaccaa agatgcttca tggttgattt  4380
gtagatgtgt gttgttgtgt tgtgtggaag cttgtgccaa tctagggttt atatagccat  4440
tgcaaagaag ggtgacgcat gtattttctt ctctaattag tgtcttggtt gttattttgg  4500
gagagggtta agtgacatga aaccggttgc tttttacagt ggcttgctct tcaattgacc  4560
atttcattaa gaaaactttg aattatttct ttttatctca attgtaattg ctatataaca  4620
tggggtatcc gacgaaccac gtcccaaccg actaattccc tcaaaaagaa tgaagattat  4680
gaatgaatgt tgaatgggag ctgggagctc ctgagtgatt ctacttcact aaaggatcag  4740
aaactcagat cagtgtttca ttaccaacat tgactaatcc aaattttaaa ggaagagatc  4800
gaccatccca aattctttta agccattcat aaagtctttt ccattggatg acaagtagga  4860
gtggactaag tagtagtcaa aaatctgtat ctattttcat gatattatgt gtggattaga  4920
tatatcaatg gtgaattctt cagaaaaatt atgtcttcca ctctcgcttt ttcgttctga  4980
ggaagaagag gagatatcca aatagttagc gagacttcaa ggccagcagc tgataagaag  5040
gtcagagtca caatcgcttt cttaattgac actacacaaa atctacatgt tcaccggcgc  5100
cgaacagatt cggttactcg caatgtaaat tgaatactat aatattgcct ggccacacaa  5160
gcaggtatat ttgagatggt aggtttctag agtatttatc accttttcaa acccgccata  5220
ccactcgacc atgcttgtgt ggttattatt tcttaagtta atatgtaaat aacaatgggg  5280
tagttttatt taaagaacga caaacacatt tttgagtttc ttaaccattg aggtttctaa  5340
tattatttct tatcaaagag agagttttta gatcctagtc ctaaaatgca tggcatgtag  5400
gtgatttgca ataaaagaca cttaacgtac aaagaacgat tcgttaattg atcggtcaac  5460
ggacaacggt gatacgatgc agcatgtgtt aaaggtatgc gcaaaagtag gatatgtccc  5520
aagattccct gtactaaagt tcctaaaaac gattccttgt atgttcaatg cctcttacgt  5580
ttgacttgga gttagaattg acgccataag ttatttaaaa atctacagta attgtatcaa  5640
gtacccacca gtctggagta acaatgacct ggttaagaaa aagaaaacag ttatcatgtg  5700
atccaaaagg ccacacctca tcacgagcct caccgctcac cagcaccgct tataactttt  5760
tgattttcgt tgctccatgc tttatcacat gaaaccactc tccaaccgat aaaataaaac  5820
aaagaccaac catatatata actttttaaa tttaccaaaa aaacatatat aactttaaaa  5880
tccttattga atagtggatg ttattcatct acttaggtga ttgaaagatg caagacaata  5940
caatagcata aatcacgatt tattaacacc ctaataatca ctattgcaag attcataagc  6000
tatccaaccc tatttttttt ttctatcgcc atgatacgtt aacctgtgaa cacttaccaa  6060
aagatttcca tttttcctct aaacaatcaa ggtaagtgtt ttgtccattc tttcgctatt  6120
ttataatgat ctacatgttc cttaaatctt agaccaagga tcatccaagg aaaccattga  6180
tgtagacaac ttctatattt ataagtgtta gttcattttt cttggaattg cacttatttt  6240
tttgttcaag gcataaactt ggttttcaag tttatcctaa tccatctcag tatcataaat  6300
ctccattcag catgcatgtt ggattagtgt tgacacaacc tgcatcagcg acttcttttt  6360
tcttttttta a                                                       6371
```

```
SEQ ID NO: 15          moltype = DNA  length = 4679
FEATURE                Location/Qualifiers
source                 1..4679
                       mol_type = other DNA
                       organism = synthetic construct
SEQUENCE: 15
aatagaacct ttgtcgaaaa gaatatctaa ttatgaaaaa tataattaaa atgtatttat  60
ttttacttaa agtatagatt taaactatag attaatatac aagtaactat ctcaggtggt  120
atacccaaac acatgttctt agtgtggttg atggtcagga acagatgccc cactcgtgac  180
aggatcctca gttggggatt acaaacagac ccccgttgcc tcctatgcaa tgttgctgat  240
gagtcaattg ctcattgttt ctttgactgt aactttgctt gggatgtttg gagaatcatg  300
gcagcaaaat gtcacttcgc ctcatctcgt caatggactg caatacttcc ccaaattaag  360
agccatactt caaacaaagt ccaaaagact tttcttcttc tatgttggca ggcgacactt  420
tatgcgctct gaacagagag gaacaatcga ctgcacaata ctcatttcac ttcaccagac  480
ggcctggtag ctcaaataaa gcttacggta aaaaacagga tctccagtct aagaatcgac  540
aggccaaatt tctcttcttc tctacttcag ttatggttct ctacgtgaaa cccatccagc  600
taattcactg attcaagttt gtatctttta gatatgtaag gccacttggc ctactgagtt  660
caatctctgt aaaatatttt cggtctcctg catttaaata gtaaaatctt tttcaaaaaa  720
aagtaactat cttatttatt cagaagtcat ggttttgtat ttattcagaa gtcatggttt  780
```

```
ttttattctc tataataaaa cgtattatta tttttattga aaatattttt atcattcgtc  840
tcggtcatac ggctctgatt atctagaaac gatagaaaaa tgcaaaaaat gtggtttgtt  900
ttggttttct ttaaaaaaaa tgcaaatttt tttgtctttc gtagagtccg gtctcatgtg  960
ataaaagcat atatagagag gtaaaaagac tcaaaaccaa aataagatat gctgtgatta  1020
tgagcggtga ggctcgtgat aagtgtggcc ttggatcagt gttagtctag attcaacact  1080
tgataatatt tcgataaaaa tcttcaataa tttatgtcgt taatcatgac gaatgtttga  1140
acattattta atacaacaaa tcttgatgaa tgatgatacg tgtcgttcta gttttgcgca  1200
aaccttcgat atatacatgc tgcattcacc actgtcgacg gatcaatttg aagatgtgag  1260
acaattcgtg ttccaagttg tgtgttccag atatggaatg taacaaaaaa aaattacact  1320
tgaaaacaat ataaataata tgacaagaaa atgacaccag atttatttgt ccaaagacgt  1380
gcttccgttc aacttcatag gttatttcct aaaattaact ctaggaaaag tagcaataaa  1440
tcattaacaa ttcatcccga taaaaaatgc aacatcttgt attttttttc ccaatgtaat  1500
ggttgattga agaacaaggc atgctaaaaa ctggaaacaa aacaaaaaaa aaaacataat  1560
caatcggtga acactgagct aaagtaaatg atcacacggg tttcatctca gctaaacctc  1620
tcccaaaata tcagaacact tagacaaaga aaaatgcata cgtcactctt cttttggaag  1680
ggctatataa accctagatg gtcacaaggt tccattaaca caacacctac atcaacagat  1740
taaccatgaa gcttcttcat ggactcgctt tagtgtttct attagctggt gcgagttgca  1800
aagctgatga agaaattact tgcgaagaga acaatccatt cacatgtagt aacactgata  1860
ttttaagcag taaaaacttc ggaaaagact tcatcttcgg tgttgcatct tctgcttacc  1920
aggcatgcaa caaatgtttt tgacgtatca ataaatacaa ttcaaaaata ctaaaatgca  1980
acttcgcatg gttgtttctt ttcatttcag atcgaaggag gaagaggtcg tggtgttaac  2040
atttgggatg gcttcagtca ccgatatcca ggtacgtcac agtgtatata tacacatgag  2100
atgaacgtcg gtttatatgt acatgtatta atgtatttgt aactactatc agagaaatca  2160
gggtcagact tgaagaatgg agacactact tgtgagtcct atacgagatg gcaggttaat  2220
acattgatac tcgtatgatt gaactatata tgtataaaaa ctatacgtgt ggaattgaca  2280
tgtgattaaa atatgtaaac tgcagaaaga tgtagacgtg atgggcgaac tcaatgctac  2340
tggctacagg ttctcctttg cgtggtcaag aatcattcca agtatgtaca tgttatccat  2400
tcgtttgtat tttaactggg atcatttagt tgaaaaagta ctaattaatg tacgacatat  2460
atatacatga gcagaaggaa aggtgagtag gggagtgaac caaggaggtc ttgattacta  2520
ccacaaactc atagatgcac tcctcgaaaa gaatataacg cctttcgtta ccctctttca  2580
ctgggacctt cctcaaacac tccaagatga gtatgaaggt ttcttggacc gccagatcat  2640
gtatgtgcca tgcagacata ttatatatga atttaagaga ttgattataa aattattaat  2700
aaaaaagaag aaggtttggt cttatttaat tacatgtatt aactgaaata attatatatt  2760
catatgcaga caagatttca aagattacgc ggatctatgt ttcaaagaat ttggtggaaa  2820
ggtaaagcga tcaaccagtt atacacagtc cctacgagag gctatgcggt cggatcacta  2880
tgatgatcca tgttttattg gagaactaaa tcattttatt ggtgattatg tcaaaaatct  2940
aagtcacagg atcgagttcc tcgaggcgaa tggtgagcca gttcctccta atgtcgctgc  3000
tacagatgcg tctggtcctt ttgttgtcgg aactgagggt ttggtaagta accctactga  3060
agcttatgat catatgcgtc aatttgatgg tatggatatg agtgtgaagg aggaagctcc  3120
tggaggtttt aatgatcatg ttcatcatca gaatatgaat catcaagaac catttcaata  3180
ccaaacttct actaactttt atgatcagac tcagcctatg ttttatggtt cgagccagga  3240
tatgaatatg aatcttgaag aaccatttca ataccaaact cctgctaact ttgatgatca  3300
gactcagcct atgttctatg gttcgagcca ggatatgtat acaggtttga atcatgatca  3360
gggacagagt tcgaatcagt atccaaattc aaaccaatcg ttcgtgggtc ttttgatggg  3420
acaacctcag cagatgagtg atggtcaaga tcctgcaacc gttgcttcga tggatgacaa  3480
aaataatggc tatcaccaac tactaatcac cagtcagatg cctctcacca ccaccgctgc  3540
cgccgctgct gatctttctg gtcataggat caacaatggt tggctaacaa ggtttggttt  3600
ggattgaagt ttttgcgttt gcaattctga attttcatat tgtaatgatt aaaggttttc  3660
gcctttaaat cagttatgat tatcaggcaa tgttgtgtcg tgtaccatat tgtccttgaa  3720
tattttattg ttttgaataa agactgttgt tttttgatat taaatcataa agagtaaatt  3780
ttttttcctt aaggccgtgg aggaagaatg caacaagcat ttcgaaaaaa aattattatc  3840
agacaaacca ttaatcaaga aatgtggcca taagacagaa atatagagtt aagttcaaaa  3900
ggaaaaaaaa aagacagaaa tatagagtta ggtgacatgt aattgcgtat ggatgtagaa  3960
tgcttattta aagatacacc attatcttcc caaagccaca tgtcatgcaa taaataatca  4020
ctcagattat caagataact atgtctgatg atatccattg tgtattaatt aaaaaatgct  4080
tcagtcttta ttcgaaacaa taaaatcatg aagtgtgtat taattaaaaa aatcttgtgt  4140
attaattaaa aaattatatt ctctccattt cattttaatt gtcatatgca cacagattaa  4200
tagaacacta ggttaagacc cgcgccttgc gcgggatgaa cattatatat ataaattatt  4260
ttatatttta tatgtttata acatattatg aaataataaa tatatattaa ataattaaaa  4320
attcattatc tactacttat ataattaaat tggtgcgaac atataaaatt tttttataaa  4380
tcgaaaaaaa aatttctatt ttatatgata tataattaaa tttaaatgat agtaacatat  4440
atatggtata ttttaatatt aatatttatt agatgatgat ttttgctcat attgtttctt  4500
atcatttgga tctgttatag caaaaagtct aaattagtga taacaaaatt ttcactgtgg  4560
gattaatggt ttaagtaatt tataatattt taaaaaatta agttgtcaat attttttcaa  4620
actttttatc aaaaaaatgt tcaaagtata tttcaaaatt aagatattta tgtattttt   4679
```

```
SEQ ID NO: 16          moltype = DNA  length = 6287
FEATURE                Location/Qualifiers
source                 1..6287
                       mol_type = other DNA
                       organism = synthetic construct
SEQUENCE: 16
ttttgcgaag aggtatacaa tcactcaaat atatacttta aacttgatta atattattac  60
taatattttc ctatattatt ttgtattaaa aatacggaca ataggattgg gatcaatcaa  120
cgattttccc agggtaacct cttcctatgt tcgttgaggt gatgttccgg ctcaactctg  180
aacggagttg acagatgctc ataacaagat ttcatcaatg aggattgatt gatccatatg  240
tttgtaaacc atatgttttt cggcatacat gtggagagac ttgacagcta ctcgagcttt  300
agagattaca cgtaaaaata ttaatatcat cataccaact ttggaggagc aagctgaccg  360
ggaattaata atggataaag cggtttgaga gactagggtc gagtttttca acgatgttga  420
```

```
ttagaaatag tttctgtatt tttattttgt tttataattt ctataaaaac tagtttaaaa  480
ttttataaaa tattcattaa ttttattgat gttctggtgt attaaatagt taattcattt  540
aaacataaac tagataccaa atgtttctat tctttaaatc caacatttgc atcaataaaa  600
taacttcgaa aatattatga tgttgtcgat aaaaatacaa aaggactttc cttttttttat  660
ttgctaatat gatcatcttt agcacattgt ctattttcac aaattcaatg tccgattaag  720
aaggcaacta caaaacgtgg aaatgaattt atacaaaata tttaaaagga cgatccagaa  780
catttttgga gttatcatat aaattcagat gttttttttag atttgtgcag acttagacat  840
ctttaagaaa tacaagatgg attttggttg aagaaatgct tgccacattt tttttcattg  900
ttggccagta agagatatat tctccctcga gatgtattca agagatcaag tttggaaaca  960
attcagagtt taataaaagg gtgttaaaca gtattggcca agtttgtagg ctaaaccagg  1020
aactgcattg cctttacaaa catgagaaac aaaagatttt attcctactt taaagtatgt  1080
aaaaattgtc ttatctattt gtttatttt atccgttaac agtttcattt atattttcag  1140
gattgtattg gagctattga tggaacatat ttctgctatt gtagtaataa ttaaataaaa  1200
ctgttagtta tcaaaacaga aatagagttt tatctatgaa tgtcctagtt gcgtgcaatt  1260
ttgatttgca gttcaaatat gttacaactg gttgggaagg ttcagctcat gatgcaaaag  1320
tgttaaatga tgcattaatg agaagtagca ataaatttga aacccccaag gtaattgcat  1380
tactcaatag aaatatatag tatgtgttta agatcggtta attaattata agttcttgat  1440
ttttcatgta ggagatttgg tagataacca tctgaaatct gaaaacttgg tagccgagtt  1500
tgtaggctaa accaggaact gcattgcatc caaataaatt tagctaaatt ccatcaaatc  1560
taaaatcctt taaaaatttc aaatccctaa tcaaataagc cctttaatat atttgaaggt  1620
atatttaagt accaaatggt tatatatttt aaaaaatcca acagttaatt caacaaaata  1680
aactttacat aattttttat ccctttcgta atttgttaaa atatgataat ctacttacaa  1740
ggttgtcatt ttattcagat aatagtccct tgttatttac aaaataaact ttacaaaaaa  1800
ataacgacca atcacaatga tgatactgat tcagctaaag taactgagcc cacggaattc  1860
accccaccaa acctctccca aaatatcaag atattgaaga aaagaaaatg tatacgtgac  1920
actactttac aaaggctata taaaccctag actagcacaa ggttccatcc aacacaaaca  1980
catacatcta cttattaacc atgaagcttc atggactagc cttgataggt tttctaattg  2040
ccgtggtgag ttgcaaagct attgaggaat gccgagagaa cgagccattc acatgtggaa  2100
acgctgatca gttaagcagt aaaagttttc caaaagactt catattcggt gttgcttctg  2160
ctgcttacca ggcatgttac aaatcaacaa tttttgacgt agaaaaccat ttaaaatatt  2220
aaatccaacg ttgcatggtt gtttcttatt attgtaggtg gaagggggca gaggacgtgg  2280
tcttaacgtt tgggatggct tcactcaccg atacccaggt atatcatcta catggtacat  2340
atatatacat atgtacaact cttatcattc ttagtataaa atgtatctgt ttactatcag  2400
agaagggagg atccgatcat gggaatggag acactacttg tgagtcatat acgagatggc  2460
aggttagttc ctcactgagt catataccag atggcaggtt aatttctcat ttcttcacta  2520
tatataatga tatccgagtg cgtgtgtaaa ctgaagaaag atatagacat catagacgaa  2580
ctcaatgcta ctggctacag attctcattt gcctggtcaa gaatcattcc aagtatgaac  2640
acataaacaa tctatttata caaaagaatt ctcgtaattt gattgtgatt gttgggaaga  2700
ttaaatatat gatatgtata catgagcaga aggaaaggtg agtaggggag tgaacaaagg  2760
aggtatcgaa tactaccaca aacttctaga tggcctcatc gctaagaata taaccccttt  2820
tgttaccctc tatcactggg accttcctca aacactgcaa gatgagtatg aaggtttctt  2880
gaaccgcacc gtcatgtatg tcatttgggc cgcgttctta gcaaggaata taagaagaaa  2940
aacatatata cataagtgat ctcatgttaa tgatttgatt ctatgctatg cacagagatg  3000
actttagaga ctatgcggat ctatgtttca aggaatttgg tggaaaggtg aagaacacga  3060
tcaaccagct gtacacagtg cctacgagag gctatgcaat cggaacagat gcacccggtc  3120
gatgttctcc ggcggttgag agatgttacg gcgggaattc ttcaacagaa ccatatatag  3180
ttgcacataa ccagcttctt gctcatgctg cggcggtcga tgtttacagg agaaaatata  3240
aggtgagagt acgtgggttt gtgaataggt gtagtcttta cgtatatgac tatatctaat  3300
catatcatta tcgtatgccg tgaccaacag ttccaaaaag ggaagatcgg accagtgatg  3360
ataaccagat ggtttcttcc atttgatgag actgatgcca gcagagatgc agctgagagg  3420
atgaaagaat tcttcttggg atggtaacgt atatgtatgt atatatcaac aaaaatgaaa  3480
tgattttctt atacgtatgt acgtcgacca ggttcatgga gccgctaaca aagggtagat  3540
acccagacat catgagggaa attgtgggta gtcggcttcc caatttcacg gaagcagaag  3600
cggaactcgt tgcgggttca tatgatttc ttggtctcaa ctactacacc actcagtacg  3660
cccaggcaaa acctaaccca gttacatggg caaatcacac tgccatgatg gacccaggcg  3720
caaagctcac atgtaccatt ctgtttcctc ttatagttac aacctttcta tatatagata  3780
tctcctttta attataacat atatgtacat tgtgagtgac catcaattat ttcatccttg  3840
ggtttacaga taacaattca cgtggtgaaa atcttggtcc actggtacgt gcatgatcca  3900
cccctgttac ttctcaatat ttttttttct ttcttgttta tgggtataat atgtacgctt  3960
ccttttctca gttcgttaaa gacgaaaaaa acgggaatgc ctattactac ccaaaaggca  4020
tctattacgt tatggactac ttcaaaacca aatacagtaa ccctttgatc tatatcactg  4080
agaacggtga ctactactca tctctttttt gcatattaat taagtaaatg tgtgtttcaa  4140
ataatgtata gttgttgatg taccatgatg gtctaattag gatttagtac tcccggtgaa  4200
gaaaaccgtg acaaagctat tgctgattcc aagcggatcg attatctctg cagtcatcta  4260
tgttttctcc gcaaggtcat caggtgaggg gaagctactt tatttttttc tcttttgaat  4320
ttgatgtatg gtcatcatca tgcataggct ttgaattatg atttttcctg tttccaggga  4380
gaagggtgtc aacataaaag gatactttgc atgggctctt ggagataatt atgaattctg  4440
caaaggtttt accgttagat tcggacttag ttacgttaac tggacagacc tcaatgatag  4500
aaatctcaaa gactctggca aatggtacca aagctttatt aacggtacca ataagaaccc  4560
tgccaaacaa tatttccgcc gcccaaacct ctccttccag aaccagaaga agaagctcgc  4620
agatgcatga aacactttat cccaccatca tgatcatctt catatctcta ctacttgctt  4680
catagataag gagcttgttg tactaaataa atattctaat aaaagatgat catttactaa  4740
tgaatatttt cgtttgagtt caatcccttc ttaccgcttc agttacgttt tactttggat  4800
gattaggtta ggttttacaa attataaaac ttggcatgtc agctattcat gtgagatttg  4860
tagatttaga taagagagag tctatgtgta aatgcgagaa ctagcaagaa tagtaacaca  4920
aagtacacaa gagaatatct ctacaaaaaa tatatgtatt tactagtatt tttaaagtaa  4980
atttactgat atcaacctta gattctgtca gcacttgctt ccaaaaaacc ctagattctt  5040
caatcgcgac ctcctctgag ctgagtctga attctgatac caatttgttc aacttaacgc  5100
tcagattacg acctagatct actcgattgc ttgaatataa aaaaaacatg caagaagaca  5160
```

```
cggtttgttc acccgtgttg gctctcccta caaaatgttg tagatcaaat gtcagtaaac  5220
ccgcatgaag caaaattatt ggctctccct tgccgtttgc gatctatgat gaatgtgaag  5280
gagaaggaaa tagtttggca gtacaaacag agacagagag acttattgaa atttctactg  5340
aacctgtgtc agtcagtcaa aacgtggagg aagaaatcca aacggagaaa cacgaggaga  5400
gacagcttag atcatctctt catcaaaatg taaaaaaaaa agattgacga aagaatagac  5460
ttatgggctg acatccggaa ctactatgat tcttctatca tttggaaaaa tctgtagatg  5520
gttgtaggag attttaatga gactttgaac attgataaac actcttcaaa tgctgtgagc  5580
tctaatgagg gagtttcaag atgtggtgca atattgttct cttctcgatt ctacctcaca  5640
tggaacaata gaagagcata aggccatata gcgaagaggt taataaataa tcacgtgtta  5700
caactatttc cgcagtctta tagtgtattg gaaggaggag gttgctagga tcacttgaga  5760
tgcagaatta agttactatc agagctttgt cgaccaaaga tgcctcttaa atttgttaac  5820
gttgtgccag agatggaaca attcaaggtc gatatttttg ggaggaatac ttatgaaata  5880
tccaaaatgg taaccggagc agaggccaac cagacacacc actcaaccaa ccaaagaatc  5940
gacatgacgt atgtgcattc taaacaccat atctcacaaa gcatgaggtc ttttgccaat  6000
atgtaaaata tatttaatat atatttatta tttgacaata tgtaaaataa tgtaaaatac  6060
ataaatatta atttatatat agaatgatca ttccgcgcaa gctgcagatc ttaacctagt  6120
tatgtattgg tttaaaattc agtgtatcac aaaaaaaata agaagtaatg aattaattat  6180
tttttaatat tgaaaagagg agtaatgttg tacgttgata tcaaatgaga gataacagaa  6240
gttgttcatc cataagcaaa gtgacccttg tatcattagt gagggat               6287

SEQ ID NO: 17          moltype = DNA  length = 6279
FEATURE                Location/Qualifiers
source                 1..6279
                       mol_type = other DNA
                       organism = synthetic construct
SEQUENCE: 17
tatacataat atataaatga atacaaataa ataataatag ataaaaatag ttttatatat  60
aacattcatc ctgcgcaatt gcccgggtct taagctagtt cattgttaac ttaacaacaa  120
attaacattg actgtcgcag ttaatttatt gctaatttaa caacaataat aaacatccac  180
gatttaaagt cttatattgt aagtcaaagt tacgaagata gtttcagcgc aaaatttata  240
tctagtttac gatgaatata tttacgacaa aataacgacg tatcatggac cttgcaactt  300
aagtctgtac gacgatcttt caataactat gtgcacttaa cgatgaagtt acattccttg  360
ttatttagtt gtagaccaga tgtctttttt agatttgtac agacttagac agagtttaat  420
aaaatattaa gggtgttaaa cagtattggc caagtttgta ggctaaacca ggaactgcat  480
tgcctttaaa aatatgagaa aacaaaagat tttgttcttg ctttaaggta tgtgaaaaat  540
tgtcttatct ttttgtttaa ttatccgtta acagttcaat ttatattctc aagattatat  600
tggagctatt gactgcatta ctcaatatat atatatatat gtattatata tgtttaatta  660
agataggtta cttaattata agtttgagtt ttatttatat ttcacattaa aaatatttca  720
tgaaaatttt atctcgcaaa ctgtgggtac ataaacaaga taaattttag agctctattt  780
cgtagtacac ataatcatat gaaataattt actggagaag gcattgatcg aagaaataaa  840
taagaattat tcaaccatcg tcattcttgt ttgagaaata tcatcgaaag gattttgggt  900
attttcaaat caagatttct tatattcaaa ttcgctccta gtttttcata aatgacacaa  960
gcagagcaag tgcttgtatc tgctgcattg cataactttt tccgtcagaa atgtcggcca  1020
gatgagtttc ttccagaaga aacatctgat gaacaaaatg ttactcaatt aagtagtaat  1080
ggttatcaat ttcttggcga acaagaacaa caaagagaac atgctactga atagagaaca  1140
accaatgctt caaatatgtg gaatgatggt actagtggat ctcaacggtg aaatatgcct  1200
gagtaagtta acatttttat gtgtttaatt ttatagttga caataatagt gaaatctcac  1260
aatgtatttt taggtgtgag atgatttatg gcattgttgg catgatatta aaaacacaca  1320
ttcgtctgtc acaataaagt caaaattgca gtcaagtatt tgtaattttt tttcatgctt  1380
ttttcgaaat tgattacact tttttgcgtg gtttcgataa attgttgtga gaaaatgttt  1440
tttaatgatc ttaggaaatc aatttttatt ttctttaaaa ttctaccaaa ttaatctcct  1500
atcaaaagct ctatcaaatt ccttaaaatc caaacaaatt tagctaaatt ccatcaaatc  1560
tgaaatcctt aaaaaaattc aaatccctaa tcaaataagc cctttaatat atttgaacct  1620
atacttaagt accaaatggt tatatattta aaaagatcca acagttaatt caacaaaata  1680
aactttacat aaatttttat ccctttcgta atttgttaaa atatgataat ctacttacaa  1740
ggttgtcatt ttattcagat aatagtccat agttatttac aaaataaact ttacaaaaaa  1800
ataacgacca atcacaatgc tgatactgat tcagctaaag taactgagcc cacggaattc  1860
accccaccaa acctctccca aaatatcaag atattgaaga aaagaaaatg tatacgtgac  1920
actactttac aaaggctata taaaccctag actagcacaa ggttccatcc aacacaaaca  1980
catacatctc cttattaacc atgaagcttc atggactagc cttgataggt tttctaattg  2040
ccgtggtgag ttgcaaagct attgaggaat gccgagagaa cgagccattc acatgtggaa  2100
acactgatca gttaagcagt aaaagtttcc caaaagactt catattcggt gttgcttctg  2160
ctgcttacca ggcatgttac aaatcaacaa tttttgacgt agaaaaccat ttaaaatatt  2220
aaatccaacg ttgcatggtt gtttcttatt attgtaggtg gaagggggca gaggacgtgg  2280
tcttaacgtt tgggatggct tcactcaccg atacccaggt atatcatcta catggtacat  2340
atatatacat atgtacaact cttatcattc ttagtataaa atgtatctgt ttactatcag  2400
agaagggagg atccgatcat gggaatggag acactacttg tgagtcatat acgagatggc  2460
aggttagttc ctcactgagt catataccag atggcaggtt aatttctgat ttcctcacta  2520
tatataatga tatccgagtg cgtgtgtaaa ctgcagaaag atatagacat catagacgaa  2580
ctcaatgcta ctggctacag attctcattt gcctggtcaa gaatcattcc aagtatgaac  2640
acataaacaa tctatttata caaaagaatt ctcgtaattt gattgtgatt gttgggaaga  2700
ttaaatatat gatatgtata catgagcaga aggaaaggtg agtaggggag tgaacaaagg  2760
aggtatcgaa tactaccaca aacttctaga tggcctcatc gctaagaata taaccccttt  2820
tgttaccctc tatcactggg accttcctca aacactgcaa gatgagtatg aaggtttctt  2880
gaaccgcacc gtcatgtatg tcatttgggc cgcgttctta gcaaggaata taagaagaaa  2940
aacatatata cataagtgat ctcatgttaa tgatttgatt ctatgctatg cacagagatg  3000
actttagaga ctatgcggat ctatgtttca aggaatttgg tggaaaggtg aaggatcacg  3060
atcaaccagc tgtacacagt gcctacgaga ggctatgcaa tcggaacaga tgcacccggt  3120
cgatgttctc cggcatgtta cggcgggaat tcttcaacag aaccatatat agttgcacat  3180
```

```
aaccagcttc ttgctcatgc tgcggcggtc gatgtttaca ggagaaaata taaggtgaga  3240
gtacgtgggt ttgtgaatag gtgtagtctt tacgtatatg actatatcta atcatatcat  3300
tatcgtatgc cgtgaccaac agttccaaaa agggaagatc ggaccagtga tgataaccag  3360
atggtttctt ccatttgatg agactgatgc cagcagagat gcagctgaga ggatgaaaga  3420
attcttcttg ggatggtaac gtatatgtat gtatatatca acaaaaatga aatgattttc  3480
ttatacgtat gtacgtcgac caggttcatg gagccgctaa caaagggtag atacccagac  3540
atcatgaggg aaattgtggg tagtcggctt cccaatttca cggaagcaga agcggaactc  3600
gttgcgggtt catatgattt tcttggtctc aactactaca ccactcagta cgcccaggca  3660
aaacctaacc cagttacatg ggcaaatcac actgccatga tggacccagg cgcaaagctc  3720
acatgtacca ttctgtttcc tcttatagtt acaacctttc tatatataga tatctccttt  3780
taattataac atatatgtac attgtgagtg accatcaatt atttcatcct tgggtttaca  3840
gataacaatt cacgtggtga aaatcttggt ccactggtac gtgcatgatc cacccctgtt  3900
acttctcaat attttttttt ctttcttgtt tatgggtata atatgtacgc ttccttttct  3960
cagttcgtta aagacgaaaa aaacgggaat gcctattact acccaaaagg catctattac  4020
gttatggact acttcaaaac caaatacagt aacccttga tctatatcac tgagaacggt  4080
gactactact catctctttt ttgcatatta attaagtaaa tgtgtgtttc aaataatgta  4140
tagttgttga tgtaccatga tggtctaatt aggatttagt actcccggtg aagaaaaccg  4200
tgacaaagct attgctgatt ccaagcggat cgattatctc tgcagtcatc tatgtttttct  4260
ccgcaaggtc atcaggtgag gggaagctac tttatttttt tctcttgtat ggtcatcatc  4320
atgcataggc tttgaattat gatttttcct gtttccaggg agaagggtgt caacataaaa  4380
ggatactttg catgggctct tggagataat tatgaattct gcaaaggttt taccgttaga  4440
ttcggactta gttacgttaa ctggacagac ctcaatgata gaaatctcaa agactctggc  4500
aaatggtacc aaagctttat taacggtacc aataagaacc ctgccaaaca atatttccgc  4560
cgcccaaacc tctccttcca gaaccagaag aagaagctcg cagatgcatg aaacacttta  4620
tcccaccatc atgatcatct tcatatctct actacttgct tcatagataa ggagcttgtt  4680
gtactaaata aatattctaa taaaagatga tcatttacta atgaatattt tcgtttgagt  4740
tcaatccctt cttaccgctt cagttacgtt ttactttgga tgattaggtt aggttttaca  4800
aattataaaa cttggcatgt cagctattca tgtgagattt gtagatttag ataagagaga  4860
gtctatgtgt aaatgcgaga actagcaaga atagtaacac aaagtacaca agagaatatc  4920
tctacaaaaa atatatgtat ttactagtat ttttaaagta aatttactga tatcaacctt  4980
agattctgtc agcacttgct tccaaaaaac cctagattct tcaatcgcga cctcctctga  5040
gctgagtctg aattctgata ccaatttgtt caacttaacg ctcagattac gacctagatc  5100
tactcgattg cttgaatata aaaaaaacat gcaagaagac acggtttgtt cacccgtgtt  5160
ggctctccct acaaaatgtt gtagatcaaa tgtcagtaaa cccgcatgaa gcaaaattat  5220
tggctctccc ttgccgtttg cgatctatga tgaatgtgaa ggagaaggaa atagtttggc  5280
agtacaaaca gagacagaga gacttattga aatttctact gaacctgtgt cagtcagtca  5340
aaacgtggag gaagaaatcc aaacggagaa acacgaggag agacagctta gatcatctct  5400
tcatcaaaat gtaaaaaaaa aagattgacg aaagaataga cttatgggct gacatccgga  5460
actactatga ttcttctatc atttggaaaa atctgtagat ggttgtagga gattttaatg  5520
agactttgaa cattgataaa cactcttcaa atgctgtgag ctctaatgag ggagtttcaa  5580
gatgtggtgc aatattgttc tcttctcgat tctacctcac atggaacaat agaagagcat  5640
aaggccatat agcgaagagg ttaataaata atcacgtgtt acaactattt ccgcagtctt  5700
atagtgtatt ggaaggagga ggttgctagg atcacttgag atgcagaatt aagttactat  5760
cagagctttg tcgaccaaag atgcctctta aatttgttaa cgttgtgcca gagatggaac  5820
aattcaaggt cgatattttt gggaggaata cttatgaaat atccaaaatg gtaaccggag  5880
cagaggccaa ccagacacac cactcaacca accaaagaat cgacatgacg tatgtgcatt  5940
ctaaacacca tatctcacaa agcatgaggt cttttgccaa tatgtaaaat atatttaata  6000
tatatttatt atttgacaat atgtaaaata atgtaaaata cataaatatt aatttatata  6060
tagaatgatc attccgctca agctgcagat cttaacctag ttatgtattg gtttaaaatt  6120
cagtgtatca caaaaaaaat aagaagtaat gaattaatta ttttttaata ttgaaaagag  6180
gagtaatgtt gtacgttgat atcaaatgag agataacaga agttgttcat ccataagcaa  6240
agtgaccatt gtatcattag tgaggaataa aattttgtt                        6279
```

```
SEQ ID NO: 18          moltype = DNA  length = 6279
FEATURE                Location/Qualifiers
source                 1..6279
                       mol_type = other DNA
                       organism = synthetic construct
SEQUENCE: 18
tatacataat atataaatga atacaaataa ataataatag ataaaaatag ttttatatat  60
aacattcatc ctgcgcaatt gcccgggtct taagctagtt cattgttaac ttaacaacaa  120
attaacattg actgtcgcag ttaatttatt gctaatttaa caacaataat aaacatccac  180
gatttaaagt cttatattgt aagtcaaagt tacgaagata gtttcagcgc aaaatttata  240
tctagtttac gatgaatata tttacgacaa aataacgacg tatcatggac cttgcaactt  300
aagtctgtac gacgatcttt caataactat gtgcacttaa cgatgaagtt acattccttg  360
ttatttagtt gtagaccaga tgtctttttt agatttgtac agacttagac agagtttaat  420
aaaatattaa gggtgttaaa cagtattggc caagtttgta ggctaaacca ggaactgcat  480
tgcctttaaa aatatgagaa aacaaaagat tttgttcttg ctttaaggta tgtgaaaaat  540
tgtcttatct ttttgtttaa ttatccgtta acagttcaat ttatattctc aagattatat  600
tggagctatt gactgcatta ctcaatatat atatatatat gtattatata tgtttaatta  660
agataggtta cttaattata agtttgagtt ttatttatat ttcacattaa aaatatttca  720
tgaaaatttt atctcgcaaa ctgtgggtac ataaacaaga taaattttag agctctattt  780
cgtagtacac ataatcatat gaaataattt actggagaag gcattgatcg aagaaataaa  840
taagaattat tcaaccatcg tcattcttgt ttgagaaata tcatcgaaag gatttgggt  900
attttcaaat caagatttct tatattcaaa ttcgctccta gtttttcata aatgacacaa  960
gcagagcaag tgcttgtatc tgctgcattg cataactttt tccgtcagaa atgtcggcca  1020
gatgagtttc ttccagaaga aacatctgat gaacaaaatg ttactcaatt aagtagtaat  1080
ggttatcaat ttcttggcga acaagaacaa caaagagaac atgctactga atagagaaca  1140
accaatgctt caaatatgtg gaatgatggt actagtggat ctcaacggtg aaatatgcct  1200
```

```
gagtaagtta acatttttat gtgtttaatt ttatagttga caataatagt gaaatctcac  1260
aatgtatttt taggtgtgag atgatttatg gcattgttgg catgatatta aaaacacaca  1320
ttcgtctgtc acaataaagt caaaattgca gtcaagtatt tgtaattttt tttcatgctt  1380
ttttcgaaat tgattacact tttttgcgtg gtttcgataa attgttgtga gaaaatgttt  1440
tttaatgatc ttaggaaatc aatttttatt ttctttaaaa ttctaccaaa ttaatctcct  1500
atcaaaagct ctatcaaatt ccttaaaatc caaacaaatt tagctaaatt ccatcaaatc  1560
tgaaatcctt aaaaaaattc aaatccctaa tcaaataagc cctttaatat atttgaacct  1620
atacttaagt accaaatggt tatatattta aaaagatcca acagttaatt caacaaaata  1680
aactttacat aaatttttat ccctttcgta atttgttaaa atatgataat ctacttacaa  1740
ggttgtcatt ttattcagat aatagtccat agttatttac aaaataaact ttacaaaaaa  1800
ataacgacca atcacaatgc tgatactgat tcagctaaag taactgagcc cacggaattc  1860
accccaccaa acctctccca aaatatcaag atattgaaga aaagaaaatg tatacgtgac  1920
actactttac aaaggctata taaaccctag actagcacaa ggttccatcc aacacaaaca  1980
catacatctc cttattaacc atgaagcttc atggactagc cttgataggt tttctaattg  2040
ccgtggtgag ttgcaaagct attgaggaat gccgagagaa cgagccattc acatgtggaa  2100
acactgatca gttaagcagt aaaagtttcc caaaagactt catattcggt gttgcttctg  2160
ctgcttacca ggcatgttac aaatcaacaa tttttgacgt agaaaaccat ttaaaatatt  2220
aaatccaacg ttgcatggtt gtttcttatt attgtaggtg gaagggggca gaggacgtgg  2280
tcttaacgtt tgggatggct tcactcaccg atacccaggt atatcatcta catggtacat  2340
atatatacat atgtacaact cttatcattc ttagtataaa atgtatctgt ttactatcag  2400
agaagggagg atccgatcat gggaatggag acactacttg tgagtcatat acgagatggc  2460
aggttagttc ctcactgagt catataccag atggcaggtt aatttctgat ttcctcacta  2520
tatataatga tatccgagtg cgtgtgtaaa ctgcagaaag atatagacat catagacgaa  2580
ctcaatgcta ctggctacag attctcattt gcctggtcaa gaatcattcc aagtatgaac  2640
acataaacaa tctatttata caaaagaatt ctcgtaattt gattgtgatt gttgggaaga  2700
ttaaatatat gatatgtata catgagcaga aggaaaggtg agtaggggag tgaacaaagg  2760
aggtatcgaa tactaccaca aacttctaga tggcctcatc gctaagaata taaccccttt  2820
tgttaccctc tatcactggg accttcctca aacactgcaa gatgagtatg aaggtttctt  2880
gaaccgcacc gtcatgtatg tcatttgggc cgcgttctta gcaaggaata taagaagaaa  2940
aacatatata cataagtgat ctcatgttaa tgatttgatt ctatgctatg cacagagatg  3000
actttagaga ctatgcggat ctatgtttca aggaatttgg tggaaaggtg aaggatcacg  3060
atcaaccagc tgtacacagt gcctacgaga ggctatgcaa tcggaacaga tgcacccggt  3120
cgatgttctc cggcatgtta cggcgggaat tcttcaacag aaccatatat agttgcacat  3180
aaccagcttc ttgctcatgc tgcggcggtc gatgtttaca ggagaaaata taaggtgaga  3240
gtacgtgggt ttgtgaatag gtgtagtctt tacgtatatg actatatcta atcatatcat  3300
tatcgtatgc cgtgaccaac agttccaaaa agggaagatc ggaccagtga tgataaccag  3360
atggtttctt ccatttgatg agactgatgc cagcagagat gcagctgaga ggatgaaaga  3420
attcttcttg ggatggtaac gtatatgtat gtatatatca acaaaaatga aatgattttc  3480
ttatacgtat gtacgtcgac caggttcatg gagccgctaa caaagggtag atacccagac  3540
atcatgaggg aaattgtggg tagtcggctt cccaatttca cggaagcaga agcggaactc  3600
gttgcgggtt catatgattt tcttggtctc aactactaca ccactcagta cgcccaggca  3660
aaacctaacc cagttacatg ggcaaatcac actgccatga tggacccagg cgcaaagctc  3720
acatgtacca ttctgtttcc tcttatagtt acaacctttc tatatataga tatctccttt  3780
taattataac atatatgtac attgtgagtg accatcaatt atttcatcct tgggtttaca  3840
gataacaatt cacgtggtga aaatcttggt ccactggtac gtgcatgatc cacccctgtt  3900
acttctcaat attttttttt ctttcttgtt tatgggtata atatgtacgc ttccttttct  3960
cagttcgtta aagacgaaaa aaacgggaat gcctattact acccaaaagg catctattac  4020
gttatggact acttcaaaac caaatacagt aacccttga tctatatcac tgagaacggt  4080
gactactact catctctttt ttgcatatta attaagtaaa tgtgtgtttc aaataatgta  4140
tagttgttga tgtaccatga tggtctaatt aggatttagt actcccggtg aagaaaaccg  4200
tgacaaagct attgctgatt ccaagcggat cgattatctc tgcagtcatc tatgttttct  4260
ccgcaaggtc atcaggtgag gggaagctac tttatttttt tctcttgtat ggtcatcatc  4320
atgcataggc tttgaattat gatttttcct gtttccaggg agaagggtgt caacataaaa  4380
ggatactttg catgggctct tggagataat tatgaattct gcaaaggttt taccgttaga  4440
ttcggactta gttacgttaa ctggacagac ctcaatgata gaaatctcaa agactctggc  4500
aaatggtacc aaagctttat taacggtacc aataagaacc ctgccaaaca atatttccgc  4560
cgcccaaacc tctccttcca gaaccagaag aagaagctcg cagatgcatg aaacacttta  4620
tcccaccatc atgatcatct tcatatctct actacttgct tcatagataa ggagcttgtt  4680
gtactaaata aatattctaa taaaagatga tcatttacta atgaatattt tcgtttgagt  4740
tcaatccctt cttaccgctt cagttacgtt ttactttgga tgattaggtt aggttttaca  4800
aattataaaa cttggcatgt cagctattca tgtgagattt gtagatttag ataagagaga  4860
gtctatgtgt aaatgcgaga actagcaaga atagtaacac aaagtacaca agagaatatc  4920
tctacaaaaa atatatgtat ttactagtat ttttaaagta aatttactga tatcaacctt  4980
agattctgtc agcacttgct tccaaaaaac cctagattct tcaatcgcga cctcctctga  5040
gctgagtctg aattctgata ccaatttgtt caacttaacg ctcagattac gacctagatc  5100
tactcgattg cttgaatata aaaaaaacat gcaagaagac acggtttgtt cacccgtgtt  5160
ggctctccct acaaaatgtt gtagatcaaa tgtcagtaaa cccgcatgaa gcaaaattat  5220
tggctctccc ttgccgtttg cgatctatga tgaatgtgaa ggagaaggaa atagtttggc  5280
agtacaaaca gagacagaga gacttattga aatttctact gaacctgtgt cagtcagtca  5340
aaacgtggag gaagaaatcc aaacggagaa acacgaggag agacagctta gatcatctct  5400
tcatcaaaat gtaaaaaaaa aagattgacg aaagaataga cttatgggct gacatccgga  5460
actactatga ttcttctatc atttggaaaa atctgtagat ggttgtagga gattttaatg  5520
agactttgaa cattgataaa cactcttcaa atgctgtgag ctctaatgag ggagtttcaa  5580
gatgtggtgc aatattgttc tcttctcgat tctacctcac atggaacaat agaagagcat  5640
aaggccatat agcgaagagg ttaataaata atcacgtgtt acaactattt ccgcagtctt  5700
atagtgtatt ggaaggagga ggttgctagg atcacttgag atgcagaatt aagttactat  5760
cagagctttg tcgaccaaag atgcctctta aatttgttaa cgttgtgcca gagatggaac  5820
aattcaaggt cgatattttt gggaggaata cttatgaaat atccaaaatg gtaaccggag  5880
cagaggccaa ccagacacac cactcaacca accaaagaat cgacatgacg tatgtgcatt  5940
```

```
ctaaacacca tatctcacaa agcatgaggt cttttgccaa tatgtaaaat atatttaata  6000
tatatttatt atttgacaat atgtaaaata atgtaaaata cataaatatt aatttatata  6060
tagaatgatc attccgctca agctgcagat cttaacctag ttatgtattg gtttaaaatt  6120
cagtgtatca caaaaaaaat aagaagtaat gaattaatta tttttaata ttgaaaagag   6180
gagtaatgtt gtacgttgat atcaaatgag agataacaga agttgttcat ccataagcaa  6240
agtgaccatt gtatcattag tgaggaataa aattttgtt                         6279

SEQ ID NO: 19           moltype = DNA  length = 6808
FEATURE                 Location/Qualifiers
source                  1..6808
                        mol_type = other DNA
                        organism = synthetic construct
SEQUENCE: 19
tccaacaaag atggaaacct agatttctaa tcaaggcgca acacaaggac gtctctctcc  60
actcatcatt actctttgaa ttgccattct ctacggcaca tggggcaatg agcttgactc  120
gtctgtgaat tgacccattt caaaatacaa tggagatgaa acgaatggtt gcaagctccc  180
caaactgctc gataaccata taacgatcca ggtttaagaa tacaaataag atataacgat  240
ccaggtttaa gaatacaaat aaggggtttt agttttgaaa caatcacagt gtgtagaaag  300
agacatgaaa agagaggaga cacgtactta gagggcaatc atctccaggg agtttgcagt  360
ctggacaaca accgtcgaat ggcatacgac atatcccaca tgtctcatcc tgagcatccc  420
atgtccatga cgcaaccgca tgccacctta cagtttattt tttcacaatg taagagttca  480
cgtattggaa ttgagaatgt atgtaacaca tgtagtggga caaagaaact tactctgttt  540
tttttttaa aaagtcagta gacattgtag cactgagagt caaggaagaa acagttcttt   600
ggaaacaaaa tcctaaatta aagaaccttt gagataatct tcgcctacct tatatgaact  660
agttgggagc tgataaccaa aatcttcacc gaaaaaaaac tattagaacg tcatctacat  720
cagtattcaa aactgaaatt catgaaaaga gaacaacttt atgaaatcat gaaacctaag  780
ctgcatcttt taaaaaaatc atgttttaaa catcaaagaa actatgtact ggaaaacatc  840
aagcattgac gtgaacattt ggatgcatga ttgacatgca gagaagatga agtagaagga  900
tacgcaagat cttgactttc atgtcttcct cctaaatgaa acataaaaat aatcttatat  960
cagttaaaca aactaaaaaa aaatagaaaa cacaaactca agaaagcaca atcctttttt  1020
actatactat aaatctaata ctactaaggc ttcatcgtct gaaaacttag acgagataaa  1080
ttcatgtttt tgacgcattc gtacactagc atgcagcaga tggcgtttcc ttagctgata  1140
gagtgatatc aacagaacgg agcaaaccca tcagaaaatt caaaaactca ccggagtttg  1200
acggagaagc gaactgcgac agagaagaag cggcgagatg tgaatagaag acacgaatta  1260
gttaagatat gggcttttat ttaaactggg ctttatttaa aattgatctc agggcccata  1320
cgtgtgctct tcttaacaag attatatatt atttataaac gacaccaata aaacgtggtt  1380
tgttttcgtt ttcttttgtc tttccgagcc tctagtttca tgtgataaaa gcaaatagag  1440
aggtcaaaag aatcaacacc aatacgatat gctgtgattt tttttttaa atatgttgta   1500
attgttagcg gtgaggctcg tgaagagtgt ggcattggtt cagctttact ttagtttcaa  1560
cactcgataa tatttcgata aaaatcttca ataactttat ggcgctatga ccaagctttg  1620
aacattattt actacagtga atcttaatga tgcgtatcat tcttgttaac cttcgatata  1680
tatatgctgc attgcaccac cgtcgacgga acaatttgaa gatgtgacgc aactcgtgtt  1740
caagtcgtac gtgttcccgt aaaggaacat aaatatttgc aatagatcat gaaagactaa  1800
acgtggaaac aagcaagaaa tttggagtaa actcggtgaa tattgagcta aagtaaccca  1860
cgggactcat cccacctaaa cctctcccaa agtatcagga caagaaatac ttacgtcact  1920
attctttagc aatggctata tataccctag atcggtacaa ggtttcatac aacaccaaca  1980
catacaacaa cagattaacc atgaagcttc ttcatggact cgctttagtt tttctattag  2040
ctgctgcgag ttgcaaagct gatgaagaaa ttacttgcga agagaacaat ccattcacat  2100
gtagtaacac tgatatttta agcagtaaaa acttcggaaa agacttcatc ttcggtgttg  2160
catcgtctgc gtaccaggca tgcaacaaat gctgccatac tatatttttg acgtatacaa  2220
aataatattc aaaaatgcta aaatatccaa ctttgcatgg ttgtttcttt tcatttcaga  2280
tcgaaggagg gagaggtcgt ggtgttaacg tttgggatgg cttcagtcac cgataccag   2340
gtatgtcact gtggcatata catatatata tatatttaaa tgagataaat gacggttata  2400
tgtatacata ttaatgtatt tgtaaattac tatcagagaa atcagggtca gatttgaaga  2460
atggagacac tacttgtgag tcatatacta gatggaaggt gaattcctca gtacatatat  2520
actcatatga ctaaactacg tataaaaagt aactgtggac tgaattgcgt ttaaaatatg  2580
taaactgcag aaagatgtag aaattatggg agaactcaat gctacaggct acagattctc  2640
cttagcgtgg tcaagaatca ttccaagtat gaacaaatta ttcattcgtt tgtattttag  2700
ttaggatcat gtagctggaa gagtactaat tgatatacaa tatacatgag cagaaggaaa  2760
ggtgagtagg ggagtgaacc aaggaggtct tgattactac cacagcctca tagatgcact  2820
cctcgaaaag aatataacgc ctttcgttac cctctttcac tgggaccttc ctcaaacact  2880
ccaagatgag tatgaaggtt ttttggaccg ccagatcatg tatgtgccat gcttcttaat  2940
catatacaaa tttttaataa gaacaagaag aagaagattt tgtcttaatt acatgcttta  3000
ctgaaagaat gattatatat taatatgcac agacaagatt tcaaagacta tgcggatcta  3060
tgtttcaaag aatttggtgg aaaggtgaag cactggatca cgatcaacca gctattcaca  3120
gtgcctacga gaggctatgc actcggaaca gatgcacccg gtcggtgttc tcctatggtt  3180
gatagcacag gtgttatggc ggaaactctt caacagaacc ctatatcgtt gcacataacc  3240
agcttcttgc tcatgccgcg gtagtggatc tttacaggaa gaactatgcg gtgagtagtc  3300
ttcatatgtg aaaaggtggt gaaaatctaa tgtatttgat cctaatttac tcatatatga  3360
tgtgaccaac aggaccaaca agggaagatt ggacctgtga tgattacaag atggtttctt  3420
ccatatgatg aggctgatcc ttcttgtata gaagcagctg acaggatgaa ccaattcttc  3480
catggatggt atatcttctt tttttgacat caaacggtta ctctattatt caaaattaaa  3540
gatggtctag gtaattagat tgattatata tattgtatgt acatataatg aaacaaaata  3600
taaatggatc aggtacatgg agccgctaac aaatggtaaa tacccagata tcatgaggaa  3660
gattgtggga agtcggcttc ccaacttcac cgaagctgaa gccgaacttg ttgctggttc  3720
atatgatttt cttggtctca actattacgt cactcagtac gcccagccga aagctaatcc  3780
attgctctca gagaaacaca ctgccatgat ggacgctggc gtaggactca catgtacgca  3840
ttactctcct ttttgttaca acatacttat ttgtgattga ccttcagtaa tttctttctt  3900
gtgtttacag atgataactc acgtggtgaa tttcttggcc cactggtata tatgcatgat  3960
```

```
ccactcttat gatttttctt tcattatttt atcttctttt cctaactgca gtgtacttgg  4020
aacacccaca ataacttttt tttctgattg atatgtatat tttgtttgct tccctttctc  4080
agtttattga agacaaaaaa gccggcaaca gctattatta cccaaaagga atttattacg  4140
tcatggaata cttcaaaacc caatacaaca accctttaat ctatgtcact gagaacggta  4200
agttctacat attactagta atctattttt atttatgcta catatcatca gataattagt  4260
gtattttgat actgagtcca aagaaactga ctttcaaata ctgtggaata tttttatgtg  4320
atggcgattt aattaggatt tagtacgccc agctcagaaa accgttgcga agctattgcc  4380
gattacaagc gaattgatta tctctgcagt catctatgtt ttctccgtaa ggtcatcaag  4440
taagtgctac tatacatgct tttcttccaa tatttatctt ctttttcttc ttctttttaa  4500
gtaatatata tatatatata tatatgtata tgattgttat tgtttccagg gagaggaatg  4560
tgaacgtgag aggatacttt gcatgggctc ttggggataa ttatgaattc tgtaaaggct  4620
ttaccgtcag atttggactc agttacgtta attgggataa tcttgacgac agaaacctca  4680
aagaatctgg caaatggtac cagagattca ttaacaggac ttccaagaac cctgcgaaac  4740
aagatttcct ccgctcaagc ctctcctctc tcaaagccag aagaagaggc ttgcttgctg  4800
atgcatgaaa cacttttccc ccttcaagat catctccacg tctctgatca ctctttttg  4860
ttgctccata gataaggagc ttctacaagt aaaaagatga tcaactacta atgaataaaa  4920
taaatttatc tacaagtaca ttatgtcaag tcaaagaggt gaggataacg cattttaaac  4980
agtaaacatc acttagacgc acatacaaaa taaaaactca aaccgccaac tagtttagtg  5040
tattaaaaat actaaggaaa tgattagcct aaattcagta attatctaat acaaatctaa  5100
aactaactaa acgaaagtat aacaataatt taacaatcca tcaagggtcg gtcgtattaa  5160
attcggaaca acaatccaac acatctttag aaatgaaaac caatgctaga tatctaatca  5220
aagcacagca caaagggttt ctctctctcc actcatcgtt actctttgaa ttgccgttct  5280
ctacggcaca tggggcaatg agcttgactc gtctgtgagt tgacccattt caatatacaa  5340
tggaggttgt cattctagac aaaatcgtta tatctaaaca attttaatga tgtctgctta  5400
ctttaatatt tgaaaacttt ttatttttct gtttctaaaa gaaaaacgaa aaaaaatatt  5460
ttaataacac ccattaagac ttttgtttga tcgtgaatta tttttatcat aaatatttgt  5520
acgtcaatgt atcttctagg ttccaatctt aaccaaatgt ataaatctat ttttttagaa  5580
tctataatat taaaacatat gtacgaattg aaaactaact ttgttcttat gtattacaaa  5640
atatatccat tttaataatc atatatatta ttttgtaaaa ataattaaaa actaaatttt  5700
aacgtaaatt aaaatattat atcaaaccaa aaaccgaact ctataaaata aattatatac  5760
gtcaaaaatt attaactata tatatttagt ttaaaattat caaatagtct aaaaatacta  5820
tttaaacatc gaactatcca aaaatcgtat tatcctatta ctttttactt gaaatatttt  5880
aaattatcct aattttagaa ctgaaccatc caatattttt tatctgaaat attaaatatc  5940
tgaattatca atattttgta aaaatatatt taaaatcaat tttatccgaa ttattcaaaa  6000
ttatccaaaa gatgagacca aacctaaacc aaattgaact caaaatttta taagattcct  6060
aacattgtta tctaaaacaa gccaaaaatc aaaattgcca aaccaaaacc aaaggtaaac  6120
ttataaataa ccaaatagtg tttatatctc ttggactaaa ataccaaaaa accaatacca  6180
caaatgaacc ggaacccaat caaaacataa aataattgaa attcaacaaa aatcaaacat  6240
ccatacctaa acatattagt aaaaaacaga tgaattcata aattatcaac acaaaatata  6300
gttcatgttt aaaggcgtaa ctttttgta acagaaaaaa aaagaatatc taattttggg  6360
aaatataact aaaaatgtat taattctaac ataaaatgta gagctaaact attaaataaa  6420
ctataggtta atacaaaagg tattttttac catatatgtg aatatctatc tatactatta  6480
aacagaaaaa tttttgagac cctttgattt ttatagtatt tacaacagtg ctattatctt  6540
ttaaattaaa ttctatatta ttataaatta ttattaaaca gaaaaattgc agggaattaa  6600
ctgcctacat acccgatttt ccttaattaa ttatagctac cataaagtgg tttctttaaa  6660
aaatagggat tatttgtaaa ttactctatt aatagtttga aatttgaaaa ctacacttct  6720
attttatttt ttgaaagcca cactttattc aatgtgaatt gacattttta tccagattag  6780
atattttaat aattaaaata taaaatcg                                    6808

SEQ ID NO: 20           moltype = DNA  length = 2191
FEATURE                 Location/Qualifiers
source                  1..2191
                        mol_type = other DNA
                        organism = synthetic construct
SEQUENCE: 20
atgaagcttc ttcatggact cgctttagtt tttctattag ctgctgcgag ttgcaaagct  60
gatgaagaaa ttacttgcga agagaacaac ccattcacat gtagtaacac tgatatttta  120
agcagtaaga acttcggaaa agatttcatc ttcggtgttg catcttctgc ttaccaggca  180
tgtagcaaat gttgtcacac cataattttg aaataaaatt taaaacacta aaatgcaact  240
ttgcatggtt gtttctattc atttcagatt gaaggaggga gaggtcgtgg tgttaacgtt  300
tgggatggct tcagtcaccg atacccaggt atgtcatttg cacagcgaca tctatattta  360
tatgtgagag gaatgttggt tacatatact catatagtca tattaatgta tttgtaatta  420
atatcagaga aagctgggtc agacttgaag aatggagaca ctacttgtga gtcatatacg  480
agatggcagg ttaatttctc agtacattga tactcatgac tgaactatat atgtataaaa  540
ctacagtgtg gattgacatg agattaaaat taatatgtaa aatgcagaaa gatgtagacg  600
tgatgggcga tctcaatgct actggctaca ggttctcctt tgcgtggtca agaatcattc  660
caagtatgta catgttatcg attcgtttgt attttaattg ggatcattta gttgaaaaag  720
tactaattaa tgtacgacat atatatacat gagcagaagg aaaggtgagt aggggagtga  780
accaaggagg tcttgattac taccacaaac tcatagatgc actcctcgaa aagaatataa  840
cgcctttcgt taccctcttt cactgggacc ttcctcaaac actccaagat gagtatgaag  900
gtttcttaga ccgccagatc atgtatgttt atatttgtgc catgcttctt atattattaa  960
taaaagaaga aaaagatttg gtttagttac atgcattaat gaaatgattc tatattaata  1020
tgcacagaca agatttcaaa gactacgcgg atctatgttt caaagaattt ggtggaaagg  1080
taaagcactg ggtatcaacc ataggagaac atcgaccggg tgcatccagt gctttacctt  1140
tccaccaaat tctttgaaac atagatccgc gtagtctttg aaatcttgtc tgtgcatatt  1200
aatatagaat catttcagta atgcatgtaa ctaaaaccaa gtctttttct tcttttatta  1260
ataaatataag aagcatggca caaatataaa catacatgat ctggcggtct aagaaacctt  1320
catactcatc ttggagtgtt tgaggaagat cccagtgaaa gagggtaacg aaaggcgtta  1380
tattcttttc gaggagtgca tctaagagtt tgtggtagta atcaagacct ccttggttca  1440
```

```
ctcccctact cacctttcct tctgctcatg tatatatatg tcgtacatta attagtactt  1500
tttcaactaa atgatcccaa ttaatataca aacgaatgga taacatgtac atacttggaa  1560
tgattcttga ccacgcaaag gagaacctgt agccagtagc attgagttcg cccatcacgt  1620
ctacatcttt ctgcagttta catattttaa tcacatgtca attccacacg tatagttttt  1680
atacatatat agttcaatca tacgagtatc aatgtattaa cctgccatct cgtataggac  1740
tcacaagtag tgtctccatt cttcaagtct gaccctgatt tctctgatag tagttacaaa  1800
tacattaata catgtacata taaaccaacg ttcatctcat gtgtatatat acactgtgac  1860
gtacctggat atcggtgact gaagccatcc caaatgttaa ctccacgacc tcttcctcct  1920
tcgatctgaa atgaaaagaa acaaccatgc gaagttgcat tttagtattt ttgaattgta  1980
tttatttata cgtcaaaaaa aatttgttac atgcctggta agcagaagat gcaacaccga  2040
agatgaagtc ttttccgaag tttttactgc ttaaaatatc agtgttacta catgtgaatg  2100
ggttgttctc ttcgcaagta atttcttcat cagctttgca actcgcagca gctaatagaa  2160
aaactaaagc gagtccatga agaagcttca t                                 2191
```

```
SEQ ID NO: 21           moltype = DNA  length = 3179
FEATURE                 Location/Qualifiers
source                  1..3179
                        mol_type = other DNA
                        organism = synthetic construct
SEQUENCE: 21
tcatgcatca gcgaacctct tcttctgact ctgggaagag aggcttgagc ggaggaaatc  60
ttgtttcaca gcgttcttaa cggtcccgtt gatgaatctc tggtaccatt tgccagattc  120
tttgaggttt ctatcgtcaa gatcttccca attaacgtaa ctgagtccaa atctgacggt  180
gaaaccttta cagaattcat aattatctcc aagagcccat gcaaagtatc ctctcacgtt  240
gacacccttc tccctgaaaa caagaagaat catatatata aatgttacca agaaagaagt  300
aacatctgta gaaaatcatt tatagtagca tccactcact tgatcacctt gcggagaaaa  360
catagatggc tgcatagata atcgattcgc ttgtagtcgg caatagcttg ctcacggttt  420
tctgaactgg gggtactaaa tcctaattaa accgacataa catgaaaaag tacacaaatat  480
ttgaaagtca gtttcttgga attatttcga aatacacaaa ttatagtaga tgttatagat  540
gaaaatatat gcatgtagaa ctcaccattt tcggtgacat agattaaagg gtcgccgtat  600
ttggttttga agtagtccat aacgtaataa atgccttttg ggtagtaata gctgttgccg  660
tttactttgt cttcaacaaa ctgagaaacg ggagttaagc gtatacatat caatcaagaa  720
aacctaatta gtggtgctta tattgaaaat tgaaaaaata aaatgaatta gaaatcatag  780
gggtggatca ttcatattat accagtggac caagaaattc accacgtgaa ttatcatctg  840
taaccacaag aatgaaataa ctgatggtca ctcacaaaaa ggagataaaa catttatata  900
tatcaaaagg ttgtaactaa gtggtaatag aaaagtacat gtgagcttta cgccagcgtc  960
catcatggca gtgtgtgtct ctgaaggata tgggttaggt tttggctggg cgtattgggt  1020
gacgtaatag tttagaccaa gaaaatcata tgaaccagca acgagttctg cttcttcctc  1080
ggtgaagttg ggaagcctac tacccacaat ctgcctcatg atgtctgggt atctacccctt  1140
tgttagcggc tccatgtacc tgatccatgt atatcttttc attatacata tatacaattt  1200
atactgatac atttttggta atataaatat atatatatac catccatgga agaattggtt  1260
catcctctca gctgcttcta tggaggcagg atcagactca tcaaatggaa gaaaccatct  1320
tgtaatcatt acaggtccaa tcttcccttt ttggaactgt tggtcacgtg atatttgact  1380
aagttagaat cagatatctt agattacatt acaccatctt tacacatatt gagacaactc  1440
accttgtatt tggtcctgta aagatcgacg accgtggcat gagcaagaag ctggttatgt  1500
gcaacgatgt agggttctgt tgaagaattt ccaccgtaac acctgtgctt ggtatcaacc  1560
ataggagaac atcgacctgg tgcatctgtt ccgatagcat agcctcttgt aggcactgtg  1620
taggtgttac ggtggaaatt cttcaacaga accctacatc gttgcacata accagcttct  1680
tgctcatgcc acggtcgtcg atctttacag gaccaaatac aaggtgagtt gtctcaatac  1740
gtgataaaga tggtgtagtg taatctaaga tatctgattc taacttagtc atatatcacg  1800
taaccaacag ttccaaaaag ggaagattgg acctgtaatg attacaagat ggtttcttcc  1860
atttgatgag tctgatcctg cctccataga agcagctgag aggatgaacc aattcttcca  1920
tggatggtat atatatatat atatattaca gaacaatgta acagtatata gtgtatgtat  1980
gtataattaa aagatataca tggatcaggt acatggagcc gctaacaaag ggtagatacc  2040
cagacatcat gaggcagatt gtgggtagta ggcttcccaa ctttaccgag gaagaagccg  2100
cactcgttgc cggttcatat gattttcttg gtctcaacta ttacgtcact cagtacgccc  2160
agccaaaacc taacccatat ccttcagaga cacacactgc catgatggac gctggcgtaa  2220
agctcacatg tactagtcta ttaccactaa ttagatacag cctttctata catataaata  2280
ttcttttatc tcctttttgt tgcaacatac tttatgagtg accatctgtt atttcatcct  2340
tgtgttacag atgataactc acgtggtgaa tttcttggtc cactggtata tatcaatgat  2400
ccaccccccta agatttgttt ttctttcatt ttttcagttt tcagtataac aaccctaatt  2460
atgtttttta attgatgtgt atatttattt acttccattt tcacagttcg ttgaagacaa  2520
ggtaaacggc aacagctatt actacccaaa aggcatttac tacgtaatgg actacttcaa  2580
aaccaaatac ggagaccctt taatctatgt caccgagaac ggtgagtttt acgaactctt  2640
tttatttata ccacataata attattgtat tttgatatta gtcgaagaaa ctgactttat  2700
tgtggaatat ttttaatgtg gcggtttatt taggatttag taccccccagt gaagaaaacc  2760
gtgagcaggc tattgccgat tacaagcgaa ttgattatct ctgcagtcat ttatgttttc  2820
tccgcaaggt catcaagtga gtggatacta ctataaatga ttttcttctt atgttatttc  2880
ttcttctttt ttgctaacat ttatatatga ttgttcttgt tttcagggag aagggtgtca  2940
acgtgagagg atacttcgca tgggctcttg gagacaatta tgaattctgt aaaggcttta  3000
ccgtcagatt tggactcagt tacgttaatt gggaagatct tgacgataga aacctcaaag  3060
aatctggcaa atggtaccag agattcatca acgggaccgt caagaacgct gtgaaacaag  3120
atttcctccg ctcaagcctc tcttcccaga gtcagaagaa gaggttcgct gatgcatga   3179
```

```
SEQ ID NO: 22           moltype = DNA  length = 2818
FEATURE                 Location/Qualifiers
source                  1..2818
                        mol_type = other DNA
                        organism = synthetic construct
```

```
SEQUENCE: 22
atgaagcttc tttatggact cgctttagtt tttctattag ctgctgcgag ttgcaaagct  60
gatgaagaaa ttacttgcga agagaacgaa ccattcacat gtagtaacac tgacatttta  120
agcagtaaga acttcggaga agacttcatc ttcggtgttg catcttctgc gtaccaggca  180
tgcaacaaat gctgccatac catatttttg acgtatagaa aataatattc aaaaatgcta  240
acatccaact ttgcatggtt gtttcttttc atttcagatc gaaggaggga gaggtcgtgg  300
tgttaacgtt tgggatggct tcagtcaccg atacccaggt atatatatat gagatgaatg  360
tcggttatat gtacacatac taatgtattt gtaattacta tcagagaaat cagggtcaga  420
tttgaagaat ggagacacta gttgtgagtc atatacgaga tggcaggtta attcttcagt  480
acatatatag attactcaaa tgactgaact atgtataaaa actacgtgtg gactgaattg  540
cgtttaaaat atgtaaactg cagaaagatg tagacattat aggcgaactc aatgctactg  600
gctacagatt ctcctttgcg tggtcaagaa tcattccaag tatgtacata aatttgtata  660
tttttattg ggatcattta gttggaagag tatacaaatt aatgtatgat atatatgagc  720
agaaggaaag gtgagtaggg gagtgaacca aggaggtctt aattactacc acagtcttat  780
agataaactc ctagaaaaga atataacgcc tttcgttact ctctttcact gggaccttcc  840
tcaaacactc caagatgagt atgaaggttt cttggaccgc cagatcatgt atgtgacatg  900
tttcttaatt atatacaatt tttaataaaa acaagaataa gaagaagatt ttgtcttaat  960
tacatgcttt actgaaagaa tgatcatata ttataatatg cacagacaag atttcaaaga  1020
ctatgcggat ctatgtttta aagaatttgg tggaaaggtg aagcactgga tcacgatcaa  1080
ccagctatac acagtgccta cgagaggcta tgcacttgga acagacgcac cgggtcgatg  1140
ttctcctatg gttgatagca caggtgttac ggcggaaact cttcaacaga accttatatt  1200
gttgcacata accagcttct tgctcatgcc acggtagttg atctttacag gaagaactat  1260
tcggtaagta gtcttcatat gtgaaaaggt ggtgtaaata taacatattt gattctaatt  1320
tactcatata tcatgtgacc aacagtccca aaatgggaag attggacctg tgatgataac  1380
aagatggttt cttccatatg atgagtttga tcctgcttgc gtagaagcag ctgagaggat  1440
gaaacacttc tttcatggat ggtatattgt ttttgtttga catcaaacaa gtattctatt  1500
aaaaacctag aggtggtcta gataactaga atgattatac tctatgtatg tataaagaaa  1560
caaaatataa atggatcagg tttatggagc cgctaacaaa gggtagatac ccagacatca  1620
tgagacagat tgtgggtagt aggcttccca gcttcaccga agctgaagcc aaactcgttg  1680
ctggttcata tgattttctt ggtctcaact attatgttac tcagtatgcg cagccaaaag  1740
ctaacccatt gctttcagag aaacacactg ccttgatgga cgctggcgta ggcctcacat  1800
gtacgcatta ctctgtttcc actttgttac aacctccttt ctatatatgt atatatattc  1860
ctttttgtta taacatactt atttgtgagt aaccatccgt taattcttcc ttgtgtttac  1920
agataataac tatctgggtg aaaatattgg tccactggta tatatcatga tccacccatg  1980
atttctcctt tcattatttg tagtgtactt aacacccaca aaaaaaaaaa actattttct  2040
gattgatatg tatattttgt ttgctccctc tctcagttca ttgaagacaa agttaacggc  2100
aacagctatt actacccaaa aggaatttat gacgtaatgg acttcttcaa aaccaattac  2160
agcaaccctt taatctatat caccgagaac ggtgagttct acataaatta ctactcatct  2220
cttttcatct attctataca tatcatcaga taactagtgt attttgatat tagttcaaga  2280
aactgatttt caaattttgt cgaatatttc catgttatgg cggtttaatt aggatttagt  2340
acgcctggtt cagaaggccg ttgcgaagct acttctgatt acaaacgaat tgattttctc  2400
tgcagtcatc tatgtttctt ccgtaaggtc atcaggtaag tggatgctac tatacatact  2460
ttcttccaat atttatcttc tttttcttct tctttttaag taatatatat atatatatat  2520
atatatatat atttatatat atatgattgt tattgttttc tgcagggaga agggtgtaaa  2580
cgtgagagga tactttgcat gggctcttgg ggataattat gaattctgta aagggtttac  2640
cgtaagattt ggactcagtt acgttaattg ggatgatctc gacgatagaa acctcaaaga  2700
atctggaaaa tggtaccaga gattcattaa cgggactgcc aagaagaatc ctgtgaaaca  2760
agatttcctc cgctcaagcc tctcctctca gagtcagaag aagaggcttg cttgctga    2818

SEQ ID NO: 23           moltype = DNA  length = 2880
FEATURE                 Location/Qualifiers
source                  1..2880
                        mol_type = other DNA
                        organism = synthetic construct
SEQUENCE: 23
atgaagcttc ttcatggact tgctttagtt ttcctattag ctgcttcgag ttgcaaagct  60
gatgaagaaa ttacatgtga agagaacact ccattcacat gtggtaacac tgatatttta  120
agcagtaaaa actttggaaa agacttcatc ttcggtgttg catcttctgc ttaccaggca  180
tgtaacaaat gttgacatac catactataa ataaatacaa ttcaaagagc taatttccaa  240
ctttgcatgg ttgtttattt tcctttcaga tcgaaggagg gagaggtcgt ggtgttaaca  300
tttgggatgg cttcagtcac cgatacccag gtatgtcgtt tttgcacggt gacgtacgtg  360
tgtatatata tatatatata taatgtacac atattaaagc atttgtaatt actatcagag  420
aaatcagggt cagatttgat gaatggagac actacttgtg agtcatatac gagatggcag  480
gtcagtacat tgatactcac atgactgaac tatgtataaa aaaacctata cgtgtgattg  540
ttgacatgcc attaaaatat gtaaactgca gaaagatgta gacattatgg gagaactcaa  600
tgctactggc tacagattct cctttgcgtg gtcaagaatc attccaagta tgtacatatt  660
attgattgtt cgtaattggg atcgtttagt tggaaaagta ctgattaatg ttttggcaaa  720
aaaaaaagta ctgattaatg tacaatatat atatgtatgc acgagcagaa ggaaaagtga  780
gtaggggagt gaaccaagga ggtcttgatt actaccacca actcatagac gccctcctag  840
aaaagaatat aacgcctttc gttaccctct tccactggga ccttcctcaa acactccaag  900
atgagtatga aggtttctta gaccgccaga tcatgtatgt ttatattttt gccatgcttc  960
ttatattatt aataaaagac gaaaaagatt tggttttagt aacatgcatt actgaaatga  1020
ttatacaata atatgcacag acaagatttc aaagattacg cggatctatg tttcaatgaa  1080
tttggtggaa aggtaaagct cacgatcaac cagctatata cagtgccgac aagaggctat  1140
gcgagcggaa cagatgcacc cggtcgatgt tcttatatgg ttgataccaa gcacaggtgt  1200
tacggcggaa attcttcaac agaaccctac atcgttgcac ataaccagct tcttgctcat  1260
gccgcagttg tcgatcttta caggaccaaa tataaggtga gtggtgctcc atatgtgaaa  1320
attagggtgg tgtaaatcta acatatatct gattctaatg tatagtcata tatatgtatc  1380
acgtgaccaa cagttccaaa acgggaagat tggacctgtg atgataacaa gatggtttct  1440
```

```
tccatttgat gagtctgatc ctgcttgcgt agaagcagct gagaggatga accaattttt  1500
ccatggatgg tatttatata tatatatata tatatatata tatatatatg tgtgtgtgtg  1560
tattaccaac aatgtatcag tatgtatttt atgtatttat aatgaaacaa aaatatacat  1620
ggatgatgga tcaggtacat ggagccgcta acaaagggta gatacccaga catcatgagg  1680
cagatcgtgg gtagtaggct ccccaacttt accgaggaag aagccgcact cgttgctggt  1740
tcatatgatt ttcttggtct caactattac gtcactcagt acgcccagcc acaacctaac  1800
ccatatcctt cagagacaca cactgccatg atggaccctg gtgtaaagct cacatgtacg  1860
tacttcagta atattaccac ttagtactta tcaaaaaaaa aaaaaattac cacttagtta  1920
caacctttct atatatgttt ttctcctttt gttaacatac tttgtgagtg actatcaatt  1980
atttcatcct tgtgtttaca gataataatt cacgtggtga attacttggt ccactggtaa  2040
tatatgaatg atccacctct acgatttctc tttttttaa tcaatatttt ctatttgcaa  2100
tagaacacca ctgattatgt tctcttgatt gatatgtata ttttgtttgg ttccctttct  2160
cagttcgctg aagacaaggt taacggcaac agctattact acccaaaagg aatgtattac  2220
gtaatggact tcttcaaaac caattacagc aacccttaa tatatatcac cgagaacggt  2280
gagttctaca tactacttac tactcatcta ttctacataa attaactagt gtattttata  2340
tattagtcca ggaaactgac tttcaaatat cgtggaatgt tttcatggtt taattaggaa  2400
ttagttcgcc cggtacagaa aaccgttgcg aagctattgc cgattacaag cgaatcgatt  2460
atctctgcag tcatctctgt tttctccgta aggtcatcag gtaagtagat gctactatac  2520
gcatgctttt tcttccaatg ttaatcaact tctttctctt ttttattttg gtaaaatctt  2580
cttcttcttt gtctttttgg taatatatat atgattattc ttgttttcag ggagaagggt  2640
gtcaacgtga gaggttattt cgcatgggct cttggagata attatgaatt ctgtaaaggc  2700
tttaccgtca gatttggact cagttatgtt aattgggatg atcttgacga cagaaatctc  2760
aaagaatctg gtaaatggta ccagagattc attaacggga ccgtcaagaa ccatgcgaac  2820
caagatttcc tccgctcaag cctttcttct cagagtcaga agaagaggct cgcttgctga  2880
```

```
SEQ ID NO: 24          moltype = DNA  length = 2730
FEATURE                Location/Qualifiers
source                 1..2730
                       mol_type = other DNA
                       organism = synthetic construct
SEQUENCE: 24
atgaagcttc ttcatggact cgctttagtg tttctattag ctggtgcgag ttgcaaagct  60
gatgaagaaa ttacttgcga agagaacaat ccattcacat gtagtaacac tgatatttta  120
agcagtaaaa acttcggaaa agacttcatc ttcggtgttg catcttctgc ttaccaggca  180
tgcaacaaat gtttttgacg tatcaataaa tacaattcaa aaatactaaa atgcaacttc  240
gcatggttgt ttcttttcat ttcagatcga aggaggaaga ggtcgtggtg ttaacatttg  300
ggatggcttc agtcaccgat atccaggtac gtcacagtgt atatatacac atgagatgaa  360
cgtcggttta tatgtacatg tattaatgta tttgtaacta ctatcagaga aatcagggtc  420
agacttgaag aatggagaca ctacttgtga gtcctatacg agatggcagg ttaatacatt  480
gatactcgta tgattgaact atatatgtat aaaaactata cgtgtggaat tgacatgtga  540
ttaaaatatg taaactgcag aaagatgtag acgtgatggg cgaactcaat gctactggct  600
acaggttctc ctttgcgtgg tcaagaatca ttccaagtat gtacatgtta tccattcgtt  660
tgtattttaa ctgggatcat ttagttgaaa aagtactaat taatgtacga catatatata  720
catgagcaga aggaaaggtg agtaggggag tgaaccaagg aggtcttgat tactaccaca  780
aactcataga tgcactcctc gaaaagaata taacgccttt cgttaccctc tttcactggg  840
accttcctca aacactccaa gatgagtatg aaggtttctt ggaccgccag atcatgtatg  900
tgccatgcag acatattata tatgaattta agagattgat tataaaatta ttaataaaaa  960
agaagaaggt ttggtcttat ttaattacat gtattaactg aaataattat atattcatat  1020
gcagacaaga tttcaaagat tacgcggatc tatgtttcaa agaatttggt ggaaaggtaa  1080
agacgatcaa ccagttatac acagtcccta cgagaggcta tgcggtcgga acagatgcac  1140
ccggtcgatg ttctcctatg gttgatacca agcacaggtg ttacggtgga aattcttcaa  1200
cagaacccta catcgttgca cataaccagc ttcttgctca tgccgtcgat ctttacagga  1260
ccaaatacaa ggtgagttgt ctcaatacgt gataaagatg gtgtagtgta atctaagata  1320
tctgattcta acttagtcat atatcacgta accaacagtt ccaaaaaggg aagattggac  1380
ctgtaatgat tacaagatgg tttcttccat ttgatgagtc tgatcctgcc tccatagaag  1440
cagctgagag gatgaaccaa ttcttccatg gatggtatat atatatattt atattaccaa  1500
aaatgtatca gtataaattg tatatatgta taatgaaaag atatacatgg atcaggtaca  1560
tggagccgct aacaaagggt agatacccag acatcatgag gcagattgtg ggtagtaggc  1620
ttcccaactt caccgaggaa gaagcagaac tcgttgctgg ttcatatgat tttcttggtc  1680
taaactatta cgtcacccaa tacgcccagc caaaacctaa cccatatcct tcagagacac  1740
acactgccat gatggacgct ggcgtaaagc tcacatgtac tagtctatta ccactaatta  1800
gatacagcct ttctatacat ataaatattc ttttatctcc tttttgttgc aacgtacttt  1860
gtgagtgacc atctgttatt tcatccttgt gtttacagat gataactcac gtggtgaatt  1920
tcttggtcca ctggtatata tcaatgatcc accccctaag atttgttttt ctttcatttt  1980
ttcagttttc agtataacaa ccctaattat gttttttaat tgatgtgtat atttatttac  2040
ttccattttc acagttcgtt gaagacaagg taaacggcaa cagctattac tacccaaaag  2100
gcatttacta cgtaatggac tacttcaaaa ccaaatacgg agacccttta atctatgtca  2160
ccgagaacgg tgagttttac gaactctttt catttatacc acataataat tattgtattt  2220
tgatattagt cgaagaaact gactttattg tggaatattt ttaatgtggc ggtttattta  2280
ggatttagta cccccagtga agaaaaccgt gagcaggcta ttgccgatta caagcgaatt  2340
gattatctct gcagtcattt atgttttctc cgcaaggtca tcaagtgagt ggatgctact  2400
ataaatgatt ttctacatct gttatattct tcttctttct tggtaacatt tttatatatg  2460
attgttcttg ttttcaggga gaagggtgtc aacgtgagag gatacttcgc atgggctctt  2520
ggagacaatt atgaattctg taaaggcttt accgtcagat ttggactcag ttacgttaat  2580
tgggaagatc ttgacgatag aaacctcaaa gaatctggca aatggtacca gagattcatc  2640
aacgggaccg tcaagaacgc tgtgaaacaa gatttcctcc gctcaagcct ctcttcccag  2700
agtcagaaga agaggttcgc tgatgcatga                                  2730
```

```
SEQ ID NO: 25          moltype = DNA  length = 2844
```

```
FEATURE                Location/Qualifiers
source                 1..2844
                       mol_type = other DNA
                       organism = synthetic construct
SEQUENCE: 25
atgaagcttc ttgggctcgc tttagttttt ctgttagctt ctgcgagttg caaagctgac  60
gaagaaatta cttgtgaaga gaacaatcca ttcacatgta gtaacactga tattttaagc  120
agtaagaact tcggaaaaga cttcatcttc ggtgttgcat cttctgctta ccaggcatgt  180
aacaaatgtt gacataccat actttttgac gtatagaaaa cactattcaa aaatgataat  240
atctaacttt gcatggttgt ttcttttcat ttcagatcga aggagggaga ggtcgtggtg  300
ttaacatttg ggatggcttc agtcaccgat acccaggtat gtcgtttgca cggtgacatc  360
tatatatata tcatatatga caggaatgtt ggttataagt actcatatta atgtatttgt  420
aattactatc agagaaatca gggtcagatt tgaagaatgg agacactact tgtgagtcat  480
atacgagatg gcaggttaat tcttcagtac atttgtagat actcatgact gaactatgta  540
tacaaactac gtgccgattg agatgcaatc aaaatatgaa actgcagaaa gatgtagacg  600
ttatgggcga actaaatgct actggctaca gattttcctt tgcgtggtcg agaatcattc  660
caagtacgta cagattatcg atcagtacat gtatatatat agttggacgt gttttaaatg  720
tacgatttat atatacatga gcagaaggaa aggtgagtag gggagtgaac caaggaggtc  780
ttgattacta ccacaaactc atagacgccc tcctcgaaaa gaatataact cctttcgtta  840
ccctctttca ctgggacctt cctcaaacac tccaagatga gtacgaaggt ttcttggacc  900
gccagatcat gtatgtttat atttgtgaca tgcttcttat attattaata agagaagaaa  960
aagatggtta attttagtta catgcattac tgaaatgatt ctatattaat atgcacagac  1020
aagatttcaa agattatgcc gatctatgtt tcaaagaatt tggtggaaag gtaaatcaac  1080
cagctataca cagtccctac gagaggctat gcagtcggaa cagatgcacc cggtcgatgt  1140
tctcctatgg ttgaggtgtt acggcggaaa ttcttcaaca gaaccctata tcgttgcaca  1200
taaccagctt cttgctcatg ccacggtcgt cgatctttac aggaccaaat ataaggtgaa  1260
tgctgtctcc atatgtgaaa attaaggtgg tgtctaacat atctgattct aatgtaaata  1320
tcacgtgacc aacagttcca aaaagggaag attggacctg tgatgataac aagatggttt  1380
cttccatttg atgagtctga tccggcctcc atagaagcag ctgagaggat gaaccaattc  1440
ttccatggat ggtatatata tatattacca aaaatgtaac agtatctact gtatttgtat  1500
gtatgtataa tggaaaaata tacatggatc aggtacatgg agccgctaac aaagggtaga  1560
tacccagaca tcatgaggca gattgtgggt agtaggcttc ccaactttac cgaggaagaa  1620
gcccaactcg ttgccggttc atatgatttt cttggtctca actattacgt cactcagtac  1680
gcccagccga aacctaaccc atatccttca gagacacaca ctgccatgat ggacgctggt  1740
gtaaagctca catgtaagta ccacacaata ttactactta gttacgacct ttctatatat  1800
tttttttctt ctttttgtta acatactttg tgagagtatc aattatttca tccttgtgtt  1860
tacagatgat aattcgcgtg gtgaatttct tggtccactg gtatatatga atgaaccacc  1920
cctatgatat ctctttcatt ttttattcta tttgcaatat atagaacacc actgattatg  1980
ttctcgtgat tgatatgtat atttgtttgc ttcccttgct cagttcgttg aagacaaaga  2040
taacggaaac agctattact atccaaaagg aatttattac gtgatggact acttcaaaac  2100
caactacggc aaccctttaa tctatgtcac cgagaacggt gagttctaca tactactact  2160
cctctatttt catttatacc acgcataata ttatgtaacc acaaaagtag accgatattc  2220
aatctaccgc agggtgaata gtaatgaaaa taattgtaaa agttatttta caattattgt  2280
attttcgaaa ttggtccaag aaactaactt acaaatattg tgtaatattt ttcatgcaat  2340
ggcggcttaa ttaggattta gtacgcccag ttcagaaaac cgtgagcagg ctattgcgga  2400
ttacaagcga attgattatc tctgcagtca tctatgtttt ctccgtaagg tcatcaagta  2460
agtaatgcta ctatatggat gcttttcttc caatgtttat caacttcttc tctttttggt  2520
aatatatata tatatatata tatatatata tatatatata tatatatata tatgattgtt  2580
cttgttttca gggagaaggg tgtcaacgtg agaggttatt ttgcatgggc tcttggagac  2640
aattacgaat tctgtaaagg ctttaccgtc agatttggac tcagttacgt taattgggac  2700
gatctcgatg atagaaacct caaagaatct ggcaaatggt accagagatt cattaacggg  2760
acagtcaaga accttgccaa acaagatttc ctccgctcaa gcctctcttc ccagagtcag  2820
aagaagaggc tgtctgatgc atga                                        2844

SEQ ID NO: 26          moltype = DNA  length = 2669
FEATURE                Location/Qualifiers
source                 1..2669
                       mol_type = other DNA
                       organism = synthetic construct
SEQUENCE: 26
atgaagcttc atggactagc cttgataggt tttctaattg ctgcggcgag ttgcaaagct  60
attgaggaca ttaattgcca agagaacgag cctttcacat gtggaaacac tgatcagtta  120
agcagtaaaa atttcccaaa agacttcatc ttcggtgttg cttctgctgc ttaccaggca  180
tgttacaaat caacaatttt tgacgtagaa aaccatttaa aatattaaat ccaacgttgc  240
atggttgttt cttattattg taggtggaag ggggcagagg acgtggtctt aacgtttggg  300
atggcttcac tcaccgatac ccaggtatat catctacatg gtacatatat atataatgtc  360
cacatctctt atatatcatt cgtagtaatg tatatgttta ctatcagaga agggtggatc  420
cgatctcggg aatggagaca ctacttgtga gtcatataca agatggcagg ttaattcctc  480
actgagtcat ataggaaaat ggcaggttaa ttccacattc ctcactatat ataaatgata  540
tccgagtgtg tatgtaaact gcgcagaaag atatagacat catggacgag ctcaatgcta  600
ctggctacag attctctttt gcgtggtcaa gaatcattcc aagtatgaac acataaacga  660
tctatttata caaaaaattc tcgtaaattg attgtgagtg ttgagaagat taaatatatg  720
atatgtatac atgagcagaa ggaaaggtga gtaggggagt gaacaaagga ggtctcgaat  780
actaccacaa actcatagat ggtctcgtcg caaagaatat aacacctttt gttaccctct  840
atcactggga cctacctcaa acactgcaag atgagtatga aggtttcttg aaccgcacca  900
tcatgtatgt catttgtgcc gcgttcttag caagaaatat aagaagaaaa acatatataa  960
gtgatctcat gttaatgatt tgtttctatg ctatgcacag agatgacttt agagattatg  1020
cggatctatg tttcaaggaa tttggtggaa aggtgaagaa ctggatcacg attaaccagc  1080
tgtacacagt gcctacgaga ggctatgcaa tcggaacaga tgcacccggt cgatgttctc  1140
```

```
cgaagttacg gcggaaattc ttcaacagaa ccttatatag ttgcacataa ccagcttctt  1200
gctcatgctg cggcggtcga tgtttacagg acaaaatata aggtgagtat atataggttt  1260
gtaaataggt gtagtctaac atatatgtca atgttctaat catatcattt catttcgtat  1320
gccgtgacaa acagttccaa ggagggaaga tcggaccagt gatgataact agatggtttc  1380
ttccatttga tgagactgat aaagctagcc tatatgcagc tgataggatg aaagaattct  1440
tcttgggatg gtacgtattt gtatgtatat gtacacaaaa atgatatgat tatttatacg  1500
tatgtacatc gatcaggttc atggagccgc taacaaaggg tagataccca gacatcatga  1560
gacaaattgt gggtagtcgg cttcccaatt tcacggaagc agaagcagaa ctagttgcgg  1620
gttcatatga ttttcttggt ctcaactact acaccactca gtatgcccag ccaaaaccta  1680
acccagttac atgggaaaat cacactgcca tgatggaccc aggcgcaaag ctcacatgta  1740
ccactcagtt tcctcttata gttacaacct ttctatatat atatatatat atataggctt  1800
ctaagtcttt taaattaagc atatatatac tttgtgagtg accactaatt atttcatcat  1860
tgggtttaca gatacgaatt cacgtggtga aaatcttggt ccactggtat atgcatgatc  1920
caccccctgac ccctgttact tattattttt tttctttcta gttgatgtgt atacgtatgc  1980
ttccttttct cagttcgtta aggacgaaat aaacggcgac tcctattact acccaaaagg  2040
catttattac gttatggact acttcaaaac caaataccgt aaccctttga tctatatcac  2100
tgaaaacggt gactactact catctctttt tccatattaa gcaaatatgt atgtttaaaa  2160
taatgtacaa gttgtttatg taccatgatg gttaaattag gatttagtac tcccggtgaa  2220
gaaacccgtg aggaagctat tgctgattcc aagcggatcg attatctctg cagtcatcta  2280
tgttttctcc gtaaggtcat caggtgagtg gaagctacta tatttttttt ttctcttttg  2340
aatttgatgc atgcatacat aaatgtatgg tcatcatcat gcataggctt aggctttgaa  2400
tgattgttcg tgtttccagg gagaagcgtg tcaacattaa aggatacttt gcatgggctc  2460
ttggagataa ttatgaattc tgcaaaggtt ttaccgttag attcggactt agttatgtta  2520
actggacaaa cctcgatgat agaaatctca aagaatctgg caaatggtac caaagcttta  2580
ttaacggtac ctctaagaac cctgctaaac aagatttcct ccgctcaaac ctctccttcc  2640
agaaccagaa gaagctcgca gatgcatga                                   2669
```

```
SEQ ID NO: 27          moltype = DNA  length = 2713
FEATURE                Location/Qualifiers
source                 1..2713
                       mol_type = other DNA
                       organism = synthetic construct
SEQUENCE: 27
atgaagcttc ttcatggact cgctttagtt tttctattag ctgctgcgag ttgcaaagct  60
gatgaagaaa ttacttgcga agagaacaat ccattcacat gtagtaacac tgatatttta  120
agcagtaaaa acttcggaaa agacttcatc ttcggtgttg catcttctgc ttaccaggca  180
tgtaacaaat tttttgacg tataaataaa tacaattcaa aaatactaaa atgcaacttc  240
gcatggttgt ttcttttcat ttcagatcga aggaggaaga ggtcgtggtg ttaacatttg  300
ggatggcttc agtcaccgat atccaggtat gtcacagcgt atatacacac atgagatgaa  360
cgtcggttta tatgtacaca tattaatgta tttgtaacta ctatcagaga aatcagggtc  420
agatttgaag aatggagaca ctacttgtga gtcatatacg agatggcagg ttaatacatt  480
gatactcata tgactgaact atatatgtat aaaaactata cgtgtggatt gacatgtgat  540
taaaatatgt aaaccgcaga aagatgtaga cgtgatgggc gaactcaatg ctactggcta  600
caggttctcc tttgcgtggt caagaatcat tccaagtatg tacatgttat cgattcgttt  660
gtattttaat tgggatcatt tagttgagaa aagtactaat taatgtacga catatatata  720
catgagcaga aggaaaggtg agtaggggag tgaaccaagg aggtcttgat tactaccaca  780
aactcataga tgcactactc gaaaagaata taacgccttt cgttaccctc tttcactggg  840
accttcctca aacactccaa gatgagtatg aaggtttctt agaccgccag atcatgtatg  900
tttatatttg ttccatgctt cttatattat aaataagaga agaaaacgtt ttggttttag  960
ttacatgcat taatgaaatg attctgtata atatgcacag acaagatttc aaagactacg  1020
cggatctatg tttcaaagaa tttggtggaa aggtatcacg atcaaccagc tatacacagt  1080
ccctacgaga ggctatgcgg tcggaacaga tgcacccggt cgatgttctc ctatggttga  1140
taccaagcac aggtgttacg gtggaaattc ttcaacagaa ccctacatcg ttgcacataa  1200
ccagcttctt gctcatgcca cggtcgtcga tctttacagg accaaatata aggtgagtgg  1260
tctctccata ttaaggtggt gcaaatctaa catatctgat tctaatgtat agtcatatat  1320
atatatatat cacgtgacca acagtttcaa aaagggaaga ttggacctgt gatgataaca  1380
agatggtttc ttccatttga tgagtctgat cctgcctcca tagaagcagc tgagaggatg  1440
aaccaattct ttcatggatg gtatatatat atattacaga acaatgtaac agtatatagt  1500
gtatgtatgt ataattaaaa gatatacatg gatcaggtac atggagccgc taacaaaggg  1560
tagataccca gacatcatga ggcagattgt gggtagtagg cttcccaact ttaccgagga  1620
agaagccgca ctcgttgccg gttcatatga ttttcttggt ctcaactatt acgtcactca  1680
gtacgcccag ccaaaaccta acccatatcc ttcagagaca cacactgcca tgatggacgc  1740
tggcgtaaag ctcacatgta ctagtctatt accactaatt agatacagcc tttctataca  1800
tataaatatt cttttatctc ctttttgttg caacatactt tgtgagtgac catctgttat  1860
ttcatccttg tgtttacaga tgataactca cgtggtgaat ttcttggtcc actggtatat  1920
atcaatgatc caccccctaa gatttgtttt tctttcattt tttcagtttt cagtataaca  1980
accctaatta tgttttttaa ttgatgtgta tatttattta cttccatttt cacagttcgt  2040
tgaagacaag gtaaacggca acagctatta ctacccaaaa ggcatttact acgtaatgga  2100
ctacttcaaa accaaatacg gagacccttt aatctatgtc accgagaacg gtgagtttta  2160
cgaactcttt tcatttatac cacataataa ttattgtatt ttgatattag tcgaagaaac  2220
tgactttatt gtggaatatt tttaatgtgg cggtttattt aggatttagt acccccagtg  2280
aagaaaaccg tgagcaggct attgccgatt acaagcgaat tgattatctc tgcagtcatt  2340
tatgttttct ccgcaaggtc atcaagtgag tggatgctac tatataaatg attttctaca  2400
tctgttatat tcttcttctt tctttgtaac atttttatat atgattgttc ttgttttcag  2460
ggagaagggt gtcaacgtga gaggatactt cgcatgggct cttggagaca attatgaatt  2520
ctgtaaaggc tttaccgtca gatttggact cagttacgtt aattgggaag atcttgacga  2580
tagaaacctc aaagaatctg gcaaatggta ccagagattc atcaacggga ccgtcaagaa  2640
cgctgtgaaa caagatttcc tccgctcaag cctctcttcc cagagtcaga agaagaggtt  2700
cgctgatgca tga                                                     2713
```

```
SEQ ID NO: 28          moltype = DNA  length = 6803
FEATURE                Location/Qualifiers
source                 1..6803
                       mol_type = genomic DNA
                       organism = Brassica juncea
SEQUENCE: 28
ttccacatca tcctctctct tccacataat ttatttaaca ttcatttcat tttaaacatc  60
tacaacattt ataatggttt gcttaaaaat ttaacactct accccaccac ttaattcata  120
ctttatcttt tacagtataa caagtacgta tattaatgat atctttgatt ataatttatt  180
taaaaattaa aataacataa ttttttaaat tttattttat ttatgtacat accttacatt  240
ttaaaaaata atactaaaat caatattgtt aaaacaatta ggatttattt aacaaaaaat  300
gtttaaaaca ctaaaataat tgattctaat gaaaaaatgg tgtttttttt tcttgtgtcc  360
aaatgaaatg agagtagttt ttatttatag atagtaaaaa atcataaatt ttttgatata  420
attaaaaatt tctattataa aataaatgat tttcagttat tgggtgaaaa taaaacttaa  480
aaatctatcc aacaatttct tccaatccaa atgcgccgtg tggcgaagct ggcccataaa  540
ataaaagttt cagctgttga taccacatag gattgttcta aaacttcaac acccttactg  600
gaagaagttc aacagttgaa tacaagattc aacaccttca ttgtaggtga tctaacaagt  660
gacaaacaaa taacacttgt gtttatctat ttggataata catagaagtg tgcacatgtt  720
tcaaagatga cgtctgtttg ttgttccgtc aacatgattg ttgtccgtaa ctagtagctt  780
tttttttca tggcagttta cactttgcag aaagaacatg ttaacctaaa caaaaatcca  840
gtataagttc gcaaagtaaa tgttacttaa agataacgaa ggcctaaagc acataaattt  900
aagtgtttta ttcttaaaat acgaacagct tatcttaatt catatttgaa ctatttcatc  960
ttgtttttc ttaaaatata aacagtttat tttaagatat ttttgattga gtctattttt  1020
gaaaagccat ggctaattta aggtttttaa aacaatttct cttagaataa gttataaaat  1080
tatttgaaat tgaaaagaaa acattaatta gttactacta tatatattta gttcataaca  1140
gttatactcg tggaagagta caggagaatc acctattgcg atattattaa atacaagtta  1200
acttatgtat atgtgctacg taaataattg atttcaaact caagttggtg gcacgtaaac  1260
agtatgaatt gtaactttat agagtaaaaa actatggaac aaactatagg ttaatacaca  1320
agtatcaatc tatttatctg gaagtcacgg atacgtatcc gttccaacct tttcaatcat  1380
ttaaaaacga taccaaaaaa agcaaaaact gtggttggtt ttcgttttct ttagtctttc  1440
ggaggcaccg gtctcatgtg ataaagcaga aatagagcga tcaaaaccaa tatgatatga  1500
tgtgattttg tgacggtaga gctcgtgata actgataagt gcggctttac accagtgtta  1560
ctctagattc aacacttgat aaaatttcga tataaatttt caataacgaa tcttgacgtt  1620
aagtgtagtt ctagttttgg cgcaaatctt acatgctgca ttgcatcatt gcatgactgt  1680
tgacggatca atttgaagat gtgtcaattc gtgtttcggt taaggaacac aacttgtgct  1740
atctaacaat tttttttgc aatagataat gaaagactaa aaagtggaaa cataacaatc  1800
agaaatatta caaaaatcgg tgaacactga gcaaaagtca gtgaacccac gggacacatg  1860
atcccaccta cacctctccc aaactatcaa gatactaaga caagaaaata catatgtcac  1920
tcttctttcg gaaaggctat ataaacccta gatgagcaca aggttccaca caacacaaca  1980
catacatcaa cagattaaac atgaagcttc ttcatggact cgctttagtt tttctattag  2040
ctgctgcgag ttgcaaagct gatgaagaaa ttacttgcga agagaacaat ccattcactt  2100
gtagtaacac tgatatttta agcagtaaga acttcggaaa agatttcatc ttcggtgttg  2160
catcttctgc ttaccaggca tgtagcaaat gttgtcacac cctaattttg aaataaaatt  2220
taaaacacta aaatgcaact ttgcatggtt gcctcttttc atttcagatc gaaggaggga  2280
gaggtcgtgg tgttaacgtt tgggatggct tcagtcaccg atacccaggt atgtcgtttg  2340
cacggtgaca tctattttat atgtgagagg aatgttggtt acatatacac atattaatgt  2400
atttgtaatt taatatcaga gaaagctggg tcagatttga agaatggaga cactacttgt  2460
gagtcatata cgagatggca ggttaatttc tcagtacatt gatactcatg actgaactat  2520
agtatgtata aaaactatac gtgtggattg acatgagatt aaaattaata tgtaaactgc  2580
agaaagatgt agacgtgatg ggcgaactca atgctactgg ctacagattc tcctttgcgt  2640
ggtcaagaat cattccaagt atgtacatat tatcgatcaa ttatatatat atatatatat  2700
ataaatatat attatttttt ttaattggga tgatttagtt ggaagagtac taattaaagt  2760
acgatgtata tatacatgag cagaaggaaa ggtgagtagg ggagtgaacc aaggaggcct  2820
tgattactac cacaaactca tagatgcact cctcgaaaaa aatataacgc ctttcgttac  2880
cctctttcac tgggatcttc ctcaaacact ccaagatgag tatgaaggtt tcttggaccg  2940
ccagatcatg tatgtgccat ccttcttaat tatatctgaa gagagtaaat ataattagtg  3000
atagaagaag aatatttggt ttaatttaca tgtattactg aaatgattct atactaatat  3060
gcacagccaa gatttcaaag attacgcgga tctatgtttc aaagaatttg gtggaaaggt  3120
aaagcattgg atcacgatca accagctata cacagtgcct acaagaggct atgcgatcgg  3180
aacagatgca cccggtcgat gttctcctat ggttgatacc aagcacaggt gttacggcgg  3240
aaattcttca acagaaccct acatcgttgc acataaccag cttcttgctc atgccacggt  3300
cgtcgatctt tacaggacca aatataaggt gagtggcctc catatgtgaa aaggtggtct  3360
aaatctaaca tatccgattc taatgtatag tcatatatat atcacgtgat gaacagttcc  3420
aaaaagggaa gattggacct gtgatgataa ctagatggtt tcttccatat gatgaatctg  3480
atcctgcctc catagaagca gctgagagga tgaaccaatt cttccatgga tggtatatat  3540
aattttatat attaccaaaa atgtatcagt ttgtatttta tgtattataa tgaaacaaaa  3600
atatacttgg atcaggtata tggagccgtt aacaaagggt agatacccag acatcatgag  3660
gcagattgtg ggtagtcggc ttcccaactt caccgaggaa gaagcggaac tcgttgctgg  3720
ttcatatgat tttcttggtc tcaactatta cgtcactcag tacgcccagc caaaaccgaa  3780
cccatatcct tcagagacac acactgccat gatggacgct ggcgtaaagc tcacatgtac  3840
tacaacatta ccacttagtt acaagctttc tatatacata tatatatgtg ctatctcctt  3900
tttgttacaa catactttct gagtgaccat caattatttc atccttgtgt ttacagatga  3960
taattcacgt ggtgaatttc ttggtccact ggtatatata aatgatcatc caccccttg  4020
atttctcttt caatttttttt ttctatttgc aatataacac cactttctcc ttgttaatat  4080
gtatatatat gtttgcttcc tttctcagtt cgttgaagac aaagtcaacg gcaacagcta  4140
ttactaccca aaagggattt attacgtaat ggactacttc aaaaccaaat acggcgaccc  4200
attaatctat gtcaccgaga atggcgagtt ctacatactt ccactactca tatttcata  4260
tataacatat cgtaattagt gtatttcgaa ataaatccaa gaaactgatt ttcaaatatt  4320
```

```
gtatactttt tcatgttatg gcggttaatt aggatttagt acccccagtt cagaaaaccg  4380
tgagcaagct attgccgatt acaagcgaat tgattatctg tgcagtcatc tatgtttttct  4440
ccgcaaggtc atcaagtgag tggatgctat tataaatgat tttcttcata tgttattttc  4500
ttcttctttt cgggtaacat ctatatatat atgattgttc ttgttttcag ggagaagggt  4560
gtcaacgtga gaggatactt tgcatgggct cttggagata attatgaatt ctgtaaaggt  4620
tttaccgtca gatttggact cagttatgtt aattgggacg atctcgacga tagaaacctc  4680
aaagaatctg gtaaatggta ccagaggttc attaacggga ccgccaagaa tcctgcgaaa  4740
caagatttcc tccgctcaag tctttcctcc cagagtcaga agaagaggct tgctgatgca  4800
tgaaacactt tccaccatcg gatcatctct atatctctca ctcttcctac ttgctccata  4860
gttaaggagc ttcttctatc tacaatatac taaataaata atctcaataa aaagatgatc  4920
aattactaat gagtaaaaat aatttatcta caactacatt atgccaagtc aagaggatga  4980
ggaaagaggg aaataacaca atttaaatag aaaacactca gaaatcccaa actagttaac  5040
ttatataata aaatgtgtat tcaagaaaca ataaccaaaa ctaatgcaaa ctcaaaagtc  5100
aaaagtaact aaaccaaagg tctatcatcc tcaactgaaa cttaatggga ttttacatat  5160
gaaattttat cactcacata aaatttacgt gagagatgac tattatagct actcttatga  5220
acctaaggaa agtaaatggg aattggagga aatgggagca aggttgtgtt gttgacaatg  5280
tattttacta ttacgatgtc tacaagaaca agttgagagc gcatgatcca aattaaggac  5340
caaagcagag gtgccggagt gtggtgaaag gtgtggaaga attgttgtct aagacgaatg  5400
gttcatgggg tacgtataca gtgcgttggg gtgagaaatt ggttcttttt cttcaggaca  5460
acgagaagat ttggtgtgcg gagattgctt tagaaacctg aatagaaaaa gagatttcgg  5520
gtaaggtgca atggtgtgat gtcgtgaatg atgatggaaa atattcggag ctcgtacaat  5580
gtttatatta gttttattta aactagggta cgttaatatt aaaagttaaa tatatttgaa  5640
tttaagtttt cgtttataat ttcacaatgt ttgggatagt tttctccgtt cctttgattt  5700
gatccattcg cagcagatca gagttttttt tttgtctatt tttatttatt tacaaagacc  5760
gcaaataaat ttattataac cgcatttgta ttagtctaag ttaatcgaaa tccacaaaat  5820
ccataaatca ttaataaatt aaaaaccgat atttcatatc ttttagttaa ttttaatagt  5880
ataaatttta tattataaaa ataaatacat attaaaatga ttttaaataa tttttattta  5940
gtattttttt atatattatc taattattat aattaaaatt taaataagta ataatattta  6000
atttttttatt tataaatctg atggactgaa ttatatcccc aattttaaat ataataaatt  6060
tacatccatt cgtatttaaa tatataatcc acatctatcc cacttcaaaa aataactgac  6120
atgcattcac ccaaggcgga tcaagaaacc catggttttg agtcaaattc ccatcactag  6180
attttttagt gtatgtacca ttcaagaaca aggagaagaa gtttcaaggg aaattgcact  6240
cattatacaa taaacaaatt ataattagtt atctaaccaa aaaaagttga cagtatattc  6300
aacatatttt ctatcatata tatcaaaata cctttgaaat caaccgtgtg atctctttct  6360
attttttttt ctttctcttc ctcttattct tcctcttctt tcggatctct gtttctcttg  6420
atcatcgaaa acataaatca taggttactc cacttcaatt acctctacct atacaatcgg  6480
ttatcaccgc cgttaacaaa cacgccaccg tcggtgttct tccatttcat aatttccatc  6540
gaataaaaca gcagttacgc aagctcagaa ttgatatcgc ttttgtatta tcttctctgt  6600
tttaaaaaaa aaatgtttta gcacttttaa attttcaagt ctatactatt attcatagtt  6660
atatagtata gtttactatt ttcatatatt aattccatta tattttaagt ttgagttcac  6720
tgattaggaa ctagggttta gtacttaaga tttagtattt gaaaggtgaa gatggaatta  6780
aaaataaagt taaaataaga ttt                                          6803
```

```
SEQ ID NO: 29          moltype = DNA  length = 9127
FEATURE                Location/Qualifiers
source                 1..9127
                       mol_type = genomic DNA
                       organism = Brassica juncea
SEQUENCE: 29
acttgaatcc taaactaaaa tctaatggga ttttgcattt gattttttta tcattcatat  60
aattttattt gattttggtt cttatataat caataaaacc aaaagaaaaa tagtcctttg  120
tctgttaaat attctatgta tataccaaat atcttccata gaaattaaat gaagttttaa  180
atataatttt actaaatttt atcgaaatgt attgaagtgt taatgaaaaa tagagatgaa  240
ttttgttatg aatataaaat aaagaataca atattttgtt tatatttata taaactttat  300
atatatataa attaataatt tatgatttta ttgggactac atatttacat aaaaaaaatt  360
aaaaaagaat attttcatat gattttatcg tttatgtcat attttaaact tgactcaact  420
cagaactgaa aaatattaat ttattgtgtt tattaattta tcgagtatta atttatagat  480
attattaatt tatcgtattt attaatttat agagtttata catgagatca tataatcaaa  540
gttgtgcgag catttatagc atccataagc aattaaaata aatatgccct caaccgtaaa  600
ataaaataaa aatgttttag aataatcatt gtcacttcaa aaaaacccag caaacttaat  660
aatggaaatt tctttctttg ttgtagtcca tttttagctt gctagtatta gtattgaact  720
aataatactc aagtgactca tgtgaccaat gtgccatgca gttttacatg tgcctgccca  780
cacagagtgg accaaaactc tttgctgcat tttttgtggt tagttactta gttatatttg  840
cattcattaa caatccatca agggtcgtac taaattcgga acaacgatcc aacacatctc  900
tagaaatgaa aaccaatgct agatatctaa tcaaaagcac agcacaaagg gtctctctcc  960
actccttgct actctttgaa ttgccattct ctacggcaca tggggcaatg agcttgacta  1020
gtctgtgaat tgacccattt caatatacaa tggagatgga acgaatggtt gcaagctccc  1080
caaactgctc gataaccata taacgatcca ggtttaagaa tacaaataag gggttttagt  1140
tttgaaacaa tcacagtgtg tagaaagaga catgaaaaga gaggagacac gtacttagag  1200
ggcaatcatc tccagggagt ttgcagtctg gacaacaacc gtcgaatggc atacgacata  1260
tcccacatgt ctcatcctga gcatcccatg tccatgacgc aaccgcatgc caccttacag  1320
tttatttttt cacaatgtaa gagttcacgt attggaattg agaatgtatg taacacatgt  1380
agtgggacaa agaaacttac tctgtttttt tttcttttttt tttaagtcag tactagacat  1440
tgtagcactg agagtcaagg aagaaacagt tctttggaca caaaatccta aattaaagaa  1500
actttgagat aatcttcgcc taccttatat aaactagtta agagttgata accaaaaatc  1560
ttcaccgaaa aaaaaaacta ttagaaagtc atctacatca gtattcaaaa ctgaaattca  1620
tgaaaagaga acaactttat gaaatcatga aacctaagct gcatctttaa aaaaacatgt  1680
tttactggaa aacatcaagc attgacgtga acatttggat gcatgattga catgcagaga  1740
agatgaagta gaaggatacg caagatcttg actttcatgt cttcctcctg aatgaaacat  1800
```

-continued

```
aaaaataatc ttatatcagt taaacaaact caacaaagag agaaaacaca aacacaagtc  1860
acgaatcacg cacacacaag acagatcaga gagattaacc taagattaac tataagatca  1920
taggtaaacc taaaatagta atatttcact gatattggtt tctctcagac atttgatcga  1980
acacctggtg gacacttcag atgtttgacg acgattccaa tcaaactcgt tctggaatac  2040
ccactaagaa gaaactcaag aaagtaaaat cctttttttat attaaactct aaatctaatg  2100
gagtgatatc aacagaacgg agcaaaccca tcagaaaatt caaaaactca ccggagtttg  2160
acggagaagc gaactgcgac agagatgaag cggcgagatg tgaatagaag acaagaatta  2220
gttaagatat gggcttttat ttaaactggg ctttatttaa aattgatctc agggcccata  2280
cgtgtgctct tcttaacaag attatatatt atttataaac gacaccaaaa aaaaacgtgg  2340
tttgttttcg ttttctttcg tctttccgag actctagttt catgtgataa aagcaaaaag  2400
agaggtcaaa agaatcaaca ccaatacgat atgctgtgat ttttttttt ttcaaatgtt  2460
gtaattgtta gcggtgaggc tcgtgaagag tgtgtcattg gttcagcgtt actttagttt  2520
caagacaaca ctcgataata tttcgataat cttcaataac tttatggcgt tatgagttat  2580
aaccaagctt tgaacattat ttactacagt gaatcttaat gatgagtatc attcttgtta  2640
accttcgata tatacatgct gcattgcacc accgtcgacg gaacaatttg aagatgtgac  2700
gcaactcgtg ttcaagtcgt acgtgttccg gtaaaggaac ataattatat gtgctacata  2760
accaaaaaat tatttgcaat agatcatgaa agactaaaac gtggaaacaa gcaagaaatt  2820
tggagtaaac tcggtgaata ttgagctaaa gtaagtgaac ccacgggact catcccacct  2880
aaacctctcc caaagtatca ggacaagaaa atacatacgt cactattctt tttgaagggc  2940
tatatataaa ccttagaagg gcacaaggtt ccgtacaaca caacacatat atcaacagat  3000
taaccatgaa gcttctttat ggactcgctt tagtttttct attagctgct gcgagttgca  3060
aagctgatga agaaattact tgcgaacaga acgaaccatt cacatgtggt aacactgata  3120
ttttaagcag taaaaacttc ggaaaagact tcatcttcgg tgttgcatcg tctgcgtacc  3180
aggcatgcaa caaatgctgc cataccatat ttttgacgta tacaaaataa tattcaaaaa  3240
tgctaaaata tccaactttg catggttgtt tctttttatt tcagatcgaa ggagggagag  3300
gtcgtggtgt taacgtttgg gatggcttca gtcaccgata cccaggtatg tccctatggc  3360
atatatctaa tctattaaaa ctaaaataca tttagtactc atatctgatt ttttctaaat  3420
aattatcata gaatgccact gagatttaat ctacacttca ctaattacta ttaggctttt  3480
acgttgtgtt gcaagaataa gtaacaagcc cactaagatt tacattcaca aaactgcatt  3540
tgtatcttct ttttttttta tcgaagcgtt tgtatatctc aaaccaataa aaatgtgttt  3600
catctttggt gcatcacatt cccaaactct tcatgaatgg tttatatgta ttagtaaacc  3660
aaaagtctaa aatcaagtgc cagaattttc actatccatt ttcaacaatt aacaataaaa  3720
ttcactacca aaattactat aataatgtaa ttcacgagaa catcactaga ccggattata  3780
tgtgtaacat gaaatataca caacttttac aaaatcgttt tagtatatag taattgtgaa  3840
tgtgatttca atttaatttt ttaacaaaga aaatcaaaga ttacagattt tctatcaatt  3900
tagttggaca cagaataaaa ataaaaaatta cagatttcct attggtttgg tatatttcga  3960
aaaatttaga tccactaaat attcctaaaa tcattgaaca tcttgctaac ttaacataac  4020
aaaccccctta attaaagtta tcatattaat aacaataata tctacttacg atggagttac  4080
ccaactatat ttgaaatata aaaatacgaa aaaatgaaag ttggtaattt caagttaaaa  4140
tattagactt cttcatattt gttttattat tctaatgctt agactataaa ctattaaaaa  4200
tattaatata taacatgacc ttagtttaaa aaaatattac catgacgtat aataagacaa  4260
aaaatgaaag ttagtgattt ttcattaaaa tattacttat tcatttgtaa aaatatcatc  4320
ttaaattttt atcaaaaagt gtttggtttc agaaaaatat taatattcac tctaattggt  4380
tatatatata aaaaatacaa tatatattat tcatgtggac aatatggatc aaatatagaa  4440
caacttaatg taatatatca ctttgatttg tttatcaaaa tacaatacta tatcgacaag  4500
acaacacata tataatctaa ccaatatttt aaaaaataag aaatattgat gtagcaattt  4560
gaataacaac cgcacggacg tgcgggtccg tacgggtaaa aatctagtat atatttatat  4620
gagataaatg acggttatgt gtatacatat taatgtattt gtaaattact atcagagaaa  4680
tcagggtcag atttgaagaa tggagacact agttgtgagt catatacgag atggaaggtg  4740
aattcttcag tacatatata gattactcaa atgactgaac tatgtataaa aactacgtgt  4800
ggactgaatt gcgtttaaaa taaactgcag aaagatgtag aaattatggg agaactcaat  4860
gctacgggct acagattctc cttagcgtgg tcaagaatca ttccaagtat gaacaaatta  4920
ttcattcgtt tgtattttag ttaggatcat gtagctggaa gagtactaat tgatatacaa  4980
tatacatgag cagaaggaaa ggtgagtagg ggagtgaacc aaggaggtct tgattactac  5040
cacagcctca tagatgcact cctcgaaaag aatataacgc ctttcgttac cctctatcac  5100
tgggaccttc ctcaaacact ccaagatgag tatgaaggtt ttttggaccg ccagatcatg  5160
tatgtgtcat gcttcttaat catatacaaa ttattaataa aaacaagcag aagaatattt  5220
tgtcttaatt acatgcttta ctgaaagaat gattatatat taatatgcac agacaagatt  5280
tcaaagacta tgcggatcta tgtttcaaag aatttggtgg aaaggtgaag cactggatca  5340
cgatcaacca gctattcaca gtgcctacga gaggctatgc actcggaaca gatgcacccg  5400
gtcggtgttc tcctatggtt gattccaagc acaggtgtta tggcggaaac tcttcaacag  5460
aaccctatat cgttgcacat aacgagcttc ttgctcatgc tgcggtagtg gatctttaca  5520
ggaagaacta tgcggtgagt agtcttcata tgtgaaaagg tggtgaaaat ctaacatatt  5580
tgatcctaat ttactcatat atgatgtgac taacaggacc aaaaagggaa gattggacct  5640
gtgatgatta caagatggtt tcttccatat gatgaggctg atccttcttg tagagaagca  5700
gctgacagga tgaaccaatt cttccatgga tggtatatct ttttttttgac atcaaacggt  5760
tattctatta ctcaaaatta aagatggtct aggtaattag attgattata ttgtatgtac  5820
atataatgaa acaaaatata aatggatcag gtacatggag ccgctaacaa agggtaaata  5880
cccagacatc atgaggaaga ttgtgggaag tcggcttccc aacttcaccg aagctgaagc  5940
caaacttgtt gctggttcat atgattttct tggtctcaac tattacgtca ctcagtacgc  6000
ccagccaaaa gctaacccat tgctctcaga gaaacacact gccatgatgg acgctggcgt  6060
aggactcaca tgtacgcatc actcgatctg ctttgttaca acttacaacc tcctttatat  6120
atgtatatat aagatgttca atatatatat atatatatat atatatatat atatatatat  6180
attccttttt gttacaacat acttatttgt gattgaccat cagttatttc ttccttgtgt  6240
ttacagatga taactcacgt ggtgaattta ttggtccact ggtatatatg catgatccac  6300
ccttatgatt tttctttcat tattttatct tcttttccta actgtagtgt acttggaaca  6360
cccacaataa cttcttattt tcttttgatt gatatgtata ttttgtttgc ttccctttct  6420
cagttcattg aagacaaaat agccggcaac agctattatt acccaaaagg aatttactac  6480
gtcatggaat acttcaaaac ccaatacaac gaccctttaa tctatgtcac cgagaatggt  6540
```

```
aagttctaca tattactagt aatctatttt tatttatgct acatatcatc agataattag  6600
tgtactttga tactgagtcc aaagaaactg actttcaaat actgtggaat atttttatgt  6660
gatggcgatt caattaggat ttagtacgcc cagctcagaa aaccgttgcg aagctattgc  6720
cgattacaag cgaattgatt atctctgcag tcatctatgt tttctccgta aggtcatcaa  6780
gtaagtccta ctatacatgc ttttcttcca atatttatct tctttttaag taatatatat  6840
atatgtatat gattgttatt gtttccaggg ataggggtgt caacgtgaga ggatactttg  6900
catgggctct tggggataat tatgaattct gtaaaggctt taccgtcaga tttggactca  6960
gttacgttaa ttgggatgat ctcgacgaca gaaacctcaa agaatctggc aaatggtacc  7020
agagattcat taacgggact tccaagaacc ctacgaaaca agatttcctc cgttcaagcc  7080
tctcctctct caaagccaga agaagaggct tgcttgctga tgcatgaaac acttttcccc  7140
cttcaagatc atctccacgt ctctgatcac tctttctagt tgctccatag ataaggagct  7200
tctaatgtac taaataaaca gatgatcaac tactaatgaa taaaataaat ttatctacaa  7260
gtacattatg tcaagtcaag gaggtgagga taacgcattt taaacagtaa acgtcactca  7320
cacgcacata caaaataaaa actcaaaccg ccaactagtt tagtgtatta aaaatattaa  7380
ggaaatgatt agcctaaatt cagtaattat ctaatacaaa tctaaaacta actaaacgaa  7440
agtacaacaa taatttaaca atccatcaag ggtcggtcgt attaaattcg gaacaacaat  7500
ccaacacatc tctagaaata aaaaccaatg ctagatatct aatcaaaaca cagcacaaag  7560
ggtttctctc gctccactca tcattactct ttgaattgcc gttctctacg gcacatgggg  7620
caatgagctt gactcgtctg tgagttgatc atttcaatat acaacggaga cggaacgaat  7680
ggttgcaagc cttccaaact gctcggtaac catatacgat acaggtttaa gaatacaaat  7740
aaggggtttt agttttgaaa cagacaaaaa aaagtttcgc atgattttca taaaaccatc  7800
agagtgtgta gagagacatg aaaaaagagg ggagaaacgt aaccatttta ggaatttgtg  7860
ggactaggtg aaaagtgctc tgttcatgct tttgtatgat gaggactgtg attctgtggg  7920
tccaaacact attgaaatgc cctgtagcat ttatacaaac tttgaaacag agcacaaagg  7980
gtctcttaat tcatgtttta ttcttcaaaa tttgaacaat ttatcttaat tcatcttttt  8040
tttttgctaa ataatctata catataagcc aaatttttgg ttgtatatat aaagggtatt  8100
taaggtttca tttcaaacta gatcctttgt caaaaagttg gtatatgcag gttgtcattc  8160
tagacaaaat cattcatatc taaacaattt taatgatgtc tgcttatttt aatatttgaa  8220
aactttttat ttttctgttt ttaaaagaaa aaacgaaaaa gaaaactttt taataatacc  8280
cattaagact tttgtttgat cgtgaattat ttttatcata aatatttgta cgtcaatgta  8340
ttttctaggt tccaatctta acaaaatgta taaatctatt tttttagaat ctgtattatt  8400
aaaacatatg tacgaattca aaactaactt tgttcttatg tattacaaaa tatatccatt  8460
ttaattatca tatatattat tttgtaaaaa taataaaaat tacatgttaa cgttagtcaa  8520
aaatcaaaat tctatcagtt gtgactatat atatcccact atcttattta atttcgtatg  8580
attataattg tatattttca gataattata gaaagtatta tatgcatagg gaaaaaaatta  8640
aggaagtccc cattaaaaat tatattcgcc ttaaacttaa ttggaaaaaa ttatataaat  8700
tttcaaattt aatatatgcc accatttatg ataatttgta atcaaaaagt atttttgaaa  8760
aaatttaagg attgcaagaa atttaatatg gaattccttt ttgaatgtat tttataattt  8820
tcaagattgc tcataaattt ttatatacga catttttgata ttacaatata aaataattta  8880
tattgtttat cctaaaataa atgtcatgta tcccataaaa tacaaaaaat attcatcaaa  8940
ataaatctca tgtactaaag ttttatagaa gaacaaaatt atgaatcatt catatttttc  9000
agtccctaaa aaatatcatg tataatttag agtcgtaaag aaatttaata ttataaaaat  9060
atgaatcata tatatagtca aaactctatc aattgatatc ttattatcct attaatttcg  9120
tataaca                                                            9127
```

```
SEQ ID NO: 30           moltype = DNA  length = 9836
FEATURE                 Location/Qualifiers
source                  1..9836
                        mol_type = genomic DNA
                        organism = Brassica juncea
SEQUENCE: 30
ttacatgaat ataatatcct ctcttacaaa ggaatcaaaa tatttctata ctaacaagtc  60
attgtttacg gtttttatta tagttatgag gaagatagtt accatttgct tccaacagcg  120
gaaacattat ttcaagacag gacattagaa catatagctt ctccattaga acatatagct  180
tccaacagcg gaaacattaa tggagtaatg aataaaagat aaaagcatta tatattaatc  240
cattttccac tccatttact ctataaatgg agtaaaatat ggagtggaga tgaaaatgcc  300
cttactatcc atccatgctt ctttatgttt caaatacatg gacgtctgac aatccaaagg  360
ttagcgaacg acttctttaa tatttgcatt taagaattgt tttggaacag tttcaatcat  420
acttaatata ggacgtacga attacacatt atgctgaata tataaatagt tgaaggaaaa  480
aaatcatctc tttcagacac acccgaaagt aatgcaagtg gcttagacat gaaagcttga  540
acctcttcca taagtggatt aagtgacaca tcggagacgt tgtatgcagt ggagatgctc  600
tgattgtcta gtgaacaatc gataactgac taccatcgag gacaccacga taactgactg  660
gctggaaacc cgtcaaatct tgcaagcgtt gtttaacaat cgctacttac agctaccagt  720
caccagtcag atgtcttcca ccaccagcac cgatgctgcc gatctttctg gtcagaacat  780
caccataaag cgttggccaa caaggttggt tttggactaa atgttttgtg tttgcatttc  840
tgaatttcat attgtaatat gtttgaaggt tgtaccttta aatctgatat cttattgtgt  900
atactattgt gtttaaattg gtaataatgt atcgtatacc ctatgtgttt gaatgtttat  960
cgtttccaaa aaaaagttgt ttttctatca tatcataaag attattgttt ccttcaggcc  1020
gtggaggaag aatgcaacgt tgcctaagat atgaaatata gagttatgcg gcatgtaatt  1080
gcgcatggat gtaggatgct tacttcagat acaaaattat cttccccaag acacaagtca  1140
tgcaataaaa agtcgctcag attatcaaga taactgaatg atatccattg atatattcaa  1200
taattcctaa atgttttctc tcactatgca gaaagatatt tacattacaa atgacagctc  1260
atgcacaaac atgtctgcac tgttcctgaa ccaatcttct caaggataga atgatagacc  1320
attttatgaa tttgtgggac taggtgaaaa gtgctctgtt catgcttttg tatgatcggg  1380
tctgtgaatc tgtgggtcca aacactattg aaatgccatg tatcttttat acaaactttg  1440
aaacacttct ctaacgtaat agaccatgtt aaactcacca cacgcagcgt aaataacaaa  1500
acctatttta acttactttt tacattttct tcattcactt tttaactaat tttaactact  1560
tcatttatga gttgattaca tagaaggaca cattttatct ttgtcttacg ctgagaaaca  1620
cttcccactt gtaggacact ttctggtggg atcaaggggt tggtttgtca aaattgccct  1680
```

```
tgtagaaaaa ggtggtgttt cgttggagat aacaaaccag tttccttttt tctttttttgt  1740
gtcactgtct tcaattaaat aacttttgtt gcatttatat ttttaggttt atagaaaaaa  1800
tggattcttg tttacaccgt tgtattaaaa aaattgctat taaatcgaat ggatgaggtt  1860
ttccaccgtt tgattaaaat ggttgctata aaatcgaatg gctgagattg aatcttggag  1920
agtaggttag tttgaccata aaaaatttcc cttgtggatg gctgagttgt ggtcggctga  1980
gtgatttatg cccaaatgat atgttgtgga cgggtgatgt ttggatgggt gaagaagcag  2040
agaagaagca gcagtggggt tttggccatt catgtggtcc acattaccgt tcctcactca  2100
ccatcaccac cagcaaaagc attgacattt tgtgggtaat gtacataaga aagtggatga  2160
attttgtaga taagagaaat ataaacaata gaactgcgta taaattcaaa ttagagatat  2220
acatcagtgt tttatcttgg tttttgtgga cataatctcc gaagcaaaat gttgtggaaa  2280
acatctaatt aacaaaaagt gtggatgtgg acaagtgaga acattctttt ttaccattct  2340
ttttcacaat tcttttttgt tttgtttcta atatctaaaa acatagataa tatataaaac  2400
atgcatatat atatttttct ttttgctatt ttataaaaaa atatcttatt agatatttta  2460
tggatataaa tagtatttat atgaattttc ttcataaaag aattgttgtt aggggtgaaa  2520
gcgtataatt aaaagtatgg gacaaaatca agagaatcta taagtaaatt aatgaatgtt  2580
ggggtcaaat tgcgtatatc caaaacttaa aggaccagat ttgtaatata gaggaacttg  2640
accattgttg tttcacgagg tttctctgca acggaaccga tgacgaaggc tcctaccagc  2700
tgcaacggcg gattcagagc atgaagatct tggtttgaga accattttgt ctttcaattt  2760
ctggaataca accactgaat cagaagaaca cagaaataat ttttcagaaa atcaaaacag  2820
ggaaatagaa ttgaatcgga gaaaaggcaa taaccagtga cctcgaggat ctggccatgg  2880
atacccaaca tttttctggg aaatcggagt gtgcaaatcc cattggagga aaagagaagg  2940
agaaagagga aaaacattcc aaaattatat aaactcttcg tgaaattgga tgaatgatgt  3000
tgtttgcagt gaatcattgt ttggttggtc gggactatgt gctcaccgac attttagagg  3060
agagagagat tcagaagact gaaatgataa ctaagcttct ctcttatttt tttttcatta  3120
cacaaaaaaa acaaatgttt agagttaaag ggtagtagag actttacaca acctaaaagt  3180
gtgccacatg ttgtaagtgc cttaaagtgt aattcaaatc acaaaatgtg tctctgaacg  3240
taaaaaaaat cttcatttat ttatttttcc aaataattcg acatcattta ttatagaagt  3300
acaaaataaa acttatctat ttttttagta tttttgtaac attttttaca tttctttttt  3360
cactattcct aactaattca ttgattgtat ttacaataat aattcgacat catttatctt  3420
acgtgttaac cataatactt tcgcatgttt gaatgaaatt gctccatttt gtaacaaata  3480
atttttggt tatctataga atcagttaga catagtgttt aggtacccat tcgggtacgg  3540
atcaattctt ttaggtatcg aatatttggg ttctaaaatt aaattatgtt cggttataat  3600
aattttatgg acgtgttcga gttggattct tccgaatccg taaaaattcg taagaaccta  3660
aaaatatcta aataatctat atatttagaa atgtcattaa acatccgcaa gaacgcgcgg  3720
gtcagtctct agtttttata aacccagaaa catataaacc tgtgtttgtc tatttgaatt  3780
ctacatggaa gttttgtacg ttttaaatat gacgactgct tgttgttcag tcaagatgat  3840
tgttatccgt aactcgtagc ttaatatcta tagtgctttt ttttcatggc agtttgtaga  3900
aagagcatgt taacctaaga aaaaaaccag tataatttcg taacataaat gttacttaaa  3960
ctcaaagtat tatttatggc ccatcctaat aaatcgaagg cctaaagcac ataaatttaa  4020
atgttttatt cttaaaaaca tgatcattta ttttagttca tgtttaaagg cgtagctttc  4080
tactgtttca agcattttaa aagttttttt ttttttttga aaaaagaata gaagaatctt  4140
ttgtcaaaaa agttgtatct aattatgaaa aatataacta aaatgtatga attctaacat  4200
aaaatgtaga attaaaacta ttgaataaac tatataggtt aatacacaag gttccttttc  4260
tttgccaaat atgtgaacta ccattaaaat gggaaagaaa atacaaaatg ttcttacatt  4320
tcaacccttc caatcatcta aaaacgatac caaaaaacgt ggttttcgtt ttctcttgtc  4380
tttcagagac tctggtctca tgtgataaaa gcaaatagag aggtcaaaag aatcaaaacc  4440
aataagatat gcatgcgggg gttttttttt tttggatatg ttgtgattgt tagcggtgag  4500
actcgtgaag agtgtgtcat tgggtcagtg ttactctagt ttcaagagtc gataatattt  4560
cgataaaaat cttaataact ttatggcgta atgaccaagc tttgaacatt atttactaca  4620
gtgaatctta agatgcgtgt cattctttta accgtcgata tatacatgct acattgcacc  4680
actgtcgacg gatcaatatg aagatgtgac gcatctcgtg ttcaagtcgt acgtgttccg  4740
gtaaaggaac acaaatatgt gctacataac cagaaaatta tatgcaatag ataacgaaag  4800
actgaaaagg tggaaaaaag caagatattt tgagcaaaat ctgtaaacat taagctaaag  4860
taagtgaacc cacaggactc atcccaccta aacctctccc aaagtatcag gacaagaaaa  4920
tacatacgtc actattcttt ttgaagggct atatataaac cttagaaggg cacaaggttc  4980
cgtacaacac aacacatata tcaacagatt aaccatgaag cttctttatg gactcgcttt  5040
agtttttcta ttagctgctg cgagttgcaa agctgatgaa gaaattactt gcgaagagaa  5100
cgaaccattc acatgtagta acactgacat tttaagcagt aagaacttcg gagaagactt  5160
catcttcggt gttgcatctt ctgcgtacca ggcatgcaac aaatgctgcc ataccatatt  5220
tttgacgtat agaaaataat attcaaaaat gctaacatcc aactttgcat ggttgtttct  5280
tttcatttca gatcgaagga gggagaggtc gtggtgttaa cgtttgggat ggcttcagtc  5340
accgataccc aggtatatat atatgagatg aatgtcggtt atatgtacac atactaatgt  5400
atttgtaatt actatcagag aaatcagggt cagatttgaa gaatggagac actagttgtg  5460
agtcatatac gagatggcag gttaattctt cagtacatat atagattact caaatgactg  5520
aactatgtat aaaaactacg tgtggactga attgcgttta aaatatgtaa actgcagaaa  5580
gatgtagaca ttataggcga actcaatgct actggctaca gattctcctt tgcgtggtca  5640
agaatcattc caagtatgta cataaatttg tatatttttt attgggatca tttagttgga  5700
agagtataca aattaatgta tgatatatat gagcagaagg aaaggtgagt aggggagtga  5760
accaaggagg tcttaattac taccacagtc ttatagataa actcctagaa aagaatataa  5820
cgcctttcgt tactctcttt cactgggacc ttcctcaaac actccaagat gagtatgaag  5880
gtttcttgga ccgccagatc atgtatgtga catgtttctt aattatatac aatttttaat  5940
aaaaacaaga ataagaagaa gattttgtct taattacatg ctttactgaa agaatgatca  6000
tatattataa tatgcacaga caagatttca aagactatgc ggatctatgt tttaaagaat  6060
ttggtggaaa ggtgaagcac tggatcacga tcaaccagct atacacagtg cctacgagag  6120
gctatgcact tggaacagac gcaccgggtc gatgttctcc tatggttgat tccaagcaca  6180
ggtgttacgg cggaaactct tcaacagaac cttatattgt tgcacataac cagcttcttg  6240
ctcatgccac ggtagttgat ctttacagga agaactattc ggtaagtagt cttcatatgt  6300
gaaaaggtgg tgtaaatata acatatttga ttctaattta ctcatatatc atgtgaccaa  6360
cagtcccaaa atgggaagat tggacctgtg atgataacaa gatggtttct tccatatgat  6420
```

```
gagtttgatc ctgcttgcgt agaagcagct gagaggatga aacacttctt tcatggatgg  6480
tatattgttt ttgtttgaca tcaaacaagt attctattaa aaacctagag gtggtctaga  6540
taactagaat gattatactc tatgtatgta taaagaaaca aaatataaat ggatcaggtt  6600
tatggagccg ctaacaaagg gtagataccc agacatcatg agacagattg tgggtagtag  6660
gcttcccagc ttcaccgaag ctgaagccaa actcgttgct ggttcatatg attttcttgg  6720
tctcaactat tatgttactc agtatgcgca gccaaaagct aacccattgc tttcagagaa  6780
acacactgcc ttgatggacg ctggcgtagg cctcacatgt acgcattact ctgtttccac  6840
tttgttacaa cctcctttct atatatgtat atatattcct ttttgttata acatacttat  6900
ttgtgagtaa ccatccgtta attcttcctt gtgtttacag ataataacta tctgggtgaa  6960
aatattggtc cactggtata tatcatgatc cacccatgat ttctcctttc attatttgta  7020
gtgtacttaa cacccacaaa aaaaaaaaac tattttctga ttgatatgta tattttgttt  7080
gctccctctc tcagttcatt gaagacaaag ttaacggcaa cagctattac tacccaaaag  7140
gaatttatga cgtaatggac ttcttcaaaa ccaattacag caacccttta atctatatca  7200
ccgagaacgg tgagttctac ataaattact actcatctct tttcatctat tctatacata  7260
tcatcagata actagtgtat tttgatatta gttcaagaaa ctgattttca aattttgtcg  7320
aatatttcca tgttatggcg gtttaattag gatttagtac gcctggttca gaaggccgtt  7380
gcgaagctac ttctgattac aaacgaattg attttctctg cagtcatcta tgttttctcc  7440
gtaaggtcat caggtaagtg gatgctacta tacatacttt cttccaatat ttatcttctt  7500
tttcttcttc tttttaagta atatatatat atatatatat atatatatat ttatatatat  7560
atgattgtta ttgttttctg cagggagaag ggtgtaaacg tgagaggata ctttgcatgg  7620
gctcttgggg ataattatga attctgtaaa gggtttaccg taagatttgg actcagttac  7680
gttaattggg atgatctcga cgatagaaac ctcaaagaat ctggaaaatg gtaccagaga  7740
ttcattaacg ggactgccaa gaagaatcct gtgaaacaag atttcctccg ctcaagcctc  7800
tcctctcaga gtcagaagaa gaggcttgct tgctgatgca taaaacactt ttccgctcgt  7860
caagatcatc tttttgtctc tcacacttcc tagttgctcc atagataagg agcttcttct  7920
acctacagtg tactaaataa aaggcctcaa taaaaagatg atcaactacg tactaaaatc  7980
tttttcagaa aaaaaaaaac tacgtactaa tgaattaaaa taaaatatct ataagtgcaa  8040
tatgtcaagt caaagagata tctataagtg caatatgtca aggcgacgca ttttaaacag  8100
aaaacaacta gttttgtgtg ataaaaatat tgaggaaatg attagcctaa attcactaat  8160
tattttaata caaactcaaa actaaactag accaaagtcc tataatccta aaataaaatt  8220
taatggtatt ttggatgtga tatattttta atcattcata taatttaatt ttattttggt  8280
tcttatataa tcaataaaac caaaagaagg tacagtagtc ctttgtgtgt ttattaatgt  8340
ttctccgttg tagttttgtc tcatagcaca tcacatgttt aaatggtcta gtaaatgttt  8400
tcgtttaggt tattaaacac taggtaagga atccgtgcga tatcgcacgg gaattcattt  8460
tgtaaaaata atataccata ttttatataa ttttttagtt agataaataa atgtgttgca  8520
aaaataatat accatagtta gataaatgtg ttacaaactt attgacttag attccctaga  8580
cactaaacca ttttgtaggt cgaggtccac gatgatccct ccattgtact gtggcttatt  8640
agggtttcct agacactaca acaggacatg caatggtttt tttttttttt gaacaaagga  8700
cattcaatgg taatcaatgt gagtttggtg ttgtggtggt tccacttacc aattgggaag  8760
ttctctccta taatcacaaa ccagcaaact caagagcatg aaatatttat agtttttaga  8820
aaatttatat gaagggtcat gttttttgtt aactgctgat gtcaactttt tttataggca  8880
aaaaatattt gtatccaaca atcacgcttg ctttaattat gtaatccaac ggacaatatt  8940
ttgttgcctt taaaaaataa cgtcaacgtt tattaaagca aacgtcatct tttgtcttcc  9000
cccgaaccaa cacctttttc agatgaaaaa tggcacctcc ttaaaagatt tatacaggtc  9060
atcctctcat aatcgtcttc ctttcaattg gtctctaata tcaacttagt tttcgtcaat  9120
caaatttgtt gtcttgctct atttgtggcg gtgacttcaa ccggcaggga gaagaggaaa  9180
tattttaaca tgtggcgaca catgaccaca tggagaaagg agaagatagg ttcacttatt  9240
aagcttctta gaagaacatg taccttgaca atctatgata aagagatgaa cagaaaaata  9300
atgcacagat gaacgaagag gttaaataga aagcagaaat tagaaatcag caaaagaaaa  9360
agaattttga aagaagagaa actatacact ggttatcaaa aatataaacg aaggaagaga  9420
tgcaaaccaa gagtcataac tctatcaatg gacacaatga ttcattaccg acataataag  9480
tcttcggatg cgtcgtcttt tgttttttgt caaaacaaaa ggtgtgctaa tctcaaccgt  9540
tacctgtttt aaaaagaaaa ttactatata tattatgaaa aggaacaagg acttcatttt  9600
ttattacggt tatgtgtaat agaaactcaa acatgaaaca tgtgtcatgt tcatgaaaaa  9660
gacaaatcaa agatacacga tttgtaatta tgagaaacaa acctttttcat ctagtaaaaa  9720
aataagacta cttatttcat tatttcgttt tggattttttg gttattcaaa cacgtataac  9780
tcttcctact atttttttgtt gacaacactt catttaaata tcttttaaaa atttgt      9836
```

```
SEQ ID NO: 31           moltype = DNA  length = 6448
FEATURE                 Location/Qualifiers
source                  1..6448
                        mol_type = genomic DNA
                        organism = Brassica juncea
SEQUENCE: 31
ttatataaat tttaccctca gttaagttgt tttaaatgtt ttcaaatgta tttgggtttg  60
ttgtatttta tccaatttta tttaaattct tttgagatct taaatattaa atgaattcga  120
agatacatac ataaaaattt caaacattat ttttgttatt ttgaataaag aaagaacgat  180
taaaactaaa actatactaa atttttaaaa gctagataaa tccttatata tatactgtat  240
ataatttatg tatacatgag tcttttcaaa tttattttac gtattaaata attttattat  300
actaagaatc tgtcatatgt aaagaattga tatttgattt attactaaat atttcaaatg  360
aatgagtgtt tcaagtttaa tttaagtact aaagtattta ttgaaatatt tatgttacga  420
tgaaaaactt tgtatataaa aaattattat ttaataatga tatttgaaag gataatgtat  480
ctatatataa atattttaaa tattattatg ctcgtccatg ctggcaaaac acctactaca  540
atatatttag aggaaaatat ttaacagtta attttttggt ttaacttatt attattaatt  600
ttcttcagtc agtttttcct agagaaaaat ctgacagtat ctttcaattt tttttaaaaa  660
aatctaaaat ataaatctta aaataagaaa attatttctt tttttcatta ccgtattaca  720
ataattgtca atggaatcta tgattttaac tcatataaaa atcgagtcct tctgatcatg  780
attactacat tttcacacta agatttaact atttaatcaa aaccacttca caacagttaa  840
accaatcaaa aaattattat attaatctga accttaaaca atcctcacgc tccaatgcat  900
```

-continued

```
cgaacgtaac ggtaacacac caaaccaccg ttaaaaagca tatatagaga ggtcaaaaga  960
atcaaaacca ataaaatata ctgtgattgt tttttttttg acatgttgtg attgttagcg  1020
gtgaggctcg tgaaaagtgt ggccttggat cagtgttact ctagattcag cacttgatag  1080
tattacgata aaaatcttca ataactttat ggcctcatga cgaagctttg aacattattt  1140
actactacgt acagccaatc ttgataattc gtgtcgttct agtttcgcac aaaccttcga  1200
tatatacatg ctgcattgag ccacagtcga cggaacaatt tgaagatgtg atacaattcg  1260
tgttccaagt cgtacatgtt ccggtaacag aacaaaaata tgtgctaaca aaaaaaaaat  1320
attcgcaata gataatgaat gactaaaaag tggaaacaga caagaaattt aaggaaaaac  1380
ggtgaacact gagctaaagt tcgtgaatcc acgagattca tctcacctaa acctctccca  1440
gaatatgaag acactaagac aagaaaattc atacatcact cttctttagg aatgtctata  1500
taaaccctag attggcacta ggtttcatac aacacaacac atacaacatc aacagactaa  1560
acatgaagct tcttcatgga cttgctttag ttttcctatt agctgcttcg agttgcaaag  1620
ctgatgaaga aattacatgt gaagagaaca ctccattcac atgtggtaac actgatattt  1680
taagcagtaa aaactttgga aaagacttca tcttcggtgt tgcatcttct gcttaccagg  1740
catgtaacaa atgttgacat accatactat aaataaatac aattcaaaga gctaatttcc  1800
aactttgcat ggttgtttat tttcctttca gatcgaagga gggagaggtc gtggtgttaa  1860
catttgggat ggcttcagtc accgataccc aggtatgtcg tttttgcacg gtgacgtacg  1920
tgtgtatata tatatatata tataatgtac acatattaaa gcatttgtaa ttactatcag  1980
agaaatcagg gtcagatttg atgaatggag acactacttg tgagtcatat acgagatggc  2040
aggtcagtac attgatactc acatgactga actatgtata aaaaaaccta tacgtgtgat  2100
tgttgacatg ccattaaaat atgtaaactg cagaaagatg tagacattat gggagaactc  2160
aatgctactg gctacagatt ctcctttgcg tggtcaagaa tcattccaag tatgtacata  2220
ttattgattg ttcgtaattg ggatcgttta gttggaaaag tactgattaa tgttttggca  2280
aaaaaaaaag tactgattaa tgtacaatat atatatgtat gcacgagcag aaggaaaagt  2340
gagtagggga gtgaaccaag gaggtcttga ttactaccac caactcatag acgccctcct  2400
agaaaagaat ataacgcctt tcgttaccct cttccactgg gaccttcctc aaacactcca  2460
agatgagtat gaaggtttct tagaccgcca gatcatgtat gtttatattt ttgccatgct  2520
tcttatatta ttaataaaag acgaaaaaga tttggtttta gtaacatgca ttactgaaat  2580
gattatacaa taatatgcac agacaagatt tcaaagatta cgcggatcta tgtttcaatg  2640
aatttggtgg aaaggtaaag cactggatca cgatcaacca gctatataca gtgccgacaa  2700
gaggctatgc gagcggaaca gatgcacccg gtcgatgttc ttatatggtt gataccaagc  2760
acaggtgtta cggcggaaat tcttcaacag aaccctacat cgttgcacat aaccagcttc  2820
ttgctcatgc cgcagttgtc gatctttaca ggaccaaata taaggtgagt ggtgctccat  2880
atgtgaaaat tagggtggtg taaatctaac atatatctga ttctaatgta tagtcatata  2940
tatgtatcac gtgaccaaca gttccaaaac gggaagattg gacctgtgat gataacaaga  3000
tggtttcttc catttgatga gtctgatcct gcttgcgtag aagcagctga gaggatgaac  3060
caatttttcc atggatggta tttatatata tatatatata tatatatata tatatatgtg  3120
tgtgtgtgta ttaccaacaa tgtatcagta tgtattttat gtatttataa tgaaacaaaa  3180
atatacatgg atgatggatc aggtacatgg agccgctaac aaagggtaga tacccagaca  3240
tcatgaggca gatcgtgggt agtaggctcc ccaactttac cgaggaagaa gccgcactcg  3300
ttgctggttc atatgatttt cttggtctca actattacgt cactcagtac gcccagccac  3360
aacctaaccc atatccttca gagacacaca ctgccatgat ggaccctggt gtaaagctca  3420
catgtacgta cttcagtaat attaccactt agtacttatc aaaaaaaaaa aaaattacca  3480
cttagttaca acctttctat atatgttttt ctccttttgt taacatactt tgtgagtgac  3540
tatcaattat ttcatccttg tgtttacaga taataattca cgtggtgaat tacttggtcc  3600
actggtaata tatgaatgat ccacctctac gatttctctt ttttttaatc aatattttct  3660
atttgcaata gaacaccact gattatgttc tcttgattga tatgtatatt ttgtttggtt  3720
ccctttctca gttcgctgaa gacaaggtta acggcaacag ctattactac ccaaaaggaa  3780
tgtattacgt aatggacttc ttcaaaacca attacagcaa ccctttaata tatatcaccg  3840
agaacggtga gttctacata ctacttacta ctcatctatt ctacataaat taactagtgt  3900
attttatata ttagtccagg aaactgactt tcaaatatcg tggaatgttt tcatggttta  3960
attaggaatt agttcgcccg gtacagaaaa ccgttgcgaa gctattgccg attacaagcg  4020
aatcgattat ctctgcagtc atctctgttt tctccgtaag gtcatcaggt aagtagatgc  4080
tactatacgc atgctttttc ttccaatgtt aatcaacttc tttctctttt ttattttggt  4140
aaaatcttct tcttctttgt ctttttggta atatatatat gattattctt gttttcaggg  4200
agaagggtgt caacgtgaga ggttatttcg catgggctct tggagataat tatgaattct  4260
gtaaaggctt taccgtcaga tttggactca gttatgttaa ttgggatgat cttgacgaca  4320
gaaatctcaa agaatctggt aaatggtacc agagattcat taacgggacc gtcaagaacc  4380
atgcgaacca agatttcctc cgctcaagcc tttcttctca gagtcagaag aagaggctcg  4440
cttgctgatg catgaaacac ttttgtcccc cgtcaagatc gtctccacgt tctcttatca  4500
ctcttactag ttgctccata gataaggagc ttcttctacc tataacaatg taataaataa  4560
atattctcaa taaaaagatg atcaaatact aatgaattaa agaataattt atctacaagt  4620
acattatgtc aaggaggtga gggggaggat aacgcatttt aaacagtaaa cgtcgtcaga  4680
cgcacatcaa aaccgatact gtaaccctgt ggttactttc ttaatttcca ctccaataag  4740
tgttatttca ccaattcacc ctattatcat catatgacaa agtgtttaaa ttgtgttaca  4800
aaaaaaaaac aaagtgttta aattatatgg caaaacctta ttatcactca ccatatgaca  4860
aagtgtttaa attgtgttac aaaaaaaaaa aagacaaagt gttttaaaca gtaaacgtca  4920
tcactctaaa aaacaaatat tttcaatacg tattgtatag tttatatgca tattgttcag  4980
aacagtgaaa ccaacatttg attatgcatg atattgtaaa aaaaaagttt tggatcttat  5040
ttatttgata tgggaaaagc ttattctccc gtcaaatagc aaaatcttat tatcatcata  5100
tgacaaaatg ttcaaattat atggcaaagg cttttacata gtctgatatt tacggatggg  5160
ttataggtat tacaaaactc tattggacct aattaagagc accctcatcc gggggtgtgg  5220
gggggggggg gggggggggg gtattaattt gaagttgtta aaaataaaaa attaatattt  5280
taatgtgttg tgtttgtgta tttaatttta attgtttcag ataaatatca actaattaaa  5340
gataaacatg tgtcatcaag tttttaaacc tgttcggaaa atgtgggtgc agagaaactc  5400
tgccattcct ctttcctact tttatatata tactagggct tggcccgccc tacgggcggg  5460
tgaaaatacc actttttact ttgttataga acacaaaatt ataaaactaa aaatttattg  5520
aaaatgcaat aatttatatt atgatcgaga tcagatagaa agcgaatccg taagattcaa  5580
atacccaatt ggatgcagaa tcagacttta tgcatgttac tactatatta agtgtaatgc  5640
```

```
gatatttaaa attaaacaaa attatcatga aaatgattgt tgcatgcttg tatatttgac  5700
actgaagatt gatctaataa tagtatatta agtacaaagt tacataagaa aattaaagat  5760
ctaaggggaa gacgaaacat tactacttca gatgcttaaa atcgtggaaa gaagtagtta  5820
tgttaacccc caaaaaaatg ataataatat aaataaagat gaaacatatt ttttccttct  5880
tggtgttgcc ttttctaatg cttttttttg tggatggaga cttagattca ccattaacag  5940
aaccatggtt caaagcccct gaactactta tcatctctcc acttctctct ttaaaagacc  6000
aaatcttcaa gaacactcta gaaacaccca acatcctcct ttcatcagtt ttcctttatt  6060
gctcttttgt ggttgattct ttgtgagtca tcgattctct aatttgcctc tcagtgctct  6120
tgtatcatct gggtcaccac acctatgtcg tctttggtgt ttgatgatct tgaagttggg  6180
gcgatctctg acatattttt ccccgcttga tgatgaacca tagttgttag ttcttacaca  6240
ttcgaagcag atcacttatc caccactcac attggtaact tctcgttttg aacagcatgt  6300
gcgcaagctt ccacccataa cttttcttca gtccattaac ttagttccaa tgggttctga  6360
cttatgatgc tatgaaccca agtataaggc tcgacactct agaaccgaac tccaaaccaa  6420
gaaacacaat cttgtgactc tttggtat                                      6448

SEQ ID NO: 32           moltype = DNA  length = 6492
FEATURE                 Location/Qualifiers
source                  1..6492
                        mol_type = genomic DNA
                        organism = Brassica juncea
SEQUENCE: 32
ggtatcatat taattgtgat atataaaatt ttcttataaa aaattatatt ttacaaaggt  60
tttaaatatg ataataaaaa acaactcaga tatcatcatt aatgtcaatt ttccatataa  120
atgtttattt ttggtaaact attaaaaata ttaaaaactc ataaatcact acgactaata  180
atatatatat atatatatca cattaataaa aagaagctaa ataagattac ttttacatca  240
acttatatag aatatttgta taaatataat tgtaaatatg catcaaaaaa tacaaaacta  300
aagtaacaac aatcgaaaaa attgatagtt aaatgtttaa acatttattt aaatttatat  360
gttcatcttc atcatgttga ttaccaaatt gatttctcag tttaacatat tttaactaaa  420
acaaacaatt ttagtaacaa tatatatata tatatatata tatatatata tatatatgta  480
tttaaaataa gtaatcatta aatatagtat aatataatta aatgtaattt tatttttatt  540
aaatttaaat ttaaataaaa tcaaatttaa atagttagac caaaccaaaa gaaataagat  600
tacaaaaatg agtttatgat tttttttaa ctattgaagt gaaaatataa aataataata  660
ttagaaatat aaatcaaaat tttcttttat ataaaaaata ttatatttaa aattattatt  720
aaaaaatatt atacacctag taaatttgga agccaatgcg aatgttcatc cacataagcg  780
gttctgcttc tattagtgtg taaatatatg ttaatatata tatatatata tattatttat  840
gtgtgtgtgc gctacgtaaa taattgcttt caaactcaag ttggtggcac gtaaccagta  900
ataatgttat ctatagaaac ttaacatatg tactatggct atttatagca aaacttatga  960
attctaactt tctagagtaa aaaactatgg aacaaactat agtttaatac acaagtatca  1020
atcttatcta tctggaagtc acggatccgt atccgttcca acccttccaa tcatttaaaa  1080
cgataccaaa aagagcaaaa aaatgtggtt agttttcgtt ttctttagtc tttcggaggc  1140
atcggtttca tgtgataaag cagaaataga gcgatcaaaa gttcaataga tattaatgtg  1200
atctgctgag cagtaaggct cgtgataatt aagtgtggct ttgcacaagt gtttctctag  1260
attcaacaat tgacaatatt tcgacataca tttttgataa cgagtcttga cgttgcgtgt  1320
cgttctagtt ttgcgcaagt cttacatgct gcattgcaac attgcatgat ggttgacgga  1380
tcaatttgaa gatgtgtcaa ttcatgtacc agttaaggaa cacaagtttg tgcgatctaa  1440
caaaatttgt ttacaataga taatgaaaga ttaaaagtgg aaacataaca atcagaaata  1500
ttacaaaaat cggtgaacac tgagccaaag taaatgaacc aacgggactc atcatgatcc  1560
cacctacacc tccccaaaaa tcaagatttt ttttccccaa atacataatc cactcttctt  1620
ttcgaaaggc tatataaaac ctagatgggc acaaggttcc acacaacaca acacaacaca  1680
tacatcaaca gattaaacat gaagcttctt catggactcg ctttagtttt tctattagct  1740
actacgagtt gcaaagcaga tgaagaaatt acttgcgaag agaacaatcc attcacctgt  1800
agtaacactg atatattaag cagtaagaac ttcggaaaaa atttcatctt cggtgttgca  1860
tcttctgctt accaggcatg tagcaaatgt tgtcataccc cacttttgaa ataaatttta  1920
aagcactaaa atgcaacttt gcatggttgt tcttcttatt tagatagaag gagggagagg  1980
tcgtggtgtt aacgtttggg atggcttcag tcaccggtac ccaggtatgt ggtttgcacg  2040
gtgacatata tatttatatg cgagaggaat gttggttaca tatacacata ttaatgtatt  2100
tgtaactaaa atcagagaaa gctgggtcag atttgaagaa tggagacact acttgtgagt  2160
catatacgag atggcaggtt aatttctcag tacattaata ctcatgactg aactatatat  2220
gtataaaaac tatacgtgtg gattgacatg agactaaaat taatatgtaa actgcagaaa  2280
gatgtagacg tgatgggcga aatcaatgct actggctaca gattctcctt tgcatggtca  2340
agaatcattc caagtatgta catatcaacg atcaatgtat atatatatat atatatatat  2400
atatatatat ttgtatttta attgggataa tttagttgga aaggtactaa ttaatgtacg  2460
atatatatct acccgagcag aaggaaaggt gagtagggga gtgaaccaag gaggtcttca  2520
atactaccac aaactcatag atgcactcct ggaaaagaat ataacgcctt tcgttaccct  2580
ctatcactgg gaccttcctc aaacactcca agatgagtat gaaggtttct tggaccgcca  2640
gatcatgtat gttccatgct tcttaattat atttgaagag agtcaatatt attagtgata  2700
gaagaagatt tagtctcaat tacatgtatt actgaaatat ttctatacta atatgcacag  2760
ccaagatttc aaagattacg cggatctatg tttcaaagaa tttggtggaa aggtaaagca  2820
ctggatcaca atcaaccagc tatacacagt gcctacgaga ggctatgcac tcggaacaga  2880
tgcacccggt cgatgttctt atatggttga taacaagcac aggtgttatg gcggaaattc  2940
ttcaacagaa ccctatatcg ttgcacataa ccagcttctt gctcatgcca cgatcgtcga  3000
tctttacagg accaaatata aggtgagtga tctccctatg tgaaaaggtg gtctaaatca  3060
aacatatccg attctaatga atagtcatat atatatatat atatatcacg tgatgagcag  3120
ttccaaaaag ggaagattgg acctgtgatg ataactagat ggtttcttcc atatgatgag  3180
tctgatcctt cttgcgtaga agcagctgag aggatgaacc aattcttcca tggatggtat  3240
atataatttt ttatatagcc aaaatatatc agtatgtatt ttatgcattt ataatgatac  3300
aaaaatatac atggatgatg gatcaggtac atggagccgc taacaaaggg tagataccca  3360
gacatcatga ggcagattgt gggtagtagg ctccccaact tcactgaagc tgaagccgaa  3420
ctcgttgctg gttcatatga ttttcttggt ctcaactatt acgtcactca gtatgcccag  3480
```

```
ccgaaaccta acccatatcc ttcagagaca cacactgcct tgatggacgc tggcgtaaag  3540
ctcacatgta cgtactacag tattaccact tagttacaac ctttctatat atctttttct  3600
cctatttgtt aacatacttt gtgagtgact atcaatttat ttcattcttg tgtttacaga  3660
tgataattca cgtggtgaat tccttggtcc actggtatat taatgatcca cccctatgat  3720
ttctctttta ttttttcta ttttcaatat aacaccactt atgctctctt tattgacatg  3780
tatatgtgtt cgcttccctt tcccagttca ttgaagacaa agacaacggc aacagctatt  3840
actacccaaa agggatttat tacgtaatgg actacttcaa aaccaaatac ggtgacccat  3900
taatctatgt caccgagaat ggtgagttct acatactact actcatcttt ttcatctata  3960
acgtatacta aataatgtat ttcggaataa atcccagaaa ctgactttca aatattgtgt  4020
acctttgcat gttatggcgg ttaggattta gcacgcccac tacagaaaac cgtggcgaag  4080
ctattgccga ttacaagcga attgattatc tttgcagtca tctatgtttt ctccgtaagg  4140
tcatcaagtg agtggatact attataaatg atttcttcca tatgttatct tcttcgtctt  4200
ttttggaaac atttatatat atatgattgt tcttgctttc agggagaagg gtgtgaacgt  4260
gagaggatac tttgcatggg ctcttgggga taattatgaa ttctgtaaag gctttaccgt  4320
caggtttgga ctcagttacg ttaactggga cgatctcgac gatagaaacc tcaaagaatc  4380
tggtaaatgg taccagagat tcattaatgg aaccgccaag aatcctgcga aacaagattt  4440
cctccgctca agcgtctcct ctcagagtca gaagaagagg cttgcttgct gatgcatgaa  4500
acacttttcc cccttcaaga tcatctccac gtctctgatc actctttcta gttgctccat  4560
agataaggag cttctgtcta taattatgta ctaaataaat attctcaata aaaagatggt  4620
ctgttactaa tgaataaaaa aattatctac aactatatta tgtcaagtca agttaaactt  4680
aaacgtcgct caggcacaca tacgaaaaca aaaacaaaaa ccccccgcaa actagtttag  4740
tgagataaat tttgcgaaaa tttggaaaaa tactttgcaa agagatttta ttttgaaaat  4800
tgctcaatat ttgatttctt ttgaaaacta cactttctct ctagctaaat gactaattta  4860
tcctattaaa atgtatatac aacaagaaaa taaatttatt ttgttaaata ttatttaaat  4920
ttatttgaaa gtaacaaaac aagatataaa ataatcatcg ttgataacat aattttacgt  4980
gaagaaattt cagtcgttta aaacttgtca aattttgatc cagtgtcttt gtgtttcata  5040
aattatgcag tagagagaaa aaaatttgaa agttgctgtt tcagtgagat ggtgagtttt  5100
taacatgtaa agttttatat tatgtatcaa aattatcttt gttatgtaat attctctagt  5160
aaaaaggttt attattttta gaaagataaa cattgaaata ttataaatat ttatccaatt  5220
atatatttta aatcaatgta tttatcttaa taatttcgaa atttgaataa aaaccattaa  5280
aatataaaat ttaacttaaa cctggttaag acgtcttttt acatattgga aaagtgtaat  5340
ttttaaaata aaattgaatc aatgtatttt tcaaattaaa aaacataaat aggatatttt  5400
cctaattagc cgaaattcac taatcaattt caaagttcaa ctttatgtac gaggatgtct  5460
tttcaacata ataataatta gtgaccaaac ctaatccaaa ctcaaaagta actaaaccag  5520
agttctatca cctcaacaaa cacttgatgg gatttcacat atgatttttt atcattcata  5580
taattttatt tgattctgtt acttttataa tcaataaaac caaaaaagct aaaccgcagt  5640
cctttgtgtt tagtgaatgt atgccgattt atgtatttca acattgtatt ctactcttga  5700
atgatggaca aatatcaaga actgaagtgt cagaagtttc cgaaagaaca tgtcaacttg  5760
ttccatggac ttctttccca aattctttta agacttctgt ggatttccta aaccaaaaat  5820
aaagacatgg tttgtcattt ccgtttttttt tttaataaaa gattcgattt atcttggatt  5880
aaacaaacta tagtaattta atgagtctca catatttata atgttggttt aattaatata  5940
atagggtttt tttctttaat tcggaaaaca agcatgtttg taatattatt agaatttcat  6000
aaatttccct ttggatatga tctgtaaatt ctcttcatac taccaacgca gcactagctg  6060
gcaacatttt cttttaaatt tgcattgaaa tttaccgttt tcttattggt tgatttaatt  6120
acttcaacaa aaggaaacaa atctagagtt atataaagta tatcttaaat tatgattgtt  6180
atctgctcta tccaatgatt ttctgaattg taaaatccat ttaaatacta gatattgtca  6240
ttcattgtat gtagaagcaa aatagaattt tgcatcttca attctccatt tatatggatg  6300
atttctaaca ctgttctaca gaaagaacac aaacactaca taacttcaaa aatttacgaa  6360
catgttaaaa attagtttca gcaaaactaa aaataagatt aataagaaaa attagattaa  6420
tatactaaga caaactaaaa cttaaaaata taacgataag tggtagctgt aattgcacaa  6480
ccgcaccaaa aa                                                     6492

SEQ ID NO: 33          moltype = DNA  length = 6769
FEATURE                Location/Qualifiers
source                 1..6769
                       mol_type = genomic DNA
                       organism = Brassica juncea
SEQUENCE: 33
ttacatataa gtaaatttct taatttctat actttcatcc ataacatcaa atattacgaa  60
tcaaagagag tatctaattg tgttacaaaa aaagagggag tatctaattg tcactattat  120
gttttttttt atttactaat tgctttcaat taaattttaa tattgttttg tttttcattt  180
ttataaatat aatatctata ataaaaatta aacatttaaa ataatttaaa ataaatttca  240
tatgtatata tatttaatat atatctgatt tcataaaaga ggaaaatgcg caaaaaaataa  300
tcttgatatc aagaaggaaa aaatcattct tctaaaacat tatcttaagc aacattctgt  360
tatatatttc ttagatgaat ataaaaaataa tttaattaac ataaagccag ttatctttag  420
ttgaatgaaa atattttata acagctgtta gtgagatgat gaattttgtt tttgtaaaac  480
atttaaccac ttttttttta ttagaataaa aataaaaata acgattaatt ttaaaatact  540
ttatttatat aacatttttc aaaaacaaag cttaaaacta gtatttattt taaaaatgtt  600
aaaaaatatt ttaaaacaga gattttaagc aagataatat atattagaaa acaaaactaa  660
aaatatcttc aaacaaaaac attttaactg acacaactct aaatacattt gataaactaa  720
aaatattata cattaccata tcgaaaaatc tttgtttttt cttaatattt cctttggttt  780
caatttaatt attttatata tttttacaat ccaatatata cattataaaa atacctaagc  840
aaatataatt cttctgttta atgttatttt aaaataattt caacatatta ttttagtaac  900
agctaaagta ttgaattccg agaaatagat acaatctaat acacctaaat aatagctaaa  960
acatctagat attatatatc taaaatcaca tgtgtaaaaa ataatataat attattaaaa  1020
ataaattata tataaattat aaaattattt aaaattgaaa gtaaaaacat taattagtta  1080
ttataatata tttagttcat aaataatttt ggtcgtgcaa tatcacgtaa gagtcaccta  1140
gtgcatcatt aaatacaagt aaataattga tttcaaactc aagttggtgg cacgtaaaca  1200
gtaataaagt tatctataga aactaaatat atgtaatatg gctatttata acaaaagtta  1260
```

-continued

```
cgaattctaa ctttctagag taaaaaacta tggaacaaac tataggttaa tatacaagta  1320
tcaatcttat ctatctggaa gtcacggatt cgtatccgtt cgaacggttc caatcattta  1380
aaacgatacc aaaaaggcca aaaatgtggt gggttaacgt tttctttagt ctttcggagg  1440
caccggtttc attgtgataa agcagaaaga gagcgatcaa aaccaataag ataagataaa  1500
tattttctca aaaaaaaaaa acaatatatc ttgtgagcgg taaggctcgt gataagtgtg  1560
gctttgcacc agtgtttctc tagattcagc acgataaaac tcgatataca tttttagtaa  1620
cgaatcttga cgttgcgcaa atcttacatg ctgcattgca tcattgcatt actgttgacg  1680
gatcaatttg aagatgtatg attcgtgttt cggttaagga acaccaatat gtgctatcta  1740
acaaaaaaaa agatttgcaa tagataatga ttaatgacta aaaggtggaa acatgacaat  1800
cagaaatatt acaaaagtcg gtgaacactg agctaaagta agtgaaccca cgggactcat  1860
gatcccacct acacctcccc aaaatgtgaa gatgctaaga caagaaaata catatgtcac  1920
ttttctttg gaaaggctat ataaacccta gatggccaca aggatccaca caacacaaca  1980
catacatcaa cagattaaac atgaagcttc ttcgtcgact cgctttagtt tttctattag  2040
ctgctgcgag ttgcaaggct gatgaagaaa ttacttgcga agagaacaat ccatttactt  2100
gtagtaacac tgatatttta agcagcaaga acttcggaaa agatttcatc tttggtgttg  2160
cgtcttctgc ttaccaggca tgtagcaaat gttgtcacac cctaattttg aaataaaatt  2220
caaagcacca atatccaatt ttgcatagtt gtttcttttc atttcagatt gaaggaggga  2280
gaggtcgtgg tgttaatgtt tgggatggtt tcagtcaccg gtacccaggt atgtcgttcg  2340
cacggtgaca tctaaactaa taatgttggt tacatataca catattaatg tatttgtaat  2400
taatattatc agagaaagct gggtcagatt tgaagaatgg agacactact tgtgagtcat  2460
atacgagatg gcaggttaat ttctgagtac actgattctc atgactgaat tatatatgta  2520
taagaactcc ctaaaaacta tacgtgtgga ttgacatgaa atttaaatta attgtaaact  2580
gcagaaagat gtagacgtga tgggcgaaat caatgctact ggctacagat tctcctttgc  2640
atggtcaaga atcattccaa gtatgtacat attaacgatc aatgtatata tatctttgta  2700
ttttaattgg gataatttag ttggaaaggt actaattaat gtacgatata tatctacccg  2760
agcagaagga aaggtgagta ggggagtgaa ccaaggaggt cttgattatt accaccaact  2820
catagatgca ctcctcgaaa agaatataac gcctttcgta accctctttc actgggacct  2880
tcctcaaaca ctccaagatg agtatgaagg tttcttggac cgccagatca tgtaggtgcc  2940
atgcttctta attatatttg aggagagtaa atattattag taatagaaga agaagattta  3000
gtcttaatta catgtttact gaaatgattc tatactaata tgaacagcca ggatttcaaa  3060
gattacgcgg atctatgttt caaagaattt ggtggaaagg taaagcattg gatcacgatc  3120
aaccagctat acacagttcc tacaagaggc tatgcagtcg gaacagatgc acccggtcga  3180
tgttctccta tggttgatac caaacacagg tgttacggcg gaaattcttc aacagaaccc  3240
tacatcgttg cacataacca gcttcttgct catgccgcgg tcgtcgatct ttacaggacc  3300
aaatataagg tgagtggtga ctccatatgt gaaaattaga gtggtgtaaa tctgatatat  3360
atctgattct aatgtatagt catatatttg gaccaacagt tccaaaacgg gaagattgga  3420
cctgtgatga taacaagatg gtttcttcca tatgatgagt ctgatcctgc ctgcatagaa  3480
gcagctgaga ggatgaacca attcttccat ggatggtata tataatttta tatattatca  3540
aaaatgtatc agtatgtatt ttatgtattt ataatgaaac aaaaatatac atggatcagg  3600
tacatggagc cgctaacgaa gggtagatac ccagacatca tgaggcaaat tgtgggtagt  3660
aggcttccca actttaccga ggaagaagcc gcactcgttg ccggttcata tgattttctt  3720
ggtctcaact attatgtcac tcagtacgcc cggccacaac ctaacccata tccttcagag  3780
acacacactg ccatgatgga cgctggagta aagctcacat gtactaattt acattaccac  3840
ttagttacaa cctttccgta catatatata tacacatgtt ctatctcctt tttgttacaa  3900
catactctgt gagtggccat caattgtttc atccttgtgt ttacagatga taattcacgt  3960
ggtgaaatac ttggtccact ggtaatatat gaatgatatc caccccctatg atttctcttt  4020
tatttttatt tttctatctg caatagaaca ccactgatta tgttctcttg attgatgtgt  4080
ttgcttccct ttctcagttc gctgaagaca aagttaatgg caacagctat tactacccaa  4140
aaggaattta ttacgtaatg gactttttca aaaccaatta cagcaaccct ttaatctata  4200
tcaccgagaa cggtgagttc tacattctac ttactactca tctattctac ataaaataat  4260
tagtgtattt ttatatatat aagtccaata aactgacttt caatattgtg gaatgttttc  4320
acggtttaat taggaattag ttcgcccagt acagaaagcc gttgtgaagc tattgccgat  4380
tacaagcgaa ttgattatct ctgcagtcat ctatgttttc tccgtaaggt catcaagtga  4440
gtggatgtta ttataaatga ttttcttcat attttatctt cttcacattt atatatatgt  4500
ttgttcttat tttcagggag aagggtgtca acgtgagagg atactttgca tgggctcttg  4560
gagataacta tgaattctgt aaaggtttta ccgtaagatt tggactcagt tacgttaatt  4620
gggacgatct cgacgataga aacctcaaag aatctggaaa atggtaccag agattcatta  4680
acgggaccgc caagaatcct gcgaaacgag atttcctccg ctcaagcctt tcctcccaga  4740
gtcagaagaa gaggcttgct gatgcatgaa acactttcca ccatcagatc atctttatat  4800
ctctcactct tcctacttgc tccatagtta aggagcttct tttatctaca atgtactaaa  4860
taaatgatct caataaaaag atgatcaatt actaatgaat aaaaataatg atctacaaac  4920
tacattatga cacaagtcaa gaggaagagg aaagagggaa ataacgaaat ttaaatagaa  4980
aacactcaga aatcccaaac tagtttagtg taaaataaac attaacgaac cgattagcct  5040
aaattcacta actagtttaa taagttcaac ttatataata aaatgtatct tcaacataat  5100
agataagaac caaacctaat acaaactcaa aactcaaaag taactaaacg taagttctat  5160
cgtcctcaac tgaaacttaa tgtgtaataa ttcatataat tttatttgat tttgttactt  5220
atataatcaa tatataaaac caaaagagct aagccgcagt cctctgtgtt taatgaatgt  5280
atgccggttt atatattaat ttaaacattg tattctactc ttgaatgatg gagaaaaaac  5340
atcaagaatt aaaggaacag aagttttctga atgaacatgt caacttgttt catggacttc  5400
tttcccaaat tctttaagac ttctgcggat ttcctaaacc aaaaataaag acgtgtttag  5460
ccatttcccc ttttctataa agattcgatg tatcttggat taaaagaact atagtaattt  5520
aatgagtttc ggatttataa ttttggttta attaataaaa tagggttttt ttctttaatt  5580
cggaaaacga gcccagatag agagattgac cgtagagaat ttatgtttga tcttctcaag  5640
ggcactatta tgatccaggt tttgttggag aactgaatct ttttgttggt ggttatgtaa  5700
taagctaact cacaggaccg tcctcgaggc gaatggtgct gtcagttcct cctcatgtcg  5760
ctgtcacagt tgcattttgt cctgttgttg gtgatgtgaa ctctgttgtt gtcagaacag  5820
agggttcggt aagaaaccct actgaatttt atgatcattt gcgtcaatat gattgtatgg  5880
atatgagtgt gaatgagcag gttcctagag gttctaagca tggagaacaa accaaatccc  5940
aagacaaagg gcacgagaca aattatcaca acaaggaaaa agatgacgct taacattgaa  6000
```

```
agtggttcct tgtggtgcac ttcaccacat tctcctacgc cgggaggtca catttcgtca  6060
caacggagct aaacatgcgt aatgaaatgc aatgcttgaa acttccagag atcgtttact  6120
tctgccaagc tataaacagt ggccttgaat acggatggcg acgagccaag aagccaccat  6180
tgggccatac attccattta ctcttggaag gtggccaaaa ggtggaggag gagattcacc  6240
gctgcccttt caaatcaatt tggaaatcgt gagatctatg taaaatagtt tttttaaaa  6300
ccccctaaac attatttgtc aagtgatttg tacatatatc atcactacaa tcattctcgc  6360
taaaaaatga tatgacactt aagaaaaaat aatatgattt tcaaaaagag tgacatggta  6420
tcatattaat tgtgatatat aaaattttct tataaaaaat tatattttac aaaggtttta  6480
aatatgataa taaaaaacaa ctcagatatc atcattaatg tcaattttcc atataaatgt  6540
ttatttttgg taaactatta aaaatattaa aaactcataa atcactacga ctaataatat  6600
atatatatat atatcacatt aataaaaaga agctaaataa gattactttt acatcaactt  6660
atatagaata tttgtataaa tataattgta aatatgcatc aaaaaataca aaactaaagt  6720
aacaacaatc gaaaaaattg atagttaaat gtttaaacat ttatttaaa             6769

SEQ ID NO: 34           moltype = DNA  length = 6528
FEATURE                 Location/Qualifiers
source                  1..6528
                        mol_type = genomic DNA
                        organism = Brassica juncea
SEQUENCE: 34
agcattttat acaaactttg aaacgcttct ctaacgtaat aaaccatgtt aaactcacca  60
cacacaccac aagtaacaaa acctatcatt ttttttagaa ctgaatgtta gatttaactt  120
ttttttaaa aaaaaaagac cgttctacat aaactcgatc aatcaaagaa aaagctctct  180
aatttgcaaa acttcaggac cttcaaaact tcaatacctt cagcttcttg tcctaaacca  240
aaatctcatc ccttcttcga aatctttatc acctctcctt tgcaaaattg tgaacttatt  300
tctcatggtt ttatcaatcc gcttaacaaa acctatcatt gctattgcaa tatgtagttt  360
gcagaaagaa catgttaatt acctaagaaa aatccagtaa aaattcgtaa cgtaaatgtt  420
acttaaactg aaatctttat ttatttccta ttctactata tcgaaggcct gaagcacata  480
aaatgaagtg tttttcctat tttaattcat gcttgaagtc atagctttga actatttcat  540
gcatttcaat agaaaaactt tttttttga aatttatttt tgttactgag acatgccatc  600
atgaccaagg tcattacagt ttaacaagct acaacaaagc aagtatatca tagaaaccca  660
gaaacaatcg aaactttcgg ttgacttaaa caaggggaga aaactagcct cttccacctc  720
tgtttccacg tccgcgattt catcatcccc gacctgtgaa ctgtaagtgc atctctttag  780
cttttgttga cagcttaacc agtccaatag aaaagctttt gtcaaaaaga atatataatt  840
acgaaaatat aagtataatg tataaattct aacataatgt gtagagttaa actaggttaa  900
tacacaagta cttatcttct tatctaacca gaagtaacag tttcgattgt atccatccca  960
acccttccaa tcatctagaa acgataccaa aaaggaaaaa aaaaagtttt cttttgtctt  1020
ttggagactc cggtctactc atgtgataaa agcatatagg gagaggtcaa aacaaataag  1080
atatgctttg attgtttttt aaaaaaatat gctgtattgt gagcggtggt gagcctcgtg  1140
ataagtttgg ctctggatca gtgttactct agattcaaca cttgataata tttcgatata  1200
aatctccaat aactttatgg cgttatgttg aagcttctaa cattatttac gacaacgaat  1260
cttttttttt tttgaaacac tacaacgaat cttgatgatg agtgtcatcc tagttcccgc  1320
aaaccttcca tatatagatg ctgcattgac agtttgacac aattcgtgtt cctagtcacg  1380
atagattgct tcgattaacc gctttaaaca aagaacgctt tagtatctaa agcaataaaa  1440
accacattca cgagacacac cgagaaaata gtgataaacc attcagcaat tcagataaag  1500
aatgcaacat ctgtattttt tccaatgaaa tggtagattg aagagaaagg cacgctaaaa  1560
agtggaaaca aaacaagaaa tttaagcaaa aatcggtgaa aactcagcta aagtaagtga  1620
gcccacgggt ttcatcccac ctaaacctct accaaatcat ctggacagaa aatgcatacg  1680
tcacaattct ttaggaaggg ctatataaac cctagattgg cacaaggttc catacaacac  1740
aacacaaaca tcaacatata ttaaccatga agattcttca tggactcgct ttagtttttc  1800
tattagctat tgcgagttgc aaagcttatg aagaaattac ttgcgaacag aacgaaccat  1860
tcacatgtgg taacactgat atcttaagca gtaaaaactt cggagaagac ttcatcttcg  1920
gtgttgcatc ttctgcgtac caggcatgca acaaatgctg ccataccata tttttgacgt  1980
atagaaaata atattcaaaa atgctaacat caaactttgc gtggttgttt ccatttcaga  2040
tcgaaggagg gagaggtcgt ggtgttaacg tttgggatgg tttcagtcac cgatacccag  2100
gtatgtcacg gtggcatata tatacatata agatgaatgt cgtttatatc tacacacatt  2160
aatgtatttg taattactat cagagaaatc agggtcagat ttgctgaatg gagacacttc  2220
ttgtgagtca tatacgagat ggaaggttag ttcctcagta catatacact catatgacta  2280
aactacgtat aaaatttacg tgtgaactga attccgttta aaatgcagaa agatgtagag  2340
attatgggag aactcaatgc tactggctac agattctcct tagcgtggtc aagaatcatt  2400
ccaagtacga acataaattt gtatttttat tgggatcctt tagctggaag agtatactaa  2460
ttaatgtatg atataaatga gcagaaggaa aggtgagtag gggagtgaac caaggaggtc  2520
ttgattacta ccaccaactc atagacgccc tcctcgaaaa gaatataact cctttcgtta  2580
ccctctttca ctgggacctt cctcaaacac tccaagatga gtatgaaggt tttttggatc  2640
gccagatcat gtatgtgcca tgcttcttaa ttatatacaa attattaata aaaacaagaa  2700
gaagaagaag aaggttttgt cttaattaca tgctttactg aaagaatgat tatatattaa  2760
tatgcacaga caagatttca aagactatgc ggatctatgt ttcaaagaat ttggtggaaa  2820
ggtaaagcac tggatcacga tcaaccagct attcacagtg cctacgagag gctatgcact  2880
cggaacagat gcacccggta gatgttctcc tatgattgat gagaggtgtt acggcggaaa  2940
ctcttcaaca gaaccctata ttgttgcaca taaccagctt ctcgctcatg ctgcggtcgt  3000
cgatctttac aggaccaact ataaggtgag tagtctccat atttaatacg atggtgtgat  3060
cttaatccat ctgattctga tctagtcata tatatcatgt gaccaacagg accaacaagg  3120
gaagattgga cctgtgatga taacaagatg gtttcttcca tatgatgagt ctgatcccgc  3180
ttgcgtagaa gcagctgaga ggatgaacca attcttccat ggatggtata tcttttttgt  3240
ttgacatcaa acaattattc ttttttttgt ttgtttacat taaatggtta ttttattatt  3300
taaaactaaa ggtggtctgt ataactagaa tgattatatt gtatgtataa tgaaaaaaat  3360
atacaccgat caggcacatg gagccgctaa caaagggtag atacccagac atcatgaggc  3420
agattgtggg tagtaggctt cccaacttta ccgaggaaga agccgcactc gttgccggtt  3480
catatgattt tcttggtctc aactattatg ttactcagta cgcccagcca caacctaacc  3540
```

```
catatccttc agagacacac actgccatga tggacgctgg agtaaagctc acatgtacca  3600
ctctgtttcc actttgttac aacctccttt ctatatatat attccttttt gttataaaac  3660
atacttaatt tgtgagtgac cataagttat ttcttccttg tgtttacaga taataactca  3720
cgtggtgaat atcttggtcc actggtaatt atgcatgatc catcctcatg atatctctct  3780
cattgatatg tatattttgt tctgattgat atgtattttt tgtttgcttc cctttcccag  3840
ttcgctgaag acaaaatagc cggcaacagc tattactacc caaaaggaat atattacgta  3900
atggacttct tcaaaaccaa ttacagcaac cctttaatct atatcaccga gaacggtgag  3960
ttctacatac tacttactac tcatctattc tacataaatt aattagtgta tttttatata  4020
ttagtcgagg aaactgattt tcaaatattg tggaatgttt tcacggttta attaggaata  4080
agttcgcccg gtacagaaaa ccgttgcgaa gctattgccg attccaagcg cattgattat  4140
ctctgcagtc atctatgttt tctccgtaag gtcatcaagt aagtggatgc tactgtacat  4200
gcttttcttc caatatttta tcatcttttt cttcttcttt ttaagtatac atatatatga  4260
ttgatttatt gtttccaggg agaggggtgt caacgtgaga ggatactttg catgggctct  4320
tggggataat tatgaattct gtaaaggctt taccgtcaga tttggtctca gttacgttaa  4380
ttgggatgat ctcgacgaca gaaacctcaa agaatctggc aaatggtacc agagattcat  4440
taacggaacc gtcaaaaacc ctgcggaaca agatttcctc cgctcaagcc tttcctctca  4500
gagtcagaag aagaggcttg cttgctgatg catgaaacac ttttccacct gtcaagatca  4560
tctctatgtc tctcacactt cctagttgct ccatagataa ggagcttctt ctactacagt  4620
gtactaaata aaaattctca acaaaaagat gatcaagaat aaaaataatt tacctacaac  4680
tacattatgt caagtcaagg ggggtgaggg ggacaataac gcaatttaaa ttgtaaaagg  4740
ctcacacaca tacaaaataa aaacccaaac cgcaaactag tttagtgtta caaaaatatt  4800
aatgggccga taagcgtaca attcactaat tagtttaata agttcaactt tatgaaataa  4860
agatgtattt tcaaccgaat agaccatgat caaacccaat ataaattcaa aaataattat  4920
accaaagttc tatcatcatt agtggaaact aaataaaaat ttacatatgt tttattttaa  4980
gtttttccta ggataggaca cgcttcaacg gaggttattt ttttattcta tttaaaaatc  5040
agcaaaataa gagtatattg attcatcttt gtcaacttat agatccatct aatctactaa  5100
ataaaaattt tggttggtaa aacttgtgtt gtaatatata cgcctcattg aaaattgatt  5160
ttattagttg gtttatatta aaacattagt tatgttattt aatgtttggt gttttaagtt  5220
atgtatttat aaataatgtt tttttcgtaa acattgtaag attttcataa ttagttaacg  5280
taatatataa tttagtcttt gaacatcttg aacacaattt acaatattga agtaatcaaa  5340
tataagataa taataataat aaaataaggc aaactaacaa gttaaatagt ttttactata  5400
tatgggtgat catttttttgt gctttttttct ttagtttttg atttttgttt tttcgaaaac  5460
catttttatc caattaaagt ataattttta tttttagttt tggtcaaaaa aaatgatttg  5520
ccaatcaaga tttttaaata aaatagtttc cctaaaattt agggaaactt attttgaaaa  5580
ctttaaccaa tttatgaaga aaaaccaaaa ccaactttta tgagctttta tgaaaaatga  5640
attttgtttc ttttggagaa aatgctcgat tttagttaac taataattaa taaataatat  5700
ttttcataaa aataaaatta tcatacaggt tttgaataat aaaatattta cataataaaa  5760
ttataattta ttttaaaatt ttgaaatatt ttttcaattat aaaatacata aaaaaacaaa  5820
tataactctg taagaaaaat tcagtatact gaaatcactg ctagaatcga ctttcaaata  5880
atataaataa taatttctta attttttaaa aatattaaat aacatataaa atatatggat  5940
caataaatcc tagctggaaa atcatccaat ttaatagaga atgttggctg atctcatatt  6000
ttttgacaaa atattttaaa accatccaat ccattttttt gacaaaatat tttaaaacca  6060
tctaatccaa tacatttgtg aatttttagt caacttgaca agtcttttgt ggaaggaatc  6120
cccatagata taaaaacatg ttgagttgga aaatttcata tactttatat attgggtgtg  6180
tatcaataaa aagttggact gagaaggcaa attaaaacag gataaaatag taaccgttaa  6240
caaagatgtt tcgcaccgac ttaaaagcaa accaaaaaga acttcgaaaa atattacttg  6300
ggcgttcata tttggtctcg tcagctttat aagtatgcag gctcaagatt ttttttttgt  6360
cacagaaatt tcattaataa taaaaaaaag acagaaagag cccaaaacat ggcccaaact  6420
cagtagtcca ttacacagaa gagaaaatat gaaaagcttt tatggctaaa ggtaacaaca  6480
atcgagttct ttgatcgggg gagatgagag aaaccgattg atgcaaat              6528
```

```
SEQ ID NO: 35          moltype = DNA  length = 6639
FEATURE                Location/Qualifiers
source                 1..6639
                       mol_type = genomic DNA
                       organism = Brassica juncea
SEQUENCE: 35
ttttgcgaag aggtatacaa tcactcaaat atatacttta aacttgatta atattattac  60
taatattttc ctatattatt ttgtattaaa aatacggaca ataggattgg gatcaatcaa  120
cgattttccc agggtaacct cttcctatgt tcgttgaggt gatgttccgg ctcaactctg  180
aacggagttg acagatgctc ataacaagat ttcatcaatg aggattgatt gatccatatg  240
tttgtaaacc atatgttttt cggcatacat gtggagagac ttgacagcta ctcgagcttt  300
agagattaca cgtaaaaata ttaatatcat catacaaact ttggaggagc aagctgaccg  360
ggaattaata atggataaag cggtttgaga gactagggtc gagtttttca acgatgttga  420
ttagaaatag tttctgtatt tttattttgt tttataattt ctataaaaac tagtttaaaa  480
ttttataaaa tattcattaa ttttattgat gttctggtgt attaaatagt taattcattt  540
aaacataaac tagataccaa atgtttctat tctttaaatc caacatttgc atcaataaaa  600
taacttcgaa aatattatga tgttgtcgat aaaaatacaa aaggactttc cttttttttat  660
ttgctaatat gatcatcttt agcacattgt ctattttcac aaattcaatg tccgattaag  720
aaggcaacta caaaacgtgg aaatgaattt atacaaaata tttaaaagga cgatccagaa  780
catttttgga gttatcatat aaattcagat gtttttttag atttgtgcag acttagacat  840
ctttaagaaa tacaagatgg attttggttg aagaaatgct tgccacattt tttttcattg  900
ttggccagta agagatatat tctccctcga gatgtattca agagatcaag tttggaaaca  960
attcagagtt taataaaagg gtgttaaaca gtattggcca agtttgtagg ctaaaccagg  1020
aactgcattg cctttacaaa catgagaaac aaaagatttt attcctactt taaagtatgt  1080
aaaaattgtc ttatctattt gtttattttt atccgttaac agtttcattt atattttcag  1140
gattgtattg gagctattga tggaacatat ttctgctatt gtagtaataa ttaaataaaa  1200
ctgttagtta tcaaaacaga aatagagttt tatctatgaa tgtcctagtt gcgtgcaatt  1260
ttgatttgca gttcaaatat gttacaactg gttgggaagg ttcagctcat gatgcaaaag  1320
```

-continued

```
tgttaaatga tgcattaatg agaagtagca ataaatttga aacccccaag gtaattgcat  1380
tactcaatag aaatatatag tatgtgttta agatcggtta attaattata agttcttgat  1440
ttttcatgta ggagatttgg tagataacca tctgaaatct gaaaacttgg tagccgagtt  1500
tgtaggctaa accaggaact gcattgcatc caaataaatt tagctaaatt ccatcaaatc  1560
taaaatcctt taaaaatttc aaatccctaa tcaaataagc cctttaatat atttgaaggt  1620
atatttaagt accaaatggt tatatatttt aaaaaatcca acagttaatt caacaaaata  1680
aactttacat aattttttat ccctttcgta atttgttaaa atatgataat ctacttacaa  1740
ggttgtcatt ttattcagat aatagtccct tgttatttac aaaataaact ttacaaaaaa  1800
ataacgacca atcacaatga tgatactgat tcagctaaag taactgagcc cacggaattc  1860
accccaccaa acctctccca aaatatcaag atattgaaga aaagaaaatg tatacgtgac  1920
actactttac aaaggctata taaaccctag actagcacaa ggttccatcc aacacaaaca  1980
catacatcta cttattaacc atgaagcttc atggactagc cttgataggt tttctaattg  2040
ccgtggtgag ttgcaaagct attgaggaat gccgagagaa cgagccattc acatgtggaa  2100
acgctgatca gttaagcagt aaaagttttc caaaagactt catattcggt gttgcttctg  2160
ctgcttacca ggcatgttac aaatcaacaa tttttgacgt agaaaaccat ttaaaatatt  2220
aaatccaacg ttgcatggtt gtttcttatt attgtaggtg gaagggggca gaggacgtgg  2280
tcttaacgtt tgggatggct tcactcaccg atacccaggt atatcatcta catggtacat  2340
atatatacat atgtacaact cttatcattc ttagtataaa atgtatctgt ttactatcag  2400
agaagggagg atccgatcat gggaatggag acactacttg tgagtcatat acgagatggc  2460
aggttagttc ctcactgagt catataccag atggcaggtt aatttctcat ttcttcacta  2520
tatataatga tatccgagtg cgtgtgtaaa ctgaagaaag atatagacat catagacgaa  2580
ctcaatgcta ctggctacag attctcattt gcctggtcaa gaatcattcc aagtatgaac  2640
acataaacaa tctatttata caaaagaatt ctcgtaattt gattgtgatt gttgggaaga  2700
ttaaatatat gatatgtata catgagcaga aggaaaggtg agtaggggag tgaacaaagg  2760
aggtatcgaa tactaccaca aacttctaga tggcctcatc gctaagaata taacccccttt  2820
tgttaccctc tatcactggg accttcctca aacactgcaa gatgagtatg aaggtttctt  2880
gaaccgcacc gtcatgtatg tcatttgggc cgcgttctta gcaaggaata taagaagaaa  2940
aacatatata cataagtgat ctcatgttaa tgatttgatt ctatgctatg cacagagatg  3000
actttagaga ctatgcggat ctatgtttca aggaatttgg tggaaaggtg aagaactgga  3060
tcacgatcaa ccagctgtac acagtgccta cgagaggcta tgcaatcgga acagatgcac  3120
ccggtcgatg ttctccggcg gttgatgaga gatgttacgg cgggaattct tcaacagaac  3180
catatatagt tgcacataac cagcttcttg ctcatgctgc ggcggtcgat gtttacagga  3240
gaaaatataa ggtgagagta cgtgggtttg tgaataggtg tagtctttac gtatatgact  3300
atatctaatc atatcattat cgtatgccgt gaccaacagt tccaaaaagg gaagatcgga  3360
ccagtgatga taaccagatg gtttcttcca tttgatgaga ctgatgccag cagagatgca  3420
gctgagagga tgaaagaatt cttcttggga tggtaacgta tatgtatgta tatatcaaca  3480
aaaatgaaat gattttctta tacgtatgta cgtcgaccag gttcatggag ccgctaacaa  3540
agggtagata cccagacatc atgagggaaa ttgtgggtag tcggcttccc aatttcacgg  3600
aagcagaagc ggaactcgtt gcgggttcat atgattttct tggtctcaac tactacacca  3660
ctcagtacgc ccaggcaaaa cctaacccag ttacatgggc aaatcacact gccatgatgg  3720
acccaggcgc aaagctcaca tgtaccattc tgtttcctct tatagttaca acctttctat  3780
atatagatat ctccttttaa ttataacata tatgtacatt gtgagtgacc atcaattatt  3840
tcatccttgg gtttacagat aacaattcac gtggtgaaaa tcttggtcca ctggtacgtg  3900
catgatccac ccctgttact tctcaatatt ttttttttctt tcttgtttat gggtataata  3960
tgtacgcttc cttttctcag ttcgttaaag acgaaaaaaa cgggaatgcc tattactacc  4020
caaaaggcat ctattacgtt atggactact tcaaaaccaa atacagtaac cctttgatct  4080
atatcactga gaacggtgac tactactcat ctctttttttg catattaatt aagtaaatgt  4140
gtgtttcaaa taatgtatag ttgttgatgt accatgatgg tctaattagg atttagtact  4200
cccggtgaag aaaaccgtga caaagctatt gctgattcca agcggatcga ttatctctgc  4260
agtcatctat gttttctccg caaggtcatc aggtgagggg aagctacttt atttttttct  4320
cttttgaatt tgatgtatgg tcatcatcat gcataggctt tgaattatga tttttcctgt  4380
ttccagggag aagggtgtca acataaaagg atactttgca tgggctcttg gagataatta  4440
tgaattctgc aaaggtttta ccgttagatt cggacttagt tacgttaact ggacagacct  4500
caatgataga aatctcaaag actctggcaa atggtaccaa agctttatta acggtaccaa  4560
taagaaccct gccaaacaat atttccgccg cccaaacctc tccttccaga accagaagaa  4620
gaagctcgca gatgcatgaa acactttatc ccaccatcat gatcatcttc atatctctac  4680
tacttgcttc atagataagg agcttgttgt actaaataaa tattctaata aaagatgatc  4740
atttactaat gaatattttc gtttgagttc aatcccttct taccgcttca gttacgtttt  4800
actttggatg attaggttag gttttacaaa ttataaaact tggcatgtca gctattcatg  4860
tgagatttgt agatttagat aagagagagt ctatgtgtaa atgcgagaac tagcaagaat  4920
agtaacacaa agtacacaag agaatatctc tacaaaaaat atatgtattt actagtattt  4980
ttaaagtaaa tttactgata tcaaccttag attctgtcag cacttgcttc caaaaaaccc  5040
tagattcttc aatcgcgacc tcctctgagc tgagtctgaa ttctgatacc aatttgttca  5100
acttaacgct cagattacga cctagatcta ctcgattgct tgaatataaa aaaaacatgc  5160
aagaagacac ggtttgttca cccgtgttgg ctctccctac aaaatgttgt agatcaaatg  5220
tcagtaaacc cgcatgaagc aaaattattg gctctccctt gccgtttgcg atctatgatg  5280
aatgtgaagg agaaggaaat agtttggcag tacaaacaga gacagagaga cttattgaaa  5340
tttctactga acctgtgtca gtcagtcaaa acgtggagga agaaatccaa acggagaaac  5400
acgaggagag acagcttaga tcatctcttc atcaaaatgt aaaaaaaaaa gattgacgaa  5460
agaatagact tatgggctga catccggaac tactatgatt cttctatcat ttggaaaaat  5520
ctgtagatgg ttgtaggaga ttttaatgag actttgaaca ttgataaaca ctcttcaaat  5580
gctgtgagct ctaatgaggg agtttcaaga tgtggtgcaa tattgttctc ttctcgattc  5640
tacctcacat ggaacaatag aagagcataa ggccatatag cgaagaggtt aataaataat  5700
cacgtgttac aactatttcc gcagtcttat agtgtattgg aaggaggagg ttgctaggat  5760
cacttgagat gcagaattaa gttactatca gagctttgtc gaccaaagat gcctcttaaa  5820
tttgttaacg ttgtgccaga gatggaacaa ttcaaggtcg atatttttgg gaggaatact  5880
tatgaaatat ccaaaatggt aaccggagca gaggccaacc agacacacca ctcaaccaac  5940
caaagaatcg acatgacgta tgtgcattct aaacaccata tctcacaaag catgaggtct  6000
tttgccaata tgtaaaatat atttaatata tatttattat ttgacaatat gtaaaataat  6060
```

```
gtaaaataca taaatattaa tttatatata gaatgatcat tccgcgcaag ctgcagatct  6120
taacctagtt atgtattggt ttaaaattca gtgtatcaca aaaaaaataa gaagtaatga  6180
attaattatt ttttaatatt gaaaagagga gtaatgttgt acgttgatat caaatgagag  6240
ataacagaag ttgttcatcc ataagcaaag tgacccttgt atcattagtg agggataaaa  6300
atttgtttgt aaagataagc attttaagta atacttaacc tataagttca tgctgatatt  6360
tttttttcat tttataaatg tatagttttg atattatcat aaacgtttga aatatatgat  6420
ttacatttta gtgttatata ttgtgtaact ttttaatttt ttgtttaagt ttttttattc  6480
aacatgatta ataatataga gtgatttttt tatatatttt aatttgtttt taatatttat  6540
tacattttca agcagggtag aataaattca taatctgaaa taatcaaata gagaatctta  6600
ttcaaaatat atatttttga tattatcata aacgtttta                         6639

SEQ ID NO: 36           moltype = DNA  length = 6628
FEATURE                 Location/Qualifiers
source                  1..6628
                        mol_type = genomic DNA
                        organism = Brassica juncea
SEQUENCE: 36
tatacataat atataaatga atacaaataa ataataatag ataaaaatag ttttatatat  60
aacattcatc ctgcgcaatt gcccgggtct taagctagtt cattgttaac ttaacaacaa  120
attaacattg actgtcgcag ttaatttatt gctaatttaa caacaataat aaacatccac  180
gatttaaagt cttatattgt aagtcaaagt tacgaagata gtttcagcgc aaaatttata  240
tctagtttac gatgaatata tttacgacaa aataacgacg tatcatggac cttgcaactt  300
aagtctgtac gacgatcttt caataactat gtgcacttaa cgatgaagtt acattccttg  360
ttatttagtt gtagaccaga tgtctttttt agatttgtac agacttagac agagtttaat  420
aaaatattaa gggtgttaaa cagtattggc caagtttgta ggctaaacca ggaactgcat  480
tgcctttaaa aatatgagaa aacaaaagat tttgttcttg ctttaaggta tgtgaaaaat  540
tgtcttatct ttttgtttaa ttatccgtta acagttcaat ttatattctc aagattatat  600
tggagctatt gactgcatta ctcaatatat atatatatat gtattatata tgtttaatta  660
agataggtta cttaattata agtttgagtt ttatttatat ttcacattaa aaatatttca  720
tgaaaatttt atctcgcaaa ctgtgggtac ataaacaaga taaattttag agctctattt  780
cgtagtacac ataatcatat gaaataattt actggagaag gcattgatcg aagaaataaa  840
taagaattat tcaaccatcg tcattcttgt ttgagaaata tcatcgaaag gattttgggt  900
attttcaaat caagatttct tatattcaaa ttcgctccta gtttttcata aatgacacaa  960
gcagagcaag tgcttgtatc tgctgcattg cataactttt tccgtcagaa atgtcggcca  1020
gatgagtttc ttccagaaga aacatctgat gaacaaaatg ttactcaatt aagtagtaat  1080
ggttatcaat ttcttggcga acaagaacaa caaagagaac atgctactga atagagaaca  1140
accaatgctt caaatatgtg gaatgatggt actagtggat ctcaacggtg aaatatgcct  1200
gagtaagtta acatttttat gtgtttaatt ttatagttga caataatagt gaaatctcac  1260
aatgtatttt taggtgtgag atgatttatg gcattgttgg catgatatta aaaacacaca  1320
ttcgtctgtc acaataaagt caaaattgca gtcaagtatt tgtaattttt tttcatgctt  1380
ttttcgaaat tgattacact tttttgcgtg gtttcgataa attgttgtga gaaaatgttt  1440
tttaatgatc ttaggaaatc aatttttatt ttctttaaaa ttctaccaaa ttaatctcct  1500
atcaaaagct ctatcaaatt ccttaaaatc caaacaaatt tagctaaatt ccatcaaatc  1560
tgaaatcctt aaaaaaattc aaatccctaa tcaaataagc cctttaatat atttgaacct  1620
atacttaagt accaaatggt tatatattta aaaagatcca acagttaatt caacaaaata  1680
aactttacat aaatttttat ccctttcgta atttgttaaa atatgataat ctacttacaa  1740
ggttgtcatt ttattcagat aatagtccat agttatttac aaaataaact ttacaaaaaa  1800
ataacgacca atcacaatgc tgatactgat tcagctaaag taactgagcc cacggaattc  1860
accccaccaa acctctccca aaatatcaag atattgaaga aaagaaaatg tatacgtgac  1920
actactttac aaaggctata taaaccctag actagcacaa ggttccatcc aacacaaaca  1980
catacatctc cttattaacc atgaagcttc atggactagc cttgataggt tttctaattg  2040
ccgtggtgag ttgcaaagct attgaggaat gccgagagaa cgagccattc acatgtggaa  2100
acactgatca gttaagcagt aaaagtttcc caaaagactt catattcggt gttgcttctg  2160
ctgcttacca ggcatgttac aaatcaacaa tttttgacgt agaaaaccat ttaaaatatt  2220
aaatccaacg ttgcatggtt gtttcttatt attgtaggtg gaagggggca gaggacgtgg  2280
tcttaacgtt tgggatggct tcactcaccg atacccaggt atatcatcta catggtacat  2340
atatatacat atgtacaact cttatcattc ttagtataaa atgtatctgt ttactatcag  2400
agaagggagg atccgatcat gggaatggag acactacttg tgagtcatat acgagatggc  2460
aggttagttc ctcactgagt catataccag atggcaggtt aatttctgat ttcctcacta  2520
tatataatga tatccgagtg cgtgtgtaaa ctgcagaaag atatagacat catagacgaa  2580
ctcaatgcta ctggctacag attctcattt gcctggtcaa gaatcattcc aagtatgaac  2640
acataaacaa tctatttata caaaagaatt ctcgtaattt gattgtgatt gttgggaaga  2700
ttaaatatat gatatgtata catgagcaga aggaaaggtg agtaggggag tgaacaaagg  2760
aggtatcgaa tactaccaca aacttctaga tggcctcatc gctaagaata taacccccttt  2820
tgttaccctc tatcactggg accttcctca aacactgcaa gatgagtatg aaggtttctt  2880
gaaccgcacc gtcatgtatg tcatttgggc cgcgttctta gcaaggaata taagaagaaa  2940
aacatatata cataagtgat ctcatgttaa tgatttgatt ctatgctatg cacagagatg  3000
actttagaga ctatgcggat ctatgtttca aggaatttgg tggaaaggtg aagaactgga  3060
tcacgatcaa ccagctgtac acagtgccta cgagaggcta tgcaatcgga acagatgcac  3120
ccggtcgatg ttctccggcg gttgatgaga gatgttacgg cgggaattct tcaacagaac  3180
catatatagt tgcacataac cagcttcttg ctcatgctgc ggcggtcgat gtttacagga  3240
gaaaatataa ggtgagagta cgtgggtttg tgaataggtg tagtctttac gtatatgact  3300
atatctaatc atatcattat cgtatgccgt gaccaacagt tccaaaaagg gaagatcgga  3360
ccagtgatga taaccagatg gtttcttcca tttgatgaga ctgatgccag cagagatgca  3420
gctgagagga tgaaagaatt cttcttggga tggtaacgta tatgtatgta tatatcaaca  3480
aaaatgaaat gattttctta tacgtatgta cgtcgaccag gttcatggag ccgctaacaa  3540
agggtagata cccagacatc atgagggaaa ttgtgggtag tcggcttccc aatttcacgg  3600
aagcagaagc ggaactcgtt gcgggttcat atgattttct tggtctcaac tactacacca  3660
ctcagtacgc ccaggcaaaa cctaacccag ttacatgggc aaatcacact gccatgatgg  3720
```

```
acccaggcgc aaagctcaca tgtaccattc tgtttcctct tatagttaca acctttctat 3780
atatagatat ctccttttaa ttataacata tatgtacatt gtgagtgacc atcaattatt 3840
tcatccttgg gtttacagat aacaattcac gtggtgaaaa tcttggtcca ctggtacgtg 3900
catgatccac ccctgttact tctcaatatt tttttttctt tcttgtttat gggtataata 3960
tgtacgcttc cttttctcag ttcgttaaag acgaaaaaaa cgggaatgcc tattactacc 4020
caaaaggcat ctattacgtt atggactact tcaaaaccaa atacagtaac cctttgatct 4080
atatcactga gaacggtgac tactactcat ctcttttttg catattaatt aagtaaatgt 4140
gtgtttcaaa taatgtatag ttgttgatgt accatgatgg tctaattagg atttagtact 4200
cccggtgaag aaaaccgtga caaagctatt gctgattcca agcggatcga ttatctctgc 4260
agtcatctat gttttctccg caaggtcatc aggtgagggg aagctacttt atttttttct 4320
cttgtatggt catcatcatg cataggcttt gaattatgat ttttcctgtt tccagggaga 4380
agggtgtcaa cataaaagga tactttgcat gggctcttgg agataattat gaattctgca 4440
aaggttttac cgttagattc ggacttagtt acgttaactg gacagacctc aatgatagaa 4500
atctcaaaga ctctggcaaa tggtaccaaa gctttattaa cggtaccaat aagaaccctg 4560
ccaaacaata tttccgccgc ccaaacctct ccttccagaa ccagaagaag aagctcgcag 4620
atgcatgaaa cactttatcc caccatcatg atcatcttca tatctctact acttgcttca 4680
tagataagga gcttgttgta ctaaataaat attctaataa aagatgatca tttactaatg 4740
aatattttcg tttgagttca atcccttctt accgcttcag ttacgtttta ctttggatga 4800
ttaggttagg ttttacaaat tataaaactt ggcatgtcag ctattcatgt gagatttgta 4860
gatttagata agagagagtc tatgtgtaaa tgcgagaact agcaagaata gtaacacaaa 4920
gtacacaaga gaatatctct acaaaaaata tatgtattta ctagtatttt taaagtaaat 4980
ttactgatat caaccttaga ttctgtcagc acttgcttcc aaaaaaccct agattcttca 5040
atcgcgacct cctctgagct gagtctgaat tctgatacca atttgttcaa cttaacgctc 5100
agattacgac ctagatctac tcgattgctt gaatataaaa aaaacatgca agaagacacg 5160
gtttgttcac ccgtgttggc tctccctaca aaatgttgta gatcaaatgt cagtaaaccc 5220
gcatgaagca aaattattgg ctctcccttg ccgtttgcga tctatgatga atgtgaagga 5280
gaaggaaata gtttggcagt acaaacagag acagagagac ttattgaaat ttctactgaa 5340
cctgtgtcag tcagtcaaaa cgtggaggaa gaaatccaaa cggagaaaca cgaggagaga 5400
cagcttagat catctcttca tcaaaatgta aaaaaaaaag attgacgaaa gaatagactt 5460
atgggctgac atccggaact actatgattc ttctatcatt tggaaaaatc tgtagatggt 5520
tgtaggagat tttaatgaga ctttgaacat tgataaacac tcttcaaatg ctgtgagctc 5580
taatgaggga gtttcaagat gtggtgcaat attgttctct tctcgattct acctcacatg 5640
gaacaataga agagcataag gccatatagc gaagaggtta ataaataatc acgtgttaca 5700
actatttccg cagtcttata gtgtattgga aggaggaggt tgctaggatc acttgagatg 5760
cagaattaag ttactatcag agctttgtcg accaaagatg cctcttaaat ttgttaacgt 5820
tgtgccagag atggaacaat tcaaggtcga tatttttggg aggaatactt atgaaatatc 5880
caaaatggta accggagcag aggccaacca gacacaccac tcaaccaacc aaagaatcga 5940
catgacgtat gtgcattcta aacaccatat ctcacaaagc atgaggtctt ttgccaatat 6000
gtaaaatata tttaatatat atttattatt tgacaatatg taaaataatg taaaatacat 6060
aaatattaat ttatatatag aatgatcatt ccgctcaagc tgcagatctt aacctagtta 6120
tgtattggtt taaaattcag tgtatcacaa aaaaaataag aagtaatgaa ttaattattt 6180
tttaatattg aaaagaggag taatgttgta cgttgatatc aaatgagaga taacagaagt 6240
tgttcatcca taagcaaagt gaccattgta tcattagtga ggaataaaat tttgtttata 6300
aagataagca ttttaagtaa tacttaacct ataagtttat gctgatattt ttttttcatt 6360
ttataaatgt atagttttga tattatcata aacgtttgaa atatatgatt tacattttag 6420
tgttatatat tgtgtaactc tttaattttt ttgtttaagt ttttttattc aacatgatta 6480
ataaatatag gtggtttttt atatatttta atttgttttt aatatttatt acattttcga 6540
gcagggtaga ataaattcat aatctgaaat aatcaaatag agaatcttat tcaaaatata 6600
tatttttgat attatcataa acgtgtta 6628

SEQ ID NO: 37           moltype = DNA  length = 6638
FEATURE                 Location/Qualifiers
source                  1..6638
                        mol_type = genomic DNA
                        organism = Brassica juncea
SEQUENCE: 37
tgttatttag tcatagaccc gatgtctttt ttagattttt aaagacttag acaactttag 60
gaaatacgag atggatttg gttgaagaaa ttcttgccac attttttctc attgttggcc 120
agtgtacgag atattattct tcctcgagat gtattcaaga gatcaagttt tgaaataatt 180
cagagtttaa taaaatatta agggtgttaa acagtattgg ccaagtttgt aggctaaacc 240
aggaactgca ttgcatttaa aaatatgaga aaacaaaagt ttttgttctt gctttaaggt 300
atgtgaaaat tgtcttatct ttttgtttaa ttatccgtta acagttcaat ttatattctc 360
aggattatat tggagctttt gatagaacat atattcctga tatggtagta gtaaataaaa 420
ctgttagcta tcgaaaccga aatggagttt tatctcagaa tgctctagct gcatgcaatt 480
tttatttgca gttcaaatat gttattactg gttgggaagg ttcagcacat gatgcaaaag 540
tgtaaaatga tgccttaacg agaagtagca aaaaatttga accccccccc cccccgaggt 600
aactgcatta ctcaatatat atatctatgt gttatatgtg tttaattaag ataggttact 660
taattataag tttgattttt atttatattt cacattaaaa atatttaagg aaaaatttat 720
ctcgcaaact gtggatacat aaacaagata aatttaaaag ctctatttcg tagtacacat 780
agttatatga aagaatttac tggaggaggc atttatctaa gaaataaata agaattattc 840
aaccattgtc attcttgctt gagatatgtc atcgaaagga ttttgggtat tttcaaatca 900
agatttctta tattcaaatt cgctcctagg ttttcataaa tgacacaagc agagcaagtg 960
cttgtatctg ctgcattgca taactttttc cgtcagaagt gtcggccaga tgagtttctt 1020
ccagaagaaa catctgatga acaaaatgtt actcaaagta gtgatggtta tcaatttctt 1080
ggcgaacaag aacaacaaag agaacatgct actgaataga gaacaaccaa tgcttcaaat 1140
acgtggaatg atgctactag tggatctcaa cggtgaaata tgcctgagta agttaacatt 1200
tttatgtgtt ctttaatttt tataattgac aataatagtg aaatctccca acgtattttt 1260
gattgatagg tgtgagatga tttatggcat tgttggcatg atattagaaa cacacattcg 1320
tctgtcacaa taaagtcaaa attacagtca agtatttgta attttttcat gctttttttcg 1380
```

```
aaattgatta cactttttg cgtggtttcg ataaattgtt gtgagaaaat gtttttaat   1440
gatcttagga aatctatttt tattttcttt aaaattctac caaattaatc tcctatcaaa  1500
agctctatca aattccttaa accccaaata aatttagcta aattccatca aatctgaaat  1560
ccttaaaaat tttcaaatcc ctaatcaaat aagcccttta atatatttga acgtatactt  1620
aagtaccaaa tggttctata tttaaaaaaa catccaacag ttaattcaag aaaacaacac  1680
tttaaatcac tttttatccc tttcgtaatt tgctaaaata tgataatcta cttacaaggt  1740
tgtcattttt ttcagataat aatagtccct tgttatttac aaaattaact ttacaaaaaa  1800
attaacgacc aatcacaatg ctgatactga ttcagctaaa gtaactgagc ccacggaatt  1860
caccccacca aacctctccc aaaatatcaa gatattaaag aaaagaaaat gtatacgtga  1920
ctctttttac aaaggctata taaaccctag tctggcacaa ggttccatac aacacaaaca  1980
aatacattta cttattaacc atgaagcttc atggactagc cttgataggt tttctaattg  2040
ccgtggtgag ttgcaaagct attgaggaat gccgagagaa cgagccattc acatgtggaa  2100
acactgatca gttaagcagt aaaagtttcc caaaagactt catattcggt gttgcttctg  2160
ctgcttacca ggcatgttac aaatcaacaa tttttgacgt agaaaaccat ttaaaatatt  2220
aaatccaacg ttgcatggtt gtttcttatt attgtaggtg gaagggggca gaggacgtgg  2280
tcttaacgtt tgggatggct tcactcaccg atacccaggt atatcatcta catggtacat  2340
atatatacat atgtacaact cttatcattc ttagtataaa atgtatctgt ttactatcag  2400
agaagggagg atccgatcat gggaatggag acactacttg tgagtcatat acgagatggc  2460
aggttagttc ctcactgagt catataccag atggcaggtt aatttctcat ttcctcacta  2520
tatataatga tatccgagtg cgtgtgtaaa ctgcagaaag atatagacat catagacgaa  2580
ctcaatgcta ctggctacag attctcattt gcctggtcaa gaatcattcc aagtatgaac  2640
acataaacaa tctatttata caaaagaatt ctcgtaattt gattgtgatt gttgggaaga  2700
ttaaatatat gatatgtata catgagcaga aggaaaggtg agtaggggag tgaacaaagg  2760
aggtatcgaa tactaccaca aacttctaga tggcctcatc gctaagaata taacccctt   2820
tgttaccctc tatcactggg accttcctca aacactgcaa gatgagtatg aaggtttctt  2880
gaaccgcacc gtcatgtatg tcatttgggc cgcgttctta gcaaggaata taagaagaaa  2940
aacatatata cataagtgat ctcatgttaa tgatttgatt ctatgctatg cacagagatg  3000
actttagaga ctatgcggat ctatgtttca aggaatttgg tggaaaggtg aagaactgga  3060
tcacgatcac cagctgtaca cagtgcctac gagaggctat gcaatcggaa cagatgcacc  3120
cggtcgatgt tctccggcgg ttgatgagag atgttacggc gggaattctt caacagaacc  3180
atatatagtt gcacataacc agcttcttgc tcatgctgcg gcggtcgatg tttacaggag  3240
aaaatataag gtgagagtac gtgggtttgt gaataggtgt agtctttacg tatatgacta  3300
tatctaatca tatcattatc gtatgccgtg accaacagtt ccaaaaaggg aagatcggac  3360
cagtgatgat aaccagatgg tttcttccat ttgatgagac tgatgccagc agagatgcag  3420
ctgagaggat gaaagaattc ttcttgggat ggtaacgtat atgtatgtat atatcaacaa  3480
aaatgaaatg attttcttat acgtatgtac gtcgaccagg ttcatggagc cgctaacaaa  3540
gggtagatac ccagacatca tgagggaaat tgtgggtagt cggcttccca atttcacgga  3600
agcagaagcg gaactcgttg cggttcata  tgattttctt ggtctcaact actacaccac  3660
tcagtacgcc caggcaaaac ctaacccagt tacatgggca aatcacactg ccatgatgga  3720
cccaggcgca aagctcacat gtaccattct gtttcctctt atagttacaa cctttctata  3780
tatagatatc tccttttaat tataacatat atgtacattg tgagtgacca tcaattattt  3840
catccttggg tttacagata acaattcacg tggtgaaaat cttggtccac tggtacgtgc  3900
atgatccacc cctgttactt ctcaatattt tttttcttt cttgtttatg ggtataaatat  3960
gtacgcttcc ttttctcagt tcgttaaaga cgaaaaaaac gggaatgcct attactaccc  4020
aaaaggcatc tattacgtta tggactactt caaaaccaaa tacagtaacc ctttgatcta  4080
tatcactgag aacggtgact actactcatc tcttttttgc atattaatta agtaaatgtg  4140
tgtttcaaat aatgtatagt tgttgatgta ccatgatggt ctaattagga tttagtactc  4200
ccggtgaaga aaaccgtgac aaagctattg ctgattccaa gcggatcgat tatctctgca  4260
gtcatctatg ttttctccgc aaggtcatca ggtgagggga agctacttta ttttttctc   4320
ttttgaattt gatgtatggt catcatcatg cataggcttt gaattatgat ttttcctgtt  4380
tccagggaga agggtgtcaa cataaaagga tactttgcat gggctcttgg agataattat  4440
gaattctgca aaggttttac cgttagattc ggacttagtt acgttaactg gacagacctc  4500
aatgatagaa atctcaaaga ctctggcaaa tggtaccaaa gctttattaa cggtaccaat  4560
aagaaccctg ccaaacaata tttccgccgc ccaaacctct ccttccagaa ccagaagaag  4620
aagctcgcag atgcatgaaa cactttatcc caccatcatg atcatcttca tatctctact  4680
acttgcttca tagataagga gcttgttgta ctaaataaat attctaataa aagatgatca  4740
tttactaatg aatattttcg tttgagttca atcccttctt accgcttcag ttacgtttta  4800
ctttggatga ttaggttagg ttttacaaat tataaaactt ggcatgtcag ctattcatgt  4860
gagatttgta ggtttagata agagagagtc tatgtgtaaa tgcgagaact agcaagaata  4920
gtaacacaaa gtacacaaga gaatatctct acaaaaaaata tgtgtattta ctagtatttt  4980
taaagtaaat ttactgatat cgaccttaga ttctgtcagc acttgcctcc aagaaaaccc  5040
tagattcttc aatcgcgacc tcctctgagc tgagcctgag ttctgatatc aatttgttca  5100
acttaacgct cagattacga cctagatctt ctcgattgct tgaatataaa aaaacatgca  5160
agaagacacg gtttgttcac ccggtgtcca actcctttt cgatgtaagt aagagatatt   5220
ctcacctggt ctggttagac cagcaataca ctatctcagc tcaaactcga gcccggatca  5280
acaaccgatc acaatcttct tctccgatct tatctctctc tctctcttat cagctagaga  5340
tataaagtga gttttaacgt cgttttacaa cactcatctc ccccccaacg tgctaacaca  5400
cgtgcaactt gaacaagcta taaccggctt aaatcacttc taatttaacc cgtcaatcaa  5460
accagtttgc atacactcgg attcctgtca tcctgagtag acccactcag cttcgtatct  5520
tgcgaactta gaaactcagt tctcagtcac cctgagaaaa gtcaattctt ccctcatctt  5580
gccaactggt aaaaccttgg taatatattt gcgggattgt actgcgaagc aatcttcaca  5640
acattgatga tcttctcact taccaactca cgaacaaagt tgtacttcac gtccacatga  5700
tttgtcctct tctgaagcac tgtgtttctt gatagtgcaa tatcactttg agaatcacaa  5760
aacacctcca cttgggttgg tcttaagcaa aacccaactc gttcataaaa cccctgagcc  5820
atactgcttc ccgagctgct tcactcaatg caatgtacct ggttgttgat agtgccacta  5880
ctttctgtaa actcgacctc cagctcacta aattctctcc aaatgtgaat accattcctg  5940
tgattgacct ctttttatcc aagtctgctc catattcttc atcacagtac ccctttataa  6000
taaaatgtca ttgcttcttg tgttaaagca tcaccttgat attatttcct ttctctttct  6060
cttcttattc tttcagatct ctgattttct tgatatcgac gaaaacataa atcacaggtt  6120
```

```
actccagtta agttacctcc acttatacaa ccagcatcac catttaccac tgcattagtt  6180
tctgctgctg tcgtcatccg tcattcaatt gatatcattt catattatct tccatgtaga  6240
tcgtactgtc caatctggtt tggaggaaac gctagacgag gttctgtcat tgccgacatt  6300
aactgacacg ccaccatcag tgttcttcca tttcctaact tccatcgaaa ttaacaaaaa  6360
tagcccggaa ttgatgtcgc tttcatattg tcttccccgt cttctttatg tttaacattt  6420
ttaagttttc aaatctgctc tattatacat acatacttat atagtatata atattatata  6480
tgattttcag attttaatta cattatattt taaatttggg tttattaatt agagtttact  6540
gagtagtgtt tagtgtttag tatttgaaag gtgaggatga aattagaaat aggttaaaat  6600
aacgtttagt attttacatt tttgtttatt gtgttcta                          6638

SEQ ID NO: 38           moltype = DNA  length = 6812
FEATURE                 Location/Qualifiers
source                  1..6812
                        mol_type = genomic DNA
                        organism = Brassica juncea
SEQUENCE: 38
tccaacaaag atggaaacct agatttctaa tcaaggcgca acacaaggac gtctctctcc  60
actcatcatt actctttgaa ttgccattct ctacggcaca tggggcaatg agcttgactc  120
gtctgtgaat tgacccattt caaaatacaa tggagatgaa acgaatggtt gcaagctccc  180
caaactgctc gataaccata taacgatcca ggtttaagaa tacaaataag atataacgat  240
ccaggtttaa gaatacaaat aaggggtttt agttttgaaa caatcacagt gtgtagaaag  300
agacatgaaa agagaggaga cacgtactta gagggcaatc atctccaggg agtttgcagt  360
ctggacaaca accgtcgaat ggcatacgac atatcccaca tgtctcatcc tgagcatccc  420
atgtccatga cgcaaccgca tgccacctta cagtttattt tttcacaatg taagagttca  480
cgtattggaa ttgagaatgt atgtaacaca tgtagtggga caaagaaact tactctgttt  540
tttttttaa aaagtcagta gacattgtag cactgagagt caaggaagaa acagttcttt  600
ggaaacaaaa tcctaaatta aagaaccttt gagataatct tcgcctacct tatatgaact  660
agttgggagc tgataaccaa aatcttcacc gaaaaaaaac tattagaacg tcatctacat  720
cagtattcaa aactgaaatt catgaaaaga gaacaacttt atgaaatcat gaaacctaag  780
ctgcatcttt taaaaaaatc atgttttaaa catcaaagaa actatgtact ggaaaacatc  840
aagcattgac gtgaacattt ggatgcatga ttgacatgca gagaagatga agtagaagga  900
tacgcaagat cttgactttc atgtcttcct cctaaatgaa acataaaaat aatcttatat  960
cagttaaaca aactaaaaaa aaatagaaaa cacaaactca agaaagcaca atcctttttt  1020
actatactat aaatctaata ctactaaggc ttcatcgtct gaaaacttag acgagataaa  1080
ttcatgtttt tgacgcattc gtacactagc atgcagcaga tggcgtttcc ttagctgata  1140
gagtgatatc aacagaacgg agcaaaccca tcagaaaatt caaaaactca ccggagtttg  1200
acggagaagc gaactgcgac agagaagaag cggcgagatg tgaatagaag acacgaatta  1260
gttaagatat gggctttttat ttaaactggg ctttatttaa aattgatctc agggcccata  1320
cgtgtgctct tcttaacaag attatatatt atttataaac gacaccaata aaacgtggtt  1380
tgttttcgtt ttcttttgtc tttccgagcc tctagtttca tgtgataaaa gcaaatagag  1440
aggtcaaaag aatcaacacc aatacgatat gctgtgattt tttttttaa atatgttgta  1500
attgttagcg gtgaggctcg tgaagagtgt ggcattggtt cagctttact ttagtttcaa  1560
cactcgataa tatttcgata aaaatcttca ataactttat ggcgctatga ccaagctttg  1620
aacattattt actacagtga atcttaatga tgcgtatcat tcttgttaac cttcgatata  1680
tatatgctgc attgcaccac cgtcgacgga acaatttgaa gatgtgacgc aactcgtgtt  1740
caagtcgtac gtgttcccgt aaaggaacat aaatatttgc aatagatcat gaaagactaa  1800
acgtggaaac aagcaagaaa tttggagtaa actcggtgaa tattgagcta aagtaaccca  1860
cgggactcat cccacctaaa cctctcccaa agtatcagga caagaaatac ttacgtcact  1920
attctttagc aatggctata tatacctag atcggtacaa ggtttcatac aacaccaaca  1980
catacaacaa cagattaacc atgaagcttc ttcatggact cgctttagtt tttctattag  2040
ctgctgcgag ttgcaaagct gatgaagaaa ttacttgcga agagaacaat ccattcacat  2100
gtagtaacac tgatatttta agcagtaaaa acttcggaaa agacttcatc ttcggtgttg  2160
catcgtctgc gtaccaggca tgcaacaaat gctgccatac tatatttttg acgtatacaa  2220
aataatattc aaaaatgcta aaatatccaa ctttgcatgg ttgtttcttt tcatttcaga  2280
tcgaaggagg gagaggtcgt ggtgttaacg tttgggatgg cttcagtcac cgatacccag  2340
gtatgtcact gtggcatata catatatata tatatttaaa tgagataaat gacggttata  2400
tgtatacata ttaatgtatt tgtaaattac tatcagagaa atcagggtca gatttgaaga  2460
atggagacac tacttgtgag tcatatacta gatggaaggt gaattcctca gtacatatat  2520
actcatatga ctaaactacg tataaaaagt aactgtggac tgaattgcgt ttaaaatatg  2580
taaactgcag aaagatgtag aaattatggg agaactcaat gctacaggct acagattctc  2640
cttagcgtgg tcaagaatca ttccaagtat gaacaaatta ttcattcgtt tgtattttag  2700
ttaggatcat gtagctggaa gagtactaat tgatatacaa tatacatgag cagaaggaaa  2760
ggtgagtagg ggagtgaacc aaggaggtct tgattactac cacagcctca tagatgcact  2820
cctcgaaaag aatataacgc ctttcgttac cctctttcac tgggaccttc ctcaaacact  2880
ccaagatgag tatgaaggtt ttttggaccg ccagatcatg tatgtgccat gcttcttaat  2940
catatacaaa tttttaataa gaacaagaag aagaagattt tgtcttaatt acatgcttta  3000
ctgaaagaat gattatatat taatatgcac agacaagatt tcaaagacta tgcggatcta  3060
tgtttcaaag aatttggtgg aaaggtgaag cactggatca cgatcaacca gctattcaca  3120
gtgcctacga gaggctatgc actcggaaca gatgcacccg gtcggtgttc tcctatggtt  3180
gatagcaagc acaggtgtta tggcggaaac tcttcaacag aaccctatat cgttgcacat  3240
aaccagcttc ttgctcatgc cgcggtagtg gatctttaca ggaagaacta tgcggtgagt  3300
agtcttcata tgtgaaaagg tggtgaaaat ctaatgtatt tgatcctaat ttactcatat  3360
atgatgtgac caacaggacc aacaagggaa gattggacct gtgatgatta caagatggtt  3420
tcttccatat gatgaggctg atccttcttg tatagaagca gctgacagga tgaaccaatt  3480
cttccatgga tggtatatct tcttttttg acatcaaacg gttactctat tattcaaaat  3540
taaagatggt ctaggtaatt agattgatta tatatattgt atgtacatat aatgaaacaa  3600
aatataaatg gatcaggtac atggagccgc taacaaatgg taaataccca gatatcatga  3660
ggaagattgt gggaagtcgg cttcccaact tcaccgaagc tgaagccgaa cttgttgctg  3720
gttcatatga ttttcttggt ctcaactatt acgtcactca gtacgcccag ccgaaagcta  3780
```

-continued

```
atccattgct ctcagagaaa cacactgcca tgatggacgc tggcgtagga ctcacatgta  3840
cgcattactc tcctttttgt tacaacatac ttatttgtga ttgaccttca gtaatttctt  3900
tcttgtgttt acagatgata actcacgtgg tgaatttctt ggcccactgg tatatatgca  3960
tgatccactc ttatgatttt tctttcatta ttttatcttc ttttcctaac tgcagtgtac  4020
ttggaacacc cacaataact tttttttctg attgatatgt atattttgtt tgcttccctt  4080
tctcagttta ttgaagacaa aaaagccggc aacagctatt attacccaaa aggaatttat  4140
tacgtcatgg aatacttcaa aacccaatac aacaaccctt taatctatgt cactgagaac  4200
ggtaagttct acatattact agtaatctat ttttatttat gctacatatc atcagataat  4260
tagtgtattt tgatactgag tccaaagaaa ctgactttca aatactgtgg aatattttta  4320
tgtgatggcg atttaattag gatttagtac gcccagctca gaaaaccgtt gcgaagctat  4380
tgccgattac aagcgaattg attatctctg cagtcatcta tgttttctcc gtaaggtcat  4440
caagtaagtg ctactataca tgcttttctt ccaatattta tcttcttttt cttcttcttt  4500
ttaagtaata tatatatata tatatatatg tatatgattg ttattgtttc cagggagagg  4560
aatgtgaacg tgagaggata ctttgcatgg gctcttgggg ataattatga attctgtaaa  4620
ggctttaccg tcagatttgg actcagttac gttaattggg ataatcttga cgacagaaac  4680
ctcaaagaat ctggcaaatg gtaccagaga ttcattaaca ggacttccaa gaaccctgcg  4740
aaacaagatt tcctccgctc aagcctctcc tctctcaaag ccagaagaag aggcttgctt  4800
gctgatgcat gaaacacttt tccccccttca agatcatctc cacgtctctg atcactcttt  4860
tttgttgctc catagataag gagcttctac aagtaaaaag atgatcaact actaatgaat  4920
aaaataaatt tatctacaag tacattatgt caagtcaaag aggtgaggat aacgcatttt  4980
aaacagtaaa catcacttag acgcacatac aaaataaaaa ctcaaaccgc caactagttt  5040
agtgtattaa aaatactaag gaaatgatta gcctaaattc agtaattatc taatacaaat  5100
ctaaaactaa ctaaacgaaa gtataacaat aatttaacaa tccatcaagg gtcggtcgta  5160
ttaaattcgg aacaacaatc caacacatct ttagaaatga aaaccaatgc tagatatcta  5220
atcaaagcac agcacaaagg gtttctctct ctccactcat cgttactctt tgaattgccg  5280
ttctctacgg cacatggggc aatgagcttg actcgtctgt gagttgaccc atttcaatat  5340
acaatggagg ttgtcattct agacaaaatc gttatatcta aacaatttta atgatgtctg  5400
cttactttaa tatttgaaaa ctttttattt ttctgtttct aaaagaaaaa cgaaaaaaaa  5460
tattttaata acacccatta agacttttgt ttgatcgtga attattttta tcataaatat  5520
ttgtacgtca atgtatcttc taggttccaa tcttaaccaa atgtataaat ctattttttt  5580
agaatctata atattaaaac atatgtacga attgaaaact aactttgttc ttatgtatta  5640
caaaatatat ccattttaat aatcatatat attattttgt aaaaataatt aaaaactaaa  5700
ttttaacgta aattaaaata ttatatcaaa ccaaaaaccg aactctataa aataaattat  5760
atacgtcaaa aattattaac tatatatatt tagtttaaaa ttatcaaata gtctaaaaat  5820
actatttaaa catcgaacta tccaaaaatc gtattatcct attacttttt acttgaaata  5880
ttttaaatta tcctaatttt agaactgaac catccaatat tttttatctg aaatattaaa  5940
tatctgaatt atcaatattt tgtaaaaata tatttaaaat caattttatc cgaattattc  6000
aaaattatcc aaaagatgag accaaaccta aaccaaattg aactcaaaat tttataagat  6060
tcctaacatt gttatctaaa acaagccaaa aatcaaaatt gccaaaccaa aaccaaaggt  6120
aaacttataa ataaccaaat agtgttata tctcttggac taaaatacca aaaaaccaat  6180
accacaaatg aaccggaacc caatcaaaac ataaaataat tgaaattcaa caaaaatcaa  6240
acatccatac ctaaacatat tagtaaaaaa cagatgaatt cataaattat caacacaaaa  6300
tatagttcat gtttaaaggc gtaacttttt tgtaacagaa aaaaaaagaa tatctaattt  6360
tgggaaatat aactaaaaat gtattaattc taacataaaa tgtagagcta aactattaaa  6420
taaactatag gttaatacaa aaggtatttt ttaccatata tgtgaatatc tatctatact  6480
attaaacaga aaaatttttg agaccctttg atttttatag tatttacaac agtgctatta  6540
tcttttaaat taaattctat attattataa attattatta aacagaaaaa ttgcagggaa  6600
ttaactgcct acatacccga ttttccttaa ttaattatag ctaccataaa gtggtttctt  6660
taaaaaatag ggattatttg taaattactc tattaatagt ttgaaatttg aaaactacac  6720
ttctatttta ttttttgaaa gccacacttt attcaatgtg aattgacatt tttatccaga  6780
ttagatattt taataattaa aatataaaat cg                                6812

SEQ ID NO: 39           moltype = DNA  length = 7414
FEATURE                 Location/Qualifiers
source                  1..7414
                        mol_type = genomic DNA
                        organism = Brassica juncea
SEQUENCE: 39
taaaatgtca gaccagaata actaaggggg ttattggtaa ggaattctca ccaattttga  60
aaattttaag aatccattgt tattggttct tggatttcaa aaatcttagt agaaactatt  120
gttattggtt taagaatttt caaaatccat aaatctcttg ttattaagtt tagttattac  180
tgattctcta attctaacta aatctagtat tattggaaga tgaattatat tcatttttac  240
tcataagact taacttttaa aatatcatat gtattcatgt gattttcaaa atctttgtga  300
taaaaaacat agaaaacaaa agaattattc ttaccaaata tctattgcac ctaaatccaa  360
attatatgtt caaaactata attcattaca tttatatact tttacatttt tgaataatta  420
ttttaaaaaa tataatatat taaaaaaatt atagttttac attacattta caaatcttaa  480
taattttgaa atattttttt ttaaatagtt tcaaaaacat tttcgaattt caaaaaaaaa  540
tcgaaaaata taaaaattat aaaaaatttt gaatttgaaa acatataatt tgaaattata  600
taaaaacaat ttttaatttt ttaatttttt attacttata catctatata gcaaggggta  660
aaataatctt ttaccttttt aatgaaattt ctttgggtca ttttttaatg ctctttttgt  720
gataaaatct tttaaaatgg ctatttaaga aaattgctca attttgtatg tatcagtatt  780
attttctttt taatttgaat gcaaaaaata aataatcatg ctatatgatt tagaaaataa  840
atagattata tatttatttt acaaaaaaat gatagaaaaa aggtaataca aattcatgaa  900
aatataaatc aatctaaaaa agtcataatc aaatttaata agcaatatat ataaattttt  960
actatccact taacttttta aaatctatca actctcaaaa ttcacaaact ctacataaat  1020
tcatctccca ataacttctc ctaaatttaa aattaaaagt aaaatattaa ttacttatta  1080
taatatttag ttcataaata gttatattca tgcaagagca cggaaaattt acctaaagca  1140
atattaaata caagttaacg tatatatgtg ctacgtaaat aatttatttc aaaaacttga  1200
tggcacgtaa acggtaatga tgttatctat agaaactaaa taatatgtaa tatggctatt  1260
```

-continued

```
tataacaaaa cgtatgtatt ctaactttat agagttaaaa actatggaac aaactatagg  1320
tcaatcttat ctatctggaa gtcggatccg tatccgttcc aacccttcca aacatttaaa  1380
acgatgccaa aaaggcaaaa aatgggttgg ttttcgtttt ctttagtctt tcggaggcac  1440
cggtctcatg tgataaagca gaaatagacc gatcaaaacc aataagatat gatgtgagat  1500
cttgtgagcg gtaaggctcg tgataagtgt ggctttgcac cagtgttaat ctagattcaa  1560
cacttgataa tatttcgata tacgtttcca gtaacgaatc ttgacgttgc gtgtcgttct  1620
agttttgcgc aaatcttaca tgctgcattg catcattgca tgactgttga cggatcaatt  1680
tgaagatgtg tcaattcgtg ttccggttaa ggaacacaaa tatatatatg tgctatctaa  1740
caaaagaata atatttgcaa tagaaaatga aagactataa agtgggaaca taacaatcac  1800
aaatattaca aaaatcggtg aacactgagc taaagtaatt aagtgaaccc acgggactca  1860
tgatcccacc tgcacctccc caaaatatca agatactaag acaaaaaaat agtggtgtca  1920
ctcttctttt ggaaaggcta tataaaccct aatgggcaca aggttccaca caacacaaca  1980
catacatcaa cagattaaac atgaagcttc ttcatggact cgctttagtt tttctattag  2040
ctgctgcgag ttgcaaagct gatgaagaaa ttacttgcga agagaacaac ccattcacat  2100
gtagtaacac tgatatttta agcagtaaga acttcggaaa agatttcatc ttcggtgttg  2160
catcttctgc ttaccaggca tgtagcaaat gttgtcacac cataattttg aaataaaatt  2220
taaaacacta aaatgcaact ttgcatggtt gtttctattc atttcagatt gaaggaggga  2280
gaggtcgtgg tgttaacgtt tgggatggct tcagtcaccg atacccaggt atgtcatttg  2340
cacagcgaca tctatattta tatgtgagag gaatgttggt tacatatact catatagtca  2400
tattaatgta tttgtaatta atatcagaga aagctgggtc agacttgaag aatggagaca  2460
ctacttgtga gtcatatacg agatggcagg ttaatttctc agtacattga tactcatgac  2520
tgaactatat atgtataaaa ctacagtgtg gattgacatg agattaaaat taatatgtaa  2580
aatgcagaaa gatgtagacg tgatgggcga tctcaatgct actggctaca ggttctcctt  2640
tgcgtggtca agaatcattc caagtatgta catgttatcg attcgtttgt attttaattg  2700
ggatcattta gttgaaaaag tactaattaa tgtacgacat atatatacat gagcagaagg  2760
aaaggtgagt aggggagtga accaaggagg tcttgattac taccacaaac tcatagatgc  2820
actcctcgaa aagaatataa cgcctttcgt taccctcttt cactgggacc ttcctcaaac  2880
actccaagat gagtatgaag gtttcttaga ccgccagatc atgtatgttt atatttgtgc  2940
catgcttctt atattattaa taaaagaaga aaaagatttg gtttagttac atgcattaat  3000
gaaatgattc tatattaata tgcacagaca agatttcaaa gactacgcgg atctatgttt  3060
caaagaattt ggtggaaagg taaagcactg gatcacgatc aaccagctat acacagtgcc  3120
tacaagaggc tatgctatcg gaacagatgc accaggtcga tgttctccta tggttgatac  3180
caagcacagg tgttacggtg gaaattcttc aacagaaccc tacatcgttg cacataacca  3240
gcttcttgct catgccacgg tcgtcgatct ttacaggacc aaatacaagg tgagttgtct  3300
caatatgtgt aaagatggtg taatgtaatc taagatatct gattctaact tagtcaaata  3360
tcacgtgacc aacagttcca aaaagggaag attggacctg taatgattac aagatggttt  3420
cttccatttg atgagtctga tcctgcctcc atagaagcag ctgagaggat gaaccaattc  3480
ttccatggat ggtatatata tatatttata ttaccaaaaa tgtatcagta taaattgtat  3540
atatgtataa tgaaaagata tacatggatc aggtacatgg agccgctaac aaagggtaga  3600
tacccagaca tcatgaggca gattgtgggt agtaggcttc ccaacttcac cgaggaagaa  3660
gcagaactcg ttgctggttc atatgatttt cttggtctaa actattacgt cacccaatac  3720
gcccagccaa aacctaaccc atatccttca gagacacaca ctgccatgat ggacgctggc  3780
gtaaagctca catgtacttt tctattacca cttagttaca acctttttgat atatataaat  3840
gttttatctc ctttttgtga gtgaccatca gttatttcat tcttgtggtt acagatgata  3900
attcacgtgg tgaatttctt ggtccactgg tataatatga atgatccacc cctatgattt  3960
ctaattcatt ttattttttc aattttcaat ataagcacca ctaattaggt tttcttgatt  4020
gatatgtata cgcttaactc ccgtttctca gtttgttgaa gacaaagtaa acggcaacag  4080
ctattactac ccaaaaggca tttattacgt tatggactac ttcaaaacca aatacggcga  4140
ccctttaatc tatgtcaccg aaaatggtga gttctacatg catatatttt catctataac  4200
atctactata atttgtgtat ttcgaaataa ttccaagaaa ctgactttca aatattgtgt  4260
actttttcat gttatgtcgg tttaattagg atttagtacc cccagttcag aaaaccgtga  4320
gcaagctatt gccgactaca agcgaatcga ttatctatgc agccatctat gttttctccg  4380
caaggtgatc aagtgagtgg atgctactat aaatgatttt ctacagatgt tacttctttc  4440
ttggtaacat ttatatatat gattcttctt gttttcaggg agaagggtgt caacgtgaga  4500
ggatactttg catgggctct tggagataat tatgaattct gtaaaggttt caccgtcaga  4560
tttggactca gttacgttaa ttgggaagat cttgacgata gaaacctcaa agaatctggc  4620
aaatggtacc agagattcat caacgggacc gttaagaacg ctgtgaaaca agatttcctc  4680
cgctcaagcc tctcttccca gagtcagaag aagaggttcg ctgatgcatg aaacactttt  4740
ccccccggtc aagatcatct ccatgtctct cactctttct agttgctcca aagataagga  4800
gcttcttcta cctacaataa tgtactaaat aaatattctc aataaaaaga tgatcagtta  4860
ctaatgaata aaaaaattgt ctacaactac attttgtcaa gatgatcgag agagagagag  4920
agtgaaataa cacaatttaa accaaaaacg tcacttagac acacatagaa aataaataaa  4980
taattacccc aaaccgcaaa ctagttttgt gtaataaata tataaacatc aaaccgatca  5040
gcttaaatta acttaataag ttcaacttta tatactagaa tagattttca acataataaa  5100
caatgaccaa accttataca aactcaaatc tagctacacc aaagttctat catcctcaac  5160
tgaaacttaa tagtatttta catatgattt tcctatcatt caaatgattt tattttattt  5220
tggttcttat acaatcaaga aaaccaaaag aaggtaaacc tcagtacttt atgttttatg  5280
aatgcttcct caaagaatct ggcaaatggt accagagatt cattaacggg actgtcaaga  5340
attctgcgaa acaagatttc ctccgctcaa gcctctcttc ccagagtcag aagaagaggc  5400
tcgctgatgc atgaaacact ttccaccatc aagatcatct ctatatctct cactcttcct  5460
acttacccca tagataagga ggttcttcta tctacaatgt actaaataaa caatctcaat  5520
aaaaagatga tcagttatta aatgaataaa aataatttgt ctacagctac attatgacaa  5580
gtgaagatga cgaggaaaga gggaaaataa caaaatttaa aacatagaac actcagaaat  5640
ctcaaactag tctagtgtta aaaaatatta acggacggat tagcctaaat tcactaatta  5700
gtttaataag tgcaacttat ataataaaag gtatcttcaa cataataaat aacaaccaaa  5760
cctaatacaa actcaaagtt tctaaaccaa agttctataa tcctcaacta aaactttatg  5820
agatcttaca tatgatcttt tatcattcat ataattttat ttgattttgt tacttttttt  5880
tttgaacaaa ctacctttca tccaataaaa tcgaaataca ctccatcgtg agtagcgaag  5940
gaattttgtt acttatataa ttaataaacc cagaagaagc taaaccccaa tcctttgttt  6000
```

```
ttatttcttt gtatttcaac attgtgaaca agaagagggt cagtagtctc tgccgttgca  6060
ggtccttctc cttccgctga gacggccctc ttttttgttt gttcaccgcg gcacgaaatc  6120
atgaagaagc tggaataact cagaaagaga gtggcaccta gccgttgaga gcgtctatta  6180
tctgagaaca gagctcccat cacaacagaa tgcacgcatg aagccgccat ccgtcccaac  6240
gtattctgct cttgaatgat ggaaaaataa tatcaagaat tgaagtatca gaagtttctg  6300
aaagaacatg tcatttccgg tttcctatat tctttaagac tttttgcgga tttcccaaaa  6360
caaaattaaa gacgtggtta gccatttctg gtttcttata aagattcgat ttatcttgta  6420
ctccttccgt tttttaatat aagtcgtttt tgaattgtct acgtagatta aaaaatcatt  6480
aattttttat attttctaaa caaaaacatc attaattatt tacataacca caaatcaacc  6540
aataaaaaaa tagaaggtat attatcactg gtcatataac attaagtgtt aataaatttt  6600
acatagaaaa ccgaaaacgt catttaattt ggaacataaa ttttttctct aaaacgactt  6660
atattaaaaa aaatagaggg agtattacac aagctataat aatttagtga gtctcaaatt  6720
tataattttg gtttaaataa tataataagt ttttttttctt taattcagaa aataagcatg  6780
tttagtagta ttattagaat tgtatgaatt ttcctttgga tatatctctg taattttagt  6840
cctactatct acgcagcatt agctggcaac attttcttct aaatttgcat tgaagtttac  6900
tgtttttttat tggttggttt aattgcttca actaagggaa acatatcttg agttatacaa  6960
ataatatcta aaattacatg attattatct gccttatcca atgatttccc gacaactgtt  7020
aatgaatata tatattcttt ttgtaactat tataattata tttactgcaa tttagcatta  7080
atgatccaaa agaaagtgat aagatctgca tacgtaatac cagcctcatt acactatata  7140
aacaagagca ttatcaagtg ccaacatatc tctatcattc accaacacaa aataatgcca  7200
aagggaagga taaaaataga gcccatgact aatagcgctg caatgaacca aactttcagg  7260
aagaggaaga aaggtttact caaaaaagcc aacgagctgt cgactctcta cggtgtcaaa  7320
gtttgtgcgg ttatcaacag ctgcgacagt acggagccgc cggagttttg gccgtcaaag  7380
gaaggcgctg aagcagtgca ctcagcgttt atgg                              7414

SEQ ID NO: 40          moltype = DNA  length = 7247
FEATURE                Location/Qualifiers
source                 1..7247
                       mol_type = genomic DNA
                       organism = Brassica juncea
SEQUENCE: 40
ccagtctaag aatcgacagg ccaaatttct catcttctct acttcagtta tggttctcta  60
cgtgaaaccc atccaactaa ttcactgatt caaatttgta tcttttagat atgtaaggcc  120
acttggccta ctgagttcaa tctctacaaa acattttcgg tctcttgcat ttaaaggcct  180
gttcgtttgt acatctggaa gatgcatcca gatggtccat ctagatgtct tatccagatg  240
atccatctgg gtgttgttcg tttcttcatt tcgtccatgc atccagatga aatcatctaa  300
atgcaactat gttcgttttt ttcatttttt aacttccata tgcatccaga tggacttatt  360
aataaaatga cttaaatata tttttacgt ttcgacggaa aaatagcatt tttacggttt  420
tggctgaaaa tatttttgcg gtttttgagg aaatatgtgt ttttcgcaaa aaagtgtatt  480
ttatggtttt ggcggaaaaa tacgttttat gggtttggcg gaaaaatacg tttttgtggt  540
ctggacggaa aaagtgtgtt ttgaagtttt ggcgggaaaa gcattttcgc gattttggcg  600
agaaaagcat ttttgcggtt ttggcgggaa aatacatttt tctggttttg gcggaaaaat  660
acattttctg gtttttggcg ggaaaatgcg ttttttccag ttttgagggg aaaatgcatt  720
tttccagttt tagcgaaaaa atgcgttttt ccggttttgg tggaaaattt tcattttcca  780
attttggcgg taaaattgac tttttcagtt ttggcggaaa aatacgtttt tccggttttg  840
gcggtaaaat tgtgtttttc agttttggcg ggaaaatgcg tttttccgga tttagcggga  900
aaattgtgtt ttccggtttt ggcgggaaaa ttgtgtttc tggttttggc gagaaaatgc  960
gttttccggt tttggcggaa aaattacgtt ttcccggttt tggcgagaaa atgtttttg  1020
cggttttggc gagaaaatgc tttttggagt tttggcggga aaatgcgttt ttttttgttt  1080
tggtcgaaaa gtgcggtttt actggtttgg ccaaaaaatg tgttttatga aaatttgtgt  1140
tttatgtttt tttttgcgga aaaacgcatt ttgcggtttt ggcgggaagt gtgtttttttc  1200
agtttttgcg agaaaatgca ttttttggtt atagcggaaa aatgtatatg caaaaaaaaa  1260
ttgaatttac ggtttaaaaa taatattttg attttaaaaa gtcatttttg tcttttatca  1320
ttttggacta aactagatgc atctggataa tgcaccatca agactcactt tcatttgggt  1380
gagaatttga gatgagtttt taaaaattca gctggatgat ctatgtggat gtagcattat  1440
aatgcacaaa acgaatatca atttgcatct tcacccagat gaatcacctg ggtgaccaaa  1500
cgaagagggc caaatagtaa aatctttttc aaaaaaaagt aactatcttg tttattcaga  1560
agtcacggtt ttttattctc tattataata tgtattatta tatttagtga aaagattttt  1620
attattcgct tcgatcaatc ataaacgcgc gtacgggtct gattatctag aaacgataga  1680
aaaaaatgca aaaaatgtgg ttggttttgg ttttctttgg tctttcgtag actccggtct  1740
catgtgataa aagtatatat agagaggtaa aaagactcaa aaccaataag atatgctgtg  1800
attatgagcg gtgaggctcg tgataagtgt ggccttggat cagtgttact ctagattcaa  1860
cacttgataa tatttcgata aaaatcttca ataatttatg tcgttaatta tgacgaatgt  1920
ttgaacatta tttaatacaa caaatcttga tgaatgatga tacgtgtcgt tctagttttg  1980
agcaaacctt cgatatatac atgctgcatt catcactgtc gacggatcaa tttgaagatg  2040
tgagacaatt cgtgttccaa gttgtgtgtt ccagatatgg aatgtaacaa aaaaaattac  2100
acttgaaaac aatataaata atatgacaag aaaatgacac cagatttaat tgtccaaaga  2160
cgtgctttcg tacaacttca taggttattt actaaaatta actctaggaa aagtagcaat  2220
aaatcattca caattcagat aaaaaatgca acatcttgta ttttttttttc ccaatgtaat  2280
ggttgattga agaacaaggc atgctaaaaa ctggaaacaa aacaaaaaaa aaaaacataa  2340
tcaatcggtg aacactgagc taaagtaaat gatcacacgg gtttcatctc agctaaacct  2400
ctcccaaaat atcagaacac ttagacaaag aaaaatgcat acaacagtct tcttttgaaa  2460
aggctatata aaccctagat gggcacaagg ttccacacaa cagaacacat acatcaacat  2520
attaaccatg aagcttcttc atggactcgc tttagttttt ctattagctg ctgcgagttg  2580
caaagctgat gaagaaatta cttgcgaaga gaacaaccca ttcacatgta gtaacactga  2640
tattttaagc agtaaaaact tcggaaaaga cttcatcttc ggtgttgcat cttctgctta  2700
ccaggcatgt aacaaatttt ttttgacgta taaataaata caattcaaaa atactaaaat  2760
gcaacttcgc atggttgttt cttttcattt cagatcgaag gaggaagagg tcgtggagtt  2820
aacatttggg atggcttcag tcaccgatat ccaggtacgt cacagtgtat atatacacat  2880
```

```
gagatgaacg ttggtttata tgtacatgta ttaatgtatt tgtaactact atcagagaaa  2940
tcagggtcag acttgaagaa tggagacact acttgtgagt cctatacgag atggcaggtt  3000
aatacattga tactcgtatg attgaactat atatgtataa aaactatacg tgtggaattg  3060
acatgtgatt aaaatatgta aactgcagaa agatgtagac gtgatgggcg aactcaatgc  3120
tactggctac aggttctcct ttgcgtggtc aagaatcatt ccaagtatgt acatgttatc  3180
cattcgtttg tatattaatt gggatcattt agttgaaaaa gtactaatta atgtacgaca  3240
tatatataca tgagcagaag gaaaggtgag taggggagtg aaccaaggag gtcttgatta  3300
ctaccacaaa ctcttagatg cactcctcga aaagaatata acgcctttcg ttaccctctt  3360
tcactgggat cttcctcaaa cactccaaga tgagtatgaa ggtttcttag accgccagat  3420
catgtatgtt tatatttgtg ccatgcttct tatattatta ataaaagaag aaaaagactt  3480
ggttttagtt acatgcatta ctgaaatgat tctatattaa tatgcacaga caagatttca  3540
aagactacgc ggatctatgt ttcaaagaat ttggtggaaa ggtaaagcac tggatcacga  3600
tcaaccagct atacacagtc cctactagag gctatgcagt tggaacagat gcacccggtc  3660
gatgttctcc tatggttgat accaagcaca ggtgttacgg tggaaattct tcaacagaac  3720
cctacatcgt tgcacataac cagcttcttg ctcatgccac ggtcgtcgat ctttacagga  3780
ccaaatacaa ggtgagttgt ctcaatacgt gataaagatg gtgtagtgta atctaagata  3840
tctgattcta acttagtcat atatcacgta accaacagtt ccaaaaaggg aagattggac  3900
ctgtaatgat tacaagatgg tttcttccat ttgatgagtc tgatcctgcc tccatagaag  3960
cagctgagag gatgaaccaa ttcttccatg gatggtatat atatatatat atattacaga  4020
acaatgtaac agtatatagt gtatgtatgt ataattaaaa gatatacatg gatcaggtac  4080
atggagccgc taacaaaggg tagataccca gacatcatga ggcagattgt gggtagtagg  4140
cttcccaact ttaccgagga agaagccgca ctcgttgccg gttcatatga ttttcttggt  4200
ctcaactatt acgtcactca gtacgcccag ccaaaaccta acccatatcc ttcagagaca  4260
cacactgcca tgatggacgc tggcgtaaag ctcacatgta ctagtctatt accactaatt  4320
agatacagcc tttctataca tataaatatt cttttatctc ctttttgttg caacatactt  4380
tatgagtgac catctgttat ttcatccttg tgttacagat gataactcac gtggtgaatt  4440
tcttggtcca ctggtatata tcaatgatcc accccctaag atttgttttt ctttcatttt  4500
ttcagttttc agtataacaa ccctaattat gttttttaat tgatgtgtat atttatttac  4560
ttccattttc acagttcgtt gaagacaagg taaacggcaa cagctattac tacccaaaag  4620
gcatttacta cgtaatggac tacttcaaaa ccaaatacgg agacccttta atctatgtca  4680
ccgagaacgg tgagttttac gaactctttt tatttatacc acataataat tattgtattt  4740
tgatattagt cgaagaaact gactttattg tggaatattt ttaatgtggc ggtttattta  4800
ggatttagta cccccagtga agaaaaccgt gagcaggcta ttgccgatta caagcgaatt  4860
gattatctct gcagtcattt atgtttctc cgcaaggtca tcaagtgagt ggatactact  4920
ataaatgatt ttcttcttat gttatttctt cttcttttt gctaacattt atatatgatt  4980
gttcttgttt tcagggagaa gggtgtcaac gtgagaggat acttcgcatg ggctcttgga  5040
gacaattatg aattctgtaa aggctttacc gtcagatttg gactcagtta cgttaattgg  5100
gaagatcttg acgatagaaa cctcaaagaa tctggcaaat ggtaccagag attcatcaac  5160
gggaccgtca agaacgctgt gaaacaagat ttcctccgct caagcctctc ttcccagagt  5220
cagaagaaga ggttcgctga tgcatgaaca ctttttcccc cggtcaagat catctccatg  5280
tctctcactc tttctagttg ctccaaagat aaggagcttc ttctacctat aataatgtac  5340
taaataaata ttctcaataa aaagatgatc agttactaat gaattaaaaa attgtctaca  5400
tctacatttt gtcaagatga tcgagagaga gagtgaaata acacaattta aaccaaaaac  5460
gtcacttaga cacacataga aaataaataa ataattaccc caaactagtt ttgtgtaata  5520
aatatataaa catcaaaccg atcagcttaa atcaacttaa taagttcaac tttatatact  5580
agaatagatt ttcaacataa taaacaatga ccaaacctta tacaaactca aatctagcta  5640
caccaaagtt ctatcatcct caactgaaat ttaatagtat tttacatatg attttcctat  5700
cattcaaatg attttatttt attttggttc ttatataatc aagaaaacca aaagaaggta  5760
aacctcagta ctttatgttt tatgaatgct tccccattct catattaaga tctcgacgac  5820
agaaacctca aagaatctgg caaatggtac cagagattca ttaacgggac tgtcaagaat  5880
tctgcgaaac aagatttcct ccgctcaagc ctatcttccc agagtcagaa gaagaggctt  5940
tctgatgcat gaaacacttt ttcccctcaa gatcatctct atgcatgtct ctcactcttt  6000
ctacttgctc catacataag gagcttttc catctataat gtactaagta aacaatctca  6060
ataaaaagat gatcaattat taatgaataa aataatttat ctacagctac attatgacaa  6120
gtcaagagga cgaggaaaga gggaaaataa cacaatttaa aacagaaaac actcagaaat  6180
ctcaaactac tctagtgtaa aaaaatatat attgacggga cggattagcc taaattcact  6240
aattagttta atgagtgcaa cttatataat aaaaggtatc ttcaacataa taaataacaa  6300
ccaaacctaa tacaaactca aaagtttcta accaaagttc tataatccaa taaaagggaa  6360
atacactcca tcctgggagg agaggttaga gtagcgaagg aatattgtta cttatataat  6420
caataaaccc aaaagaatct aaaccgcaat cctttgtttt tatttgtttg tatttcaaca  6480
ttgtattcta ctctttaatg atggaaaaat aatatcaaga attgaagtat cagaagtttc  6540
tgaaagaaca tatcatttcc ggtttcctat attctgtaag actttttgcg gatttcccaa  6600
acctaaaata aagacgtgat tagccatttc cggtttctta taaagattcg atttatcttg  6660
tgttacacaa gctatagtaa tttaatgagt caaaaattta taattttggt ttaactaata  6720
taataagttt ttttctttaa ttcagaaaat aagcatgttt agtagtatta ctagggatta  6780
acccgggcta cgcccgggat ttttattttt ttctaattta agttgttaaa ttatttatat  6840
ttaggttatg atatatattt atataaatat taagatgcat gtcataatta aaatttattt  6900
ttaaatttta acacgttaaa ttaacatatt tttttactat ttaaataatt ttttttgtaa  6960
ttttgttggc tatctagtta tcatatttag taaaactatc tgttgagtat tagaataaaa  7020
gttttagata tttaattaaa ctgcagagta ttttcggatc gaccacatgc tcaacaatcg  7080
atcgatccgt aaaaagatgg tcgatttcct tggccaggta agtacaattt tagcaaaaat  7140
atcttagatt ttcaaatatt aagtatataa ctattatttt gaataatatt tttttgaatt  7200
gtattttttg attaaattat tgtattataa tgtttatgta aatattt                7247
```

```
SEQ ID NO: 41          moltype = DNA  length = 8661
FEATURE                Location/Qualifiers
source                 1..8661
                       mol_type = genomic DNA
                       organism = Brassica juncea
```

```
SEQUENCE: 41
aatagaacct ttgtcgaaaa gaatatctaa ttatgaaaaa tataattaaa atgtatttat  60
ttttacttaa agtatagatt taaactatag attaatatac aagtaactat ctcaggtggt  120
atacccaaac acatgttctt agtgtggttg atggtcagga acagatgccc cactcgtgac  180
aggatcctca gttggggatt acaaacagac ccccgttgcc tcctatgcaa tgttgctgat  240
gagtcaattg ctcattgttt ctttgactgt aactttgctt gggatgtttg gagaatcatg  300
gcagcaaaat gtcacttcgc ctcatctcgt caatggactg caatacttcc ccaaattaag  360
agccatactt caaacaaagt ccaaaagact tttcttcttc tatgttggca ggcgacactt  420
tatgcgctct gaacagagag gaacaatcga ctgcacaata ctcatttcac ttcaccagac  480
ggcctggtag ctcaaataaa gcttacggta aaaaacagga tctccagtct aagaatcgac  540
aggccaaatt tctcttcttc tctacttcag ttatggttct ctacgtgaaa cccatccagc  600
taattcactg attcaagttt gtatctttta gatatgtaag gccacttggc ctactgagtt  660
caatctctgt aaaatatttt cggtctcctg catttaaata gtaaaatctt tttcaaaaaa  720
aagtaactat cttatttatt cagaagtcat ggttttgtat ttattcagaa gtcatggttt  780
ttttattctc tataataaaa cgtattatta tttttattga aaatattttt atcattcgtc  840
tcggtcatac ggctctgatt atctagaaac gatagaaaaa tgcaaaaaat gtggtttgtt  900
ttggttttct ttaaaaaaaa tgcaaatttt tttgtctttc gtagagtccg gtctcatgtg  960
ataaaagcat atatagagag gtaaaaagac tcaaaaccaa aataagatat gctgtgatta  1020
tgagcggtga ggctcgtgat aagtgtggcc ttggatcagt gttagtctag attcaacact  1080
tgataatatt tcgataaaaa tcttcaataa tttatgtcgt taatcatgac gaatgtttga  1140
acattattta atacaacaaa tcttgatgaa tgatgatacg tgtcgttcta gttttgcgca  1200
aaccttcgat atatacatgc tgcattcacc actgtcgacg gatcaatttg aagatgtgag  1260
acaattcgtg ttccaagttg tgtgttccag atatggaatg taacaaaaaa aaattacact  1320
tgaaaacaat ataaataata tgacaagaaa atgacaccag atttatttgt ccaaagacgt  1380
gcttccgttc aacttcatag gttatttcct aaaattaact ctaggaaaag tagcaataaa  1440
tcattaacaa ttcatcccga taaaaaatgc aacatcttgt atttttttttc ccaatgtaat  1500
ggttgattga agaacaaggc atgctaaaaa ctggaaacaa aacaaaaaaa aaaacataat  1560
caatcggtga acactgagct aaagtaaatg atcacacggg tttcatctca gctaaacctc  1620
tcccaaaata tcagaacact tagacaaaga aaaatgcata cgtcactctt cttttggaag  1680
ggctatataa accctagatg gtcacaaggt tccattaaca caacacctac atcaacagat  1740
taaccatgaa gcttcttcat ggactcgctt tagtgtttct attagctggt gcgagttgca  1800
aagctgatga agaaattact tgcgaagaga acaatccatt cacatgtagt aacactgata  1860
ttttaagcag taaaaacttc ggaaaagact tcatcttcgg tgttgcatct tctgcttacc  1920
aggcatgcaa caaatgtttt tgacgtatca ataaatacaa ttcaaaaata ctaaaatgca  1980
acttcgcatg gttgtttctt ttcatttcag atcgaaggag gaagaggtcg tggtgttaac  2040
atttgggatg gcttcagtca ccgatatcca ggtacgtcac agtgtatata tacacatgag  2100
atgaacgtcg gtttatatgt acatgtatta atgtatttgt aactactatc agagaaatca  2160
gggtcagact tgaagaatgg agacactact tgtgagtcct atacgagatg gcaggttaat  2220
acattgatac tcgtatgatt gaactatata tgtataaaaa ctatacgtgt ggaattgaca  2280
tgtgattaaa atatgtaaac tgcagaaaga tgtagacgtg atgggcgaac tcaatgctac  2340
tggctacagg ttctcctttg cgtggtcaag aatcattcca agtatgtaca tgttatccat  2400
tcgtttgtat tttaactggg atcatttagt tgaaaaagta ctaattaatg tacgacatat  2460
atatacatga gcagaaggaa aggtgagtag gggagtgaac caaggaggtc ttgattacta  2520
ccacaaactc atagatgcac tcctcgaaaa gaatataacg cctttcgtta ccctctttca  2580
ctgggacctt cctcaaacac tccaagatga gtatgaaggt ttcttggacc gccagatcat  2640
gtatgtgcca tgcagacata ttatatatga atttaagaga ttgattataa aattattaat  2700
aaaaaagaag aaggtttggt cttatttaat tacatgtatt aactgaaata attatatatt  2760
catatgcaga caagatttca aagattacgc ggatctatgt ttcaaagaat ttggtggaaa  2820
ggtaaagcac tggatcacga tcaaccagtt atacacagtc cctacgagag gctatgcggt  2880
cggaacagat gcacccggtc gatgttctcc tatggttgat accaagcaca ggtgttacgg  2940
tggaaattct tcaacagaac cctacatcgt tgcacataac cagcttcttg ctcatgccac  3000
ggtcgtcgat ctttacagga ccaaatacaa ggtgagttgt ctcaatacgt gataaagatg  3060
gtgtagtgta atctaagata tctgattcta acttagtcat atatcacgta accaacagtt  3120
ccaaaaaggg aagattggac ctgtaatgat tacaagatgg tttcttccat ttgatgagtc  3180
tgatcctgcc tccatagaag cagctgagag gatgaaccaa ttcttccatg gatggtatat  3240
atatatattt atattaccaa aaatgtatca gtataaattg tatatatgta taatgaaaag  3300
atatacatgg atcaggtaca tggagccgct aacaaagggt agatacccag acatcatgag  3360
gcagattgtg ggtagtaggc ttcccaactt caccgaggaa gaagcagaac tcgttgctgg  3420
ttcatatgat tttcttggtc taaactatta cgtcacccaa tacgcccagc caaaacctaa  3480
cccatatcct tcagagacac acactgccat gatggacgct ggcgtaaagc tcacatgtac  3540
tagtctatta ccactaatta gatacagcct ttctatacat ataaatattc ttttatctcc  3600
tttttgttgc aacgtacttt gtgagtgacc atctgttatt tcatccttgt gtttacagat  3660
gataactcac gtggtgaatt tcttggtcca ctggtatata tcaatgatcc accccctaag  3720
atttgttttt ctttcatttt ttcagttttc agtataacaa ccctaattat gttttttaat  3780
tgatgtgtat atttatttac ttccattttc acagttcgtt gaagacaagg taaacggcaa  3840
cagctattac tacccaaaag gcatttacta cgtaatggac tacttcaaaa ccaaatacgg  3900
agaccctta atctatgtca ccgagaacgg tgagttttac gaactctttt catttatacc  3960
acataataat tattgtattt tgatattagt cgaagaaact gactttattg tggaatattt  4020
ttaatgtggc ggtttattta ggatttagta cccccagtga agaaaaccgt gagcaggcta  4080
ttgccgatta caagcgaatt gattatctct gcagtcattt atgttttctc cgcaaggtca  4140
tcaagtgagt ggatgctact ataaatgatt ttctacatct gttatattct tcttctttct  4200
tggtaacatt tttatatatg attgttcttg ttttcaggga gaagggtgtc aacgtgagag  4260
gatacttcgc atgggctctt ggagacaatt atgaattctg taaaggcttt accgtcagat  4320
ttggactcag ttacgttaat tgggaagatc ttgacgatag aaacctcaaa gaatctggca  4380
aatggtacca gagattcatc aacgggaccg tcaagaacgc tgtgaaacaa gatttcctcc  4440
gctcaagcct ctcttcccag agtcagaaga agaggttcgc tgatgcatga acactttttc  4500
ccccggtcaa gatcatctcc atgtctctca ctctttctag ttgctccaaa gataaggagc  4560
ttcttctacc tataataatg tactaaataa atattctcaa taaaaagatg atcagttact  4620
aatgaattaa aaaattgtct acatctacat tttgtcaaga tgatcgagag agagagtgaa  4680
```

-continued

```
ataacacaat ttaaaccaaa aacgtcactt agacacacat agaaaataaa taaataatta  4740
ccccaaacta gttttgtgta ataaatatat aaacatcaaa ccgatcagct taaatcaact  4800
taataagttc aactttatat actagaatag attttcaaca taataaacaa tgaccaaacc  4860
ttatacaaac tcaaatctag ctacaccaaa gttctatcat cctcaactga aatttaatag  4920
tattttacat atgattttcc tatcattcaa atgattttat tttattttgg ttcttatata  4980
atcaagaaaa ccaaaagaag ctaaacctca gtaatttatg ttttatgaat gcttccccat  5040
tctcatatta agatctcgac gacagaaacc tcaaagaatc tggcaaatgg taccagagat  5100
tcattaacgg gactgtcaag aattctgcga aacaagattt cctccgctca agcctatctt  5160
cccagagtca gaagaagagg ctttctgatg catgaaacac tttttcccct caagatcatc  5220
tctatgcatg tctctcactc tttctacttg ctccatacat aaggagcttt ttccatctat  5280
aatgtactaa gtaaacaatc tcaataaaaa gatgatcaat tattaatgaa taaaataatt  5340
tatctacagc tacattatga caagtcaaga ggacgaggaa agagggaaaa taacacaatt  5400
taaaacagaa aacactcaga aatctcaaac tactctagtg taaaaaaata tatattgacg  5460
ggacggatta gcctaaattc actaattagt ttaatgagtg caacttatat aataaaaggt  5520
atcttcaaca taataaatag caaccaaacc taatacaaac tcaaaagttt ctaaccaaag  5580
ttctataatc ctcaactaaa actttatgag atattgcata tgatcttttt ttaacaaact  5640
acctttcatc caataaaagg gaaatatcct gggaggagag gtttagagta gcgaaggaat  5700
tttgttactt atataatcaa taaacccaaa agaagctaaa ccgcaatcct ttgtttttat  5760
ttgtttgtat ttcaacattg tattctactc ttaaatgatg gaaaataata tcaagaattg  5820
aagtatcaga agtttctgaa agaacatgtc atttccggtt tcctatattc tttaagactt  5880
tttgcggatt tccaaaccaa aaataaagac ttgattagcc atttccggtt tcttataaag  5940
attcgattta tcttgtgtta cacaagctat agtaatttaa tgagtctcaa atttataatt  6000
ttggtttaac taatataata agtttttttc tttaattcag aaaataagca tgtttagtag  6060
tattattaga attgtataaa ttttcctttg gatatatctc tgtaatttta gttctactac  6120
ctacgcagca ttagctggca acatttttctt ctaaatttgc tttgaaattt actgtttcct  6180
tattggttgg ttaaattgct tcaactaaga gaaacatatc ttgagttata caaataatat  6240
ctaaagttac atgattatta tctgctctat ccaacgattt cctgacaact gttaatgagt  6300
atatatacat tctttttgta actattataa ttatacatta ctgcaattta gcattaatga  6360
tcccaaagaa agtgataaga cctgcatacg taataccagc ctcattacac tatataaaca  6420
agagcattat caagtaccaa catatctcta tcattcacca acacaaaaca atgccaaggg  6480
gaaggataaa aatagagccc atgactaata gcactgcaag gaaccaaact ttcaggaaga  6540
ggaagaaagg tttacttaaa aaagccaacg agctgtcgac tctctgcggt gtcaaagttt  6600
gtgtggttat caacagctgc gacaacacgg agacggagtt ttggccgtca agggaaggcg  6660
ctgaagcagt gcactcggcg tttatgggtg ttctgccgga ggaacggtgc aagaagatgt  6720
acgaccaaga gaggcatctg gaggagagga tccagaaggg acaagcgaaa gcgatgaggc  6780
tacaagcgga gaatcgagag attgagctca gagaggttat gttcaatctt ttcaaggggg  6840
agacgctaaa gccgcatcac tatgatgatc catgttttat tggagaacta aatcatttta  6900
ttggtgatta tgtcaaaaat ctaagtcaca ggatcgagtt cctcgaggcg aatggtgagc  6960
cagttcctcc taatgtcgct gctacagatg cgtctggtcc ttttgttgtc ggaactgagg  7020
gtttggtaag taaccctact gaagcttatg atcatatgcg tcaatttgat ggtatggata  7080
tgagtgtgaa ggaggaagct cctggaggtt ttaatgatca tgttcatcat cagaatatga  7140
atcatcaaga accatttcaa taccaaactt ctactaactt ttatgatcag actcagccta  7200
tgttttatgg ttcgagccag gatatgaata tgaatcttga agaaccattt caataccaaa  7260
ctcctgctaa ctttgatgat cagactcagc ctatgttcta tggttcgagc caggatatgt  7320
atacaggttt gaatcatgat cagggacaga gttcgaatca gtatccaaat tcaaaccaat  7380
cgttcgtggg tcttttgatg ggacaacctc agcagatgag tgatggtcaa gatcctgcaa  7440
ccgttgcttc gatggatgac aaaaataatg gctatcacca actactaatc accagtcaga  7500
tgcctctcac caccaccgct gccgccgctg ctgatctttc tggtcatagg atcaacaatg  7560
gttggctaac aaggtttggt ttggattgaa gtttttgcgt ttgcaattct gaattttcat  7620
attgtaatga ttaaaggttt tcgcctttaa atcagttatg attatcaggc aatgttgtgt  7680
cgtgtaccat attgtccttg aatattttat tgttttgaat aaagactgtt gtttttttgat  7740
attaaatcat aaagagtaaa ttttttttcc ttaaggccgt ggaggaagaa tgcaacaagc  7800
atttcgaaaa aaaattatta tcagacaaac cattaatcaa gaaatgtggc cataagacag  7860
aaatatagag ttaagttcaa aaggaaaaaa aaaagacaga aatatagagt taggtgacat  7920
gtaattgcgt atggatgtag aatgcttatt taaagataca ccattatctt cccaaagcca  7980
catgtcatgc aataaataat cactcagatt atcaagataa ctatgtctga tgatatccat  8040
tgtgtattaa ttaaaaaatg cttcagtctt tattcgaaac aataaaatca tgaagtgtgt  8100
attaattaaa aaaatcttgt gtattaatta aaaaattata ttctctccat ttcattttaa  8160
ttgtcatatg cacacagatt aatagaacac taggttaaga cccgcgcctt gcgcgggatg  8220
aacattatat atataaatta ttttatattt tatatgttta taacatatta tgaaataata  8280
aatatatatt aaataattaa aaattcatta tctactactt atataattaa attggtgcga  8340
acatataaaa tttttttata aatcgaaaaa aaaatttcta ttttatatga tatataatta  8400
aatttaaatg atagtaacat atatatggta tattttaata ttaatattta ttagatgatg  8460
atttttgctc atattgtttc ttatcatttg gatctgttat agcaaaaagt ctaaattagt  8520
gataacaaaa ttttcactgt gggattaatg gtttaagtaa tttataatat tttaaaaaat  8580
taagttgtca atattttttc aaacttttta tcaaaaaaat gttcaaagta tatttcaaaa  8640
ttaagatatt tatgtatttt t                                             8661
```

```
SEQ ID NO: 42          moltype = DNA  length = 6684
FEATURE                Location/Qualifiers
source                 1..6684
                       mol_type = genomic DNA
                       organism = Brassica juncea
SEQUENCE: 42
aatatatata tatattagta tttatattat ctcatttaaa aaaatattta aaattatttg  60
tttttatatt tttataattt tacaataaat aaaaaattac cataccacaa ccacccataa  120
ccacaaacgc tagctgtaac cagcttttga tttagtgaag tttagaacgg tgtaaagcgg  180
tttgtattgt tttttgtgat tgttgtgaaa caccaacaac tgatatcagc cgcaaaagat  240
gtgtttgcga gtgatagcat ataaaccagt tagatcctaa atgagaggtt tgaggaaact  300
```

```
ggcaaaatat gtcatattta aaataaattt gtccatgtat aactttctac tagtttgtca  360
atatttaaaa aataactatt attttaatga aaacaattaa atatatatat attgatgggg  420
ataatttatc cacaataaga gcttgcgggt tagaacatgg cgccaatatc ttggttccga  480
cttctgacct ccggcctccg ggttcaggct ttcaggtcaa gtgattttta ccgcctaatg  540
ataaatggaa tcttctttaa tataaaatat gttgtttaga caatcttcct agagagaaca  600
aaaagaagta ttataatata tatagccatg cttaaaggat tatatatata acttgtataa  660
atgttatatt ttatacattt ttataatatt tatgtattaa atatattata ctagttatta  720
taatttaaaa ataaaataat ttttgtaatg agattattat tattttttgg atttttattt  780
ttatttatat tttaatttta attttttttg tattgttcaa attggatatc cagttaaaaa  840
tttaaaattt ctggatattc aagtgaatgg aaatcgaatc gaataactga ttattcaaac  900
gaaatgtata aaatcataaa tatcttaaaa atctcgtata ttcgatacgt gtccaccttt  960
ttcgtatgat aaagcaggga gcaacgaaaa tcaaaaagat atgcggtgat ggtgagcggc  1020
gaggctcgtg atgagtgtgg ctttttggat gacatgataa ttgttttttt ttcttagtca  1080
ttgttactcc agactacttg ataatattac tggagacttt ttcaataact tagggcgtca  1140
gttctaactc caagtcaaac gtaagagcca ttgagcatca tctactacaa ggaatcgttt  1200
tttggaactt tactataggg aatcttgaga catgtccttt tacttttgcg cagtgccggc  1260
tcttaccctg tgcacaaggc acatttgcac agggtcccca aaaaataaat aaaatttagt  1320
tagaatttaa gatctaattt tatagaattt aggacctttt tttgcaaatt acttttattg  1380
tttctgaaag ttagaacttg cacaaggtcc actcaaaaat taagccgggc ctgcttttgc  1440
gcataccttt gtcacatgct gcatcgtatc actgttgacc gatcaattaa cgaatagttc  1500
tttgtatgtt aagtgttttt tctttttttgc aaattacatg ccatgcattt ttaggactag  1560
gatctaaaaa ctctctcttt ttttggtaaa aaaaaaaact gtctctttga taagaaaaga  1620
gtattagaga aacctcaatg gttaagaaac tcaaaaagta cgtttgtcgt tctacaaata  1680
aatctacccc atcgttattt acagattaac ttcgaaaaat gatagtaatc tagcaatcac  1740
aattgagata aaagaaatag tcaaaagttt tcttaatgaa atgatcaatt gaagagcaag  1800
ccactgtaaa acgccacggg tttcatgtca cctaaccctc tcccaaaata ttgatcaaga  1860
cacttattag agaagaaaat gcatagatca ccaagttgca aaaaaaaaat gcatagatca  1920
ccctccgttg caatggctat ataaacccta gattggcaga aggttccata caacataaga  1980
aacacatcta caaattaacc atgaagcatc tttggctcac attagctttt ctattggctt  2040
tggcgacttg caaagctgat gaagaaatta cttgcgaaga gaacctgcca ttcacatgtg  2100
gtcaaactga tcgtttcaac agtagcagtt tcgagaaaga cttcatcttc ggtcttgcat  2160
cttctgctta ccaggcatgt aacatatata tatcaaccat tagtattatg ttgccagacg  2220
tcatatttta cgtataaaac atcatatata aacattaaaa tctaacgttg catggttgtt  2280
tcttttcatt tcagatcgaa ggtagcataa atcgtggagt taacgtttgg gatggcttca  2340
ctcaccgatt cccacgtttg ttttttgcat ggttactcat cacatataca tattatgtcg  2400
gttatatgtc tccatgcatt tatagttatg tatttattta ctatcagata aagcaggacc  2460
cgatcatgga aatggagaca ctacttgtaa ctcatattcg tactgggagg taattaaatt  2520
cctcaatata tatgtgtgtg catattaata ttactcactg aattatttat caactaccaa  2580
cctagtgtgg attgacatgc gattatatgt gaactgcaga aagatataga ggtaatggat  2640
gaactcaaag ctactggcta cagattctcc attgcctggt caagaatcat tccaagtatg  2700
tgaacgttat tgatccatgt atatatataa atcatatatg gtaatattcg attatgattc  2760
tttcgaaaga ttaaatatag gatacatatg agcaggagga aagaggagca ggggagtaca  2820
ccaaggaggt attaactact accacggact cataaatggc ctcatcgaca agggtataac  2880
gcctttagtt acgctctttc actgggacct tcctcaagta ctacaagatg actatgaagg  2940
tttcttggac cctcagatca tgtatgttat atttatgcca tgctgcttat taagaaggac  3000
gacaatatat aaagatttgt tctgggatta atgaaatgac tataatattc gcagagatga  3060
tttcagagat ttcgcggatc tatgttttga agaatatggt gataaagtaa agcactggtt  3120
cacaatcaac cagctctact cagtgcctac gagaggctat ggattaggat cagatgcacc  3180
tggtcgatgt tctccaaagg ttgattctac atgttacgcc ggaaattctt caacggaacc  3240
ctatattgtt gcacataacc agctccttgc tcatgccacg gtggtcgatc tttacaggac  3300
aaaatataag gcaggttctc cattttatga aaggtgtatt atctgattct aaattaatct  3360
tatcgttggg tatatatatc tgcgtgacca cagcatcaag gaggtaagat tggacctgtg  3420
atgataacta gatggtttct tccatataat gacactgatc cagactccat agctgcaacc  3480
gagaggatga aagaattctt cttgggatgg tatatgtttt ataaaatgaa atgatattct  3540
taacatgaat atatgctgta tatatgaact gacgaaaaat atgtatttat atgtacacca  3600
ggtacatggg gccgctaaca aatggtacat accctcaaat catgatagac actgtgggtg  3660
agcggcttcc atcgttcact ccagaggaat ccaaactcgt aaagggttca tatgattttc  3720
ttggtctcaa ctattacttc actcagtatg tccagccaag tcctaatcat gttgattcgg  3780
atggtcacac tgccatgatg gacgctggca caaggctcac atgtatccat ctatatattt  3840
cgacttagtt acaaccttaa tttatatcta cctaacgcct tttgttaatt acaataattt  3900
gtgttaacag atcgtaatgc aagtaatcat gccattggcc cagtggtata tatatgcatc  3960
aaccatccct attctttcat ttttttttcta agcaaaattc agttttctga tactaatttg  4020
cttccctttc taagttcact gaacacaaag atgacgagac caaaaacacc tattactacc  4080
caaaaggcat ttattatgtg atggatcact tcaaaaccaa ttacaatgac cctgtaatct  4140
atataaccga gaacggtggg ttctactact catctctaaa ttcatcttta catgttaaat  4200
gtaatttgaa atttgttgaa attgttcatg ttatgacggt taactaggat tcagtacctc  4260
cggtgatgaa acccgtgagg aggctaagtt tgattacagg cggattgatt atctctgcag  4320
tcatctctgt ttcctcagta aagtcatcaa gtgagttgat gcttctctct tttgcttctt  4380
gtgttttatg tatatacttg tatgtacgta tggcgtctaa tgatttattg ttcctgcttt  4440
tagggagaca ggtgtcaagg tgaaaggata ctgtgcgtgg tctcttgggg ataattatga  4500
attcgggcta ggatttaccg tcagattcgg actcacttac attgactgga acaatgtcac  4560
tgatagagat ctcaaagagt ctggcaaatg gtataagaag ttcattgcaa ccaagaacct  4620
tgcaaagcca aattttctgc gctccagcct cacctttgag aagaagaagt tcgcagatgc  4680
atgaaagatc cagtccacta tatttacctc atcaagatca tctcatgttc cctctttcta  4740
cttgctccat agataaggag cttcatctac ctaccactgt atactaaata aaaaatctca  4800
ataaaagaag atatggattt gggataagtg gacactgcaa gaaaacaaaa tgttttgtat  4860
ggataatttt gtcggaaatt catcggaaaa aaagaagcaa tttccaacga aattttttcg  4920
tttggtttta tttcgttaaa aaattcgata aaactttttt ggacaattcg acgaatttcc  4980
agcagattcc gacatatgca ttcccgacga gatactgaca aaaatagccg aaagacatta  5040
```

```
tcaagaattc ggcaatattt tcaacgaata tcatccatca gaaattggac aatatttgtc  5100
aaaacctttg taaattatta aaagatatat ttaaattaat taacaattta acaaactaaa  5160
tttacatatc tagataaaaa ttgtttataa taatttttaa tcttatatat aaatataata  5220
actattaaaa ttaaaaaaaa acgcttttta aaaagtgaaa aacttttttta taaattctag  5280
aaaaaccatt aaacgtttta taaattgaaa gcgtttttcg aaaagtgaaa aaaagttgta  5340
taaattataa aatagtaaaa atattataaa cagaaacatt tttagaaagt gaaaaaaatg  5400
ttttctataa attccagaaa cataaaaact ttttataaat tacagaacat aaaaatgttt  5460
tataaaatct tacgttttat aaaaccgtaa gaacatttta aaacaacata aataataaaa  5520
catcaaaaat ataaaataag ttttcaaatc ctaaatctaa aatgtgaaat cctaaaacaa  5580
acaattctaa cacaaatata acatataaat cctaaatcaa ccaacctaat tcatttctaa  5640
catttcaatc cctaaaatct atcaactcta ataaccaaac acatatacaa attaacatat  5700
atgattatta agaggataac atatgactaa catgatttaa taagagttgt agggaaggat  5760
tcacatctgt ttttcgagag agggagagtt gaaatgaaga agaaaaagaa aactatttgg  5820
ttcttatgtt aaaatatttt gacgaatcaa gtttgcaatc cattagaaat tttttaattt  5880
ggtgcttcac aaaagtttag gtgattcttt tttccggaca aatttcaatt tctgacaaat  5940
tttcaaaaaa atataaagaa tttctgataa actttattta ttgaattact taactatttt  6000
cgatatatga atatatccta ttcgttgaaa attcataaat tcactcagac tgacaaattc  6060
agtttattct ctgcatgaat tataatcggc caaaacacag ttttgaaaaa aaatcccacg  6120
gaatatggat tgcggtttca aaacataata aaaatagact gatattatct attgataata  6180
tttgggaaaa ttccatataa tatttcaact aaattttgtt aagcttttta atacacaaat  6240
tttttcacta cctagtttaa taccccaact aattattttg ctcattttaa aacacaaact  6300
tttaaaactt gtgcttattt taacatccaa actttgttta tctatactat tatttgagaa  6360
gtgaatttgc ttagttgtca tattctccat gattttagga taaattatta gtttaattaa  6420
tattattatt ttaaattttc ttttaatata tgtatttatc atgatattta agataattaa  6480
taaacattaa cctattctac tgatatacat ataatattat tttaaaaaat atatatttaa  6540
tatatataat tatcatgata tttaaaacat ttaattaata aataaatatt aacaattgat  6600
attaacaata tctactggta ttatcataat tatggaggaa tttcatgttt accactttca  6660
ttatttatct ttaccaccac aaaa                                        6684
```

```
SEQ ID NO: 43          moltype = DNA  length = 6962
FEATURE                Location/Qualifiers
source                 1..6962
                       mol_type = genomic DNA
                       organism = Brassica juncea
SEQUENCE: 43
tatcgaatga aacaaaagta caatcacagt tcatatagaa aggagataag attggatcaa  60
acaatacctt tgtttcaact ttggaggtgc gaaggagagc ttggaggtgc aaaggaaagc  120
caattgaaca aacaatacgt ttgtttcaac cttggaggtg cgtaggagag aacgacagcc  180
atcgtcgtct tgcgtcttgc ggagacaacg agggaagcgg cggagaagcc gagagaaacc  240
aaagaaaaga aaaagagaaa agaaaaatag aaaaatatat gctttgcctt tcgttagctg  300
acacgtggag gaaaaacccc tttagttatc gatcacaaaa atcctttctt aaggatcgat  360
aactcccctt ttatttagtt ttcatttaat taaataccca attaacttta aaaccccact  420
taaaatcccc cgttaaagat gctcttaggt cttatttaca aaattttccc aaatcgattc  480
aaaactacta cttgtaagaa ataaaacaat tgaaatgatt attgtgaaaa aatgaaatca  540
tatgtatatg tctcgataat ttttatttta ttgaatgaaa aataagagta ttacagtcta  600
tgttattgat aattcatggt gcatggatag tttttatttt attgaatgaa cattaagaga  660
attccatagt agttctcaaa aacaaaccaa aaagttattt aaactgaaac tattatttag  720
gtgatgattg tttacatggt ttttggattt tagtttttat tttttagatt tggtttttac  780
attttagttt ctgattttg aattttgatt ttgctatata ttttaatttt tcaaaaaaac  840
ttgaatggtg attctagatt ttgctttttg gtttttaatt aattttttta aaatatattg  900
gaatctaaag tttgataact aattatttaa ttttaaagtt attttttatt tttaagaact  960
tcactcataa gttaatttc ttttaaacaa acttaaaatt actaaaataa atatcatttt  1020
aaataagtaa taccaataga actcttaaca aatatgcaaa atttacataa actaattaac  1080
caaattttaa atttatttta tccaaatgcc taaagcacag aaatttaata aaatgtttta  1140
ttcttgaaat aatacgaaca gtttatttta attcatgttt gaactttgaa aacatagctt  1200
tgtactgtca tagaagaatt ttttcaaaaa taatatctaa ttataaaaaa tatatataac  1260
taaagtttat gaattcttac ataagtgtta aactataggt taatacacaa gattcttgca  1320
tttcaaccct tccaatcata tctagaaacg ttaccaaaaa aagcaaaaaa tgttgttggt  1380
tttcgttttc gttttctttt gtctttcgga tactgtggtc tcatgtgata aagcatatat  1440
agagaggtca aaagaatcaa aacaaataag atatgctatg attgtttttt cttgataatg  1500
ttgattatta gcggtgatct catgaaaagt gtggccttgg atcagtgtta ctctagattt  1560
agcacttgat aatatttcga taaaagtctt caataacttt atggcgttat gacgacgctt  1620
tgaacattat ttactgcagc taatcttgat atataattcg tcttttctag ttcgcgcacg  1680
ccttccacat atacatgctg catcgcacca ctggtcgacg gatcaatttg aagatgtgac  1740
acaattcgtc ttccaagtcg tacgtcttcc aagtcgtacg tgttccaagt cgtacgtgtt  1800
cccgtaattt gaagatggaa cacaactatg tgctatgtaa caaaaaaaaa ttatttgcaa  1860
tagataatga aaaactaaaa agtggaagca aacaagaaat ttaagcaaaa tcggtgaaca  1920
ctgagctaaa gtaagtgaac ccacgggact catgatccca cctaaacctc cccaaaatgt  1980
cgagatacta agacaagaaa atgtatgtgt cactcttctt taggaagggc tatataaacc  2040
gtagatggac acaaggttcc atacaacaca acacatacat caacatatta actatgaagc  2100
ttcttgggct cgctttagtt tttctgttag cttctgcgag ttgcaaagct gacgaagaaa  2160
ttacttgtga agagaacaat ccattcacat gtagtaacac tgatatttta agcagtaaga  2220
acttcggaaa agacttcatc ttcggtgttg catcttctgc ttaccaggca tgtaacaaat  2280
gttgacatac catacttttt gacgtataga aaacactatt caaaaatgat aatatctaac  2340
tttgcatggt tgtttctttt catttcagat cgaaggaggg agaggtcgtg gtgttaacat  2400
ttgggatggc ttcagtcacc gatacccagg tatgtcgttt gcacggtgac atctatatat  2460
atatcatata tgacaggaat gttggttata agtactcata ttaatgtatt tgtaattact  2520
atcagagaaa tcagggtcag atttgaagaa tggagacact acttgtgagt catatacgag  2580
atggcaggtt aattcttcag tacatttgta gatactcatg actgaactat gtatacaaac  2640
```

```
tacgtgccga ttgagatgca atcaaaatat gaaactgcag aaagatgtag acgttatggg  2700
cgaactaaat gctactggct acagattttc ctttgcgtgg tcgagaatca ttccaagtac  2760
gtacagatta tcgatcagta catgtatata tatagttgga cgtgttttaa atgtacgatt  2820
tatatataca tgagcagaag gaaaggtgag taggggagtg aaccaaggag gtcttgatta  2880
ctaccacaaa ctcatagacg ccctcctcga aaagaatata actcctttcg ttaccctctt  2940
tcactgggac cttcctcaaa cactccaaga tgagtacgaa ggtttcttgg accgccagat  3000
catgtatgtt tatatttgtg acatgcttct tatattatta ataagagaag aaaaagatgg  3060
ttaattttag ttacatgcat tactgaaatg attctatatt aatatgcaca gacaagattt  3120
caaagattat gccgatctat gtttcaaaga atttggtgga aaggtaaagc actggatcac  3180
gatcaaccag ctatacacag tccctacgag aggctatgca gtcggaacag atgcacccgg  3240
tcgatgttct cctatggttg atactaagca caggtgttac ggcggaaatt cttcaacaga  3300
accctatatc gttgcacata accagcttct tgctcatgcc acggtcgtcg atctttacag  3360
gaccaaatat aaggtgaatg ctgtctccat atgtgaaaat taaggtggtg tctaacatat  3420
ctgattctaa tgtaaatatc acgtgaccaa cagttccaaa aagggaagat tggacctgtg  3480
atgataacaa gatggtttct tccatttgat gagtctgatc cggcctccat agaagcagct  3540
gagaggatga accaattctt ccatggatgg tatatatata tattaccaaa aatgtaacag  3600
tatctactgt atttgtatgt atgtataatg gaaaaatata catggatcag gtacatggag  3660
ccgctaacaa agggtagata cccagacatc atgaggcaga ttgtgggtag taggcttccc  3720
aactttaccg aggaagaagc ccaactcgtt gccggttcat atgattttct tggtctcaac  3780
tattacgtca ctcagtacgc ccagccgaaa cctaacccat atccttcaga gacacacact  3840
gccatgatgg acgctggtgt aaagctcaca tgtaagtacc acacaatatt actacttagt  3900
tacgaccttt ctatatattt tttttcttct ttttgttaac atactttgtg agagtatcaa  3960
ttatttcatc cttgtgttta cagatgataa ttcgcgtggt gaatttcttg gtccactggt  4020
atatatgaat gaaccacccc tatgatatct ctttcatttt ttattctatt tgcaatatat  4080
agaacaccac tgattatgtt ctcgtgattg atatgtatat ttgtttgctt cccttgctca  4140
gttcgttgaa gacaaagata acggaaacag ctattactat ccaaaaggaa tttattacgt  4200
gatggactac ttcaaaacca actacggcaa ccctttaatc tatgtcaccg agaacggtga  4260
gttctacata ctactactcc tctattttca tttataccac gcataatatt atgtaaccac  4320
aaaagtagac cgatattcaa tctaccgcag ggtgaatagt aatgaaaata attgtaaaag  4380
ttattttaca attattgtat tttcgaaatt ggtccaagaa actaacttac aaatattgtg  4440
taatattttt catgcaatgg cggcttaatt aggatttagt acgcccagtt cagaaaaccg  4500
tgagcaggct attgcggatt acaagcgaat tgattatctc tgcagtcatc tatgttttct  4560
ccgtaaggtc atcaagtaag taatgctact atatggatgc ttttcttcca atgtttatca  4620
acttcttctc tttttggtaa tatatatata tatatatata tatatatata tatatatata  4680
tatatatata tgattgttct tgttttcagg gagaagggtg tcaacgtgag aggttatttt  4740
gcatgggctc ttggagacaa ttacgaattc tgtaaaggct ttaccgtcag atttggactc  4800
agttacgtta attgggacga tctcgatgat agaaacctca aagaatctgg caaatggtac  4860
cagagattca ttaacgggac agtcaagaac cttgccaaac aagatttcct ccgctcaagc  4920
ctctcttccc agagtcagaa gaagaggctg tctgatgcat gaaacacttc cccccctca   4980
agatcatctc catgtctctc actctttata cttgctcaac cgataaagag cttcttctac  5040
ctatagtaat gtactaaata aatattctca ataaaaagat gatcagttac taatgaataa  5100
aaaatttatc taccactaca ttatgtcaag tcaagaagat cgagagaggg agacagaggg  5160
aaataacaca atttaaacca aaaacgtcac ccatacaaaa taaaaaaaaa aatacacggt  5220
ttatgcgaga aacttaagag caaccttatg gttgatacta aatttagata tctcaaacca  5280
aaaatattgt tagtttaatc tgtttttacc taaagttcaa ttttattttt tattttttaa  5340
gtcaatctaa ttggtgaaag acaatatgcg gccatatgag atttgttaaa aacttaaaat  5400
cgtgttaaaa gttctcgcat gcgaacctgc ttctcttctc tttcgtgttt tttgtatttt  5460
tgaatttttt taatctaaga tactctatct aaaacgtatc cattttgttt atcaatgtta  5520
tcaaggtctt atttttttcg agattccaca ttgatatgta agaccatcca ctacaagaaa  5580
acacgccgaa ttccgacgga gattccgacg gacgtcacag gcgtcggaca atttagacga  5640
aattctgacc gatttccgac gaaaacaaaa aatctgaagt cgtcggaatt ccgtcggcta  5700
attccgacga acttccgaga aaacaagggt cgtcggaata ttccgacgac ttttcgacga  5760
catccgataa acaatataac cgttgtagtc gtcgaaaagt cgtcggaata tccgacgatt  5820
ttggccatca gaatccccct gttttcttgt agtgatctca actctatttt atttttcact  5880
tttttgcttc attttgaaag aacttttgtt ccaattctac ctcatttctt gcttcaacaa  5940
agcaataaac aatatatctt caaatttaaa aatatatcgt tcacgttttc aattttataa  6000
gataaaattt taactataaa ttgattctta atttttagtt atttttattt tgtcaccata  6060
aattatataa tattaattac ccaatcaatt tcaaaatttt tgactattgt tttcatctaa  6120
tattaattac ccaataaatt ttgactattt agcttgatta agaaaaatca aagataaata  6180
gtctcatatt tttatttcaa aacacttttg ttaactcata gaaaaatatt ttctttctaa  6240
aatatgatat tctttgtttg tttcttgtgt tatgtaataa ttttattaaa tgataatgtt  6300
taatatatat taaactctaa ttgtgataga ttattggtaa aataataatt gagtaacatt  6360
tataaatatg aaaaagtaca aatgtaatta ataactaata attattggag atagaatata  6420
gttagaatat tctttttaca gaaaataaaa aaaaaaccat tgaaataaat gttatttcat  6480
tttttttat  aaaagtgaac tctgaaaaat aaaaatgaaa ccaatcttaa gagatgccct  6540
aaatccatga gtcttttttt aataagaaaa atatatttca tcaatatgtt ggaagctgaa  6600
gtaatataaa tagtatctcc taacgagaat tgaactcaaa tggtgatatg tctactagac  6660
agatttttac tgctaaacca acatatagtt ggttccatga atctcttcaa tcttattttc  6720
catatacaaa aagaaaataa ataattttaa aactaactca tgcacattcg tgaatgttta  6780
ttttacgata gatatataga tatttctaaa cacaacaatt tagtagttgc atttgtatta  6840
ctttagtgta tcgttgagac catatattgt attactggat catgtgatat atttttctta  6900
ttagatatgt gttggatgag ttatgtaatt ataaatatga ttagatctat gtattgatat  6960
gc                                                                 6962
```

```
SEQ ID NO: 44          moltype = DNA  length = 6731
FEATURE                Location/Qualifiers
source                 1..6731
                       mol_type = genomic DNA
                       organism = Brassica juncea
```

SEQUENCE: 44
```
cgaccagtca caattctgat actgatttag ctgaagtaac tgagcccacg gaattcaccc 60
aaccaaacct ctcctaaaat atcaagatat taaagaaaag aaaatacttg tattggaact 120
atcgatgaaa catatatttc tgctatggta gtaggaaatt aaattgttag gtatcaaaac 180
ataatagagt tttatctgag aatgtgttag ctgcatgcaa ttttgatttg aaactcatat 240
attttcaaac tagctgggaa ggatcagttc ataatgcaaa agtgttaaat gatgcattaa 300
cggaaagtag caatatattt gaaattctcc tgggtaaatg tgttacttaa taaatatata 360
cattattgtt gtttaagata ggatatttta ctataaattt tatgattttt atatttattt 420
tacatcaaaa aaaaatcatg aaaattttat atagcatatt gtggatatga aaatgagtta 480
aatattctaa ctcaatttca aagtacccat tatcatctga aagaatttac tggaaggggc 540
agtgatccag gaaataaaga agaattattc aactatcatc atgcttgttt gagaaatgtc 600
gtcaaatgtc ttttagtatt ttctaatcaa gatttgtgat atccaaatct gcttcaagtt 660
ttccatataa gacagaagca gaattagagc ttgtatgtgc tgcagtgcat aactttctcc 720
atcagaagtg tcggccaaat gagtttcctc cagaagaaac ctctaatgaa taaaatgtta 780
ctcaaccaag taccgatggt catcaatttt ttaggctctc agaaacaaca aagagaacat 840
gctaataatg taattaaaac aacaattgat gttacaacaa aaaaaaacaa caacaattgc 900
ttcaaatatg taaaatgatt gtattagtgg atctcaacgg tggtatatgc atgagtaagt 960
tatcattttt atgtgttctt tgaattttat ggttgataag aatggtaaaa tatcacaacg 1020
tatttttggc tgatatgtgt tgagatgatt tatggcattg ttaacatgat gtattaaaaa 1080
aaatcgactc tcacagtaaa gtcaaaattg caaatcaagt gaagtatttg tcacttgtaa 1140
tgatattttt gaaaacagat tacacttttt gcctggtttt actaaattgt gtttatttta 1200
tgttgttaga aaatgttttt aagaaaacat tagcaaaact attttttatt tttattttaa 1260
aattctatca aatgtcctat caaaatctct atcaaaatcc attaaatcca aataatttag 1320
aatctgaaat ccttaaagtt ttttccaaat ccctaatcta ataagctcct ttagtatatt 1380
tgaacgtata tttatattta gtaccaaatg gttatatata tatatatata tatatatatt 1440
taaaaatcca gcggttaatt caataaaata acactttaaa tattttttta tgccctttcg 1500
ttatttgcta atactccttc cgtttacttt tataagtcgt tttagaacct tgcacataga 1560
ttaagaaaaa acataaattt tttatatttt ctaaacaaaa acatcattaa ttatttacct 1620
aaccacaaat caatcaatga aaaaatagaa gacatattat catttggtca tacaacatta 1680
actattaaga aattttacat agaaaaccga aaacgtcata taatttggaa caaaattttt 1740
tctctaaaac gacttataaa agaaaacgga gggagtatat gataatttac ttacaattca 1800
ttttattcag ataaacttag tcccttgtta tttacaaaat taacttcaca aaaataacga 1860
ccggtcacaa ttctgatact gatttagcta aagtaactca gcccacggaa ttcacccaac 1920
caaacctctc ccaaaatatc aagatattaa agaaaagaaa atacgtgact cttctttaca 1980
aaggctatat aaacccttga atggcacaag gttccatcaa cacaaacaca tacatttact 2040
tattaaccat gaagcttcat ggactagcct tgataggttt tctaattgct gcggcgagtt 2100
gcaaagctat tgaggacatt aattgccaag agaacgagcc tttcacatgt ggaaacactg 2160
atcagttaag cagtaaaaat ttcccaaaag acttcatctt cggtgttgct tctgctgctt 2220
accaggcatg ttacaaatca acaatttttg acgtagaaaa ccatttaaaa tattaaatcc 2280
aacgttgcat ggttgtttct tattattgta ggtggaaggg ggcagaggac gtggtcttaa 2340
cgtttgggat ggcttcactc accgataccc aggtatatca tctacatggt acatatatat 2400
ataatgtcca catctcttat atatcattcg tagtaatgta tatgtttact atcagagaag 2460
ggtggatccg atctcgggaa tggagacact acttgtgagt catatacaag atggcaggtt 2520
aattcctcac tgagtcatat aggaaaatgg caggttaatt cccacattcct cactatatat 2580
aaatgatatc cgagtgtgta tgtaaactgc gcagaaagat atagacatca tggacgagct 2640
caatgctact ggctacagat tctcttttgc gtggtcaaga atcattccaa gtatgaacac 2700
ataaacgatc tatttataca aaaaattctc gtaaattgat tgtgagtgtt gagaagatta 2760
aatatatgat atgtatacat gagcagaagg aaaggtgagt aggggagtga acaaaggagg 2820
tctcgaatac taccacaaac tcatagatgg tctcgtcgca aagaatataa caccttttgt 2880
taccctctat cactgggacc tacctcaaac actgcaagat gagtatgaag gtttcttgaa 2940
ccgcaccatc atgtatgtca tttgtgccgc gttcttagca agaaatataa gaagaaaaac 3000
atatataagt gatctcatgt taatgatttg tttctatgct atgcacagag atgactttag 3060
agattatgcg gatctatgtt tcaaggaatt tggtggaaag gtgaagaact ggatcacgat 3120
taaccagctg tacacagtgc ctacgagagg ctatgcaatc ggaacagatg caccccggtcg 3180
atgttctccg aaggttgatg agagatgtta cggcggaaat tcttcaacag aaccttatat 3240
agttgcacat aaccagcttc ttgctcatgc tgcggcggtc gatgtttaca ggacaaaata 3300
taaggtgagt atatataggt ttgtaaatag gtgtagtcta acatatatgt caatgttcta 3360
atcatatcat ttcatttcgt atgccgtgac aaacagttcc aaggagggaa gatcggacca 3420
gtgatgataa ctagatggtt tcttccattt gatgagactg ataaagctag cctatatgca 3480
gctgatagga tgaaagaatt cttcttggga tggtacgtat ttgtatgtat atgtacacaa 3540
aaatgatatg attatttata cgtatgtaca tcgatcaggt tcatggagcc gctaacaaag 3600
ggtagatacc cagacatcat gagacaaatt gtgggtagtc ggcttcccaa tttcacggaa 3660
gcagaagcag aactagttgc gggttcatat gattttcttg gtctcaacta ctacaccact 3720
cagtatgccc agccaaaacc taacccagtt acatgggaaa atcacactgc catgatggac 3780
ccaggcgcaa agctcacatg taccactcag tttcctctta tagttacaac ctttctatat 3840
atatatatat atatataggc ttctaagtct tttaaattaa gcatatatat actttgtgag 3900
tgaccactaa ttatttcatc attgggttta cagatacgaa ttcacgtggt gaaaatcttg 3960
gtccactggt atatgcatga tccacccctg acccctgtta cttattattt tttttcttc 4020
tagttgatgt gtatacgtat gcttcctttt ctcagttcgt taaggacgaa ataaacggcg 4080
actcctatta ctacccaaaa ggcatttatt acgttatgga ctacttcaaa accaaatacc 4140
gtaacccttt gatctatatc actgaaaacg gtgactacta ctcatctctt tttccatatt 4200
aagcaaatat gtatgtttaa aataatgtac aagttgttta tgtaccatga tggttaaatt 4260
aggatttagt actcccggtg aagaaacccg tgaggaagct attgctgatt ccaagcggat 4320
cgattatctc tgcagtcatc tatgttttct ccgtaaggtc atcaggtgag tggaagctac 4380
tatatttttt ttttctcttt tgaatttgat gcatgcatac ataaatgtat ggtcatcatc 4440
atgcataggc ttaggctttg aatgattgtt cgtgtttcca gggagaagcg tgtcaacatt 4500
aaaggatact ttgcatgggc tcttggagat aattatgaat tctgcaaagg ttttaccgtt 4560
agattcggac ttagttatgt taactggaca aacctcgatg atagaaatct caaagaatct 4620
ggcaaatggt accaaagctt tattaacggt acctctaaga accctgctaa acaagatttc 4680
```

```
ctccgctcaa acctctcctt ccagaaccag aagaagctcg cagatgcatg aaacacttta  4740
tcccaccatc atgatcatct tcatatctct actacttgct tcatagataa ggagcttgtt  4800
ctatcaatat tgtactaaat aaatattcca ataaaagatg atcatttact gatgactatt  4860
ttcgtttgag ttcgatccta cttacacgat gaattacttt tacttgggat tattagcatt  4920
tttaagttat aaaacttggc acagatcagc tatctaaggg gtaagtattt aactgatcgt  4980
cgggataaaa ctaaattaat catgttcggg tccctgattc atgaaaatca tgagcctagg  5040
ctccttccct gcttctagct ggtttttgac ttgaggtttt cttggttgat ttctgtaaaa  5100
ctgtagctag taataatttt ttcatttggt ttttaaatta acctaattta atgatctcaa  5160
tagaaaaaaa aagagaacaa ttcagtggcc acaaaagatt catgctttgc agatatgata  5220
aatcacttac tatatttatt ggcgatttac agaataaaga tattggttgt ttttgcattt  5280
tgtttgcgaa tttcattatg agaatgagaa agcttgtaaa tattaccaag agttatgatc  5340
acgatgttga acttttctct tggctttacc tctcactcat ggcaagcctc tcttgttctc  5400
tctgttttta tgcttgtgtt aatttctttg tacacaagct tactcttttt actctcactt  5460
gtcgcttgtt ctgttcctat agatagaaga gagaactctt tgtttgtcta gatttcttac  5520
attgatcatc tcaaggatgt ttttacacaa cattgcacac acatatttat acaagaaaac  5580
atgatagcaa tctctgtttt ctccactctc tcccacactt tttgacctag acttaggagt  5640
ataatctcca tatcttgcct atacttttttg actcagcctt ggctaataca gcaagcaaac  5700
ttagagactt ttacatacca aaacaaaagc tttcactaac tcccttgact tgttgcttct  5760
tccacatttt tcttattctt attttctttt tgtttctttt tcttatttaa tcaaaggata  5820
caattccaac acatgagaca tgcttggaaa aaaaataaaa acaaggaagt catatggagt  5880
aaaagatgaa agaagcaaag attagactag agtcagtcat tgttgcatat ggttcctgaa  5940
agcttttcga ttcctatccc ccaggatggt gtcaatgatc agccggtcta atattttgaa  6000
aattgcagca tgtctagaag caacattgtt gtggaggcga tagcaaataa actgtacctt  6060
gagcagctag ccgaggaagt ttctcaagca aatgttgtca ctgataccca aaccaggtgg  6120
agaaagcggg ccatgcatgc atggaaagta aaatgactgt agccaagtcg tccaattgac  6180
caagagccac tgttgttcgc tcacgtccca cctaaggaac attgcaaatc aaaaagaaaa  6240
tggtttgaca atgatacaat ataaaaagag ataatgattc gtcgtcgtta ccatctaaaa  6300
aagaatatat ataatatata taatatatat atatagcaat gtatgagtta aataataagc  6360
atcatgacag aaaaagcata tagttcaaaa gaagttgtat gacccattca attttaaggt  6420
ttcagaagtt aaatcttctc catcttttgg gtattttttta agaaatgcat tctcaaattt  6480
atcataatct agttattttc tcagctaaag attccaccgt ctgatttgtc acccaactca  6540
gtgtttgtca accttcattt ccttatagga agcacgaaaa aacagagatg tattgaggac  6600
agaagtgtag ctttcccgtg ggtcctctgg aatatctgga aatcaaggaa ttgattggtc  6660
tttgagaact ccaggtcttc tccgtctgaa tgcgctgaga atgccataga agatgcatag  6720
atatggctat c                                                      6731

SEQ ID NO: 45           moltype = DNA  length = 6723
FEATURE                 Location/Qualifiers
source                  1..6723
                        mol_type = genomic DNA
                        organism = Brassica juncea
SEQUENCE: 45
aaagctttag tgggttttat tgtgttacat gcaatagttt tctacgtgct ttgttatttt  60
ccaagaaatt tttatagttt ggctttggtg tgtgaaagag tttcagagag atttaatggt  120
gtcagtcccc tgacctttga cgtgtgcacc cgtgagtgag gtcaaagtgc cgagaaaggt  180
atgtggtgga tgatcacatt tgcacgatat cgcgaaccga taaaggttat caagacgcac  240
gagatctatt tggtgggtga cctcattcgc acgatatcgc gaatcacttt ctgataggtc  300
actcatcttt ctactactcc agctcaaata tgattaactc tagagttcta aacggacatg  360
tgcccgaaaa gataaacgca ctttgttgaa ataagtagcc aaatcaattc tcagtctttc  420
cacatataat agaaattaga gtgttacaaa ttttgtctaa gatttattta taatatgaat  480
atctcaaagt gttgttttc cattgtttga gatttgttgg ttatagtttc cattatgggg  540
gagtttttgt aggaaacgct tgcttttttta ggtcaatttg tttaattcaa gttttggatt  600
gacagagata aggaagatta tttacgggtc tatagttgag ctcacataat gtattctcat  660
tatcaagacc aaatatgagc tgaagtttc atctttccat atctaagagt ttttgcccaa  720
aaaagtttat tgacattttt gtacattatt gacatagtgt ccacgatata cgtagtttac  780
tttgtaattg cagatttgtt tgttgcatcc acatttatcg tgtagggaag tattgaagat  840
atattagaaa acaagatatg tatcttacga accaactgag gaccgttgaa atctgattat  900
gaagtgaagc acataaagtc tatgaaatcc aaaccgaaaa tttattgata agttatattc  960
gtaattgaga tagatctaag tcttgtgtat atatagaaat ctcttgtaac ttataagaca  1020
caacacaata atatatttat tctataattc tacaattaat cttatcttag agcatgagta  1080
gtgagagtac ctcccatgat ttttcaagat aaaaatagtt aaaaaaatca gagaagagta  1140
agagagaaag agaaaataga agggacgatt cttgaaagga gacgtctctt aacaattcat  1200
gacaatggtc atgttgtgag tggttacaat tttattgtgt ttaaaattta atgatattaa  1260
taaaataaat caagagactt ttgttagaga tgtaaccaat gtggatgccc taagggttcc  1320
gtatccttcc caacccttcc aatcatttta aaacaatacc aaaaaaggca aaaaaacaaa  1380
tgtagttggt tttcgtttc ttttgtcttt cagagacacc agtctcatgt gataaagaag  1440
cagatataga gccaacgaaa ccaatatgat atgatgtgat tgtgaacggt gagctcgtga  1500
taagtgtggc tttggatcag atttactata gattcaccac ttgataatat ttcgataaca  1560
aaaaaatgta tatttcgata cacattttca gtaacgagtc ttgacgatgc gtgtcgttct  1620
agttttgcgc atattccttc aatatataca tgctgcactg catcactgtc gacggatcaa  1680
tttgaatatg tgacaaaaat catgttcgtg tgttccgatt aaggaacaca gatatgtgct  1740
atgtaacaaa agaaaaatca gcaatagaaa atgaaagact aaaaagtgga aacaaaacaa  1800
caaatataac aacaatgggt gaacactgag gttaaagtaa gtgaacccac gggattcatg  1860
atcccaccta aacctctccc aaaatatcaa gatactaaga caagaaaata caaacgtcac  1920
tcttctttag gaatggctat ataaaccta gattggcaca aggtttcata caacacaaca  1980
catacatcaa catattagcc atgaagcttc ttcatggact cgctttagtt tttctattag  2040
ctgctgcgag ttgcaaagct gatgaagaaa ttacttgcga agagaacaat ccattcacat  2100
gtagtaacac tgatatttta agcagtaaaa acttcggaaa agacttcatc ttcggtgttg  2160
catcttctgc ttaccaggca tgtaacaaat ttttttgacg tataaataaa tacaattcaa  2220
```

```
aaatactaaa atgcaacttc gcatggttgt ttcttttcat ttcagatcga aggaggaaga  2280
ggtcgtggtg ttaacatttg ggatggcttc agtcaccgat atccaggtat gtcacagcgt  2340
atatacacac atgagatgaa cgtcggttta tatgtacaca tattaatgta tttgtaacta  2400
ctatcagaga aatcagggtc agatttgaag aatggagaca ctacttgtga gtcatatacg  2460
agatggcagg ttaatacatt gatactcata tgactgaact atatatgtat aaaaactata  2520
cgtgtggatt gacatgtgat taaaatatgt aaaccgcaga aagatgtaga cgtgatgggc  2580
gaactcaatg ctactggcta caggttctcc tttgcgtggt caagaatcat tccaagtatg  2640
tacatgttat cgattcgttt gtattttaat tgggatcatt tagttgagaa aagtactaat  2700
taatgtacga catatatata catgagcaga aggaaaggtg agtaggggag tgaaccaagg  2760
aggtcttgat tactaccaca aactcataga tgcactactc gaaaagaata taacgccttt  2820
cgttaccctc tttcactggg accttcctca aacactccaa gatgagtatg aaggtttctt  2880
agaccgccag atcatgtatg tttatatttg ttccatgctt cttatattat aaataagaga  2940
agaaaacgtt ttggttttag ttacatgcat taatgaaatg attctgtata atatgcacag  3000
acaagatttc aaagactacg cggatctatg tttcaaagaa tttggtggaa aggtaaagca  3060
ctggatcacg atcaaccagc tatacacagt ccctacgaga ggctatgcgg tcggaacaga  3120
tgcacccggt cgatgttctc ctatggttga taccaagcac aggtgttacg gtggaaattc  3180
ttcaacagaa ccctacatcg ttgcacataa ccagcttctt gctcatgcca cggtcgtcga  3240
tctttacagg accaaatata aggtgagtgg tctctccata ttaaggtggt gcaaatctaa  3300
catatctgat tctaatgtat agtcatatat atatatatat cacgtgacca acagtttcaa  3360
aaagggaaga ttggacctgt gatgataaca agatggtttc ttccatttga tgagtctgat  3420
cctgcctcca tagaagcagc tgagaggatg aaccaattct ttcatggatg gtatatatat  3480
atattacaga acaatgtaac agtatatagt gtatgtatgt ataattaaaa gatatacatg  3540
gatcaggtac atggagccgc taacaaaggg tagataccca gacatcatga ggcagattgt  3600
gggtagtagg cttcccaact ttaccgagga agaagccgca ctcgttgccg gttcatatga  3660
ttttcttggt ctcaactatt acgtcactca gtacgcccag ccaaaaccta acccatatcc  3720
ttcagagaca cacactgcca tgatggacgc tggcgtaaag ctcacatgta ctagtctatt  3780
accactaatt agatacagcc tttctataca tataaatatt cttttatctc ctttttgttg  3840
caacatactt tgtgagtgac catctgttat ttcatccttg tgtttacaga tgataactca  3900
cgtggtgaat ttcttggtcc actggtatat atcaatgatc cacccccctaa gatttgtttt  3960
tctttcattt tttcagtttt cagtataaca accctaatta tgttttttaa ttgatgtgta  4020
tatttattta cttccatttt cacagttcgt tgaagacaag gtaaacggca acagctatta  4080
ctacccaaaa ggcatttact acgtaatgga ctacttcaaa accaaatacg gagacccttt  4140
aatctatgtc accgagaacg gtgagtttta cgaactcttt tcatttatac cacataataa  4200
ttattgtatt ttgatattag tcgaagaaac tgactttatt gtggaatatt tttaatgtgg  4260
cggtttattt aggatttagt acccccagtg aagaaaaccg tgagcaggct attgccgatt  4320
acaagcgaat tgattatctc tgcagtcatt tatgttttct ccgcaaggtc atcaagtgag  4380
tggatgctac tatataaatg attttctaca tctgttatat tcttcttctt tctttgtaac  4440
atttttatat atgattgttc ttgttttcag ggagaagggt gtcaacgtga gaggatactt  4500
cgcatgggct cttggagaca attatgaatt ctgtaaaggc tttaccgtca gatttggact  4560
cagttacgtt aattgggaag atcttgacga tagaaacctc aaagaatctg gcaaatggta  4620
ccagagattc atcaacggga ccgtcaagaa cgctgtgaaa caagatttcc tccgctcaag  4680
cctctcttcc cagagtcaga agaagaggtt cgctgatgca tgaaacactt tttccccccgg  4740
tcaagatcat ctccatgtct ctcactcttt ctagttgctc caaaaataag gagcttcttc  4800
tacctataat aatgtactaa ataaatattc tcaataaaaa gatgatcagt tactaatgaa  4860
taaaaaaatt gtctacagct acattttgtc aagatgatcg agagagagag agagtgaaat  4920
aacacaattt aaaccaaaaa cgtcacttag acacacatag aaaataaata aataattacc  4980
ccaaaccgca aactagtttt gtgtaataaa tatataaaca tcaaaccgat cagcttaaat  5040
tcactaatta acttaataag ttcaacttta tatactagaa tagattttca acataataaa  5100
caatgaccaa accttataca aactcaaatc tagctacacc aaagttctat catcctcaac  5160
tgaaacttaa tagtatttta catatgattt tcctatcatt caaatgattt tattttattt  5220
tggttcttat ataatcaaga aaaccaaaag aagctaaacc tcagtacttt agagtgtgat  5280
gattcaacca cactggttgt gattcaagcc ggctagctca ttcattaaga gaggtgttgt  5340
gacttgcact ctttttcttg gtttggtttt gttccactag gttttccaaa caaagttttt  5400
aatgaggctt agacacaaca ctacacatga gcctctcgat gaaatcagac caatctctat  5460
tctaattttt gtccataaag aaggatccag aagcttatct tttaaattgt tttcaattgt  5520
ttatggacct gttttcaatt gttgcgtggt gaatcacatt aattaacaac agaacaaatg  5580
catttggtct cataagcttt ataagtatga aggctcaaga ttcaaagcct atatctataa  5640
ctattctttg catcgtagga aaactatag ataaagccgc aatgagattg atcctaatct  5700
ttgtgattat gtgtggcttt tacaacgaaa catatgggga agtttcatta gatatcgaca  5760
agaaattgag gactcttaat aagccagcct tagagacgat caaggtatgt atgggatctg  5820
aaggcgcaat ataatatttc atgtgtagaa tttgtttcgg tttctgagtt ccgaaaattg  5880
attgtaatat atttgtagag tgaagatgga gatgtaatag actgcataga tatctacaaa  5940
caacatgctt ttgatcatcc tgccttaaga aaccataaga ttcaggtaaa catattctac  6000
atattaatga cattttgttt tcgtactcat attatattta aattatttat aaaagattta  6060
ttcatgaatt ttcagtccta aatacttata aattctatac actgatgcca tgcagatgaa  6120
acctagtgca gaatttgatg caaagacgac tactattcca aacaacggtt cttctaaacc  6180
aatcacgtcc cagatttggt ccaaatctgg aaactgtccc gttgggacaa taccagttcg  6240
cagagtcaga agagaagaca taatgagagc ctcttcaccg tctcattttg gaagaaaaac  6300
tcatcacaga tacagtttc tcgacaatgc acttcaacac aaggccaatt tcaatttaac  6360
tgctaaaaga ttacgcgaac cccgctcaaa caaccgatcg gtacgtacac ttttgctttt  6420
tttgactaaa gattagtgtc acttttatct ctttaccaca ctacaagaaa acagcgacat  6480
accgagggaa aaaatcgtcg gtatgtcgtc ggaataatac tattccaacg acataccgac  6540
gaaacaagtc ctcggaaata actcctcgga aattcatttt tcttcggaaa tctctcggaa  6600
atttccgacg gaattccgag aaaactccga ggaccaccaa ttcgtcggaa tataccgagg  6660
aaagacttct tcggaatatt tcgatggact ttccgatggt ctaatcctcg gaagtcccga  6720
cga                                                                6723
```

```
SEQ ID NO: 46          moltype = DNA  length = 6734
FEATURE                Location/Qualifiers
```

```
source                  1..6734
                        mol_type = genomic DNA
                        organism = Brassica juncea
SEQUENCE: 46
ttaaaaaaag aaaaaagaag tcgctgatgc aggttgtgtc aacactaatc caacatgcat  60
gctgaatgga gatttatgat actgagatgg attaggataa acttgaaaac caagtttatg  120
ccttgaacaa aaaaataagt gcaattccaa gaaaaatgaa ctaacactta taaatataga  180
agttgtctac atcaatggtt tccttggatg atccttggtc taagatttaa ggaacatgta  240
gatcattata aaatagcgaa agaatggaca aaacacttac cttgattgtt tagaggaaaa  300
atgaaaatct tttggtaagt gttcacaggt taacgtatca tggcgataga aaaaaaaaat  360
agggttggat agcttatgaa tcttgcaata gtgattatta gggtgttaat aaatcgtgat  420
ttatgctatt gtattgtctt gcatctttca atcacctaag tagatgaata acatccacta  480
ttcaataagg attttaaagt tatatatgtt tttttggtaa atttaaaaag ttatatatat  540
ggttggtctt tgttttattt tatcggttgg agagtggttt catgtgataa agcatggagc  600
aacgaaaatc aaaaagttat aagcggtgct ggtgagcggt gaggctcgtg atgaggtgtg  660
gccttttgga tcacatgata actgttttct ttttcttaac caggtcattg ttactccaga  720
ctggtgggta cttgatacaa ttactgtaga tttttaaata acttatggcg tcaattctaa  780
ctccaagtca aacgtaagag gcattgaaca tacaaggaat cgtttttagg aactttagta  840
cagggaatct tgggacatat cctacttttg cgcatacctt taacacatgc tgcatcgtat  900
caccgttgtc cgttgaccga tcaattaacg aatcgttctt tgtacgttaa gtgtctttta  960
ttgcaaatca cctacatgcc atgcatttta ggactaggat ctaaaaactc tctctttgat  1020
aagaaataat attagaaacc tcaatggtta agaaactcaa aaatgtgttt gtcgttcttt  1080
aaataaaact accccattgt tatttacata ttaacttaag aaataataac cacacaagca  1140
tggtcgagtg gtatggcggg tttgaaaagg tgataaatac tctagaaacc taccatctca  1200
aatataccctg cttgtgtggc caggcaatat tatagtattc aatttacatt gcgagtaacc  1260
gaatctgttc ggcgccggtg aacatgtaga ttttgtgtag tgtcaattaa gaaagcgatt  1320
gtgactctga ccttcttatc agctgctggc cttgaagtct cgctaactat ttggatatct  1380
cctcttcttc ctcagaacga aaaagcgaga gtggaagaca taatttttct gaagaattca  1440
ccattgatat atctaatcca cacataatat catgaaaata gatacagatt tttgactact  1500
acttagtcca ctcctacttg tcatccaatg gaaaagactt tatgaatggc ttaaaagaat  1560
ttgggatggt cgatctcttc ctttaaaatt tggattagtc aatgttggta atgaaacact  1620
gatctgagtt tctgatcctt tagtgaagta gaatcactca ggagctccca gctcccattc  1680
aacattcatt cataatcttc attctttttg agggaattag tcggttggga cgtggttcgt  1740
cggatacccc atgttatata gcaattacaa ttgagataaa aagaaataat tcaaagtttt  1800
cttaatgaaa tggtcaattg aagagcaagc cactgtaaaa agcaaccggt ttcatgtcac  1860
ttaaccctct cccaaaataa caaccaagac actaattaga gaagaaaata catgcgtcac  1920
ccttctttgc aatggctata taaaccctag attggcacaa gcttccacac aacacaacaa  1980
cacacatcta caaatcaacc atgaagcatc tttggttcgc attagctttt ctattagctt  2040
tggcgatttg caaagctgat gaagaaatta cctgcgaaga gaacctgcca ttcacatgtg  2100
gtcaaactga tcgtttcaac agtagcagtt tcgagaaaga cttcatcttc ggtcttgcat  2160
cttctgctta ccaggcatgt aacatatgct acatatcaac cattagtatt atgttgccag  2220
acgtcatatt aatttaacgt ataaataaca tcatatacga acattaaaat ccaacgttgc  2280
atggttgttt cgtttcattt cagatcgaag gtagcataaa tcgtggactt aacgtttggg  2340
atggcttcac tcaccgattc ccacgtttgt tttttgcatt actcatcaca tatgcatatt  2400
atctcggtta catgtctcca cgcacttata gtactgtatt tgtttactat cagataaagc  2460
aggacccgat catggaaatg gagacactac ttgtaactca tattcatact gggaggtaat  2520
taaattcctc tatatgaata tgtgtgtgct aactaatatt actcactgaa ttatctatca  2580
actgccaacc tagtgtggat tgacatgcga ttgtatgtga actgcagaaa gatatagagg  2640
tgatggacga actcaaagct actggctaca gattctccat tgcctggtca agaatcattc  2700
caagtatgtg aacgttattg atttatgtat atatatatat atatcatata tggtaatatt  2760
cgattgtgat tctttggaaa gattatatat tacgatacat atgagcagga ggaaagagga  2820
gcaggggagt acaccaagga ggtattaact actaccacgg actcataaat ggcctcatcg  2880
aaaagggtat aacgccttta gttacgctct ttcactggga ccttcctcaa gtactacaag  2940
atgattatga aggtttctta gacccccaga tcatgtatgt taattatatt tatggcatac  3000
tgcttattaa gaaagacgat aatatataga tatttgttct tggattaatg aaatgattct  3060
ataatactcg cagagatgat ttcagagatt acgcggatct atgtttcgaa gaatttggtg  3120
acaaagtaaa gcactggttc acaatcaacc agctctactc agtgcctacg agaggctatg  3180
gattaggatc agatgcacct ggtcgatgtt ctccaaaggt tgatcctaca tgttacgccg  3240
gaaattcttc aacggaaccc tatatcgttg cacataacca gctccttgct catgccaggg  3300
tggtcgatct ttacaggaca aaatataagg tagattaatt ctccattttg tgaaaggtgt  3360
attctaacat atctgattct aaattaatca tatcactgtg tatatttatc tgcgtgacca  3420
cagcatcaag gaggtaagat tggacctgtg atgataacta gatggtttct tccatataat  3480
gacactgatc aagacagcat agctgcaacc gagaggatga aagaattctt cttgggatgg  3540
taaatgctta taaaatgaaa ttatattctt aacattaata tatgttgtat ttatgaactg  3600
acgaaaaata tgtatttatg tacaccaggt tcatggggcc tctaacaaat ggtacatacc  3660
ctcaaatcat gatagacact gtgggtgagc ggcttccatc cttcactcca gaggaatcca  3720
aactcgtaaa gggttcatat gattttcttg gtctcaacta ttacttcagt cagtatgtcc  3780
aaccaagtcc taatcgtgtt gattgggatc gtcacattgc catgatggac gctggcacaa  3840
agctcacatg tatccatcta tatatatttc gacttattta caaccttaat ttgccttttg  3900
ttaagtacaa taatttgtga ccatcaatta tttgtgttaa cagatcgtaa tgcaagtaat  3960
catctcattg gtccagtggt atatatgcat ccatccctat tctttcattt ttttctaagc  4020
aaaattcagt tttctgatac tatttcgctt ctctttctaa gttcgctgaa cacagggaag  4080
acgagaccag aaacatctat tactacccaa aaggcattta ttatgtgatg gattacttca  4140
aaaccaagta caataaccct ttaatctata taaccgagaa cggtgggttc tactactcta  4200
tctctaaatt catctctaca tgttaaatgt aatttgaaat ttgttgaaat gatttcatgt  4260
tatgacggtt taactaggaa tccttacctc cggtgatgaa acccgtgagg aggctaagtt  4320
tgattacaga cggattgatt atctctgcag tcatctctgt tttctcagta aagtcatcaa  4380
gtgagttgat gcttctctct tttccttctt gtgcgtttta tatatatata tatatatata  4440
tacatgtatg acgtatcata tgacgtctaa tgattcattg ttcctgcttt tagggagaca  4500
```

```
ggtgtcaagg tgaaaggata ctgtgcgtgg tctcttgggg ataattatga atttggacaa  4560
ggatttaccg tcagattcgg actcacttac attgactgga ataatgtcac tgatagagat  4620
ctcaaagagt ctggccaatg gtttaagaag ttcattgcca ccaagaacct tgcgaagaaa  4680
gattttcttc gctccagcct cacctttgag aagaagaagt tcgcagatgc atgaaagatc  4740
caatccactt tatttacctc atcaagatca tcttcatgtc ccctctttct acttgctcca  4800
tagataagga gctagctttg tctacctacc actgtataac taaataaaaa acctcaataa  4860
aagaagatat ggggtttggg atatgtgggc actacaagaa aacagactct ttcatatata  4920
tatacgaagg attttgtcag aaattcattg gaaaaaaaaa accattttca acgaaagtcc  4980
aaccaatttt tttttttgt ctgttctatt tcgtctaaaa gtattttcca attatccaca  5040
gaatttccga tggacacatt tccaacggac tccgtcggac acattcccag tgaactccgt  5100
ccgacacatt cccaacaaaa taccaacaag aacagccgtc gtaaaacact gtctagaatt  5160
tgtcagcaac attttcgatg tgtatcatcc atcaaaaaat tttgacaaat gattttagcg  5220
ggaaattttg ttaaacattt tttagaaaaa ttaaaattta ataattagat aattaacttt  5280
tttgaaacac aattaattaa ctatttaaaa aacaaattta catattagat gaaaaaattg  5340
tttatgataa ataatctata aaaatatttt atatatatac ataataaaat taaaatttga  5400
aatcattttt attatgtaat tattcttaaa cgtttttaca atatattatt tgattttttt  5460
tattaaattc ccaaaaagca acttaaacat tttataaatt gaaaaaaaaa attaagtgaa  5520
tttttttttt acaaatttta aataacactt aaacgtttga tcaattaaac atttttaagt  5580
gaaaatattt ttgtaaattc caaaaaaaaa aacataaaac gttctataaa ttgaaaacag  5640
ttcttttta aagtgaaatc cgtttttata aattacattt ttaagtaaaa atacattttt  5700
ataaattaaa aaaaaacact aaaacttttt ataaattgaa aacagttttt tttttaagtg  5760
aataccgttt ttataaattc taagaaacat taaacgtttt atgaattaca acaaaaaaac  5820
ataaaaacgt tttataaaaa cttgagaaca ttttataaa aactttaaaa cattttataa  5880
aatcttaaaa acgcttaaaa aaaataaaaa taacaaaaca tcaaaaacat aaaacaagtt  5940
ttcaaatcct aaaactaaca attctcacat aaatctaaca tattaaatcc tataccaacc  6000
aacctaactc atatctaaca tttcaattcc taaaatctat taattataat aaccacacaa  6060
atatacaaac taatatatat aactattaag aggataatag atgattaaca tgatttaaga  6120
gaacttttag agaaggagtc acgtatgttc ttcgactaag agggagaaat gaaagaaaga  6180
gttgaaatga aagaaagagt tgaaatgaaa tagaagaaga aaactatcat gttcttatgt  6240
taaaaaatcg attgatcaag ttcgtcggaa atttatggtt ttttaaaaaa aaaatttggc  6300
gtttcacaaa aattaggcgg tttttttttc cgggaaaatt ttaatttcta acgaatgtac  6360
ccttctcggg tttttagacc caacatatcc cagataaatt taaacctaag acatttaatg  6420
ttcaaataaa cttaatccga aaatcataaa tttttgatgg acgtattccg gccttagagc  6480
atcttcaaga gcaaccttaa aatttcaaat ataaggtttt atgtgctcca agagaaacct  6540
taaaacctca aattataagg ttttgtacag tgaaacctta tatttgaggt ttcaatgtac  6600
aaaaccttat atttgaggtt tcatattttt ttagtccttg tatttgtata tcttttagat  6660
tatcttgata attttcttgt ttatcatttt agtccataca gttttgtatc ttttatatat  6720
tttatatatg ttct                                                   6734
```

```
SEQ ID NO: 47          moltype = DNA  length = 6684
FEATURE                Location/Qualifiers
source                 1..6684
                       mol_type = genomic DNA
                       organism = Brassica juncea
SEQUENCE: 47
aatatatata tatattagta tttatattat ctcatttaaa aaaatattta aaattatttg  60
tttttatatt tttataattt tacaataaat aaaaaattac cataccacaa ccacccataa  120
ccacaaacgc tagctgtaac cagcttttga tttagtgaag tttagaacgg tgtaaagcgg  180
tttgtattgt tttttgtgat tgttgtgaaa caccaacaac tgatatcagc cgcaaaagat  240
gtgtttgcga gtgatagcat ataaaccagt tagatcctaa atgagaggtt tgaggaaact  300
ggcaaaatat gtcatattta aaataaattt gtccatgtat aactttctac tagtttgtca  360
atatttaaaa aataactatt attttaatga aaacaattaa atatatatat attgatgggg  420
ataatttatc cacaataaga gcttgcgggt tagaacatgg cgccaatatc ttggttccga  480
cttctgacct ccggcctccg ggttcaggct ttcaggtcaa gtgattttta ccgcctaatg  540
ataaatggaa tcttctttaa tataaaatat gttgtttaga caatcttcct agagagaaca  600
aaaagaagta ttataatata tatagccatg cttaaaggat tatatatata acttgtataa  660
atgttatatt tttatacatt tttataatatt tatgtattaa atatattata ctagttatta  720
taatttaaaa ataaaataat ttttgtaatg agattattat tattttttgg atttttattt  780
ttatttatat tttaatttta atttttttg tattgttcaa attggatatc cagttaaaaa  840
tttaaaattt ctggatattc aagtgaatgg aaatcgaatc gaataactga ttattcaaac  900
gaaatgtata aaatcataaa tatcttaaaa atctcgtata ttcgatacgt gtccaccttt  960
ttcgtatgat aaagcaggga gcaacgaaaa tcaaaaagat atgcggtgat ggtgagcggc  1020
gaggctcgtg atgagtgtgg ctttttggat gacatgataa ttgttttttt ttcttagtca  1080
ttgttactcc agactacttg ataatattac tggagacttt ttcaataact tagggcgtca  1140
gttctaactc caagtcaaac gtaagagcca ttgagcatca tctactacaa ggaatcgttt  1200
tttggaactt tactataggg aatcttgaga catgtccttt tacttttgcg cagtgccggc  1260
tcttaccctg tgcacaaggc acatttgcac agggtcccca aaaaataaat aaaatttagt  1320
tagaatttaa gatctaattt tatagaattt aggacctttt tttgcaaatt actttttattg  1380
tttctgaaag ttagaacttg cacaaggtcc actcaaaaat taagccgggc ctgcttttgc  1440
gcataccttt gtcacatgct gcatcgtatc actgttgacc gatcaattaa cgaatagttc  1500
tttgtatgtt aagtgttttt tcttttttgc aaattacatg ccatgcattt ttaggactag  1560
gatctaaaaa ctctctcttt ttttggtaaa aaaaaaaact gtctctttga taagaaaaga  1620
gtattagaga aacctcaatg gttaagaaac tcaaaaagta cgtttgtcgt tctacaaata  1680
aatctacccc atcgttattt acagattaac ttcgaaaaat gatagtaatc tagcaatcac  1740
aattgagata aaagaaatag tcaaaagttt tcttaatgaa atgatcaatt gaagagcaag  1800
ccactgtaaa acgccacggg tttcatgtca cctaaccctc tcccaaaata ttgatcaaga  1860
cacttattag agaagaaaat gcatagatca ccaagttgca aaaaaaaaat gcatagatca  1920
ccctccgttg caatggctat ataaacccta gattggcaga aggttccata caacataaga  1980
aacacatcta caaattaacc atgaagcatc tttggctcac attagctttt ctattggctt  2040
```

-continued

```
tggcgacttg caaagctgat gaagaaatta cttgcgaaga gaacctgcca ttcacatgtg  2100
gtcaaactga tcgtttcaac agtagcagtt tcgagaaaga cttcatcttc ggtcttgcat  2160
cttctgctta ccaggcatgt aacatatata tatcaaccat tagtattatg ttgccagacg  2220
tcatatttta cgtataaaac atcatatata aacattaaaa tctaacgttg catggttgtt  2280
tcttttcatt tcagatcgaa ggtagcataa atcgtggagt taacgtttgg gatggcttca  2340
ctcaccgatt cccacgtttg ttttttgcat ggttactcat cacatataca tattatgtcg  2400
gttatatgtc tccatgcatt tatagttatg tatttattta ctatcagata aagcaggacc  2460
cgatcatgga aatggagaca ctacttgtaa ctcatattcg tactgggagg taattaaatt  2520
cctcaatata tatgtgtgtg catattaata ttactcactg aattatttat caactaccaa  2580
cctagtgtgg attgacatgc gattatatgt gaactgcaga aagatataga ggtaatggat  2640
gaactcaaag ctactggcta cagattctcc attgcctggt caagaatcat tccaagtatg  2700
tgaacgttat tgatccatgt atatatataa atcatatatg gtaatattcg attatgattc  2760
tttcgaaaga ttaaatatag gatacatatg agcaggagga aagaggagca ggggagtaca  2820
ccaaggaggt attaactact accacggact cataaatggc ctcatcgaca agggtataac  2880
gcctttagtt acgctctttc actgggacct tcctcaagta ctacaagatg actatgaagg  2940
tttcttggac cctcagatca tgtatgttat atttatgcca tgctgcttat taagaaggac  3000
gacaatatat aaagatttgt tctgggatta atgaaatgac tataatattc gcagagatga  3060
tttcagagat ttcgcggatc tatgttttga agaatatggt gataaagtaa agcactggtt  3120
cacaatcaac cagctctact cagtgcctac gagaggctat ggattaggat cagatgcacc  3180
tggtcgatgt tctccaaagg ttgattctac atgttacgcc ggaaattctt caacggaacc  3240
ctatattgtt gcacataacc agctccttgc tcatgccacg gtggtcgatc tttacaggac  3300
aaaatataag gcaggttctc cattttatga aaggtgtatt atctgattct aaattaatct  3360
tatcgttggg tatatatatc tgcgtgacca cagcatcaag gaggtaagat tggacctgtg  3420
atgataacta gatggtttct tccatataat gacactgatc cagactccat agctgcaacc  3480
gagaggatga aagaattctt cttgggatgg tatatgtttt ataaaatgaa atgatattct  3540
taacatgaat atatgctgta tatatgaact gacgaaaaat atgtatttat atgtacacca  3600
ggtacatggg gccgctaaca aatggtacat accctcaaat catgatagac actgtgggtg  3660
agcggcttcc atcgttcact ccagaggaat ccaaactcgt aaagggttca tatgattttc  3720
ttggtctcaa ctattacttc actcagtatg tccagccaag tcctaatcat gttgattcgg  3780
atggtcacac tgccatgatg gacgctggca caaggctcac atgtatccat ctatatattt  3840
cgacttagtt acaaccttaa tttatatcta cctaacgcct tttgttaatt acaataattt  3900
gtgttaacag atcgtaatgc aagtaatcat gccattggcc cagtggtata tatatgcatc  3960
aaccatccct attctttcat tttttttcta agcaaaattc agttttctga tactaatttg  4020
cttccctttc taagttcact gaacacaaag atgacgagac caaaaacacc tattactacc  4080
caaaaggcat ttattatgtg atggatcact tcaaaaccaa ttacaatgac cctgtaatct  4140
atataaccga gaacggtggg ttctactact catctctaaa ttcatcttta catgttaaat  4200
gtaatttgaa atttgttgaa attgttcatg ttatgacggt taactaggat tcagtacctc  4260
cggtgatgaa acccgtgagg aggctaagtt tgattacagg cggattgatt atctctgcag  4320
tcatctctgt ttcctcagta aagtcatcaa gtgagttgat gcttctctct tttgcttctt  4380
gtgttttatg tatatacttg tatgtacgta tggcgtctaa tgatttattg ttcctgcttt  4440
tagggagaca ggtgtcaagg tgaaaggata ctgtgcgtgg tctcttgggg ataattatga  4500
attcgggcta ggatttaccg tcagattcgg actcacttac attgactgga acaatgtcac  4560
tgatagagat ctcaaagagt ctggcaaatg gtataagaag ttcattgcaa ccaagaacct  4620
tgcaaagcca aattttctgc gctccagcct cacctttgag aagaagaagt tcgcagatgc  4680
atgaaagatc cagtccacta tatttacctc atcaagatca tctcatgttc cctctttcta  4740
cttgctccat agataaggag cttcatctac ctaccactgt atactaaata aaaaatctca  4800
ataaaagaag atatggattt gggataagtg gacactgcaa gaaaacaaaa tgttttgtat  4860
ggataatttt gtcggaaatt catcggaaaa aaagaagcaa tttccaacga aattttttcg  4920
tttggtttta tttcgttaaa aaattcgata aaactttttt ggacaattcg acgaatttcc  4980
agcagattcc gacatatgca ttcccgacga gatactgaca aaaatagccg aaagacatta  5040
tcaagaattc ggcaatattt tcaacgaata tcatccatca gaaattggac aatatttgtc  5100
aaaacctttg taaattatta aaagatatat ttaaattaat taacaattta acaaactaaa  5160
tttacatatc tagataaaaa ttgtttataa taatttttaa tcttatatat aaatataata  5220
actattaaaa ttaaaaaaaa acgcttttta aaaagtgaaa aacttttttta taaattctag  5280
aaaaaccatt aaacgtttta taaattgaaa gcgtttttcg aaaagtgaaa aaaagttgta  5340
taaattataa aatagtaaaa atattataaa cagaaacatt tttagaaagt gaaaaaaatg  5400
ttttctataa attccagaaa cataaaaact ttttataaat tacagaacat aaaaatgttt  5460
tataaaatct tacgttttat aaaaccgtaa gaacatttta aaacaacata aataataaaa  5520
catcaaaaat ataaaataag ttttcaaatc ctaaatctaa aatgtgaaat cctaaaacaa  5580
acaattctaa cacaaatata acatataaat cctaaatcaa ccaacctaat tcatttctaa  5640
catttcaatc cctaaaatct atcaactcta ataaccaaac acatatacaa attaacatat  5700
atgattatta agaggataac atatgactaa catgatttaa taagagttgt agggaaggat  5760
tcacatctgt ttttcgagag agggagagtt gaaatgaaga agaaaaagaa aactatttgg  5820
ttcttatgtt aaaatatttt gacgaatcaa gtttgcaatc cattagaaat tttttaattt  5880
ggtgcttcac aaaagtttag gtgattcttt tttccggaca aatttcaatt tctgacaaat  5940
tttcaaaaaa atataaagaa tttctgataa actttattta ttgaattact taactatttt  6000
cgatatatga atatatccta ttcgttgaaa attcataaat tcactcagac tgacaaattc  6060
agtttattct ctgcatgaat tataatcggc caaaacacag ttttgaaaaa aaatcccacg  6120
gaatatggat tgcggtttca aaacataata aaaatagact gatattatct attgataata  6180
tttgggaaaa ttccatataa tatttcaact aaattttgtt aagcttttta atacacaaat  6240
tttttcacta cctagtttaa taccccaact aattattttg ctcattttaa aacacaaact  6300
tttaaaactt gtgcttattt taacatccaa actttgttta tctatactat tatttgagaa  6360
gtgaatttgc ttagttgtca tattctccat gattttagga taaattatta gtttaattaa  6420
tattattatt ttaaattttc ttttaatata tgtatttatc atgatattta agataattaa  6480
taaacattaa cctattctac tgatatacat ataatattat tttaaaaaat atatatttaa  6540
tatatataat tatcatgata tttaaaacat ttaattaata aataaatatt aacaattgat  6600
attaacaata tctactggta ttatcataat tatggaggaa tttcatgttt accaytttca  6660
ttatttatct ttaccaccac aaaa                                          6684
```

```
SEQ ID NO: 48           moltype = DNA  length = 6734
FEATURE                 Location/Qualifiers
source                  1..6734
                        mol_type = genomic DNA
                        organism = Brassica juncea
SEQUENCE: 48
ttaaaaaaag aaaaaagaag tcgctgatgc aggttgtgtc aacactaatc caacatgcat  60
gctgaatgga gatttatgat actgagatgg attaggataa acttgaaaac caagtttatg  120
ccttgaacaa aaaaataagt gcaattccaa gaaaaatgaa ctaacactta taaatataga  180
agttgtctac atcaatggtt tccttggatg atccttggtc taagatttaa ggaacatgta  240
gatcattata aaatagcgaa agaatggaca aaacacttac cttgattgtt tagaggaaaa  300
atgaaaatct tttggtaagt gttcacaggt taacgtatca tggcgataga aaaaaaaaat  360
agggttggat agcttatgaa tcttgcaata gtgattatta gggtgttaat aaatcgtgat  420
ttatgctatt gtattgtctt gcatctttca atcacctaag tagatgaata acatccacta  480
ttcaataagg attttaaagt tatatatgtt tttttggtaa atttaaaaag ttatatatat  540
ggttggtctt tgttttattt tatcggttgg agagtggttt catgtgataa agcatggagc  600
aacgaaaatc aaaaagttat aagcggtgct ggtgagcggt gaggctcgtg atgaggtgtg  660
gccttttgga tcacatgata actgttttct ttttcttaac caggtcattg ttactccaga  720
ctggtgggta cttgatacaa ttactgtaga tttttaaata acttatggcg tcaattctaa  780
ctccaagtca aacgtaagag gcattgaaca tacaaggaat cgtttttagg aactttagta  840
cagggaatct tgggacatat cctacttttg cgcatacctt taacacatgc tgcatcgtat  900
caccgttgtc cgttgaccga tcaattaacg aatcgttctt tgtacgttaa gtgtctttta  960
ttgcaaatca cctacatgcc atgcatttta ggactaggat ctaaaaactc tctctttgat  1020
aagaaataat attagaaacc tcaatggtta agaaactcaa aaatgtgttt gtcgttcttt  1080
aaataaaact accccattgt tatttacata ttaacttaag aaataataac cacacaagca  1140
tggtcgagtg gtatggcggg tttgaaaagg tgataaatac tctagaaacc taccatctca  1200
aatatacctg cttgtgtggc caggcaatat tatagtattc aatttacatt gcgagtaacc  1260
gaatctgttc ggcgccggtg aacatgtaga ttttgtgtag tgtcaattaa gaaagcgatt  1320
gtgactctga ccttcttatc agctgctggc cttgaagtct cgctaactat ttggatatct  1380
cctcttcttc ctcagaacga aaaagcgaga gtggaagaca taatttttct gaagaattca  1440
ccattgatat atctaatcca cacataatat catgaaaata gatacagatt tttgactact  1500
acttagtcca ctcctacttg tcatccaatg gaaaagactt tatgaatggc ttaaaagaat  1560
ttgggatggt cgatctcttc ctttaaaatt tggattagtc aatgttggta atgaaacact  1620
gatctgagtt tctgatcctt tagtgaagta gaatcactca ggagctccca gctcccattc  1680
aacattcatt cataatcttc attctttttg agggaattag tcggttggga cgtggttcgt  1740
cggatacccc atgttatata gcaattacaa ttgagataaa aagaaaataat tcaaagtttt  1800
cttaatgaaa tggtcaattg aagagcaagc cactgtaaaa agcaaccggt ttcatgtcac  1860
ttaaccctct cccaaaataa caaccaagac actaattaga gaagaaaata catgcgtcac  1920
ccttctttgc aatggctata taaaccctag attggcacaa gcttccacac aacacaacaa  1980
cacacatcta caaatcaacc atgaagcatc tttggttcgc attagctttt ctattagctt  2040
tggcgatttg caaagctgat gaagaaatta cctgcgaaga gaacctgcca ttcacatgtg  2100
gtcaaactga tcgtttcaac agtagcagtt tcgagaaaga cttcatcttc ggtcttgcat  2160
cttctgctta ccaggcatgt aacatatgct acatatcaac cattagtatt atgttgccag  2220
acgtcatatt aatttaacgt ataaataaca tcatatacga acattaaaat ccaacgttgc  2280
atggttgttt cgtttcattt cagatcgaag gtagcataaa tcgtggactt aacgtttggg  2340
atggcttcac tcaccgattc ccacgtttgt tttttgcatt actcatcaca tatgcatatt  2400
atctcggtta catgtctcca cgcacttata gtactgtatt tgtttactat cagataaagc  2460
aggacccgat catggaaatg gagacactac ttgtaactca tattcatact gggaggtaat  2520
taaattcctc tatatgaata tgtgtgtgct aactaatatt actcactgaa ttatctatca  2580
actgccaacc tagtgtggat tgacatgcga ttgtatgtga actgcagaaa gatatagagg  2640
tgatggacga actcaaagct actggctaca gattctccat tgcctggtca agaatcattc  2700
caagtatgtg aacgttattg atttatgtat atatatatat atatcatata tggtaatatt  2760
cgattgtgat tctttggaaa gattatatat tacgatacat atgagcagga ggaaagagga  2820
gcaggggagt acaccaagga ggtattaact actaccacgg actcataaat ggcctcatcg  2880
aaaagggtat aacgccttta gttacgctct ttcactggga ccttcctcaa gtactacaag  2940
atgattatga aggtttctta gacccccaga tcatgtatgt taattatatt tatggcatac  3000
tgcttattaa gaaagacgat aatatataga tatttgttct tggattaatg aaatgattct  3060
ataatactcg cagagatgat ttcagagatt acgcggatct atgtttcgaa gaatttggtg  3120
acaaagtaaa gcactggttc acaatcaacc agctctactc agtgcctacg agaggctatg  3180
gattaggatc agatgcacct ggtcgatgtt ctccaaaggt tgatcctaca tgttacgccg  3240
gaaattcttc aacggaaccc tatatcgttg cacataacca gctccttgct catgccaggg  3300
tggtcgatct ttacaggaca aaatataagg tagattaatt ctccattttg tgaaaggtgt  3360
attctaacat atctgattct aaattaatca tatcactgtg tatatttatc tgcgtgacca  3420
cagcatcaag gaggtaagat tggacctgtg atgataacta gatggtttct tccatataat  3480
gacactgatc aagacagcat agctgcaacc gagaggatga aagaattctt cttgggatgg  3540
taaatgctta taaaatgaaa ttatattctt aacattaata tatgttgtat ttatgaactg  3600
acgaaaaata tgtatttatg tacaccaggt tcatggggcc tctaacaaat ggtacatacc  3660
ctcaaatcat gatagacact gtgggtgagc ggcttccatc cttcactcca gaggaatcca  3720
aactcgtaaa gggttcatat gattttcttg gtctcaacta ttacttcagt cagtatgtcc  3780
aaccaagtcc taatcgtgtt gattgggatc gtcacattgc catgatggac gctggcacaa  3840
agctcacatg tatccatcta tatatatttc gacttattta caaccttaat ttgccttttg  3900
ttaagtacaa taatttgtga ccatcaatta tttgtgttaa cagatcgtaa tgcaagtaat  3960
catctcattg gtccagtggt atatatgcat ccatccctat tctttcattt ttttctaagc  4020
aaaattcagt tttctgatac tatttcgctt ctctttctaa gttcgctgaa cacagggaag  4080
acgagaccag aaacatctat tactacccaa aaggcattta ttatgtgatg gattacttca  4140
aaaccaagta caataaccct ttaatctata taaccgagaa cggtgggttc tactactcta  4200
tctctaaatt catctctaca tgttaaatgt aatttgaaat ttgttgaaat gatttcatgt  4260
tatgacggtt taactaggaa tccttacctc cggtgatgaa acccgtgagg aggctaagtt  4320
tgattacaga cggattgatt atctctgcag tcatctctgt tttctcagta aagtcatcaa  4380
```

```
gtgagttgat gcttctctct tttccttctt gtgcgtttta tatatatata tatatatata  4440
tacatgtatg acgtatcata tgacgtctaa tgattcattg ttcctgcttt tagggagaca  4500
ggtgtcaagg tgaaaggata ctgtgcgtgg tctcttgggg ataattatga atttggacaa  4560
ggatttaccg tcagattcgg actcacttac attgactgga ataatgtcac tgatagagat  4620
ctcaaagagt ctggccaatg gtttaagaag ttcattgcca ccaagaacct tgcgaagaaa  4680
gattttcttc gctccagcct caccttttgag aagaagaagt tcgcagatgc atgaaagatc  4740
caatccactt tatttacctc atcaagatca tcttcatgtc cctctttct acttgctcca  4800
tagataagga gctagctttg tctacctacc actgtataac taaataaaaa acctcaataa  4860
aagaagatat ggggtttggg atatgtgggc actacaagaa aacagactct ttcatatata  4920
tatacgaagg attttgtcag aaattcattg gaaaaaaaaa accattttca acgaaagtcc  4980
aaccaatttt tttttttgt ctgttctatt tcgtctaaaa gtattttcca attatccaca  5040
gaatttccga tggacacatt tccaacggac tccgtcggac acattcccag tgaactccgt  5100
ccgacacatt cccaacaaaa taccaacaag aacagccgtc gtaaaacact gtctagaatt  5160
tgtcagcaac attttcgatg tgtatcatcc atcaaaaaat tttgacaaat gattttagcg  5220
ggaaattttg ttaaacattt tttagaaaaa ttaaaattta ataattagat aattaacttt  5280
tttgaaacac aattaattaa ctatttaaaa aacaaattta catattagat gaaaaaattg  5340
tttatgataa ataatctata aaaatatttt atatatatac ataataaaat taaaatttga  5400
aatcattttt attatgtaat tattcttaaa cgtttttaca atatattatt tgattttttt  5460
tattaaattc ccaaaaagca acttaaacat tttataaatt gaaaaaaaaa attaagtgaa  5520
ttttttttt acaaatttta aataacactt aaacgtttga tcaattaaac atttttaagt  5580
gaaaatattt ttgtaaattc caaaaaaaaa aacataaaac gttctataaa ttgaaaacag  5640
ttcttttta aagtgaaatc cgtttttata aattacattt ttaagtaaaa atacattttt  5700
ataaattaaa aaaaaacact aaaacttttt ataaattgaa aacagttttt tttttaagtg  5760
aataccgttt ttataaattc taagaaacat taaacgtttt atgaattaca acaaaaaaac  5820
ataaaaacgt tttataaaaa cttgagaaca tttttataaa aactttaaaa cattttataa  5880
aatcttaaaa acgcttaaaa aaaataaaaa taacaaaaca tcaaaaacat aaaacaagtt  5940
ttcaaatcct aaaactaaca attctcacat aaatctaaca tattaaatcc tataccaacc  6000
aacctaactc atatctaaca tttcaattcc taaaatctat taattataat aaccacacaa  6060
atatacaaac taatatatat aactattaag aggataatag atgattaaca tgatttaaga  6120
gaacttttag agaaggagtc acgtatgttc ttcgactaag agggagaaat gaaagaaaga  6180
gttgaaatga aagaaagagt tgaaatgaaa tagaagaaga aaactatcat gttcttatgt  6240
taaaaaatcg attgatcaag ttcgtcggaa atttatggtt ttttaaaaaa aaaatttggc  6300
gtttcacaaa aattaggcgg ttttttttc cgggaaaatt ttaatttcta acgaatgtac  6360
ccttctcggg tttttagacc caacatatcc cagataaatt taaacctaag acatttaatg  6420
ttcaaataaa cttaatccga aaatcataaa tttttgatgg acgtattccg gccttagagc  6480
atcttcaaga gcaaccttaa aatttcaaat ataaggtttt atgtgctcca agagaaacct  6540
taaaacctca aattataagg ttttgtacag tgaaacctta tatttgaggt ttcaatgtac  6600
aaaaccttat atttgaggtt tcatattttt ttagtccttg tatttgtata tcttttagat  6660
tatcttgata attttcttgt ttatcatttt agtccataca gttttgtatc ttttatatat  6720
tttatatatg ttct                                                    6734
```

```
SEQ ID NO: 49           moltype = DNA  length = 6731
FEATURE                 Location/Qualifiers
source                  1..6731
                        mol_type = genomic DNA
                        organism = Brassica juncea
SEQUENCE: 49
cgaccagtca caattctgat actgatttag ctgaagtaac tgagcccacg gaattcaccc  60
aaccaaacct ctcctaaaat atcaagatat taaagaaaag aaaatacttg tattggaact  120
atcgatgaaa catatatttc tgctatggta gtaggaaatt aaattgttag gtatcaaaac  180
ataatagagt tttatctgag aatgtgttag ctgcatgcaa ttttgatttg aaactcatat  240
attttcaaac tagctgggaa ggatcagttc ataatgcaaa agtgttaaat gatgcattaa  300
cggaaagtag caatatattt gaaattctcc tgggtaaatg tgttacttaa taaatatata  360
cattattgtt gtttaagata ggatatttta ctataaattt tatgattttt atatttattt  420
tacatcaaaa aaaaatcatg aaaattttat atagcatatt gtggatatga aaatgagtta  480
aatattctaa ctcaatttca aagtacccat tatcatctga aagaatttac tggaaggggc  540
agtgatccag gaaataaaga agaattattc aactatcatc atgcttgttt gagaaatgtc  600
gtcaaatgtc ttttagtatt ttctaatcaa gatttgtgat atccaaatct gcttcaagtt  660
ttccatataa gacagaagca gaattagagc ttgtatgtgc tgcagtgcat aactttctcc  720
atcagaagtg tcggccaaat gagtttcctc cagaagaaac ctctaatgaa taaaatgtta  780
ctcaaccaag taccgatggt catcaatttt ttaggctctc agaaacaaca aagagaacat  840
gctaataatg taattaaaac aacaattgat gttacaacaa aaaaaaacaa caacaattgc  900
ttcaaatatg taaaatgatt gtattagtgg atctcaacgg tggtatatgc atgagtaagt  960
tatcattttt atgtgttctt tgaattttat ggttgataag aatggtaaaa tatcacaacg  1020
tatttttggc tgatatgtgt tgagatgatt tatggcattg ttaacatgat gtattaaaaa  1080
aaatcgactc tcacagtaaa gtcaaaattg caaatcaagt gaagtatttg tcacttgtaa  1140
tgatattttt gaaaacagat tacacttttt gcctggtttt actaaattgt gtttatttta  1200
tgttgttaga aaatgttttt aagaaaacat tagcaaaact atttttttatt tttattttaa  1260
aattctatca aatgtcctat caaaatctct atcaaaatcc attaaatcca aataatttag  1320
aatctgaaat ccttaaagtt ttttccaaat ccctaatcta ataagctcct ttagtatatt  1380
tgaacgtata tttatattta gtaccaaatg gttatatata tatatatata tatatatatt  1440
taaaaatcca gcggttaatt caataaaata acactttaaa tattttttta tgccctttcg  1500
ttatttgcta atactccttc cgtttacttt tataagtcgt tttagaacct tgcacataga  1560
ttaagaaaaa acataaattt tttatatttt ctaaacaaaa acatcattaa ttatttacct  1620
aaccacaaat caatcaatga aaaaatagaa gacatattat catttggtca tacaacatta  1680
actattaaga aattttacat agaaaaccga aaacgtcata taatttggaa caaaattttt  1740
tctctaaaac gacttataaa agaaaacgga gggagtatat gataatttac ttacaattca  1800
ttttattcag ataaacttag tcccttgtta tttacaaaat taacttcaca aaaataacga  1860
ccggtcacaa ttctgatact gatttagcta aagtaactca gcccacggaa ttcacccaac  1920
```

```
caaacctctc ccaaaatatc aagatattaa agaaaagaaa atacgtgact cttctttaca  1980
aaggctatat aaacccttga atggcacaag gttccatcaa cacaaacaca tacatttact  2040
tattaaccat gaagcttcat ggactagcct tgataggttt tctaattgct gcggcgagtt  2100
gcaaagctat tgaggacatt aattgccaag agaacgagcc tttcacatgt ggaaacactg  2160
atcagttaag cagtaaaaat ttcccaaaag acttcatctt cggtgttgct tctgctgctt  2220
accaggcatg ttacaaatca acaatttttg acgtagaaaa ccatttaaaa tattaaatcc  2280
aacgttgcat ggttgtttct tattattgta ggtggaaggg ggcagaggac gtggtcttaa  2340
cgtttgggat ggcttcactc accgataccc aggtatatca tctacatggt acatatatat  2400
ataatgtcca catctcttat atatcattcg tagtaatgta tatgtttact atcagagaag  2460
ggtggatccg atctcgggaa tggagacact acttgtgagt catatacaag atggcaggtt  2520
aattcctcac tgagtcatat aggaaaatgg caggttaatt ccacattcct cactatatat  2580
aaatgatatc cgagtgtgta tgtaaactgc gcagaaagat atagacatca tggacgagct  2640
caatgctact ggctacagat tctcttttgc gtggtcaaga atcattccaa gtatgaacac  2700
ataaacgatc tatttataca aaaaattctc gtaaattgat tgtgagtgtt gagaagatta  2760
aatatatgat atgtatacat gagcagaagg aaaggtgagt aggggagtga acaaaggagg  2820
tctcgaatac taccacaaac tcatagatgg tctcgtcgca aagaatataa cacctttttgt  2880
taccctctat cactgggacc tacctcaaac actgcaagat gagtatgaag gtttcttgaa  2940
ccgcaccatc atgtatgtca tttgtgccgc gttcttagca agaaatataa gaagaaaaac  3000
atatataagt gatctcatgt taatgatttg tttctatgct atgcacagag atgactttag  3060
agattatgcg gatctatgtt tcaaggaatt tggtggaaag gtgaagaact ggatcacgat  3120
taaccagctg tacacagtgc ctacgagagg ctatgcaatc ggaacagatg cacccggtcg  3180
atgttctccg aaggttgatg agagatgtta cggcggaaat tcttcaacag aaccttatat  3240
agttgcacat aaccagcttc ttgctcatgc tgcggcggtc gatgtttaca ggacaaaata  3300
taaggtgagt atatataggt ttgtaaatag gtgtagtcta acatatatgt caatgttcta  3360
atcatatcat ttcatttcgt atgccgtgac aaacagttcc aaggagggaa gatcggacca  3420
gtgatgataa ctagatggtt tcttccattt gatgagactg ataaagctag cctatatgca  3480
gctgatagga tgaaagaatt cttcttggga tggtacgtat ttgtatgtat atgtacacaa  3540
aaatgatatg attatttata cgtatgtaca tcgatcaggt tcatggagcc gctaacaaag  3600
ggtagatacc cagacatcat gagacaaatt gtgggtagtc ggcttcccaa tttcacggaa  3660
gcagaagcag aactagttgc gggttcatat gattttcttg gtctcaacta ctacaccact  3720
cagtatgccc agccaaaacc taacccagtt acatgggaaa atcacactgc catgatggac  3780
ccaggcgcaa agctcacatg taccactcag tttcctctta tagttacaac ctttctatat  3840
atatatatat atatataggc ttctaagtct tttaaattaa gcatatatat actttgtgag  3900
tgaccactaa ttatttcatc attgggttta cagatacgaa ttcacgtggt gaaaatcttg  3960
gtccactggt atatgcatga tccacccctg acccctgtta cttattattt tttttctttc  4020
tagttgatgt gtatacgtat gcttcctttt ctcagttcgt taaggacgaa ataaacggcg  4080
actcctatta ctacccaaaa ggcatttatt acgttatgga ctacttcaaa accaaatacc  4140
gtaacccttt gatctatatc actgaaaacg gtgactacta ctcatctctt tttccatatt  4200
aagcaaatat gtatgtttaa aataatgtac aagttgttta tgtaccatga tggttaaatt  4260
aggatttagt actcccggtg aagaaacccg tgaggaagct attgctgatt ccaagcggat  4320
cgattatctc tgcagtcatc tatgttttct ccgtaaggtc atcaggtgag tggaagctac  4380
tatatttttt ttttctcttt tgaatttgat gcatgcatac ataaatgtat ggtcatcatc  4440
atgcataggc ttaggctttg aatgattgtt cgtgtttcca gggagaagcg tgtcaacatt  4500
aaaggatact ttgcatgggc tcttggagat aattatgaat tctgcaaagg ttttaccgtt  4560
agattcggac ttagttatgt taactggaca aacctcgatg atagaaatct caaagaatct  4620
ggcaaatggt accaaagctt tattaacggt acctctaaga accctgctaa acaagatttc  4680
ctccgctcaa acctctcctt ccagaaccag aagaagctcg cagatgcatg aaacacttta  4740
tcccaccatc atgatcatct tcatatctct actacttgct tcatagataa ggagcttgtt  4800
ctatcaatat tgtactaaat aaatattcca ataaaagatg atcatttact gatgactatt  4860
ttcgtttgag ttcgatccta cttacacgat gaattacttt tacttgggat tattagcatt  4920
tttaagttat aaaacttggc acagatcagc tatctaaggg gtaagtattt aactgatcgt  4980
cgggataaaa ctaaattaat catgttcggg tccctgattc atgaaaatca tgagcctagg  5040
ctccttccct gcttctagct ggtttttgac ttgaggtttt cttggttgat ttctgtaaaa  5100
ctgtagctag taataatttt ttcatttggt ttttaaatta acctaattta atgatctcaa  5160
tagaaaaaaa aagagaacaa ttcagtggcc acaaaagatt catgctttgc agatatgata  5220
aatcacttac tatatttatt ggcgatttac agaataaaga tattggttgt ttttgcattt  5280
tgtttgcgaa tttcattatg agaatgagaa agcttgtaaa tattaccaag agttatgatc  5340
acgatgttga acttttctct tggctttacc tctcactcat ggcaagcctc tcttgttctc  5400
tctgttttta tgcttgtgtt aatttctttg tacacaagct tactcttttt actctcactt  5460
gtcgcttgtt ctgttcctat agatagaaga gagaactctt tgtttgtcta gatttcttac  5520
attgatcatc tcaaggatgt ttttacacaa cattgcacac acatatttat acaagaaaac  5580
atgatagcaa tctctgtttt ctccactctc tcccacactt tttgacctag acttaggagt  5640
ataatctcca tatcttgcct atactttttg actcagcctt ggctaataca gcaagcaaac  5700
ttagagactt ttacatacca aaacaaaagc tttcactaac tcccttgact tgttgcttct  5760
tccacatttt tcttattctt attttctttt tgtttctttt tcttatttaa tcaaaggata  5820
caattccaac acatgagaca tgcttggaaa aaaaataaaa acaaggaagt catatggagt  5880
aaaagatgaa agaagcaaag attagactag agtcagtcat tgttgcatat ggttcctgaa  5940
agcttttcga ttcctatccc ccaggatggt gtcaatgatc agccggtcta atattttgaa  6000
aattgcagca tgtctagaag caacattgtt gtggaggcga tagcaaataa actgtacctt  6060
gagcagctag ccgaggaagt ttctcaagca aatgttgtca ctgataccca aaccaggtgg  6120
agaaagcggg ccatgcatgc atggaaagta aaatgactgt agccaagtcg tccaattgac  6180
caagagccac tgttgttcgc tcacgtccca cctaaggaac attgcaaatc aaaaagaaaa  6240
tggtttgaca atgatacaat ataaaaagag ataatgattc gtcgtcgtta ccatctaaaa  6300
aagaatatat ataatatata taatatatat atatagcaat gtatgagtta aataataagc  6360
atcatgacag aaaaagcata tagttcaaaa gaagttgtat gacccattca attttaaggt  6420
ttcagaagtt aaatcttctc catcttttgg gtatttttta agaaatgcat tctcaaattt  6480
atcataatct agttattttc tcagctaaag attccaccgt ctgatttgtc acccaactca  6540
gtgtttgtca accttcattt ccttatagga agcacgaaaa aacagagatg tattgaggac  6600
agaagtgtag ctttcccgtg ggtcctctgg aatatctgga aatcaaggaa ttgattggtc  6660
```

```
tttgagaact ccaggtcttc tccgtctgaa tgcgctgaga atgccataga agatgcatag  6720
atatggctat c                                                       6731

SEQ ID NO: 50          moltype = DNA  length = 6638
FEATURE                Location/Qualifiers
source                 1..6638
                       mol_type = genomic DNA
                       organism = Brassica juncea
SEQUENCE: 50
tgttatttag tcatagaccc gatgtctttt ttagattttt aaagacttag acaactttag  60
gaaatacgag atggattttg gttgaagaaa ttcttgccac attttttctc attgttggcc  120
agtgtacgag atattattct tcctcgagat gtattcaaga gatcaagttt tgaaataatt  180
cagagtttaa taaaatatta agggtgttaa acagtattgg ccaagtttgt aggctaaacc  240
aggaactgca ttgcatttaa aaatatgaga aaacaaaagt ttttgttctt gctttaaggt  300
atgtgaaaat tgtcttatct ttttgtttaa ttatccgtta acagttcaat ttatattctc  360
aggattatat tggagctttt gatagaacat atattcctga tatggtagta gtaaataaaa  420
ctgttagcta tcgaaaccga aatggagttt tatctcagaa tgctctagct gcatgcaatt  480
tttatttgca gttcaaatat gttattactg gttgggaagg ttcagcacat gatgcaaaag  540
tgtaaaatga tgccttaacg agaagtagca aaaaatttga accccccccc cccccgaggt  600
aactgcatta ctcaatatat atatctatgt gttatatgtg tttaattaag ataggttact  660
taattataag tttgattttt atttatattt cacattaaaa atatttaagg aaaaatttat  720
ctcgcaaact gtggatacat aaacaagata aatttaaaag ctctatttcg tagtacacat  780
agttatatga aagaatttac tggaggaggc atttatctaa gaaataaata agaattattc  840
aaccattgtc attcttgctt gagatatgtc atcgaaagga ttttgggtat tttcaaatca  900
agatttctta tattcaaatt cgctcctagg ttttcataaa tgacacaagc agagcaagtg  960
cttgtatctg ctgcattgca taacttttttc cgtcagaagt gtcggccaga tgagtttctt  1020
ccagaagaaa catctgatga acaaaatgtt actcaaagta gtgatggtta tcaatttctt  1080
ggcgaacaag aacaacaaag agaacatgct actgaataga gaacaaccaa tgcttcaaat  1140
acgtggaatg atgctactag tggatctcaa cggtgaaata tgcctgagta agttaacatt  1200
tttatgtgtt ctttaatttt tataattgac aataatagtg aaatctccca acgtattttt  1260
gattgatagg tgtgagatga tttatggcat tgttggcatg atattagaaa cacacattcg  1320
tctgtcacaa taaagtcaaa attacagtca agtatttgta attttttcat gctttttttcg  1380
aaattgatta cactttttttg cgtggtttcg ataaattgtt gtgagaaaat gtttttttaat  1440
gatcttagga aatctatttt tattttcttt aaaattctac caaattaatc tcctatcaaa  1500
agctctatca aattccttaa accccaaata aatttagcta aattccatca aatctgaaat  1560
ccttaaaaat tttcaaatcc ctaatcaaat aagcccttta atatatttga acgtatactt  1620
aagtaccaaa tggttctata tttaaaaaaa catccaacag ttaattcaag aaaacaacac  1680
tttaaatcac tttttatccc tttcgtaatt tgctaaaata tgataatcta cttacaaggt  1740
tgtcattttt ttcagataat aatagtccct tgttatttac aaaattaact ttacaaaaaa  1800
attaacgacc aatcacaatg ctgatactga ttcagctaaa gtaactgagc ccacggaatt  1860
caccccacca aacctctccc aaaatatcaa gatattaaag aaaagaaaat gtatacgtga  1920
ctctttttac aaaggctata taaaccctag tctggcacaa ggttccatac aacacaaaca  1980
aatacattta cttattaacc atgaagcttc atggactagc cttgataggt tttctaattg  2040
ccgtggtgag ttgcaaagct attgaggaat gccgagagaa cgagccattc acatgtggaa  2100
acactgatca gttaagcagt aaaagtttcc caaaagactt catattcggt gttgcttctg  2160
ctgcttacca ggcatgttac aaatcaacaa tttttgacgt agaaaaccat ttaaaatatt  2220
aaatccaacg ttgcatggtt gtttcttatt attgtaggtg gaagggggca gaggacgtgg  2280
tcttaacgtt tgggatggct tcactcaccg atacccaggt atatcatcta catggtacat  2340
atatatacat atgtacaact cttatcattc ttagtataaa atgtatctgt ttactatcag  2400
agaagggagg atccgatcat gggaatggag acactacttg tgagtcatat acgagatggc  2460
aggttagttc ctcactgagt catataccag atggcaggtt aatttctcat ttcctcacta  2520
tatataatga tatccgagtg cgtgtgtaaa ctgcagaaag atatagacat catagacgaa  2580
ctcaatgcta ctggctacag attctcattt gcctggtcaa gaatcattcc aagtatgaac  2640
acataaacaa tctatttata caaaagaatt ctcgtaattt gattgtgatt gttgggaaga  2700
ttaaatatat gatatgtata catgagcaga aggaaaggtg agtaggggag tgaacaaagg  2760
aggtatcgaa tactaccaca aacttctaga tggcctcatc gctaagaata taacccccttt  2820
tgttaccctc tatcactggg accttcctca aacactgcaa gatgagtatg aaggtttctt  2880
gaaccgcacc gtcatgtatg tcatttgggc cgcgttctta gcaaggaata taagaagaaa  2940
aacatatata cataagtgat ctcatgttaa tgatttgatt ctatgctatg cacagagatg  3000
actttagaga ctatgcggat ctatgtttca aggaatttgg tggaaaggtg aagaactgga  3060
tcacgatcac cagctgtaca cagtgcctac gagaggctat gcaatcggaa cagatgcacc  3120
cggtcgatgt tctccggcgg ttgatgagag atgttacggc gggaattctt caacagaacc  3180
atatatagtt gcacataacc agcttcttgc tcatgctgcg gcggtcgatg tttacaggag  3240
aaaatataag gtgagagtac gtgggtttgt gaataggtgt agtctttacg tatatgacta  3300
tatctaatca tatcattatc gtatgccgtg accaacagtt ccaaaaaggg aagatcggac  3360
cagtgatgat aaccagatgg tttcttccat ttgatgagac tgatgccagc agagatgcag  3420
ctgagaggat gaaagaattc ttcttgggat ggtaacgtat atgtatgtat atatcaacaa  3480
aaatgaaatg attttcttat acgtatgtac gtcgaccagg ttcatggagc cgctaacaaa  3540
gggtagatac ccagacatca tgagggaaat tgtgggtagt cggcttccca atttcacgga  3600
agcagaagcg gaactcgttg cgggttcata tgattttctt ggtctcaact actacaccac  3660
tcagtacgcc caggcaaaac ctaacccagt tacatgggca aatcacactg ccatgatgga  3720
cccaggcgca aagctcacat gtaccattct gtttcctctt atagttacaa cctttctata  3780
tatagatatc tccttttaat tataacatat atgtacattg tgagtgacca tcaattattt  3840
catccttggg tttacagata acaattcacg tggtgaaaat cttggtccac tggtacgtgc  3900
atgatccacc cctgttactt ctcaatattt ttttttcttt cttgtttatg ggtataatat  3960
gtacgcttcc ttttctcagt tcgttaaaga cgaaaaaaac gggaatgcct attactaccc  4020
aaaaggcatc tattacgtta tggactactt caaaaccaaa tacagtaacc ctttgatcta  4080
tatcactgag aacggtgact actactcatc tctttttttgc atattaatta agtaaatgtg  4140
tgtttcaaat aatgtatagt tgttgatgta ccatgatggt ctaattagga tttagtactc  4200
```

```
ccggtgaaga aaaccgtgac aaagctattg ctgattccaa gcggatcgat tatctctgca  4260
gtcatctatg ttttctccgc aaggtcatca ggtgaggga agctacttta ttttttctc  4320
ttttgaattt gatgtatggt catcatcatg cataggcttt gaattatgat ttttcctgtt  4380
tccagggaga agggtgtcaa cataaaagga tactttgcat gggctcttgg agataattat  4440
gaattctgca aaggttttac cgttagattc ggacttagtt acgttaactg gacagacctc  4500
aatgatagaa atctcaaaga ctctggcaaa tggtaccaaa gctttattaa cggtaccaat  4560
aagaaccctg ccaaacaata tttccgccgc ccaaacctct ccttccagaa ccagaagaag  4620
aagctcgcag atgcatgaaa cactttatcc caccatcatg atcatcttca tatctctact  4680
acttgcttca tagataagga gcttgttgta ctaaataaat attctaataa aagatgatca  4740
tttactaatg aatattttcg tttgagttca atcccttctt accgcttcag ttacgtttta  4800
ctttggatga ttaggttagg ttttacaaat tataaaactt ggcatgtcag ctattcatgt  4860
gagatttgta ggtttagata agagagagtc tatgtgtaaa tgcgagaact agcaagaata  4920
gtaacacaaa gtacacaaga gaatatctct acaaaaaata tgtgtattta ctagtatttt  4980
taaagtaaat ttactgatat cgaccttaga ttctgtcagc acttgcctcc aagaaaaccc  5040
tagattcttc aatcgcgacc tcctctgagc tgagcctgag ttctgatatc aatttgttca  5100
acttaacgct cagattacga cctagatctt ctcgattgct tgaatataaa aaaacatgca  5160
agaagacacg gtttgttcac ccggtgtcca actccttttt cgatgtaagt aagagatatt  5220
ctcacctggt ctggttagac cagcaataca ctatctcagc tcaaactcga gcccggatca  5280
acaaccgatc acaatcttct tctccgatct tatctctctc tctctcttat cagctagaga  5340
tataaagtga gttttaacgt cgttttacaa cactcatctc ccccccaacg tgctaacaca  5400
cgtgcaactt gaacaagcta taaccggctt aaatcacttc taatttaacc cgtcaatcaa  5460
accagtttgc atacactcgg attcctgtca tcctgagtag acccactcag cttcgtatct  5520
tgcgaactta gaaactcagt tctcagtcac cctgagaaaa gtcaattctt ccctcatctt  5580
gccaactggt aaaaccttgg taatatattt gcgggattgt actgcgaagc aatcttcaca  5640
acattgatga tcttctcact taccaactca cgaacaaagt tgtacttcac gtccacatga  5700
tttgtcctct tctgaagcac tgtgtttctt gatagtgcaa tatcactttg agaatcacaa  5760
aacacctcca cttgggttgg tcttaagcaa aacccaactc gttcataaaa cccctgagcc  5820
atactgcttc ccgagctgct tcactcaatg caatgtacct ggttgttgat agtgccacta  5880
ctttctgtaa actcgacctc cagctcacta aattctctcc aaatgtgaat accattcctg  5940
tgattgacct ctttttatcc aagtctgctc catattcttc atcacagtac ccctttataa  6000
taaaatgtca ttgcttcttg tgttaaagca tcaccttgat attatttcct ttctctttct  6060
cttcttattc tttcagatct ctgattttct tgatatcgac gaaaacataa atcacaggtt  6120
actccagtta agttacctcc acttatacaa ccagcatcac catttaccac tgcattagtt  6180
tctgctgctg tcgtcatccg tcattcaatt gatatcattt catattatct tccatgtaga  6240
tcgtactgtc caatctggtt tggaggaaac gctagacgag gttctgtcat tgccgacatt  6300
aactgacacg ccaccatcag tgttcttcca tttcctaact tccatcgaaa ttaacaaaaa  6360
tagcccggaa ttgatgtcgc tttcatattg tcttccccgt cttctttatg tttaacattt  6420
ttaagtttc aaatctgctc tattatacat acatacttat atagtatata atattatata  6480
tgattttcag attttaatta cattatattt taaatttggg tttattaatt agagtttact  6540
gagtagtgtt tagtgtttag tatttgaaag gtgaggatga aattagaaat aggttaaaat  6600
aacgtttagt attttacatt tttgtttatt gtgttcta                        6638

SEQ ID NO: 51          moltype = DNA  length = 6639
FEATURE                Location/Qualifiers
source                 1..6639
                       mol_type = genomic DNA
                       organism = Brassica juncea
SEQUENCE: 51
ttttgcgaag aggtatacaa tcactcaaat atatacttta aacttgatta atattattac  60
taatattttc ctatattatt ttgtattaaa aatacggaca ataggattgg gatcaatcaa  120
cgattttccc agggtaacct cttcctatgt tcgttgaggt gatgttccgg ctcaactctg  180
aacggagttg acagatgctc ataacaagat ttcatcaatg aggattgatt gatccatatg  240
tttgtaaacc atatgttttt cggcatacat gtggagagac ttgacagcta ctcgagcttt  300
agagattaca cgtaaaaata ttaatatcat cataccaact ttggaggagc aagctgaccg  360
ggaattaata atggataaag cggtttgaga gactagggtc gagtttttca acgatgttga  420
ttagaaatag tttctgtatt tttattttgt tttataattt ctataaaaac tagtttaaaa  480
ttttataaaa tattcattaa ttttattgat gttctggtgt attaaatagt taattcattt  540
aaacataaac tagataccaa atgtttctat tctttaaatc caacatttgc atcaataaaa  600
taacttcgaa aatattatga tgttgtcgat aaaaatacaa aaggactttc cttttttat  660
ttgctaatat gatcatcttt agcacattgt ctattttcac aaattcaatg tccgattaag  720
aaggcaacta caaaacgtgg aaatgaattt atacaaaata tttaaaagga cgatccagaa  780
catttttgga gttatcatat aaattcagat gttttttag atttgtgcag acttagacat  840
ctttaagaaa tacaagatgg attttggttg aagaaatgct tgccacattt tttttcattg  900
ttggccagta agagatatat tctccctcga gatgtattca agagatcaag tttggaaaca  960
attcagagtt taataaaagg gtgttaaaca gtattggcca agtttgtagg ctaaaccagg  1020
aactgcattg cctttacaaa catgagaaac aaaagatttt attcctactt taaagtatgt  1080
aaaaattgtc ttatctattt gtttattttt atccgttaac agtttcattt atattttcag  1140
gattgtattg gagctattga tggaacatat ttctgctatt gtagtaataa ttaaataaaa  1200
ctgttagtta tcaaaacaga aatagagttt tatctatgaa tgtcctagtt gcgtgcaatt  1260
ttgatttgca gttcaaatat gttacaactg gttgggaagg ttcagctcat gatgcaaaag  1320
tgttaaatga tgcattaatg agaagtagca ataaatttga aacccccaag gtaattgcat  1380
tactcaatag aaatatatag tatgtgttta agatcggtta attaattata agttcttgat  1440
ttttcatgta ggagatttgg tagataacca tctgaaatct gaaaacttgg tagccgagtt  1500
tgtaggctaa accaggaact gcattgcatc caaataaatt tagctaaatt ccatcaaatc  1560
taaaatcctt taaaaatttc aaatccctaa tcaaataagc cctttaatat atttgaaggt  1620
atatttaagt accaaatggt tatatatttt aaaaaatcca acagttaatt caacaaaata  1680
aactttacat aattttttat ccctttcgta atttgttaaa atatgataat ctacttacaa  1740
ggttgtcatt ttattcagat aatagtccct tgttatttac aaaataaact ttacaaaaaa  1800
ataacgacca atcacaatga tgatactgat tcagctaaag taactgagcc cacggaattc  1860
```

-continued

```
accccaccaa acctctccca aaatatcaag atattgaaga aaagaaaatg tatacgtgac  1920
actactttac aaaggctata taaaccctag actagcacaa ggttccatcc aacacaaaca  1980
catacatcta cttattaacc atgaagcttc atggactagc cttgataggt tttctaattg  2040
ccgtggtgag ttgcaaagct attgaggaat gccgagagaa cgagccattc acatgtggaa  2100
acgctgatca gttaagcagt aaaagttttc caaaagactt catattcggt gttgcttctg  2160
ctgcttacca ggcatgttac aaatcaacaa tttttgacgt agaaaaccat ttaaaatatt  2220
aaatccaacg ttgcatggtt gtttcttatt attgtaggtg gaagggggca gaggacgtgg  2280
tcttaacgtt tgggatggct tcactcaccg atacccaggt atatcatcta catggtacat  2340
atatatacat atgtacaact cttatcattc ttagtataaa atgtatctgt ttactatcag  2400
agaagggagg atccgatcat gggaatggag acactacttg tgagtcatat acgagatggc  2460
aggttagttc ctcactgagt catataccag atggcaggtt aatttctcat ttcttcacta  2520
tatataatga tatccgagtg cgtgtgtaaa ctgaagaaag atatagacat catagacgaa  2580
ctcaatgcta ctggctacag attctcattt gcctggtcaa gaatcattcc aagtatgaac  2640
acataaacaa tctatttata caaaagaatt ctcgtaattt gattgtgatt gttgggaaga  2700
ttaaatatat gatatgtata catgagcaga aggaaaggtg agtaggggag tgaacaaagg  2760
aggtatcgaa tactaccaca aacttctaga tggcctcatc gctaagaata taaccccttt  2820
tgttaccctc tatcactggg accttcctca aacactgcaa gatgagtatg aaggtttctt  2880
gaaccgcacc gtcatgtatg tcatttgggc cgcgttctta gcaaggaata taagaagaaa  2940
aacatatata cataagtgat ctcatgttaa tgatttgatt ctatgctatg cacagagatg  3000
actttagaga ctatgcggat ctatgtttca aggaatttgg tggaaaggtg aagaactgga  3060
tcacgatcaa ccagctgtac acagtgccta cgagaggcta tgcaatcgga acagatgcac  3120
ccggtcgatg ttctccggcg gttgatgaga gatgttacgg cgggaattct tcaacagaac  3180
catatatagt tgcacataac cagcttcttg ctcatgctgc ggcggtcgat gtttacagga  3240
gaaaatataa ggtgagagta cgtgggtttg tgaataggtg tagtctttac gtatatgact  3300
atatctaatc atatcattat cgtatgccgt gaccaacagt tccaaaaagg gaagatcgga  3360
ccagtgatga taaccagatg gtttcttcca tttgatgaga ctgatgccag cagagatgca  3420
gctgagagga tgaaagaatt cttcttggga tggtaacgta tatgtatgta tatatcaaca  3480
aaaatgaaat gattttctta tacgtatgta cgtcgaccag gttcatggag ccgctaacaa  3540
agggtagata cccagacatc atgagggaaa ttgtgggtag tcggcttccc aatttcacgg  3600
aagcagaagc ggaactcgtt gcgggttcat atgattttct tggtctcaac tactacacca  3660
ctcagtacgc ccaggcaaaa cctaacccag ttacatgggc aaatcacact gccatgatgg  3720
acccaggcgc aaagctcaca tgtaccattc tgtttcctct tatagttaca acctttctat  3780
atatagatat ctccttttaa ttataacata tatgtacatt gtgagtgacc atcaattatt  3840
tcatccttgg gtttacagat aacaattcac gtggtgaaaa tcttggtcca ctggtacgtg  3900
catgatccac ccctgttact tctcaatatt ttttttcttt tcttgtttat gggtataata  3960
tgtacgcttc cttttctcag ttcgttaaag acgaaaaaaa cgggaatgcc tattactacc  4020
caaaaggcat ctattacgtt atggactact tcaaaaccaa atacagtaac cctttgatct  4080
atatcactga gaacggtgac tactactcat ctctttttg catattaatt aagtaaatgt  4140
gtgtttcaaa taatgtatag ttgttgatgt accatgatgg tctaattagg atttagtact  4200
cccggtgaag aaaaccgtga caaagctatt gctgattcca agcggatcga ttatctctgc  4260
agtcatctat gttttctccg caaggtcatc aggtgagggg aagctacttt attttttttct  4320
cttttgaatt tgatgtatgg tcatcatcat gcataggctt tgaattatga tttttcctgt  4380
ttccagggag aagggtgtca acataaaagg atactttgca tgggctcttg gagataatta  4440
tgaattctgc aaaggtttta ccgttagatt cggacttagt tacgttaact ggacagacct  4500
caatgataga aatctcaaag actctggcaa atggtaccaa agctttatta acggtaccaa  4560
taagaaccct gccaaacaat atttccgccg cccaaacctc tccttccaga accagaagaa  4620
gaagctcgca gatgcatgaa acactttatc ccaccatcat gatcatcttc atatctctac  4680
tacttgcttc atagataagg agcttgttgt actaaataaa tattctaata aaagatgatc  4740
atttactaat gaatattttc gtttgagttc aatcccttct taccgcttca gttacgtttt  4800
actttggatg attaggttag gttttacaaa ttataaaact tggcatgtca gctattcatg  4860
tgagatttgt agatttagat aagagagagt ctatgtgtaa atgcgagaac tagcaagaat  4920
agtaacacaa agtacacaag agaatatctc tacaaaaaat atatgtattt actagtattt  4980
ttaaagtaaa tttactgata tcaaccttag attctgtcag cacttgcttc caaaaaaccc  5040
tagattcttc aatcgcgacc tcctctgagc tgagtctgaa ttctgatacc aatttgttca  5100
acttaacgct cagattacga cctagatcta ctcgattgct tgaatataaa aaaaacatgc  5160
aagaagacac ggtttgttca cccgtgttgg ctctccctac aaaatgttgt agatcaaatg  5220
tcagtaaacc cgcatgaagc aaaattattg gctctccctt gccgtttgcg atctatgatg  5280
aatgtgaagg agaaggaaat agtttggcag tacaaacaga gacagagaga cttattgaaa  5340
tttctactga acctgtgtca gtcagtcaaa acgtggagga agaaatccaa acggagaaac  5400
acgaggagag acagcttaga tcatctcttc atcaaaatgt aaaaaaaaaa gattgacgaa  5460
agaatagact tatgggctga catccggaac tactatgatt cttctatcat ttggaaaaat  5520
ctgtagatgg ttgtaggaga ttttaatgag actttgaaca ttgataaaca ctcttcaaat  5580
gctgtgagct ctaatgaggg agtttcaaga tgtggtgcaa tattgttctc ttctcgattc  5640
tacctcacat ggaacaatag aagagcataa ggccatatag cgaagaggtt aataaataat  5700
cacgtgttac aactatttcc gcagtcttat agtgtattgg aaggaggagg ttgctaggat  5760
cacttgagat gcagaattaa gttactatca gagctttgtc gaccaaagat gcctcttaaa  5820
tttgttaacg ttgtgccaga gatggaacaa ttcaaggtcg atatttttgg gaggaatact  5880
tatgaaatat ccaaaatggt aaccggagca gaggccaacc agacacacca ctcaaccaac  5940
caaagaatcg acatgacgta tgtgcattct aaacaccata tctcacaaag catgaggtct  6000
tttgccaata tgtaaaatat atttaatata tatttattat ttgacaatat gtaaaataat  6060
gtaaaataca taaatattaa tttatatata gaatgatcat tccgcgcaag ctgcagatct  6120
taacctagtt atgtattggt ttaaaattca gtgtatcaca aaaaaaaataa gaagtaatga  6180
attaattatt ttttaatatt gaaaagagga gtaatgttgt acgttgatat caaatgagag  6240
ataacagaag ttgttcatcc ataagcaaag tgacccttgt atcattagtg agggataaaa  6300
atttgtttgt aaagataagc attttaagta atacttaacc tataagttca tgctgatatt  6360
tttttttcat tttataaatg tatagttttg atattatcat aaacgtttga aatatatgat  6420
ttacatttta gtgttatata ttgtgtaact ttttaatttt ttgtttaagt ttttttattc  6480
aacatgatta ataatataga gtgatttttt tatatatttt aatttgtttt taatatttat  6540
tacattttca agcagggtag aataaattca taatctgaaa taatcaaata gagaatctta  6600
```

```
ttcaaaatat atatttttga tattatcata aacgtttta                        6639

SEQ ID NO: 52          moltype = DNA  length = 6628
FEATURE                Location/Qualifiers
source                 1..6628
                       mol_type = genomic DNA
                       organism = Brassica juncea
SEQUENCE: 52
tatacataat atataaatga atacaaataa ataataatag ataaaaatag ttttatatat  60
aacattcatc ctgcgcaatt gcccgggtct taagctagtt cattgttaac ttaacaacaa  120
attaacattg actgtcgcag ttaatttatt gctaatttaa caacaataat aaacatccac  180
gatttaaagt cttatattgt aagtcaaagt tacgaagata gtttcagcgc aaaatttata  240
tctagtttac gatgaatata tttacgacaa aataacgacg tatcatggac cttgcaactt  300
aagtctgtac gacgatcttt caataactat gtgcacttaa cgatgaagtt acattccttg  360
ttatttagtt gtagaccaga tgtctttttt agatttgtac agacttagac agagtttaat  420
aaaatattaa gggtgttaaa cagtattggc caagtttgta ggctaaacca ggaactgcat  480
tgcctttaaa aatatgagaa aacaaaagat tttgttcttg ctttaaggta tgtgaaaaat  540
tgtcttatct ttttgtttaa ttatccgtta acagttcaat ttatattctc aagattatat  600
tggagctatt gactgcatta ctcaatatat atatatatat gtattatata tgtttaatta  660
agataggtta cttaattata agtttgagtt ttatttatat ttcacattaa aaatatttca  720
tgaaaatttt atctcgcaaa ctgtgggtac ataaacaaga taaattttag agctctattt  780
cgtagtacac ataatcatat gaaataattt actggagaag gcattgatcg aagaaataaa  840
taagaattat tcaaccatcg tcattcttgt ttgagaaata tcatcgaaag gattttgggt  900
attttcaaat caagatttct tatattcaaa ttcgctccta gtttttcata aatgacacaa  960
gcagagcaag tgcttgtatc tgctgcattg cataactttt tccgtcagaa atgtcggcca  1020
gatgagtttc ttccagaaga aacatctgat gaacaaaatg ttactcaatt aagtagtaat  1080
ggttatcaat ttcttggcga acaagaacaa caaagagaac atgctactga atagagaaca  1140
accaatgctt caaatatgtg gaatgatggt actagtggat ctcaacggtg aaatatgcct  1200
gagtaagtta acatttttat gtgtttaatt ttatagttga caataatagt gaaatctcac  1260
aatgtatttt taggtgtgag atgatttatg gcattgttgg catgatatta aaaacacaca  1320
ttcgtctgtc acaataaagt caaaattgca gtcaagtatt tgtaattttt tttcatgctt  1380
ttttcgaaat tgattacact tttttgcgtg gtttcgataa attgttgtga gaaaatgttt  1440
tttaatgatc ttaggaaatc aatttttatt ttctttaaaa ttctaccaaa ttaatctcct  1500
atcaaaagct ctatcaaatt ccttaaaatc caaacaaatt tagctaaatt ccatcaaatc  1560
tgaaatcctt aaaaaaattc aaatccctaa tcaaataagc cctttaatat atttgaacct  1620
atacttaagt accaaatggt tatatattta aaaagatcca acagttaatt caacaaaata  1680
aactttacat aaatttttat ccctttcgta atttgttaaa atatgataat ctacttacaa  1740
ggttgtcatt ttattcagat aatagtccat agttatttac aaaataaact ttacaaaaaa  1800
ataacgacca atcacaatgc tgatactgat tcagctaaag taactgagcc cacggaattc  1860
accccaccaa acctctccca aaatatcaag atattgaaga aaagaaaatg tatacgtgac  1920
actactttac aaaggctata taaaccctag actagcacaa ggttccatcc aacacaaaca  1980
catacatctc cttattaacc atgaagcttc atggactagc cttgataggt tttctaattg  2040
ccgtggtgag ttgcaaagct attgaggaat gccgagagaa cgagccattc acatgtggaa  2100
acactgatca gttaagcagt aaaagtttcc caaaagactt catattcggt gttgcttctg  2160
ctgcttacca ggcatgttac aaatcaacaa tttttgacgt agaaaaccat ttaaaatatt  2220
aaatccaacg ttgcatggtt gtttcttatt attgtaggtg gaagggggca gaggacgtgg  2280
tcttaacgtt tgggatggct tcactcaccg atacccaggt atatcatcta catggtacat  2340
atatatacat atgtacaact cttatcattc ttagtataaa atgtatctgt ttactatcag  2400
agaagggagg atccgatcat gggaatggag acactacttg tgagtcatat acgagatggc  2460
aggttagttc ctcactgagt catataccag atggcaggtt aatttctgat ttcctcacta  2520
tatataatga tatccgagtg cgtgtgtaaa ctgcagaaag atatagacat catagacgaa  2580
ctcaatgcta ctggctacag attctcattt gcctggtcaa gaatcattcc aagtatgaac  2640
acataaacaa tctatttata caaaagaatt ctcgtaattt gattgtgatt gttgggaaga  2700
ttaaatatat gatatgtata catgagcaga aggaaaggtg agtaggggag tgaacaaagg  2760
aggtatcgaa tactaccaca aacttctaga tggcctcatc gctaagaata taacccccttt  2820
tgttaccctc tatcactggg accttcctca aacactgcaa gatgagtatg aaggtttctt  2880
gaaccgcacc gtcatgtatg tcatttgggc cgcgttctta gcaaggaata taagaagaaa  2940
aacatatata cataagtgat ctcatgttaa tgatttgatt ctatgctatg cacagagatg  3000
actttagaga ctatgcggat ctatgtttca aggaatttgg tggaaaggtg aagaactgga  3060
tcacgatcaa ccagctgtac acagtgccta cgagaggcta tgcaatcgga acagatgcac  3120
ccggtcgatg ttctccggcg gttgatgaga gatgttacgg cgggaattct tcaacagaac  3180
catatatagt tgcacataac cagcttcttg ctcatgctgc ggcggtcgat gtttacagga  3240
gaaaatataa ggtgagagta cgtgggtttg tgaataggtg tagtctttac gtatatgact  3300
atatctaatc atatcattat cgtatgccgt gaccaacagt tccaaaaagg gaagatcgga  3360
ccagtgatga taaccagatg gtttcttcca tttgatgaga ctgatgccag cagagatgca  3420
gctgagagga tgaaagaatt cttcttggga tggtaacgta tatgtatgta tatatcaaca  3480
aaaatgaaat gattttctta tacgtatgta cgtcgaccag gttcatggag ccgctaacaa  3540
agggtagata cccagacatc atgagggaaa ttgtgggtag tcggcttccc aatttcacgg  3600
aagcagaagc ggaactcgtt gcgggttcat atgattttct tggtctcaac tactacacca  3660
ctcagtacgc ccaggcaaaa cctaacccag ttacatgggc aaatcacact gccatgatgg  3720
acccaggcgc aaagctcaca tgtaccattc tgtttcctct tatagttaca acctttctat  3780
atatagatat ctccttttaa ttataacata tatgtacatt gtgagtgacc atcaattatt  3840
tcatccttgg gtttacagat aacaattcac gtggtgaaaa tcttggtcca ctggtacgtg  3900
catgatccac ccctgttact tctcaatatt tttttttctt tcttgtttat gggtataata  3960
tgtacgcttc cttttctcag ttcgttaaag acgaaaaaaa cgggaatgcc tattactacc  4020
caaaaggcat ctattacgtt atggactact tcaaaaccaa atacagtaac cctttgatct  4080
atatcactga gaacggtgac tactactcat ctcttttttg catattaatt aagtaaatgt  4140
gtgtttcaaa taatgtatag ttgttgatgt accatgatgg tctaattagg atttagtact  4200
cccggtgaag aaaaccgtga caaagctatt gctgattcca agcggatcga ttatctctgc  4260
```

```
agtcatctat gttttctccg caaggtcatc aggtgagggg aagctacttt attttttttct  4320
cttgtatggt catcatcatg cataggcttt gaattatgat ttttcctgtt tccagggaga  4380
agggtgtcaa cataaaagga tactttgcat gggctcttgg agataattat gaattctgca  4440
aaggttttac cgttagattc ggacttagtt acgttaactg gacagacctc aatgatagaa  4500
atctcaaaga ctctggcaaa tggtaccaaa gctttattaa cggtaccaat aagaaccctg  4560
ccaaacaata tttccgccgc ccaaacctct ccttccagaa ccagaagaag aagctcgcag  4620
atgcatgaaa cactttatcc caccatcatg atcatcttca tatctctact acttgcttca  4680
tagataagga gcttgttgta ctaaataaat attctaataa aagatgatca tttactaatg  4740
aatattttcg tttgagttca atcccttctt accgcttcag ttacgtttta ctttggatga  4800
ttaggttagg ttttacaaat tataaaactt ggcatgtcag ctattcatgt gagatttgta  4860
gatttagata agagagagtc tatgtgtaaa tgcgagaact agcaagaata gtaacacaaa  4920
gtacacaaga gaatatctct acaaaaaata tatgtattta ctagtatttt taaagtaaat  4980
ttactgatat caaccttaga ttctgtcagc acttgcttcc aaaaaaccct agattcttca  5040
atcgcgacct cctctgagct gagtctgaat tctgatacca atttgttcaa cttaacgctc  5100
agattacgac ctagatctac tcgattgctt gaatataaaa aaaacatgca agaagacacg  5160
gtttgttcac ccgtgttggc tctccctaca aaatgttgta gatcaaatgt cagtaaaccc  5220
gcatgaagca aaattattgg ctctcccttg ccgtttgcga tctatgatga atgtgaagga  5280
gaaggaaata gtttggcagt acaaacagag acagagagac ttattgaaat ttctactgaa  5340
cctgtgtcag tcagtcaaaa cgtggaggaa gaaatccaaa cggagaaaca cgaggagaga  5400
cagcttagat catctcttca tcaaaatgta aaaaaaaaag attgacgaaa gaatagactt  5460
atgggctgac atccggaact actatgattc ttctatcatt tggaaaaatc tgtagatggt  5520
tgtaggagat tttaatgaga ctttgaacat tgataaacac tcttcaaatg ctgtgagctc  5580
taatgaggga gtttcaagat gtggtgcaat attgttctct tctcgattct acctcacatg  5640
gaacaataga agagcataag gccatatagc gaagaggtta ataaataatc acgtgttaca  5700
actatttccg cagtcttata gtgtattgga aggaggaggt tgctaggatc acttgagatg  5760
cagaattaag ttactatcag agctttgtcg accaaagatg cctcttaaat ttgttaacgt  5820
tgtgccagag atggaacaat tcaaggtcga tatttttggg aggaatactt atgaaatatc  5880
caaaatggta accggagcag aggccaacca gacacaccac tcaaccaacc aaagaatcga  5940
catgacgtat gtgcattcta aacaccatat ctcacaaagc atgaggtctt ttgccaatat  6000
gtaaaatata tttaatatat atttattatt tgacaatatg taaaataatg taaaatacat  6060
aaatattaat ttatatatag aatgatcatt ccgctcaagc tgcagatctt aacctagtta  6120
tgtattggtt taaaattcag tgtatcacaa aaaaaataag aagtaatgaa ttaattattt  6180
tttaatattg aaaagaggag taatgttgta cgttgatatc aaatgagaga taacagaagt  6240
tgttcatcca taagcaaagt gaccattgta tcattagtga ggaataaaat tttgtttata  6300
aagataagca ttttaagtaa tacttaacct ataagtttat gctgatattt ttttttcatt  6360
ttataaatgt atagttttga tattatcata aacgtttgaa atatatgatt tacattttag  6420
tgttatatat tgtgtaactc tttaattttt ttgtttaagt ttttttattc aacatgatta  6480
ataatataga gtggtttttt atatatttta atttgttttt aatatttatt acattttcga  6540
gcagggtaga ataaattcat aatctgaaat aatcaaatag agaatcttat tcaaaatata  6600
tatttttgat attatcataa acgtgtta                                    6628
```

```
SEQ ID NO: 53           moltype = DNA  length = 6528
FEATURE                 Location/Qualifiers
source                  1..6528
                        mol_type = genomic DNA
                        organism = Brassica juncea
SEQUENCE: 53
agcattttat acaaactttg aaacgcttct ctaacgtaat aaaccatgtt aaactcacca  60
cacacaccac aagtaacaaa acctatcatt ttttttagaa ctgaatgtta gatttaactt  120
tttttttaaa aaaaaaagac cgttctacat aaactcgatc aatcaaagaa aaagctctct  180
aatttgcaaa acttcaggac cttcaaaact tcaatacctt cagcttcttg tcctaaacca  240
aaatctcatc ccttcttcga aatctttatc acctctcctt tgcaaaattg tgaacttatt  300
tctcatggtt ttatcaatcc gcttaacaaa acctatcatt gctattgcaa tatgtagttt  360
gcagaaagaa catgttaatt acctaagaaa aatccagtaa aaattcgtaa cgtaaatgtt  420
acttaaactg aaatctttat ttatttccta ttctactata tcgaaggcct gaagcacata  480
aaatgaagtg tttttcctat tttaattcat gcttgaagtc atagctttga actatttcat  540
gcatttcaat agaaaaactt ttttttttga aatttatttt tgttactgag acatgccatc  600
atgaccaagg tcattacagt ttaacaagct acaacaaagc aagtatatca tagaaaccca  660
gaaacaatcg aaactttcgg ttgacttaaa caaggggaga aaactagcct cttccacctc  720
tgtttccacg tccgcgattt catcatcccc gacctgtgaa ctgtaagtgc atctctttag  780
cttttgttga cagcttaacc agtccaatag aaaagctttt gtcaaaaaga atatataatt  840
acgaaaatat aagtataatg tataaattct aacataatgt gtagagttaa actaggttaa  900
tacacaagta cttatcttct tatctaacca gaagtaacag tttcgattgt atccatccca  960
acccttccaa tcatctagaa acgataccaa aaaggaaaaa aaaaagtttt cttttgtctt  1020
ttggagactc cggtctactc atgtgataaa agcatatagg gagaggtcaa aacaaataag  1080
atatgctttg attgtttttt aaaaaaatat gctgtattgt gagcggtggt gagcctcgtg  1140
ataagtttgg ctctggatca gtgttactct agattcaaca cttgataata tttcgatata  1200
aatctccaat aactttatgg cgttatgttg aagcttctaa cattatttac gacaacgaat  1260
cttttttttt tttgaaacac tacaacgaat cttgatgatg agtgtcatcc tagttcccgc  1320
aaaccttcca tatatagatg ctgcattgac agtttgacac aattcgtgtt cctagtcacg  1380
atagattgct tcgattaacc gctttaaaca aagaacgctt tagtatctaa agcaataaaa  1440
accacattca cgagacacac cgagaaaata gtgataaacc attcagcaat tcagataaag  1500
aatgcaacat ctgtattttt tccaatgaaa tggtagattg aagagaaagg cacgctaaaa  1560
agtggaaaca aaacaagaaa tttaagcaaa aatcggtgaa aactcagcta aagtaagtga  1620
gcccacgggt ttcatcccac ctaaacctct accaaatcat ctggacagaa aatgcatacg  1680
tcacaattct ttaggaaggg ctatataaac cctagattgg cacaaggttc catacaacac  1740
aacacaaaca tcaacatata ttaaccatga agattcttca tggactcgct ttagtttttc  1800
tattagctat tgcgagttgc aaagcttatg aagaaattac ttgcgaacag aacgaaccat  1860
tcacatgtgg taacactgat atcttaagca gtaaaaactt cggagaagac ttcatcttcg  1920
```

```
gtgttgcatc ttctgcgtac caggcatgca acaaatgctg ccataccata tttttgacgt  1980
atagaaaata atattcaaaa atgctaacat caaactttgc gtggttgttt ccatttcaga  2040
tcgaaggagg gagaggtcgt ggtgttaacg tttgggatgg tttcagtcac cgatacccag  2100
gtatgtcacg gtggcatata tatacatata agatgaatgt cgtttatatc tacacacatt  2160
aatgtatttg taattactat cagagaaatc agggtcagat ttgctgaatg gagacacttc  2220
ttgtgagtca tatacgagat ggaaggttag ttcctcagta catatacact catatgacta  2280
aactacgtat aaaatttacg tgtgaactga attccgttta aaatgcagaa agatgtagag  2340
attatgggag aactcaatgc tactggctac agattctcct tagcgtggtc aagaatcatt  2400
ccaagtacga acataaattt gtatttttat tgggatcctt tagctggaag agtatactaa  2460
ttaatgtatg atataaatga gcagaaggaa aggtgagtag gggagtgaac caaggaggtc  2520
ttgattacta ccaccaactc atagacgccc tcctcgaaaa gaatataact cctttcgtta  2580
ccctctttca ctgggacctt cctcaaacac tccaagatga gtatgaaggt tttttggatc  2640
gccagatcat gtatgtgcca tgcttcttaa ttatatacaa attattaata aaaacaagaa  2700
gaagaagaag aaggttttgt cttaattaca tgctttactg aaagaatgat tatatattaa  2760
tatgcacaga caagatttca aagactatgc ggatctatgt ttcaaagaat ttggtggaaa  2820
ggtaaagcac tggatcacga tcaaccagct attcacagtg cctacgagag gctatgcact  2880
cggaacagat gcacccggta gatgttctcc tatgattgat gagaggtgtt acggcggaaa  2940
ctcttcaaca gaaccctata ttgttgcaca taaccagctt ctcgctcatg ctgcggtcgt  3000
cgatctttac aggaccaact ataaggtgag tagtctccat atttaatacg atggtgtgat  3060
cttaatccat ctgattctga tctagtcata tatatcatgt gaccaacagg accaacaagg  3120
gaagattgga cctgtgatga taacaagatg gtttcttcca tatgatgagt ctgatcccgc  3180
ttgcgtagaa gcagctgaga ggatgaacca attcttccat ggatggtata tctttttgt  3240
ttgacatcaa acaattattc tttttttgt ttgtttacat taaatggtta ttttattatt  3300
taaaactaaa ggtggtctgt ataactagaa tgattatatt gtatgtataa tgaaaaaaat  3360
atacaccgat caggcacatg gagccgctaa caaagggtag atacccagac atcatgaggc  3420
agattgtggg tagtaggctt cccaacttta ccgaggaaga agccgcactc gttgccggtt  3480
catatgattt tcttggtctc aactattatg ttactcagta cgcccagcca caacctaacc  3540
catatccttc agagacacac actgccatga tggacgctgg agtaaagctc acatgtacca  3600
ctctgtttcc actttgttac aacctccttt ctatatatat attccttttt gttataaaac  3660
atacttaatt tgtgagtgac cataagttat ttcttccttg tgtttacaga taataactca  3720
cgtggtgaat atcttggtcc actggtaatt atgcatgatc catcctcatg atatctctct  3780
cattgatatg tatattttgt tctgattgat atgtattttt tgtttgcttc cctttcccag  3840
ttcgctgaag acaaaaatagc cggcaacagc tattactacc caaaaggaat atattacgta  3900
atggacttct tcaaaaccaa ttacagcaac cctttaatct atatcaccga gaacggtgag  3960
ttctacatac tacttactac tcatctattc tacataaatt aattagtgta tttttatata  4020
ttagtcgagg aaactgattt tcaaatattg tggaatgttt tcacggttta attaggaata  4080
agttcgcccg gtacagaaaa ccgttgcgaa gctattgccg attccaagcg cattgattat  4140
ctctgcagtc atctatgttt tctccgtaag gtcatcaagt aagtggatgc tactgtacat  4200
gcttttcttc caatatttta tcatcttttt cttcttcttt ttaagtatac atatatatga  4260
ttgatttatt gtttccaggg agaggggtgt caacgtgaga ggatactttg catgggctct  4320
tggggataat tatgaattct gtaaaggctt taccgtcaga tttggtctca gttacgttaa  4380
ttgggatgat ctcgacgaca gaaacctcaa agaatctggc aaatggtacc agagattcat  4440
taacggaacc gtcaaaaacc ctgcggaaca agatttcctc cgctcaagcc tttcctctca  4500
gagtcagaag aagaggcttg cttgctgatg catgaaacac ttttccacct gtcaagatca  4560
tctctatgtc tctcacactt cctagttgct ccatagataa ggagcttctt ctactacagt  4620
gtactaaata aaaattctca acaaaaagat gatcaagaat aaaaataatt tacctacaac  4680
tacattatgt caagtcaagg ggggtgaggg ggacaataac gcaatttaaa ttgtaaaagg  4740
ctcacacaca tacaaaataa aaacccaaac cgcaaactag tttagtgtta caaaaatatt  4800
aatgggccga taagcgtaca attcactaat tagtttaata agttcaactt tatgaaataa  4860
agatgtattt tcaaccgaat agaccatgat caaacccaat ataaattcaa aaataattat  4920
accaaagttc tatcatcatt agtggaaact aaataaaaat ttacatatgt tttattttaa  4980
gtttttccta ggataggaca cgcttcaacg gaggttattt ttttattcta tttaaaaatc  5040
agcaaaataa gagtatattg attcatcttt gtcaacttat agatccatct aatctactaa  5100
ataaaaattt tggttggtaa aacttgtgtt gtaatatata cgcctcattg aaaattgatt  5160
ttattagttg gtttatatta aaacattagt tatgttattt aatgtttggt gttttaagtt  5220
atgtatttat aaataatgtt tttttcgtaa acattgtaag attttcataa ttagttaacg  5280
taatatataa tttagtcttt gaacatcttg aacacaattt acaatattga agtaatcaaa  5340
tataagataa taataataat aaaataaggc aaactaacaa gttaaatagt ttttactata  5400
tatgggtgat catttttgt gctttttctt ttagttttg attttgttt tttcgaaaac  5460
catttttatc caattaaagt ataattttta tttttagttt tggtcaaaaa aaatgatttg  5520
ccaatcaaga tttttaaata aaatagtttc cctaaaattt agggaaactt attttgaaaa  5580
ctttaaccaa tttatgaaga aaaaccaaaa ccaactttta tgagctttta tgaaaaatga  5640
attttgtttc ttttggagaa aatgctcgat tttagttaac taataattaa taaataatat  5700
ttttcataaa aataaaatta tcatacaggt tttgaataat aaaatattta cataataaaa  5760
ttataattta ttttaaaatt ttgaaatatt tttcaattat aaaatacata aaaaaacaaa  5820
tataactctg taagaaaaat tcagtatact gaaatcactg ctagaatcga ctttcaaata  5880
atataaataa taatttctta attttttaaa aatattaaat aacatataaa atatatggat  5940
caataaatcc tagctggaaa atcatccaat ttaatagaga atgttggctg atctcatatt  6000
ttttgacaaa atattttaaa accatccaat ccattttttt gacaaaatat tttaaaacca  6060
tctaatccaa tacatttgtg aatttttagt caacttgaca agtcttttgt ggaaggaatc  6120
cccatagata taaaaacatg ttgagttgga aaatttcata tactttatat attgggtgtg  6180
tatcaataaa aagttggact gagaaggcaa attaaaacag gataaaatag taaccgttaa  6240
caaagatgtt tcgcaccgac ttaaaagcaa accaaaaaga acttcgaaaa atattacttg  6300
ggcgttcata tttggtctcg tcagctttat aagtatgcag gctcaagatt tttttttgt  6360
cacagaaatt tcattaataa taaaaaaaag acagaaagag cccaaaacat ggcccaaact  6420
cagtagtcca ttacacagaa gagaaaatat gaaaagcttt tatggctaaa ggtaacaaca  6480
atcgagttct ttgatcgggg gagatgagag aaaccgattg atgcaaat              6528

SEQ ID NO: 54          moltype = DNA  length = 9127
```

```
FEATURE                Location/Qualifiers
source                 1..9127
                       mol_type = genomic DNA
                       organism = Brassica juncea
SEQUENCE: 54
acttgaatcc taaactaaaa tctaatggga ttttgcattt gattttttta tcattcatat  60
aattttattt gattttggtt cttatataat caataaaacc aaaagaaaaa tagtcctttg  120
tctgttaaat attctatgta tataccaaat atcttccata gaaattaaat gaagttttaa  180
atataatttt actaaatttt atcgaaatgt attgaagtgt taatgaaaaa tagagatgaa  240
ttttgttatg aatataaaat aaagaataca atattttgtt tatatttata taaactttat  300
atatatataa attaataatt tatgatttta ttgggactac atatttacat aaaaaaaatt  360
aaaaaagaat attttcatat gattttatcg tttatgtcat attttaaact tgactcaact  420
cagaactgaa aaatattaat ttattgtgtt tattaattta tcgagtatta atttatagat  480
attattaatt tatcgtattt attaatttat agagtttata catgagatca tataatcaaa  540
gttgtgcgag catttatagc atccataagc aattaaaata aatatgccct caaccgtaaa  600
ataaaataaa aatgttttag aataatcatt gtcacttcaa aaaaacccag caaacttaat  660
aatggaaatt tctttctttg ttgtagtcca ttttagcttt gctagtatta gtattgaact  720
aataatactc aagtgactca tgtgaccaat gtgccatgca gttttacatg tgcctgccca  780
cacagagtgg accaaaactc tttgctgcat tttttgtggt tagttactta gttatatttg  840
cattcattaa caatccatca agggtcgtac taaattcgga acaacgatcc aacacatctc  900
tagaaatgaa aaccaatgct agatatctaa tcaaaagcac agcacaaagg gtctctctcc  960
actccttgct actctttgaa ttgccattct ctacggcaca tggggcaatg agcttgacta  1020
gtctgtgaat tgacccattt caatatacaa tggagatgga acgaatggtt gcaagctccc  1080
caaactgctc gataaccata taacgatcca ggtttaagaa tacaaataag gggttttagt  1140
tttgaaacaa tcacagtgtg tagaaagaga catgaaaaga gaggagacac gtacttagag  1200
ggcaatcatc tccagggagt ttgcagtctg gacaacaacc gtcgaatggc atacgacata  1260
tcccacatgt ctcatcctga gcatcccatg tccatgacgc aaccgcatgc caccttacag  1320
tttatttttt cacaatgtaa gagttcacgt attggaattg agaatgtatg taacacatgt  1380
agtgggacaa agaaacttac tctgtttttt tttctttttt tttaagtcag tactagacat  1440
tgtagcactg agagtcaagg aagaaacagt tctttggaca caaaatccta aattaaagaa  1500
actttgagat aatcttcgcc taccttatat aaactagtta agagttgata accaaaaatc  1560
ttcaccgaaa aaaaaaacta ttagaaagtc atctacatca gtattcaaaa ctgaaattca  1620
tgaaaagaga acaactttat gaaatcatga aacctaagct gcatctttaa aaaaacatgt  1680
tttactggaa aacatcaagc attgacgtga acatttggat gcatgattga catgcagaga  1740
agatgaagta gaaggatacg caagatcttg actttcatgt cttcctcctg aatgaaacat  1800
aaaaataatc ttatatcagt taaacaaact caacaaagag agaaaacaca aacacaagtc  1860
acgaatcacg cacacacaag acagatcaga gagattaacc taagattaac tataagatca  1920
taggtaaacc taaaatagta atatttcact gatattggtt tctctcagac atttgatcga  1980
acacctggtg gacacttcag atgtttgacg acgattccaa tcaaactcgt tctggaatac  2040
ccactaagaa gaaactcaag aaagtaaaat cctttttat attaaactct aaatctaatg  2100
gagtgatatc aacagaacgg agcaaaccca tcagaaaatt caaaaactca ccggagtttg  2160
acggagaagc gaactgcgac agagatgaag cggcgagatg tgaatagaag acaagaatta  2220
gttaagatat gggcttttat ttaaactggg ctttatttaa aattgatctc agggcccata  2280
cgtgtgctct tcttaacaag attatatatt atttataaac gacaccaaaa aaaaacgtgg  2340
tttgttttcg ttttctttcg tctttccgag actctagttt catgtgataa aagcaaaaag  2400
agaggtcaaa agaatcaaca ccaatacgat atgctgtgat tttttttttt ttcaaatgtt  2460
gtaattgtta gcggtgaggc tcgtgaagag tgtgtcattg gttcagcgtt actttagttt  2520
caagacaaca ctcgataata tttcgataat cttcaataac tttatggcgt tatgagttat  2580
aaccaagctt tgaacattat ttactacagt gaatcttaat gatgagtatc attcttgtta  2640
accttcgata tatacatgct gcattgcacc accgtcgacg gaacaatttg aagatgtgac  2700
gcaactcgtg ttcaagtcgt acgtgttccg gtaaaggaac ataattatat gtgctacata  2760
accaaaaaat tatttgcaat agatcatgaa agactaaaac gtggaaacaa gcaagaaatt  2820
tggagtaaac tcggtgaata ttgagctaaa gtaagtgaac ccacgggact catcccacct  2880
aaacctctcc caaagtatca ggacaagaaa atacatacgt cactattctt tttgaagggc  2940
tatatataaa ccttagaagg gcacaaggtt ccgtacaaca caacacatat atcaacagat  3000
taaccatgaa gcttctttat ggactcgctt tagtttttct attagctgct gcgagttgca  3060
aagctgatga agaaattact tgcgaacaga acgaaccatt cacatgtggt aacactgata  3120
ttttaagcag taaaaacttc ggaaaagact tcatcttcgg tgttgcatcg tctgcgtacc  3180
aggcatgcaa caaatgctgc cataccatat ttttgacgta tacaaaataa tattcaaaaa  3240
tgctaaaata tccaactttg catggttgtt tctttttatt tcagatcgaa ggagggagag  3300
gtcgtggtgt taacgtttgg gatggcttca gtcaccgata cccaggtatg tccctatggc  3360
atatatctaa tctattaaaa ctaaaataca tttagtactc atatctgatt ttttctaaat  3420
aattatcata gaatgccact gagatttaat ctacacttca ctaattacta ttaggctttt  3480
acgttgtgtt gcaagaataa gtaacaagcc cactaagatt tacattcaca aaactgcatt  3540
tgtatcttct tttttttta tcgaagcgtt tgtatatctc aaaccaataa aaatgtgttt  3600
catctttggt gcatcacatt cccaaactct tcatgaatgg tttatatgta ttagtaaacc  3660
aaaagtctaa aatcaagtgc cagaattttc actatccatt ttcaacaatt aacaataaaa  3720
ttcactacca aaattactat aataatgtaa ttcacgagaa catcactaga ccggattata  3780
tgtgtaacat gaaatataca caacttttac aaaatcgttt tagtatatag taattgtgaa  3840
tgtgatttca atttaatttt ttaacaaaga aaatcaaaga ttacagattt tctatcaatt  3900
tagttggaca cagaataaaa ataaaaatta cagatttcct attggtttgg tatatttcga  3960
aaaatttaga tccactaaat attcctaaaa tcattgaaca tcttgctaac ttaacataac  4020
aaacccctta attaaagtta tcatattaat aacaataata tctacttacg atggagttac  4080
ccaactatat ttgaaatata aaaatacgaa aaaatgaaag ttggtaattt caagttaaaa  4140
tattagactt cttcatattt gttttattat tctaatgctt agactataaa ctattaaaaa  4200
tattaatata taacatgacc ttagtttaaa aaaatattac catgacgtat aataagacaa  4260
aaaatgaaag ttagtgattt ttcattaaaa tattacttat tcatttgtaa aaatatcatc  4320
ttaaattttt atcaaaaagt gtttggtttc agaaaaatat taatattcac tctaattggt  4380
tatatatata aaaaatacaa tatatattat tcatgtggac aatatggatc aaatatagaa  4440
```

```
caacttaatg taatatatca ctttgatttg tttatcaaaa tacaatacta tatcgacaag  4500
acaacacata tataatctaa ccaatatttt aaaaaaataag aaatattgat gtagcaattt  4560
gaataacaac cgcacggacg tgcgggtccg tacgggtaaa aatctagtat atatttatat  4620
gagataaatg acggttatgt gtatacatat taatgtattt gtaaattact atcagagaaa  4680
tcagggtcag atttgaagaa tggagacact agttgtgagt catatacgag atggaaggtg  4740
aattcttcag tacatatata gattactcaa atgactgaac tatgtataaa aactacgtgt  4800
ggactgaatt gcgtttaaaa taaactgcag aaagatgtag aaattatggg agaactcaat  4860
gctacgggct acagattctc cttagcgtgg tcaagaatca ttccaagtat gaacaaatta  4920
ttcattcgtt tgtattttag ttaggatcat gtagctggaa gagtactaat tgatatacaa  4980
tatacatgag cagaaggaaa ggtgagtagg ggagtgaacc aaggaggtct tgattactac  5040
cacagcctca tagatgcact cctcgaaaag aatataacgc ctttcgttac cctctatcac  5100
tgggaccttc ctcaaacact ccaagatgag tatgaaggtt ttttggaccg ccagatcatg  5160
tatgtgtcat gcttcttaat catatacaaa ttattaataa aaacaagcag aagaatattt  5220
tgtcttaatt acatgcttta ctgaaagaat gattatatat taatatgcac agacaagatt  5280
tcaaagacta tgcggatcta tgtttcaaag aatttggtgg aaaggtgaag cactggatca  5340
cgatcaacca gctattcaca gtgcctacga gaggctatgc actcggaaca gatgcacccg  5400
gtcggtgttc tcctatggtt gattccaagc acaggtgtta tggcggaaac tcttcaacag  5460
aaccctatat cgttgcacat aacgagcttc ttgctcatgc tgcggtagtg gatctttaca  5520
ggaagaacta tgcggtgagt agtcttcata tgtgaaaagg tggtgaaaat ctaacatatt  5580
tgatcctaat ttactcatat atgatgtgac taacaggacc aaaaagggaa gattggacct  5640
gtgatgatta caagatggtt tcttccatat gatgaggctg atccttcttg tagagaagca  5700
gctgacagga tgaaccaatt cttccatgga tggtatatct tttttttgac atcaaacggt  5760
tattctatta ctcaaaatta aagatggtct aggtaattag attgattata ttgtatgtac  5820
atataatgaa acaaaatata aatggatcag gtacatggag ccgctaacaa agggtaaata  5880
cccagacatc atgaggaaga ttgtgggaag tcggcttccc aacttcaccg aagctgaagc  5940
caaacttgtt gctggttcat atgattttct tggtctcaac tattacgtca ctcagtacgc  6000
ccagccaaaa gctaacccat tgctctcaga gaaacacact gccatgatgg acgctggcgt  6060
aggactcaca tgtacgcatc actcgatctg ctttgttaca acttacaacc tcctttatat  6120
atgtatatat aagatgttca atatatatat atatatatat atatatatat atatatatat  6180
attccttttt gttacaacat acttatttgt gattgaccat cagttatttc ttccttgtgt  6240
ttacagatga taactcacgt ggtgaattta ttggtccact ggtatatatg catgatccac  6300
ccttatgatt tttctttcat tattttatct tcttttccta actgtagtgt acttggaaca  6360
cccacaataa cttcttattt tcttttgatt gatatgtata ttttgtttgc ttccctttct  6420
cagttcattg aagacaaaat agccggcaac agctattatt acccaaaagg aatttactac  6480
gtcatggaat acttcaaaac ccaatacaac gacccttttaa tctatgtcac cgagaatggt  6540
aagttctaca tattactagt aatctatttt tatttatgct acatatcatc agataattag  6600
tgtactttga tactgagtcc aaagaaactg actttcaaat actgtggaat atttttatgt  6660
gatggcgatt caattaggat ttagtacgcc cagctcagaa aaccgttgcg aagctattgc  6720
cgattacaag cgaattgatt atctctgcag tcatctatgt tttctccgta aggtcatcaa  6780
gtaagtccta ctatacatgc ttttcttcca atatttatct tctttttaag taatatatat  6840
atatgtatat gattgttatt gtttccaggg ataggggtgt caacgtgaga ggatactttg  6900
catgggctct tggggataat tatgaattct gtaaaggctt taccgtcaga tttggactca  6960
gttacgttaa ttgggatgat ctcgacgaca gaaacctcaa agaatctggc aaatggtacc  7020
agagattcat taacgggact tccaagaacc ctacgaaaca agatttcctc cgttcaagcc  7080
tctcctctct caaagccaga agaagaggct tgcttgctga tgcatgaaac acttttcccc  7140
cttcaagatc atctccacgt ctctgatcac tctttctagt tgctccatag ataaggagct  7200
tctaatgtac taaataaaca gatgatcaac tactaatgaa taaaataaat ttatctacaa  7260
gtacattatg tcaagtcaag gaggtgagga taacgcattt taaacagtaa acgtcactca  7320
cacgcacata caaaataaaa actcaaaccg ccaactagtt tagtgtatta aaaatattaa  7380
ggaaatgatt agcctaaatt cagtaattat ctaatacaaa tctaaaacta actaaacgaa  7440
agtacaacaa taatttaaca atccatcaag ggtcggtcgt attaaattcg gaacaacaat  7500
ccaacacatc tctagaaata aaaaccaatg ctagatatct aatcaaaaca cagcacaaag  7560
ggtttctctc gctccactca tcattactct ttgaattgcc gttctctacg gcacatgggg  7620
caatgagctt gactcgtctg tgagttgatc atttcaatat acaacggaga cggaacgaat  7680
ggttgcaagc cttccaaact gctcggtaac catatacgat acaggtttaa gaatacaaat  7740
aaggggtttt agttttgaaa cagacaaaaa aaagtttcgc atgattttca taaaaccatc  7800
agagtgtgta gagagacatg aaaaaagagg ggagaaacgt aaccatttta ggaatttgtg  7860
ggactaggtg aaaagtgctc tgttcatgct tttgtatgat gaggactgtg attctgtggg  7920
tccaaacact attgaaatgc cctgtagcat ttatacaaac tttgaaacag agcacaaagg  7980
gtctcttaat tcatgtttta ttcttcaaaa tttgaacaat ttatcttaat tcatcttttt  8040
tttttgctaa ataatctata catataagcc aaatttttgg ttgtatatat aaagggtatt  8100
taaggtttca tttcaaacta gatcctttgt caaaaagttg gtatatgcag gttgtcattc  8160
tagacaaaat cattcatatc taaacaattt taatgatgtc tgcttatttt aatatttgaa  8220
aactttttat ttttctgttt ttaaaagaaa aaacgaaaaa gaaaactttt taataatacc  8280
cattaagact tttgtttgat cgtgaattat ttttatcata aatatttgta cgtcaatgta  8340
ttttctaggt tccaatctta acaaaatgta taaatctatt tttttagaat ctgtattatt  8400
aaaacatatg tacgaattca aaactaactt tgttcttatg tattacaaaa tatatccatt  8460
ttaattatca tatatattat tttgtaaaaa taataaaaat tacatgttaa cgttagtcaa  8520
aaatcaaaat tctatcagtt gtgactatat atatcccact atcttattta atttcgtatg  8580
attataattg tatattttca gataattata gaaagtatta tatgcatagg gaaaaaatta  8640
aggaagtccc cattaaaaat tatattcgcc ttaaacttaa ttggaaaaaa ttatataaat  8700
tttcaaattt aatatatgcc accatttatg ataatttgta atcaaaaagt atttttgaaa  8760
aaatttaagg attgcaagaa atttaatatg gaattccttt ttgaatgtat tttataattt  8820
tcaagattgc tcataaattt ttatatacga catttttgata ttacaatata aaataattta  8880
tattgtttat cctaaaataa atgtcatgta tcccataaaa tacaaaaaat attcatcaaa  8940
ataaatctca tgtactaaag ttttatagaa gaacaaaatt atgaatcatt catatttttc  9000
agtccctaaa aaatatcatg tataatttag agtcgtaaag aaatttaata ttataaaaat  9060
atgaatcata tatatagtca aaactctatc aattgatatc ttattatcct attaatttcg  9120
tataaca                                                            9127
```

```
SEQ ID NO: 55          moltype = DNA  length = 9836
FEATURE                Location/Qualifiers
source                 1..9836
                       mol_type = genomic DNA
                       organism = Brassica juncea
SEQUENCE: 55
ttacatgaat ataatatcct ctcttacaaa ggaatcaaaa tatttctata ctaacaagtc  60
attgtttacg gtttttatta tagttatgag gaagatagtt accatttgct tccaacagcg  120
gaaacattat ttcaagacag gacattagaa catatagctt ctccattaga acatatagct  180
tccaacagcg gaaacattaa tggagtaatg aataaaagat aaaagcatta tatattaatc  240
cattttccac tccatttact ctataaatgg agtaaaatat ggagtggaga tgaaaatgcc  300
cttactatcc atccatgctt ctttatgttt caaatacatg gacgtctgac aatccaaagg  360
ttagcgaacg acttctttaa tatttgcatt taagaattgt tttggaacag tttcaatcat  420
acttaatata ggacgtacga attacacatt atgctgaata tataaatagt tgaaggaaaa  480
aaatcatctc tttcagacac acccgaaagt aatgcaagtg gcttagacat gaaagcttga  540
acctcttcca taagtggatt aagtgacaca tcggagacgt tgtatgcagt ggagatgctc  600
tgattgtcta gtgaacaatc gataactgac taccatcgag gacaccacga taactgactg  660
gctggaaacc cgtcaaatct tgcaagcgtt gtttaacaat cgctacttac agctaccagt  720
caccagtcag atgtcttcca ccaccagcac cgatgctgcc gatctttctg gtcagaacat  780
caccataaag cgttggccaa caaggttggt tttggactaa atgttttgtg tttgcatttc  840
tgaatttcat attgtaatat gtttgaaggt tgtaccttta aatctgatat cttattgtgt  900
atactattgt gtttaaattg gtaataatgt atcgtatacc ctatgtgttt gaatgtttat  960
cgtttccaaa aaaaagttgt ttttctatca tatcataaag attattgttt ccttcaggcc  1020
gtggaggaag aatgcaacgt tgcctaagat atgaaatata gagttatgcg gcatgtaatt  1080
gcgcatggat gtaggatgct tacttcagat acaaaattat cttccccaag acacaagtca  1140
tgcaataaaa agtcgctcag attatcaaga taactgaatg atatccattg atatattcaa  1200
taattcctaa atgttttctc tcactatgca gaaagatatt tacattacaa atgacagctc  1260
atgcacaaac atgtctgcac tgttcctgaa ccaatcttct caaggataga atgatagacc  1320
attttatgaa tttgtgggac taggtgaaaa gtgctctgtt catgcttttg tatgatcggg  1380
tctgtgaatc tgtgggtcca aacactattg aaatgccatg tatcttttat acaaactttg  1440
aaacacttct ctaacgtaat agaccatgtt aaactcacca cacgcagcgt aaataacaaa  1500
acctatttta acttactttt tacattttct tcattcactt tttaactaat tttaactact  1560
tcatttatga gttgattaca tagaaggaca cattttatct ttgtcttacg ctgagaaaca  1620
cttcccactt gtaggacact ttctggtggg atcaaggggt tggtttgtca aaattgccct  1680
tgtagaaaaa ggtggtgttt cgttggagat aacaaaccag tttccttttt tcttttttgt  1740
gtcactgtct tcaattaaat aacttttgtt gcatttatat ttttaggttt atagaaaaaa  1800
tggattcttg tttacaccgt tgtattaaaa aaattgctat taaatcgaat ggatgaggtt  1860
ttccaccgtt tgattaaaat ggttgctata aaatcgaatg gctgagattg aatcttggag  1920
agtaggttag tttgaccata aaaaatttcc cttgtggatg gctgagttgt ggtcggctga  1980
gtgatttatg cccaaatgat atgttgtgga cgggtgatgt ttggatgggt gaagaagcag  2040
agaagaagca gcagtggggt tttggccatt catgtggtcc acattaccgt tcctcactca  2100
ccatcaccac cagcaaaagc attgacattt tgtgggtaat gtacataaga aagtggatga  2160
attttgtaga taagagaaat ataaacaata gaactgcgta taaattcaaa ttagagatat  2220
acatcagtgt tttatcttgg tttttgtgga cataatctcc gaagcaaaat gttgtggaaa  2280
acatctaatt aacaaaaagt gtggatgtgg acaagtgaga acattctttt ttaccattct  2340
ttttcacaat tctttttttgt tttgtttcta atatctaaaa acatagataa tatataaaac  2400
atgcatatat atatttttct ttttgctatt ttataaaaaa atatcttatt agatatttta  2460
tggatataaa tagtatttat atgaattttc ttcataaaag aattgttgtt aggggtgaaa  2520
gcgtataatt aaaagtatgg gacaaaatca agagaatcta taagtaaatt aatgaatgtt  2580
ggggtcaaat tgcgtatatc caaaacttaa aggaccagat ttgtaatata gaggaacttg  2640
accattgttg tttcacgagg tttctctgca acggaaccga tgacgaaggc tcctaccagc  2700
tgcaacggcg gattcagagc atgaagatct tggtttgaga accattttgt ctttcaattt  2760
ctggaataca accactgaat cagaagaaca cagaaataat ttttcagaaa atcaaaacag  2820
ggaaatagaa ttgaatcgga gaaaaggcaa taaccagtga cctcgaggat ctggccatgg  2880
atacccaaca tttttctggg aaatcggagt gtgcaaatcc cattggagga aaagagaagg  2940
agaaagagga aaaacattcc aaaattatat aaactcttcg tgaaattgga tgaatgatgt  3000
tgtttgcagt gaatcattgt ttggttggtc gggactatgt gctcaccgac attttagagg  3060
agagagagat tcagaagact gaaatgataa ctaagcttct ctcttatttt tttttcatta  3120
cacaaaaaaa acaaatgttt agagttaaag ggtagtagag actttacaca acctaaaagt  3180
gtgccacatg ttgtaagtgc cttaaagtgt aattcaaatc acaaaatgtg tctctgaacg  3240
taaaaaaaat cttcatttat ttatttttcc aaataattcg acatcattta ttatagaagt  3300
acaaaataaa acttatctat ttttttagta tttttgtaac attttttaca tttctttttt  3360
cactattcct aactaattca ttgattgtat ttacaataat aattcgacat catttatctt  3420
acgtgttaac cataatactt tcgcatgttt gaatgaaatt gctccatttt gtaacaaata  3480
atttttttggt tatctataga atcagttaga catagtgttt aggtacccat tcgggtacgg  3540
atcaattctt ttaggtatcg aatatttggg ttctaaaatt aaattatgtt cggttataat  3600
aattttatgg acgtgttcga gttggattct tccgaatccg taaaaattcg taagaaccta  3660
aaaatatcta aataatctat atatttagaa atgtcattaa acatccgcaa gaacgcgcgg  3720
gtcagtctct agtttttata aacccagaaa catataaacc tgtgtttgtc tatttgaatt  3780
ctacatggaa gttttgtacg ttttaaatat gacgactgct tgttgttcag tcaagatgat  3840
tgttatccgt aactcgtagc ttaatatcta tagtgctttt ttttcatggc agtttgtaga  3900
aagagcatgt taacctaaga aaaaaaccag tataatttcg taacataaat gttacttaaa  3960
ctcaaagtat tatttatggc ccatcctaat aaatcgaagg cctaaagcac ataaatttaa  4020
atgttttatt cttaaaaaca tgatcattta ttttagttca tgtttaaagg cgtagctttc  4080
tactgtttca agcattttaa aagttttttt tttttttttga aaaaagaata gaagaatctt  4140
ttgtcaaaaa agttgtatct aattatgaaa aatataacta aaatgtatga attctaacat  4200
aaaatgtaga attaaaacta ttgaataaac tatataggtt aatacacaag gttccttttc  4260
tttgccaaat atgtgaacta ccattaaaat gggaaagaaa atacaaaatg ttcttacatt  4320
```

-continued

```
tcaacccttc caatcatcta aaaacgatac caaaaaacgt ggttttcgtt ttctcttgtc  4380
tttcagagac tctggtctca tgtgataaaa gcaaatagag aggtcaaaag aatcaaaacc  4440
aataagatat gcatgcgggg gttttttttt tttggatatg ttgtgattgt tagcggtgag  4500
actcgtgaag agtgtgtcat tgggtcagtg ttactctagt ttcaagagtc gataatattt  4560
cgataaaaat cttaataact ttatggcgta atgaccaagc tttgaacatt atttactaca  4620
gtgaatctta agatgcgtgt cattctttta accgtcgata tatacatgct acattgcacc  4680
actgtcgacg gatcaatatg aagatgtgac gcatctcgtg ttcaagtcgt acgtgttccg  4740
gtaaaggaac acaaatatgt gctacataac cagaaaatta tatgcaatag ataacgaaag  4800
actgaaaagg tggaaaaaag caagatattt tgagcaaaat ctgtaaacat taagctaaag  4860
taagtgaacc cacaggactc atcccaccta aacctctccc aaagtatcag gacaagaaaa  4920
tacatacgtc actattcttt ttgaagggct atatataaac cttagaaggg cacaaggttc  4980
cgtacaacac aacacatata tcaacagatt aaccatgaag cttctttatg gactcgcttt  5040
agtttttcta ttagctgctg cgagttgcaa agctgatgaa gaaattactt gcgaagagaa  5100
cgaaccattc acatgtagta acactgacat tttaagcagt aagaacttcg gagaagactt  5160
catcttcggt gttgcatctt ctgcgtacca ggcatgcaac aaatgctgcc ataccatatt  5220
tttgacgtat agaaaataat attcaaaaat gctaacatcc aactttgcat ggttgtttct  5280
tttcatttca gatcgaagga gggagaggtc gtggtgttaa cgtttgggat ggcttcagtc  5340
accgataccc aggtatatat atatgagatg aatgtcggtt atatgtacac atactaatgt  5400
atttgtaatt actatcagag aaatcagggt cagatttgaa gaatggagac actagttgtg  5460
agtcatatac gagatggcag gttaattctt cagtacatat atagattact caaatgactg  5520
aactatgtat aaaaactacg tgtggactga attgcgttta aaatatgtaa actgcagaaa  5580
gatgtagaca ttataggcga actcaatgct actggctaca gattctcctt tgcgtggtca  5640
agaatcattc caagtatgta cataaatttg tatatttttt attgggatca tttagttgga  5700
agagtataca aattaatgta tgatatatat gagcagaagg aaaggtgagt aggggagtga  5760
accaaggagg tcttaattac taccacagtc ttatagataa actcctagaa aagaatataa  5820
cgcctttcgt tactctcttt cactgggacc ttcctcaaac actccaagat gagtatgaag  5880
gtttcttgga ccgccagatc atgtatgtga catgtttctt aattatatac aatttttaat  5940
aaaaacaaga ataagaagaa gattttgtct taattacatg ctttactgaa agaatgatca  6000
tatattataa tatgcacaga caagatttca aagactatgc ggatctatgt tttaaagaat  6060
ttggtggaaa ggtgaagcac tggatcacga tcaaccagct atacacagtg cctacgagag  6120
gctatgcact tggaacagac gcaccgggtc gatgttctcc tatggttgat tccaagcaca  6180
ggtgttacgg cggaaactct tcaacagaac cttatattgt tgcacataac cagcttcttg  6240
ctcatgccac ggtagttgat ctttacagga agaactattc ggtaagtagt cttcatatgt  6300
gaaaaggtgg tgtaaatata acatatttga ttctaattta ctcatatatc atgtgaccaa  6360
cagtcccaaa atgggaagat tggacctgtg atgataacaa gatggtttct tccatatgat  6420
gagtttgatc ctgcttgcgt agaagcagct gagaggatga aacacttctt tcatggatgg  6480
tatattgttt ttgtttgaca tcaaacaagt attctattaa aaacctagag gtggtctaga  6540
taactagaat gattatactc tatgtatgta taaagaaaca aaatataaat ggatcaggtt  6600
tatggagccg ctaacaaagg gtagataccc agacatcatg agacagattg tgggtagtag  6660
gcttcccagc ttcaccgaag ctgaagccaa actcgttgct ggttcatatg attttcttgg  6720
tctcaactat tatgttactc agtatgcgca gccaaaagct aacccattgc tttcagagaa  6780
acacactgcc ttgatggacg ctggcgtagg cctcacatgt acgcattact ctgtttccac  6840
tttgttacaa cctcctttct atatatgtat atatattcct ttttgttata acatacttat  6900
ttgtgagtaa ccatccgtta attcttcctt gtgtttacag ataataacta tctgggtgaa  6960
aatattggtc cactggtata tatcatgatc cacccatgat ttctcctttc attatttgta  7020
gtgtacttaa cacccacaaa aaaaaaaaac tattttctga ttgatatgta tattttgttt  7080
gctccctctc tcagttcatt gaagacaaag ttaacggcaa cagctattac tacccaaaag  7140
gaatttatga cgtaatggac ttcttcaaaa ccaattacag caacccttta atctatatca  7200
ccgagaacgg tgagttctac ataaattact actcatctct tttcatctat tctatacata  7260
tcatcagata actagtgtat tttgatatta gttcaagaaa ctgattttca aattttgtcg  7320
aatatttcca tgttatggcg gtttaattag gatttagtac gcctggttca gaaggccgtt  7380
gcgaagctac ttctgattac aaacgaattg attttctctg cagtcatcta tgtttctcc  7440
gtaaggtcat caggtaagtg gatgctacta tacatacttt cttccaatat ttatcttctt  7500
tttcttcttc tttttaagta atatatatat atatatatat atatatatat ttatatatat  7560
atgattgtta ttgttttctg cagggagaag ggtgtaaacg tgagaggata ctttgcatgg  7620
gctcttgggg ataattatga attctgtaaa gggtttaccg taagatttgg actcagttac  7680
gttaattggg atgatctcga cgatagaaac ctcaaagaat ctggaaaatg gtaccagaga  7740
ttcattaacg ggactgccaa gaagaatcct gtgaaacaag atttcctccg ctcaagcctc  7800
tcctctcaga gtcagaagaa gaggcttgct tgctgatgca taaaacactt ttccgctcgt  7860
caagatcatc tttttgtctc tcacacttcc tagttgctcc atagataagg agcttcttct  7920
acctacagtg tactaaataa aaggcctcaa taaaaagatg atcaactacg tactaaaatc  7980
tttttcagaa aaaaaaaaac tacgtactaa tgaattaaaa taaaatatct ataagtgcaa  8040
tatgtcaagt caaagagata tctataagtg caatatgtca aggcgacgca ttttaaacag  8100
aaaacaacta gttttgtgtg ataaaaatat tgaggaaatg attagcctaa attcactaat  8160
tattttaata caaactcaaa actaaactag accaaagtcc tataatccta aaataaaatt  8220
taatggtatt ttggatgtga tatattttta atcattcata taatttaatt ttattttggt  8280
tcttatataa tcaataaaac caaaagaagg tacagtagtc ctttgtgtgt ttattaatgt  8340
ttctccgttg tagttttgtc tcatagcaca tcacatgttt aaatggtcta gtaaatgttt  8400
tcgtttaggt tattaaacac taggtaagga atccgtgcga tatcgcacgg gaattcattt  8460
tgtaaaaata atataccata ttttatataa ttttttagtt agataaataa atgtgttgca  8520
aaaataatat accatagtta gataaatgtg ttacaaactt attgacttag attccctaga  8580
cactaaacca ttttgtaggt cgaggtccac gatgatccct ccattgtact gtggcttatt  8640
agggtttcct agacactaca acaggacatg caatggtttt tttttttttt gaacaaagga  8700
cattcaatgg taatcaatgt gagtttggtg ttgtggtggt tccacttacc aattgggaag  8760
ttctctccta taatcacaaa ccagcaaact caagagcatg aaatatttat agtttttaga  8820
aaatttatat gaagggtcat gttttttgtt aactgctgat gtcaactttt tttataggca  8880
aaaaatattt gtatccaaca atcacgcttg ctttaattat gtaatccaac ggacaatatt  8940
ttgttgcctt taaaaaataa cgtcaacgtt tattaaagca aacgtcatct tttgtcttcc  9000
cccgaaccaa cacctttttc agatgaaaaa tggcacctcc ttaaaagatt tatacaggtc  9060
```

```
atcctctcat aatcgtcttc ctttcaattg gtctctaata tcaacttagt tttcgtcaat  9120
caaatttgtt gtcttgctct atttgtggcg gtgacttcaa ccggcaggga gaagaggaaa  9180
tattttaaca tgtggcgaca catgaccaca tggagaaagg agaagatagg ttcacttatt  9240
aagcttctta gaagaacatg taccttgaca atctatgata aagagatgaa cagaaaaata  9300
atgcacagat gaacgaagag gttaaataga aagcagaaat tagaaatcag caaaagaaaa  9360
agaattttga aagaagagaa actatacact ggttatcaaa aatataaacg aaggaagaga  9420
tgcaaaccaa gagtcataac tctatcaatg gacacaatga ttcattaccg acataataag  9480
tcttcggatg cgtcgtcttt tgttttttgt caaaacaaaa ggtgtgctaa tctcaaccgt  9540
tacctgtttt aaaaagaaaa ttactatata tattatgaaa aggaacaagg acttcatttt  9600
ttattacggt tatgtgtaat agaaactcaa acatgaaaca tgtgtcatgt tcatgaaaaa  9660
gacaaatcaa agatacacga tttgtaatta tgagaaacaa accttttcat ctagtaaaaa  9720
aataagacta cttatttcat tatttcgttt tggattttg gttattcaaa cacgtataac  9780
tcttcctact attttttgtt gacaacactt catttaaata tcttttaaaa atttgt      9836

SEQ ID NO: 56          moltype = DNA  length = 6812
FEATURE                Location/Qualifiers
source                 1..6812
                       mol_type = genomic DNA
                       organism = Brassica juncea
SEQUENCE: 56
tccaacaaag atggaaacct agatttctaa tcaaggcgca acacaaggac gtctctctcc  60
actcatcatt actctttgaa ttgccattct ctacggcaca tggggcaatg agcttgactc  120
gtctgtgaat tgacccattt caaaatacaa tggagatgaa acgaatggtt gcaagctccc  180
caaactgctc gataaccata taacgatcca ggtttaagaa tacaaataag atataacgat  240
ccaggtttaa gaatacaaat aaggggtttt agttttgaaa caatcacagt gtgtagaaag  300
agacatgaaa agagaggaga cacgtactta gagggcaatc atctccaggg agtttgcagt  360
ctggacaaca accgtcgaat ggcatacgac atatcccaca tgtctcatcc tgagcatccc  420
atgtccatga cgcaaccgca tgccacctta cagtttattt tttcacaatg taagagttca  480
cgtattggaa ttgagaatgt atgtaacaca tgtagtggga caaagaaact tactctgttt  540
ttttttttaa aaagtcagta gacattgtag cactgagagt caaggaagaa acagttcttt  600
ggaaacaaaa tcctaaatta aagaaccttt gagataatct tcgcctacct tatatgaact  660
agttgggagc tgataaccaa aatcttcacc gaaaaaaaac tattagaacg tcatctacat  720
cagtattcaa aactgaaatt catgaaaaga gaacaacttt atgaaatcat gaaacctaag  780
ctgcatcttt taaaaaaatc atgttttaaa catcaaagaa actatgtact ggaaaacatc  840
aagcattgac gtgaacattt ggatgcatga ttgacatgca gagaagatga agtagaagga  900
tacgcaagat cttgactttc atgtcttcct cctaaatgaa acataaaaat aatcttatat  960
cagttaaaca aactaaaaaa aaatagaaaa cacaaactca agaaagcaca atcctttttt  1020
actatactat aaatctaata ctactaaggc ttcatcgtct gaaaacttag acgagataaa  1080
ttcatgtttt tgacgcattc gtacactagc atgcagcaga tggcgtttcc ttagctgata  1140
gagtgatatc aacagaacgg agcaaaccca tcagaaaatt caaaaactca ccggagtttg  1200
acggagaagc gaactgcgac agagaagaag cggcgagatg tgaatagaag acacgaatta  1260
gttaagatat gggcttttat ttaaactggg ctttatttaa aattgatctc agggcccata  1320
cgtgtgctct tcttaacaag attatatatt atttataaac gacaccaata aaacgtggtt  1380
tgttttcgtt ttcttttgtc tttccgagcc tctagtttca tgtgataaaa gcaaatagag  1440
aggtcaaaag aatcaacacc aatacgatat gctgtgattt tttttttaa atatgttgta  1500
attgttagcg gtgaggctcg tgaagagtgt ggcattggtt cagctttact ttagtttcaa  1560
cactcgataa tatttcgata aaaatcttca ataactttat ggcgctatga ccaagctttg  1620
aacattattt actacagtga atcttaatga tgcgtatcat tcttgttaac cttcgatata  1680
tatatgctgc attgcaccac cgtcgacgga acaatttgaa gatgtgacgc aactcgtgtt  1740
caagtcgtac gtgttcccgt aaaggaacat aaatatttgc aatagatcat gaaagactaa  1800
acgtggaaac aagcaagaaa tttggagtaa actcggtgaa tattgagcta aagtaaccca  1860
cgggactcat cccacctaaa cctctcccaa agtatcagga caagaaatac ttacgtcact  1920
attctttagc aatggctata tataccctag atcggtacaa ggtttcatac aacaccaaca  1980
catacaacaa cagattaacc atgaagcttc ttcatggact cgctttagtt tttctattag  2040
ctgctgcgag ttgcaaagct gatgaagaaa ttacttgcga agagaacaat ccattcacat  2100
gtagtaacac tgatatttta agcagtaaaa acttcggaaa agacttcatc ttcggtgttg  2160
catcgtctgc gtaccaggca tgcaacaaat gctgccatac tatatttttg acgtatacaa  2220
aataatattc aaaaatgcta aaatatccaa ctttgcatgg ttgtttcttt tcatttcaga  2280
tcgaaggagg gagaggtcgt ggtgttaacg tttgggatgg cttcagtcac cgatacccag  2340
gtatgtcact gtggcatata catatatata tatatttaaa tgagataaat gacggttata  2400
tgtatacata ttaatgtatt tgtaaattac tatcagagaa atcagggtca gatttgaaga  2460
atggagacac tacttgtgag tcatatacta gatggaaggt gaattcctca gtacatatat  2520
actcatatga ctaaactacg tataaaaagt aactgtggac tgaattgcgt ttaaaatatg  2580
taaactgcag aaagatgtag aaattatggg agaactcaat gctacaggct acagattctc  2640
cttagcgtgg tcaagaatca ttccaagtat gaacaaatta ttcattcgtt tgtattttag  2700
ttaggatcat gtagctggaa gagtactaat tgatatacaa tatacatgag cagaaggaaa  2760
ggtgagtagg ggagtgaacc aaggaggtct tgattactac cacagcctca tagatgcact  2820
cctcgaaaag aatataacgc ctttcgttac cctctttcac tgggaccttc ctcaaacact  2880
ccaagatgag tatgaaggtt ttttggaccg ccagatcatg tatgtgccat gcttcttaat  2940
catatacaaa tttttaataa gaacaagaag aagaagattt tgtcttaatt acatgcttta  3000
ctgaaagaat gattatatat taatatgcac agacaagatt tcaaagacta tgcggatcta  3060
tgtttcaaag aatttggtgg aaaggtgaag cactggatca cgatcaacca gctattcaca  3120
gtgcctacga gaggctatgc actcggaaca gatgcacccg gtcggtgttc tcctatggtt  3180
gatagcaagc acaggtgtta tggcggaaac tcttcaacag aaccctatat cgttgcacat  3240
aaccagcttc ttgctcatgc cgcggtagtg gatctttaca ggaagaacta tgcggtgagt  3300
agtcttcata tgtgaaaagg tggtgaaaat ctaatgtatt tgatcctaat ttactcatat  3360
atgatgtgac caacaggacc aacaagggaa gattggacct gtgatgatta caagatggtt  3420
tcttccatat gatgaggctg atccttcttg tatagaagca gctgacagga tgaaccaatt  3480
cttccatgga tggtatatct tcttttttg acatcaaacg gttactctat tattcaaaat  3540
```

```
taaagatggt ctaggtaatt agattgatta tatatattgt atgtacatat aatgaaacaa  3600
aatataaatg gatcaggtac atggagccgc taacaaatgg taaataccca gatatcatga  3660
ggaagattgt gggaagtcgg cttcccaact tcaccgaagc tgaagccgaa cttgttgctg  3720
gttcatatga ttttcttggt ctcaactatt acgtcactca gtacgcccag ccgaaagcta  3780
atccattgct ctcagagaaa cacactgcca tgatggacgc tggcgtagga ctcacatgta  3840
cgcattactc tcctttttgt tacaacatac ttatttgtga ttgaccttca gtaatttctt  3900
tcttgtgttt acagatgata actcacgtgg tgaatttctt ggcccactgg tatatatgca  3960
tgatccactc ttatgatttt tctttcatta ttttatcttc ttttcctaac tgcagtgtac  4020
ttggaacacc cacaataact ttttttctg attgatatgt atattttgtt tgcttccctt  4080
tctcagttta ttgaagacaa aaaagccggc aacagctatt attacccaaa aggaatttat  4140
tacgtcatgg aatacttcaa aacccaatac aacaaccctt taatctatgt cactgagaac  4200
ggtaagttct acatattact agtaatctat ttttatttat gctacatatc atcagataat  4260
tagtgtattt tgatactgag tccaaagaaa ctgactttca aatactgtgg aatattttta  4320
tgtgatggcg atttaattag gatttagtac gcccagctca gaaaaccgtt gcgaagctat  4380
tgccgattac aagcgaattg attatctctg cagtcatcta tgttttctcc gtaaggtcat  4440
caagtaagtg ctactataca tgcttttctt ccaatattta tcttcttttt cttcttcttt  4500
ttaagtaata tatatatata tatatatatg tatatgattg ttattgtttc cagggagagg  4560
aatgtgaacg tgagaggata ctttgcatgg gctcttgggg ataattatga attctgtaaa  4620
ggctttaccg tcagatttgg actcagttac gttaattggg ataatcttga cgacagaaac  4680
ctcaaagaat ctggcaaatg gtaccagaga ttcattaaca ggacttccaa gaaccctgcg  4740
aaacaagatt tcctccgctc aagcctctcc tctctcaaag ccagaagaag aggcttgctt  4800
gctgatgcat gaaacacttt tccccccttca agatcatctc cacgtctctg atcactcttt  4860
tttgttgctc catagataag gagcttctac aagtaaaaag atgatcaact actaatgaat  4920
aaaataaatt tatctacaag tacattatgt caagtcaaag aggtgaggat aacgcatttt  4980
aaacagtaaa catcacttag acgcacatac aaaataaaaa ctcaaaccgc caactagttt  5040
agtgtattaa aaatactaag gaaatgatta gcctaaattc agtaattatc taatacaaat  5100
ctaaaactaa ctaaacgaaa gtataacaat aatttaacaa tccatcaagg gtcggtcgta  5160
ttaaattcgg aacaacaatc caacacatct ttagaaatga aaaccaatgc tagatatcta  5220
atcaaagcac agcacaaagg gtttctctct ctccactcat cgttactctt tgaattgccg  5280
ttctctacgg cacatggggc aatgagcttg actcgtctgt gagttgaccc atttcaatat  5340
acaatggagg ttgtcattct agacaaaatc gttatatcta aacaatttta atgatgtctg  5400
cttactttaa tatttgaaaa ctttttattt ttctgtttct aaaagaaaaa cgaaaaaaaa  5460
tattttaata acacccatta agacttttgt ttgatcgtga attatttta tcataaatat  5520
ttgtacgtca atgtatcttc taggttccaa tcttaaccaa atgtataaat ctattttttt  5580
agaatctata atattaaaac atatgtacga attgaaaact aactttgttc ttatgtatta  5640
caaaatatat ccattttaat aatcatatat attattttgt aaaaataatt aaaaactaaa  5700
ttttaacgta aattaaaata ttatatcaaa ccaaaaaccg aactctataa aataaattat  5760
atacgtcaaa aattattaac tatatatatt tagtttaaaa ttatcaaata gtctaaaaat  5820
actatttaaa catcgaacta tccaaaaatc gtattatcct attacttttt acttgaaata  5880
ttttaaatta tcctaatttt agaactgaac catccaatat tttttatctg aaatattaaa  5940
tatctgaatt atcaatattt tgtaaaaata tatttaaaat caattttatc cgaattattc  6000
aaaattatcc aaaagatgag accaaaccta aaccaaattg aactcaaaat tttataagat  6060
tcctaacatt gttatctaaa acaagccaaa aatcaaaatt gccaaaccaa aaccaaaggt  6120
aaacttataa ataaccaaat agtgtttata tctcttggac taaaatacca aaaaaccaat  6180
accacaaatg aaccggaacc caatcaaaac ataaaataat tgaaattcaa caaaaatcaa  6240
acatccatac ctaaacatat tagtaaaaaa cagatgaatt cataaattat caacacaaaa  6300
tatagttcat gtttaaaggc gtaacttttt tgtaacagaa aaaaaaagaa tatctaattt  6360
tgggaaatat aactaaaaat gtattaattc taacataaaa tgtagagcta aactattaaa  6420
taaactatag gttaatacaa aaggtatttt ttaccatata tgtgaatatc tatctatact  6480
attaaacaga aaaatttttg agaccctttg atttttatag tatttacaac agtgctatta  6540
tcttttaaat taaattctat attattataa attattatta aacagaaaaa ttgcagggaa  6600
ttaactgcct acatacccga ttttccttaa ttaattatag ctaccataaa gtggtttctt  6660
taaaaaatag ggattatttg taaattactc tattaatagt ttgaaatttg aaaactacac  6720
ttctatttta ttttttgaaa gccacacttt attcaatgtg aattgacatt tttatccaga  6780
ttagatattt taataattaa aatataaaat cg                                6812
```

```
SEQ ID NO: 57          moltype = DNA  length = 6448
FEATURE                Location/Qualifiers
source                 1..6448
                       mol_type = genomic DNA
                       organism = Brassica juncea
SEQUENCE: 57
ttatataaat tttaccctca gttaagttgt tttaaatgtt ttcaaatgta tttgggtttg  60
ttgtatttta tccaatttta tttaaattct tttgagatct taaatattaa atgaattcga  120
agatacatac ataaaaattt caaacattat ttttgttatt ttgaataaag aaagaacgat  180
taaaactaaa actatactaa atttttaaaa gctagataaa tccttatata tatactgtat  240
ataatttatg tatacatgag tcttttcaaa tttattttac gtattaaata attttattat  300
actaagaatc tgtcatatgt aaagaattga tatttgattt attactaaat atttcaaatg  360
aatgagtgtt tcaagtttaa tttaagtact aaagtattta ttgaaatatt tatgttacga  420
tgaaaaactt tgtatataaa aaattattat ttaataatga tatttgaaag gataatgtat  480
ctatatataa atattttaaa tattattatg ctcgtccatg ctggcaaaac acctactaca  540
atatatttag aggaaaatat ttaacagtta attttttggt ttaacttatt attattaatt  600
ttcttcagtc agtttttcct agagaaaaat ctgacagtat ctttcaattt tttttaaaaa  660
aatctaaaat ataaatctta aaataagaaa attatttctt tttttcatta ccgtattaca  720
ataattgtca atggaatcta tgattttaac tcatataaaa atcgagtcct tctgatcatg  780
attactacat tttcacacta agatttaact atttaatcaa aaccacttca caacagttaa  840
accaatcaaa aaattattat attaatctga accttaaaca atcctcacgc tccaatgcat  900
cgaacgtaac ggtaacacac caaaccaccg ttaaaaagca tatatagaga ggtcaaaaga  960
atcaaaacca ataaaatata ctgtgattgt tttttttttg acatgttgtg attgttagcg  1020
```

```
gtgaggctcg tgaaaagtgt ggccttggat cagtgttact ctagattcag cacttgatag  1080
tattacgata aaaatcttca ataactttat ggcctcatga cgaagctttg aacattattt  1140
actactacgt acagccaatc ttgataattc gtgtcgttct agtttcgcac aaaccttcga  1200
tatatacatg ctgcattgag ccacagtcga cggaacaatt tgaagatgtg atacaattcg  1260
tgttccaagt cgtacatgtt ccggtaacag aacaaaaata tgtgctaaca aaaaaaaaat  1320
attcgcaata gataatgaat gactaaaaag tggaaacaga caagaaattt aaggaaaaac  1380
ggtgaacact gagctaaagt tcgtgaatcc acgagattca tctcacctaa acctctccca  1440
gaatatgaag acactaagac aagaaaattc atacatcact cttctttagg aatgtctata  1500
taaaccctag attggcacta ggtttcatac aacacaacac atacaacatc aacagactaa  1560
acatgaagct tcttcatgga cttgctttag ttttcctatt agctgcttcg agttgcaaag  1620
ctgatgaaga aattacatgt gaagagaaca ctccattcac atgtggtaac actgatattt  1680
taagcagtaa aaactttgga aaagacttca tcttcggtgt tgcatcttct gcttaccagg  1740
catgtaacaa atgttgacat accatactat aaataaatac aattcaaaga gctaatttcc  1800
aactttgcat ggttgtttat tttcctttca gatcgaagga gggagaggtc gtggtgttaa  1860
catttgggat ggcttcagtc accgataccc aggtatgtcg tttttgcacg gtgacgtacg  1920
tgtgtatata tatatatata tataatgtac acatattaaa gcatttgtaa ttactatcag  1980
agaaatcagg gtcagatttg atgaatggag acactacttg tgagtcatat acgagatggc  2040
aggtcagtac attgatactc acatgactga actatgtata aaaaaaccta tacgtgtgat  2100
tgttgacatg ccattaaaat atgtaaactg cagaaagatg tagacattat gggagaactc  2160
aatgctactg gctacagatt ctcctttgcg tggtcaagaa tcattccaag tatgtacata  2220
ttattgattg ttcgtaattg ggatcgttta gttggaaaag tactgattaa tgttttggca  2280
aaaaaaaaag tactgattaa tgtacaatat atatatgtat gcacgagcag aaggaaaagt  2340
gagtagggga gtgaaccaag gaggtcttga ttactaccac caactcatag acgccctcct  2400
agaaaagaat ataacgcctt tcgttaccct cttccactgg gaccttcctc aaacactcca  2460
agatgagtat gaaggtttct tagaccgcca gatcatgtat gtttatattt ttgccatgct  2520
tcttatatta ttaataaaag acgaaaaaga tttggtttta gtaacatgca ttactgaaat  2580
gattatacaa taatatgcac agacaagatt tcaaagatta cgcggatcta tgtttcaatg  2640
aatttggtgg aaaggtaaag cactggatca cgatcaacca gctatataca gtgccgacaa  2700
gaggctatgc gagcggaaca gatgcacccg gtcgatgttc ttatatggtt gataccaagc  2760
acaggtgtta cggcggaaat tcttcaacag aaccctacat cgttgcacat aaccagcttc  2820
ttgctcatgc cgcagttgtc gatctttaca ggaccaaata taaggtgagt ggtgctccat  2880
atgtgaaaat tagggtggtg taaatctaac atatatctga ttctaatgta tagtcatata  2940
tatgtatcac gtgaccaaca gttccaaaac gggaagattg gacctgtgat gataacaaga  3000
tggtttcttc catttgatga gtctgatcct gcttgcgtag aagcagctga gaggatgaac  3060
caatttttcc atggatggta tttatatata tatatatata tatatatata tatatatgtg  3120
tgtgtgtgta ttaccaacaa tgtatcagta tgtattttat gtatttataa tgaaacaaaa  3180
atatacatgg atgatggatc aggtacatgg agccgctaac aaagggtaga tacccagaca  3240
tcatgaggca gatcgtgggt agtaggctcc ccaactttac cgaggaagaa gccgcactcg  3300
ttgctggttc atatgatttt cttggtctca actattacgt cactcagtac gcccagccac  3360
aacctaaccc atatccttca gagacacaca ctgccatgat ggaccctggt gtaaagctca  3420
catgtacgta cttcagtaat attaccactt agtacttatc aaaaaaaaaa aaaattacca  3480
cttagttaca acctttctat atatgttttt ctccttttgt taacatactt tgtgagtgac  3540
tatcaattat ttcatccttg tgtttacaga taataattca cgtggtgaat tacttggtcc  3600
actggtaata tatgaatgat ccacctctac gatttctctt ttttttaatc aatattttct  3660
atttgcaata gaacaccact gattatgttc tcttgattga tatgtatatt ttgtttggtt  3720
ccctttctca gttcgctgaa gacaaggtta acggcaacag ctattactac ccaaaaggaa  3780
tgtattacgt aatggacttc ttcaaaacca attacagcaa ccctttaata tatatcaccg  3840
agaacggtga gttctacata ctacttacta ctcatctatt ctacataaat taactagtgt  3900
attttatata ttagtccagg aaactgactt tcaaatatcg tggaatgttt tcatggttta  3960
attaggaatt agttcgcccg gtacagaaaa ccgttgcgaa gctattgccg attacaagcg  4020
aatcgattat ctctgcagtc atctctgttt tctccgtaag gtcatcaggt aagtagatgc  4080
tactatacgc atgctttttc ttccaatgtt aatcaacttc tttctctttt ttattttggt  4140
aaaatcttct tcttctttgt ctttttggta atatatatat gattattctt gttttcaggg  4200
agaagggtgt caacgtgaga ggttatttcg catgggctct tggagataat tatgaattct  4260
gtaaaggctt taccgtcaga tttggactca gttatgttaa ttgggatgat cttgacgaca  4320
gaaatctcaa agaatctggt aaatggtacc agagattcat taacgggacc gtcaagaacc  4380
atgcgaacca agatttcctc cgctcaagcc tttcttctca gagtcagaag aagaggctcg  4440
cttgctgatg catgaaacac ttttgtcccc cgtcaagatc gtctccacgt tctcttatca  4500
ctcttactag ttgctccata gataaggagc ttcttctacc tataacaatg taataaataa  4560
atattctcaa taaaaagatg atcaaatact aatgaattaa agaataattt atctacaagt  4620
acattatgtc aaggaggtga gggggaggat aacgcatttt aaacagtaaa cgtcgtcaga  4680
cgcacatcaa aaccgatact gtaaccctgt ggttactttc ttaatttcca ctccaataag  4740
tgttatttca ccaattcacc ctattatcat catatgacaa agtgtttaaa ttgtgttaca  4800
aaaaaaaaac aaagtgttta aattatatgg caaaacctta ttatcactca ccatatgaca  4860
aagtgtttaa attgtgttac aaaaaaaaaa aagacaaagt gttttaaaca gtaaacgtca  4920
tcactctaaa aaacaaatat tttcaatacg tattgtatag tttatatgca tattgttcag  4980
aacagtgaaa ccaacatttg attatgcatg atattgtaaa aaaaaagttt tggatcttat  5040
ttatttgata tgggaaaagc ttattctccc gtcaaatagc aaaatcttat tatcatcata  5100
tgacaaaatg ttcaaattat atggcaaagg cttttacata gtctgatatt tacggatggg  5160
ttataggtat tacaaaactc tattggacct aattaagagc accctcatcc gggggtgtgg  5220
gggggggggg gggggggggg gtattaattt gaagttgtta aaaataaaaa attaatattt  5280
taatgtgttg tgtttgtgta tttaatttta attgtttcag ataaatatca actaattaaa  5340
gataaacatg tgtcatcaag tttttaaacc tgttcggaaa atgtgggtgc agagaaactc  5400
tgccattcct ctttcctact tttatatata tactagggct tggcccgccc tacgggcggg  5460
tgaaaatacc actttttact ttgttataga acacaaaatt ataaaactaa aaatttattg  5520
aaaatgcaat aatttatatt atgatcgaga tcagatagaa agcgaatccg taagattcaa  5580
atacccaatt ggatgcagaa tcagacttta tgcatgttac tactatatta agtgtaatgc  5640
gatatttaaa attaaacaaa attatcatga aaatgattgt tgcatgcttg tatatttgac  5700
actgaagatt gatctaataa tagtatatta agtacaaagt tacataagaa aattaaagat  5760
```

```
ctaaggggaa gacgaaacat tactacttca gatgcttaaa atcgtggaaa gaagtagtta  5820
tgttaacccc caaaaaaatg ataataatat aaataaagat gaaacatatt ttttccttct  5880
tggtgttgcc ttttctaatg cttttttttg tggatggaga cttagattca ccattaacag  5940
aaccatggtt caaagcccct gaactactta tcatctctcc acttctctct ttaaaagacc  6000
aaatcttcaa gaacactcta gaaacaccca acatcctcct ttcatcagtt ttcctttatt  6060
gctcttttgt ggttgattct ttgtgagtca tcgattctct aatttgcctc tcagtgctct  6120
tgtatcatct gggtcaccac acctatgtcg tctttggtgt ttgatgatct tgaagttggg  6180
gcgatctctg acatattttt ccccgcttga tgatgaacca tagttgttag ttcttacaca  6240
ttcgaagcag atcacttatc caccactcac attggtaact tctcgttttg aacagcatgt  6300
gcgcaagctt ccacccataa cttttcttca gtccattaac ttagttccaa tgggttctga  6360
cttatgatgc tatgaaccca agtataaggc tcgacactct agaaccgaac tccaaaccaa  6420
gaaacacaat cttgtgactc tttggtat                                     6448

SEQ ID NO: 58           moltype = DNA  length = 6769
FEATURE                 Location/Qualifiers
source                  1..6769
                        mol_type = genomic DNA
                        organism = Brassica juncea
SEQUENCE: 58
ttacatataa gtaaatttct taatttctat actttcatcc ataacatcaa atattacgaa  60
tcaaagagag tatctaattg tgttacaaaa aaagagggag tatctaattg tcactattat  120
gttttttttt atttactaat tgctttcaat taaattttaa tattgttttg tttttcattt  180
ttataaatat aatatctata ataaaaatta aacatttaaa ataatttaaa ataaatttca  240
tatgtatata tatttaatat atatctgatt tcataaaaga ggaaaatgcg caaaaaataa  300
tcttgatatc aagaaggaaa aaatcattct tctaaaacat tatcttaagc aacattctgt  360
tatatatttc ttagatgaat ataaaaataa tttaattaac ataaagccag ttatctttag  420
ttgaatgaaa atattttata acagctgtta gtgagatgat gaattttgtt tttgtaaaac  480
atttaaccac ttttttttta ttagaataaa aataaaaata acgattaatt ttaaaatact  540
ttatttatat aacatttttc aaaaacaaag cttaaaacta gtatttattt taaaaatgtt  600
aaaaaatatt ttaaaacaga gattttaagc aagataaatat atattagaaa acaaaactaa  660
aaatatcttc aaacaaaaac atttaactg acacaactct aaatacattt gataaactaa  720
aaatattata cattaccata tcgaaaaatc tttgtttttt cttaatattt cctttggttt  780
caatttaatt attttatata tttttacaat ccaatatata cattataaaa atacctaagc  840
aaatataatt cttctgttta atgttatttt aaaataattt caacatatta ttttagtaac  900
agctaaagta ttgaattccg agaaatagat acaatctaat acacctaaat aatagctaaa  960
acatctagat attatatatc taaaatcaca tgtgtaaaaa ataatataat attattaaaa  1020
ataaattata tataaattat aaaattattt aaaattgaaa gtaaaaacat taattagtta  1080
ttataatata tttagttcat aaataatttt ggtcgtgcaa tatcacgtaa gagtcaccta  1140
gtgcatcatt aaatacaagt aaataattga tttcaaactc aagttggtgg cacgtaaaca  1200
gtaataaagt tatctataga aactaaatat atgtaatatg gctatttata acaaaagtta  1260
cgaattctaa ctttctagag taaaaaaacta tggaacaaac tataggttaa tatacaagta  1320
tcaatcttat ctatctggaa gtcacggatt cgtatccgtt cgaacggttc caatcattta  1380
aaacgatacc aaaaaggcca aaaatgtggt gggttaacgt tttctttagt ctttcggagg  1440
caccggtttc attgtgataa agcagaaaga gagcgatcaa aaccaataag ataagataaa  1500
tattttctca aaaaaaaaaa acaatatatc ttgtgagcgg taaggctcgt gataagtgtg  1560
gctttgcacc agtgtttctc tagattcagc acgataaaac tcgatataca tttttagtaa  1620
cgaatcttga cgttgcgcaa atcttacatg ctgcattgca tcattgcatt actgttgacg  1680
gatcaatttg aagatgtatg attcgtgttt cggttaagga acaccaatat gtgctatcta  1740
acaaaaaaaa agatttgcaa tagataatga ttaatgacta aaaggtggaa acatgacaat  1800
cagaaatatt acaaaagtcg gtgaacactg agctaaagta agtgaaccca cgggactcat  1860
gatcccacct acacctcccc aaaatgtgaa gatgctaaga caagaaaata catatgtcac  1920
ttttcttttg gaaaggctat ataaacccta gatggccaca aggatccaca caacacaaca  1980
catacatcaa cagattaaac atgaagcttc ttcgtcgact cgctttagtt tttctattag  2040
ctgctgcgag ttgcaaggct gatgaagaaa ttacttgcga agagaacaat ccatttactt  2100
gtagtaacac tgatatttta agcagcaaga acttcggaaa agatttcatc tttggtgttg  2160
cgtcttctgc ttaccaggca tgtagcaaat gttgtcacac cctaattttg aaataaaatt  2220
caaagcacca atatccaatt ttgcatagtt gtttcttttc atttcagatt gaaggaggga  2280
gaggtcgtgg tgttaatgtt tgggatggtt tcagtcaccg gtacccaggt atgtcgttcg  2340
cacggtgaca tctaaactaa taatgttggt tacatataca catattaatg tatttgtaat  2400
taatattatc agagaaagct gggtcagatt tgaagaatgg agacactact tgtgagtcat  2460
atacgagatg gcaggttaat ttctgagtac actgattctc atgactgaat tatatatgta  2520
taagaactcc ctaaaaacta tacgtgtgga ttgacatgaa atttaaatta attgtaaact  2580
gcagaaagat gtagacgtga tgggcgaaat caatgctact ggctacagat tctcctttgc  2640
atggtcaaga atcattccaa gtatgtacat attaacgatc aatgtatata tatctttgta  2700
ttttaattgg gataatttag ttggaaaggt actaattaat gtacgatata tatctacccg  2760
agcagaagga aaggtgagta ggggagtgaa ccaaggaggt cttgattatt accaccaact  2820
catagatgca ctcctcgaaa agaatataac gcctttcgta accctctttc actgggacct  2880
tcctcaaaca ctccaagatg agtatgaagg tttcttggac cgccagatca tgtaggtgcc  2940
atgcttctta attatatttg aggagagtaa atattattag taatagaaga agaagattta  3000
gtcttaatta catgtttact gaaatgattc tatactaata tgaacagcca ggatttcaaa  3060
gattacgcgg atctatgttt caaagaattt ggtggaaagg taaagcattg gatcacgatc  3120
aaccagctat acacagttcc tacaagaggc tatgcagtcg gaacagatgc acccggtcga  3180
tgttctccta tggttgatac caaacacagg tgttacggcg gaaattcttc aacagaaccc  3240
tacatcgttg cacataacca gcttcttgct catgccgcgg tcgtcgatct ttacaggacc  3300
aaatataagg tgagtggtga ctccatatgt gaaaattaga gtggtgtaaa tctgatatat  3360
atctgattct aatgtatagt catatatttg gaccaacagt tccaaaacgg gaagattgga  3420
cctgtgatga taacaagatg gtttcttcca tatgatgagt ctgatcctgc ctgcatagaa  3480
gcagctgaga ggatgaacca attcttccat ggatggtata tataatttta tatattatca  3540
aaaatgtatc agtatgtatt ttatgtattt ataatgaaac aaaaatatac atggatcagg  3600
```

```
tacatggagc cgctaacgaa gggtagatac ccagacatca tgaggcaaat tgtgggtagt  3660
aggcttccca actttaccga ggaagaagcc gcactcgttg ccggttcata tgattttctt  3720
ggtctcaact attatgtcac tcagtacgcc cggccacaac ctaacccata tccttcagag  3780
acacacactg ccatgatgga cgctggagta aagctcacat gtactaattt acattaccac  3840
ttagttacaa cctttccgta catatatata tacacatgtt ctatctcctt tttgttacaa  3900
catactctgt gagtggccat caattgtttc atccttgtgt ttacagatga taattcacgt  3960
ggtgaaatac ttggtccact ggtaatatat gaatgatatc cacccctatg atttctcttt  4020
tatttttatt tttctatctg caatagaaca ccactgatta tgttctcttg attgatgtgt  4080
ttgcttccct ttctcagttc gctgaagaca aagttaatgg caacagctat tactacccaa  4140
aaggaattta ttacgtaatg gacttttttca aaaccaatta cagcaaccct ttaatctata  4200
tcaccgagaa cggtgagttc tacattctac ttactactca tctattctac ataaaataat  4260
tagtgtattt ttatatatat aagtccaata aactgacttt caatattgtg gaatgttttc  4320
acggtttaat taggaattag ttcgcccagt acagaaagcc gttgtgaagc tattgccgat  4380
tacaagcgaa ttgattatct ctgcagtcat ctatgttttc tccgtaaggt catcaagtga  4440
gtggatgtta ttataaatga ttttcttcat attttatctt cttcacattt atatatatgt  4500
ttgttcttat tttcagggag aagggtgtca acgtgagagg atactttgca tgggctcttg  4560
gagataacta tgaattctgt aaaggtttta ccgtaagatt tggactcagt tacgttaatt  4620
gggacgatct cgacgataga aacctcaaag aatctggaaa atggtaccag agattcatta  4680
acgggaccgc caagaatcct gcgaaacgag atttcctccg ctcaagcctt tcctcccaga  4740
gtcagaagaa gaggcttgct gatgcatgaa acactttcca ccatcagatc atctttatat  4800
ctctcactct tcctacttgc tccatagtta aggagcttct tttatctaca atgtactaaa  4860
taaatgatct caataaaaag atgatcaatt actaatgaat aaaaataatg atctacaaac  4920
tacattatga cacaagtcaa gaggaagagg aaagagggaa ataacgaaat ttaaatagaa  4980
aacactcaga aatcccaaac tagtttagtg taaaataaac attaacgaac cgattagcct  5040
aaattcacta actagtttaa taagttcaac ttatataata aaatgtatct tcaacataat  5100
agataagaac caaacctaat acaaactcaa aactcaaaag taactaaacg taagttctat  5160
cgtcctcaac tgaaacttaa tgtgtaataa ttcatataat tttatttgat tttgttactt  5220
atataatcaa tatataaaac caaaagagct aagccgcagt cctctgtgtt taatgaatgt  5280
atgccggttt atatattaat ttaaacattg tattctactc ttgaatgatg gagaaaaaac  5340
atcaagaatt aaaggaacag aagtttctga atgaacatgt caacttgttt catggacttc  5400
tttcccaaat tctttaagac ttctgcggat ttcctaaacc aaaaataaag acgtgtttag  5460
ccatttcccc ttttctataa agattcgatg tatcttggat taaaagaact atagtaattt  5520
aatgagtttc ggatttataa ttttggttta attaataaaa tagggttttt ttctttaatt  5580
cggaaaacga gcccagatag agagattgac cgtagagaat ttatgtttga tcttctcaag  5640
ggcactatta tgatccaggt tttgttggag aactgaatct ttttgttggt ggttatgtaa  5700
taagctaact cacaggaccg tcctcgaggc gaatggtgct gtcagttcct cctcatgtcg  5760
ctgtcacagt tgcattttgt cctgttgttg gtgatgtgaa ctctgttgtt gtcagaacag  5820
agggttcggt aagaaaccct actgaatttt atgatcattt gcgtcaatat gattgtatgg  5880
atatgagtgt gaatgagcag gttcctagag gttctaagca tggagaacaa accaaatccc  5940
aagacaaagg gcacgagaca aattatcaca acaaggaaaa agatgacgct taacattgaa  6000
agtggttcct tgtggtgcac ttcaccacat tctcctacgc cgggaggtca catttcgtca  6060
caacggagct aaacatgcgt aatgaaatgc aatgcttgaa acttccagag atcgtttact  6120
tctgccaagc tataaacagt ggccttgaat acggatggcg acgagccaag aagccaccat  6180
tgggccatac attccattta ctcttggaag gtggccaaaa ggtggaggag gagattcacc  6240
gctgcccttt caaatcaatt tggaaatcgt gagatctatg taaaatagtt tttttaaaa   6300
cccccctaaac attatttgtc aagtgatttg tacatatatc atcactacaa tcattctcgc  6360
taaaaaatga tatgacactt aagaaaaaat aatatgattt tcaaaaagag tgacatggta  6420
tcatattaat tgtgatatat aaaattttct tataaaaaat tatattttac aaaggtttta  6480
aatatgataa taaaaaacaa ctcagatatc atcattaatg tcaattttcc atataaatgt  6540
ttatttttgg taaactatta aaaatattaa aaactcataa atcactacga ctaataatat  6600
atatatatat atatcacatt aataaaaaga agctaaataa gattactttt acatcaactt  6660
atatagaata tttgtataaa tataattgta aatatgcatc aaaaaataca aaactaaagt  6720
aacaacaatc gaaaaaattg atagttaaat gtttaaacat ttatttaaa             6769

SEQ ID NO: 59           moltype = DNA  length = 6803
FEATURE                 Location/Qualifiers
source                  1..6803
                        mol_type = genomic DNA
                        organism = Brassica juncea
SEQUENCE: 59
ttccacatca tcctctctct tccacataat ttatttaaca ttcatttcat tttaaacatc  60
tacaacattt ataatggttt gcttaaaaat ttaacactct accccaccac ttaattcata  120
ctttatcttt tacagtataa caagtacgta tattaatgat atctttgatt ataatttatt  180
taaaaattaa aataacataa ttttttaaat tttattttat ttatgtacat accttacatt  240
ttaaaaaata atactaaaat caatattgtt aaaacaatta ggatttattt aacaaaaaat  300
gtttaaaaca ctaaaataat tgattctaat gaaaaaatgg tgtttttttt tcttgtgtcc  360
aaatgaaatg agagtagttt ttatttatag atagtaaaaa atcataaatt ttttgatata  420
attaaaaatt tctattataa aataaatgat tttcagttat tgggtgaaaa taaaacttaa  480
aaatctatcc aacaatttct tccaatccaa atgcgccgtg tggcgaagct ggcccataaa  540
ataaaagttt cagctgttga taccacatag gattgttcta aaacttcaac acccttactg  600
gaagaagttc aacagttgaa tacaagattc aacaccttca ttgtaggtga tctaacaagt  660
gacaaacaaa taacacttgt gtttatctat ttggataata catagaagtg tgcacatgtt  720
tcaaagatga cgtctgtttg ttgttccgtc aacatgattg ttgtccgtaa ctagtagctt  780
ttttttttca tggcagttta cactttgcag aaagaacatg ttaacctaaa caaaaatcca  840
gtataagttc gcaaagtaaa tgttacttaa agataacgaa ggcctaaagc acataaattt  900
aagtgtttta ttcttaaaat acgaacagct tatcttaatt catatttgaa ctatttcatc  960
ttgtttttc ttaaaatata aacagtttat tttaagatat ttttgattga gtctattttt  1020
gaaaagccat ggctaattta aggtttttaa aacaatttct cttagaataa gttataaaat  1080
tatttgaaat tgaaaagaaa acattaatta gttactacta tatatattta gttcataaca  1140
```

-continued

```
gttatactcg tggaagagta caggagaatc acctattgcg atattattaa atacaagtta  1200
acttatgtat atgtgctacg taaataattg atttcaaact caagttggtg gcacgtaaac  1260
agtatgaatt gtaactttat agagtaaaaa actatggaac aaactatagg ttaatacaca  1320
agtatcaatc tatttatctg gaagtcacgg atacgtatcc gttccaacct tttcaatcat  1380
ttaaaaacga taccaaaaaa agcaaaaact gtggttggtt ttcgttttct ttagtctttc  1440
ggaggcaccg gtctcatgtg ataaagcaga aatagagcga tcaaaaccaa tatgatatga  1500
tgtgattttg tgacggtaga gctcgtgata actgataagt gcggctttac accagtgtta  1560
ctctagattc aacacttgat aaaatttcga tataaatttt caataacgaa tcttgacgtt  1620
aagtgtagtt ctagttttgg cgcaaatctt acatgctgca ttgcatcatt gcatgactgt  1680
tgacggatca atttgaagat gtgtcaattc gtgtttcggt taaggaacac aacttgtgct  1740
atctaacaat tttttttgc aatagataat gaaagactaa aaagtggaaa cataacaatc  1800
agaaatatta caaaaatcgg tgaacactga gcaaaagtca gtgaacccac gggacacatg  1860
atcccaccta cacctctccc aaactatcaa gatactaaga caagaaaata catatgtcac  1920
tcttctttcg gaaaggctat ataaacccta gatgagcaca aggttccaca caacacaaca  1980
catacatcaa cagattaaac atgaagcttc ttcatggact cgctttagtt tttctattag  2040
ctgctgcgag ttgcaaagct gatgaagaaa ttacttgcga agagaacaat ccattcactt  2100
gtagtaacac tgatatttta agcagtaaga acttcggaaa agatttcatc ttcggtgttg  2160
catcttctgc ttaccaggca tgtagcaaat gttgtcacac cctaattttg aaataaaatt  2220
taaaacacta aaatgcaact ttgcatggtt gcctcttttc atttcagatc gaaggaggga  2280
gaggtcgtgg tgttaacgtt tgggatggct tcagtcaccg atacccaggt atgtcgtttg  2340
cacggtgaca tctattttat atgtgagagg aatgttggtt acatatacac atattaatgt  2400
atttgtaatt taatatcaga gaaagctggg tcagatttga agaatggaga cactacttgt  2460
gagtcatata cgagatggca ggttaatttc tcagtacatt gatactcatg actgaactat  2520
agtatgtata aaaactatac gtgtggattg acatgagatt aaaattaata tgtaaactgc  2580
agaaagatgt agacgtgatg ggcgaactca atgctactgg ctacagattc tcctttgcgt  2640
ggtcaagaat cattccaagt atgtacatat tatcgatcaa ttatatatat atatatatat  2700
ataaatatat attatttttt ttaattggga tgatttagtt ggaagagtac taattaaagt  2760
acgatgtata tatacatgag cagaaggaaa ggtgagtagg ggagtgaacc aaggaggcct  2820
tgattactac cacaaactca tagatgcact cctcgaaaaa aatataacgc ctttcgttac  2880
cctctttcac tgggatcttc ctcaaacact ccaagatgag tatgaaggtt tcttggaccg  2940
ccagatcatg tatgtgccat ccttcttaat tatatctgaa gagagtaaat ataattagtg  3000
atagaagaag aatatttggt ttaatttaca tgtattactg aaatgattct atactaatat  3060
gcacagccaa gatttcaaag attacgcgga tctatgtttc aaagaatttg gtggaaaggt  3120
aaagcattgg atcacgatca accagctata cacagtgcct acaagaggct atgcgatcgg  3180
aacagatgca cccggtcgat gttctcctat ggttgatacc aagcacaggt gttacggcgg  3240
aaattcttca acagaaccct acatcgttgc acataaccag cttcttgctc atgccacggt  3300
cgtcgatctt tacaggacca aatataaggt gagtggcctc catatgtgaa aaggtggtct  3360
aaatctaaca tatccgattc taatgtatag tcatatatat atcacgtgat gaacagttcc  3420
aaaaagggaa gattggacct gtgatgataa ctagatggtt tcttccatat gatgaatctg  3480
atcctgcctc catagaagca gctgagagga tgaaccaatt cttccatgga tggtatatat  3540
aattttatat attaccaaaa atgtatcagt ttgtatttta tgtattataa tgaaacaaaa  3600
atatacttgg atcaggtata tggagccgtt aacaaagggt agatacccag acatcatgag  3660
gcagattgtg ggtagtcggc ttcccaactt caccgaggaa gaagcggaac tcgttgctgg  3720
ttcatatgat ttcttggtc tcaactatta cgtcactcag tacgcccagc caaaaccgaa  3780
cccatatcct tcagagacac acactgccat gatggacgct ggcgtaaagc tcacatgtac  3840
tacaacatta ccacttagtt acaagctttc tatatacata tatatatgtg ctatctcctt  3900
tttgttacaa catactttct gagtgaccat caattatttc atccttgtgt ttacagatga  3960
taattcacgt ggtgaatttc ttggtccact ggtatatata aatgatcatc cacccctttg  4020
atttctcttt caattttttt ttctatttgc aatataacac cactttctcc ttgttaatat  4080
gtatatatat gtttgcttcc tttctcagtt cgttgaagac aaagtcaacg gcaacagcta  4140
ttactaccca aaagggattt attacgtaat ggactacttc aaaaccaaat acggcgaccc  4200
attaatctat gtcaccgaga atggcgagtt ctacatactt ccactactca tattttcata  4260
tataacatat cgtaattagt gtatttcgaa ataaatccaa gaaactgatt ttcaaatatt  4320
gtatactttt tcatgttatg gcggttaatt aggatttagt acccccagtt cagaaaaccg  4380
tgagcaagct attgccgatt acaagcgaat tgattatctg tgcagtcatc tatgttttct  4440
ccgcaaggtc atcaagtgag tggatgctat tataaatgat tttcttcata tgttattttc  4500
ttcttctttt cgggtaacat ctatatatat atgattgttc ttgttttcag ggagaagggt  4560
gtcaacgtga gaggatactt tgcatgggct cttggagata attatgaatt ctgtaaaggt  4620
tttaccgtca gatttggact cagttatgtt aattgggacg atctcgacga tagaaacctc  4680
aaagaatctg gtaaatggta ccagaggttc attaacggga ccgccaagaa tcctgcgaaa  4740
caagatttcc tccgctcaag tctttcctcc cagagtcaga agaagaggct tgctgatgca  4800
tgaaacactt tccaccatcg gatcatctct atatctctca ctcttcctac ttgctccata  4860
gttaaggagc ttcttctatc tacaatatac taaataaata atctcaataa aaagatgatc  4920
aattactaat gagtaaaaat aatttatcta caactacatt atgccaagtc aagaggatga  4980
ggaaagaggg aaataacaca atttaaatag aaaacactca gaaatcccaa actagttaac  5040
ttatataata aaatgtgtat tcaagaaaca ataaccaaaa ctaatgcaaa ctcaaaagtc  5100
aaaagtaact aaaccaaagg tctatcatcc tcaactgaaa cttaatggga ttttacatat  5160
gaaattttat cactcacata aaatttacgt gagagatgac tattatagct actcttatga  5220
acctaaggaa agtaaatggg aattggagga aatgggagca aggttgtgtt gttgacaatg  5280
tattttacta ttacgatgtc tacaagaaca agttgagagc gcatgatcca aattaaggac  5340
caaagcagag gtgccggagt gtggtgaaag gtgtggaaga attgttgtct aagacgaatg  5400
gttcatgggg tacgtataca gtgcgttggg gtgagaaatt ggttcttttt cttcaggaca  5460
acgagaagat ttggtgtgcg gagattgctt tagaaacctg aatagaaaaa gagatttcgg  5520
gtaaggtgca atggtgtgat gtcgtgaatg atgatggaaa atattcggag ctcgtacaat  5580
gtttatatta gttttattta aactagggta cgttaatatt aaaagttaaa tatatttgaa  5640
tttaagtttt cgtttataat ttcacaatgt ttgggatagt tttctccgtt cctttgattt  5700
gatccattcg cagcagatca gagttttttt tttgtctatt tttatttatt tacaaagacc  5760
gcaaataaat ttattataac cgcatttgta ttagtctaag ttaatcgaaa tccacaaaat  5820
ccataaatca ttaataaatt aaaaaccgat atttcatatc ttttagttaa ttttaatagt  5880
```

```
ataaatttta tattataaaa ataaatacat attaaaatga ttttaaataa tttttattta  5940
gtattttttt atatattatc taattattat aattaaaatt taaataagta ataatattta  6000
attttttatt tataaatctg atggactgaa ttatatcccc aattttaaat ataataaatt  6060
tacatccatt cgtatttaaa tatataatcc acatctatcc cacttcaaaa aataactgac  6120
atgcattcac ccaaggcgga tcaagaaacc catggttttg agtcaaattc ccatcactag  6180
atttttagt  gtatgtacca ttcaagaaca aggagaagaa gtttcaaggg aaattgcact  6240
cattatacaa taaacaaatt ataattagtt atctaaccaa aaaaagttga cagtatattc  6300
aacatatttt ctatcatata tatcaaaata cctttgaaat caaccgtgtg atctctttct  6360
attttttttt ctttctcttc ctcttattct tcctcttctt tcggatctct gtttctcttg  6420
atcatcgaaa acataaatca taggttactc cacttcaatt acctctacct atacaatcgg  6480
ttatcaccgc cgttaacaaa cacgccaccg tcggtgttct tccatttcat aatttccatc  6540
gaataaaaca gcagttacgc aagctcagaa ttgatatcgc ttttgtatta tcttctctgt  6600
tttaaaaaaa aaatgtttta gcacttttaa attttcaagt ctatactatt attcatagtt  6660
atatagtata gtttactatt ttcatatatt aattccatta tattttaagt ttgagttcac  6720
tgattaggaa ctagggttta gtacttaaga tttagtattt gaaaggtgaa gatggaatta  6780
aaaataaagt taaaataaga ttt                                         6803
```

```
SEQ ID NO: 60          moltype = DNA  length = 6492
FEATURE                Location/Qualifiers
source                 1..6492
                       mol_type = genomic DNA
                       organism = Brassica juncea
SEQUENCE: 60
ggtatcatat taattgtgat atataaaatt ttcttataaa aaattatatt ttacaaaggt  60
tttaaatatg ataataaaaa acaactcaga tatcatcatt aatgtcaatt ttccatataa  120
atgtttattt ttggtaaact attaaaaata ttaaaaactc ataaatcact acgactaata  180
atatatatat atatatatca cattaataaa aagaagctaa ataagattac ttttacatca  240
acttatatag aatatttgta taaatataat tgtaaatatg catcaaaaaa tacaaaacta  300
aagtaacaac aatcgaaaaa attgatagtt aaatgtttaa acatttattt aaatttatat  360
gttcatcttc atcatgttga ttaccaaatt gatttctcag tttaacatat tttaactaaa  420
acaaacaatt ttagtaacaa tatatatata tatatatata tatatatata tatatatgta  480
tttaaaataa gtaatcatta aatatagtat aatataatta aatgtaattt tatttttatt  540
aaatttaaat ttaaataaaa tcaaatttaa atagttagac caaaccaaaa gaaataagat  600
tacaaaaatg agtttatgat tttttttaa ctattgaagt gaaaatataa aataataata  660
ttagaaatat aaatcaaaat tttcttttat ataaaaaata ttatatttaa aattattatt  720
aaaaaatatt atacacctag taaatttgga agccaatgcg aatgttcatc cacataagcg  780
gttctgcttc tattagtgtg taaatatatg ttaatatata tatatatata tattatttat  840
gtgtgtgtgc gctacgtaaa taattgcttt caaactcaag ttggtggcac gtaaccagta  900
ataatgttat ctatagaaac ttaacatatg tactatggct atttatagca aaacttatga  960
attctaactt tctagagtaa aaaactatgg aacaaactat agtttaatac acaagtatca  1020
atcttatcta tctggaagtc acggatccgt atccgttcca acccttccaa tcatttaaaa  1080
cgataccaaa aagagcaaaa aaatgtggtt agttttcgtt ttctttagtc tttcggaggc  1140
atcggtttca tgtgataaag cagaaataga gcgatcaaaa gttcaataga tattaatgtg  1200
atctgctgag cagtaaggct cgtgataatt aagtgtggct ttgcacaagt gtttctctag  1260
attcaacaat tgacaatatt tcgacataca tttttgataa cgagtcttga cgttgcgtgt  1320
cgttctagtt ttgcgcaagt cttacatgct gcattgcaac attgcatgat ggttgacgga  1380
tcaatttgaa gatgtgtcaa ttcatgtacc agttaaggaa cacaagtttg tgcgatctaa  1440
caaaatttgt ttacaataga taatgaaaga ttaaaagtgg aaacataaca atcagaaata  1500
ttacaaaaat cggtgaacac tgagccaaag taaatgaacc aacgggactc atcatgatcc  1560
cacctacacc tccccaaaaa tcaagatttt ttttccccaa atacataatc cactcttctt  1620
ttcgaaaggc tatataaaac ctagatgggc acaaggttcc acacaacaca acacaacaca  1680
tacatcaaca gattaaacat gaagcttctt catggactcg ctttagtttt tctattagct  1740
actacgagtt gcaaagcaga tgaagaaatt acttgcgaag agaacaatcc attcacctgt  1800
agtaacactg atatattaag cagtaagaac ttcggaaaaa atttcatctt cggtgttgca  1860
tcttctgctt accaggcatg tagcaaatgt tgtcataccc cacttttgaa ataaatttta  1920
aagcactaaa atgcaacttt gcatggttgt tcttcttatt tagatagaag gagggagagg  1980
tcgtggtgtt aacgtttggg atggcttcag tcaccggtac ccaggtatgt ggtttgcacg  2040
gtgacatata tatttatatg cgagaggaat gttggttaca tatacacata ttaatgtatt  2100
tgtaactaaa atcagagaaa gctgggtcag atttgaagaa tggagacact acttgtgagt  2160
catatacgag atggcaggtt aatttctcag tacattaata ctcatgactg aactatatat  2220
gtataaaaac tatacgtgtg gattgacatg agactaaaat taatatgtaa actgcagaaa  2280
gatgtagacg tgatgggcga aatcaatgct actggctaca gattctcctt tgcatggtca  2340
agaatcattc caagtatgta catatcaacg atcaatgtat atatatatat atatatatat  2400
atatatatat ttgtatttta attgggataa tttagttgga aaggtactaa ttaatgtacg  2460
atatatatct acccgagcag aaggaaaggt gagtagggga gtgaaccaag gaggtcttca  2520
atactaccac aaactcatag atgcactcct ggaaaagaat ataacgcctt tcgttaccct  2580
ctatcactgg gaccttcctc aaacactcca agatgagtat gaaggtttct tggaccgcca  2640
gatcatgtat gttccatgct tcttaattat atttgaagag agtcaatatt attagtgata  2700
gaagaagatt tagtctcaat tacatgtatt actgaaatat ttctatacta atatgcacag  2760
ccaagatttc aaagattacg cggatctatg tttcaaagaa tttggtggaa aggtaaagca  2820
ctggatcaca atcaaccagc tatacacagt gcctacgaga ggctatgcac tcggaacaga  2880
tgcacccggt cgatgttctt atatggttga taacaagcac aggtgttatg gcggaaattc  2940
ttcaacagaa ccctatatcg ttgcacataa ccagcttctt gctcatgcca cgatcgtcga  3000
tctttacagg accaaatata aggtgagtga tctccctatg tgaaaaggtg gtctaaatca  3060
aacatatccg attctaatga atagtcatat atatatatat atatatcacg tgatgagcag  3120
ttccaaaaag ggaagattgg acctgtgatg ataactagat ggtttcttcc atatgatgag  3180
tctgatcctt cttgcgtaga agcagctgag aggatgaacc aattcttcca tggatggtat  3240
atataatttt ttatatagcc aaaatatatc agtatgtatt ttatgcattt ataatgatac  3300
aaaaatatac atggatgatg gatcaggtac atggagccgc taacaaaggg tagataccca  3360
```

```
gacatcatga ggcagattgt gggtagtagg ctccccaact tcactgaagc tgaagccgaa  3420
ctcgttgctg gttcatatga ttttcttggt ctcaactatt acgtcactca gtatgcccag  3480
ccgaaaccta acccatatcc ttcagagaca cacactgcct tgatggacgc tggcgtaaag  3540
ctcacatgta cgtactacag tattaccact tagttacaac ctttctatat atctttttct  3600
cctatttgtt aacatacttt gtgagtgact atcaatttat ttcattcttg tgtttacaga  3660
tgataattca cgtggtgaat tccttggtcc actggtatat taatgatcca cccctatgat  3720
ttctctttta tttttttcta ttttcaatat aacaccactt atgctctctt tattgacatg  3780
tatatgtgtt cgcttccctt tcccagttca ttgaagacaa agacaacggc aacagctatt  3840
actacccaaa agggatttat tacgtaatgg actacttcaa aaccaaatac ggtgacccat  3900
taatctatgt caccgagaat ggtgagttct acatactact actcatcttt ttcatctata  3960
acgtatacta aataatgtat ttcggaataa atcccagaaa ctgactttca aatattgtgt  4020
acctttgcat gttatggcgg ttaggattta gcacgcccac tacagaaaac cgtggcgaag  4080
ctattgccga ttacaagcga attgattatc tttgcagtca tctatgtttt ctccgtaagg  4140
tcatcaagtg agtggatact attataaatg attttcttca tatgttatct tcttcgtctt  4200
ttttggaaac atttatatat atatgattgt tcttgctttc agggagaagg gtgtgaacgt  4260
gagaggatac tttgcatggg ctcttgggga taattatgaa ttctgtaaag gctttaccgt  4320
caggtttgga ctcagttacg ttaactggga cgatctcgac gatagaaacc tcaaagaatc  4380
tggtaaatgg taccagagat tcattaatgg aaccgccaag aatcctgcga aacaagattt  4440
cctccgctca agcgtctcct ctcagagtca gaagaagagg cttgcttgct gatgcatgaa  4500
acacttttcc cccttcaaga tcatctccac gtctctgatc actctttcta gttgctccat  4560
agataaggag cttctgtcta taattatgta ctaaataaat attctcaata aaaagatggt  4620
ctgttactaa tgaataaaaa aattatctac aactatatta tgtcaagtca agttaaactt  4680
aaacgtcgct caggcacaca tacgaaaaca aaaacaaaaa ccccccgcaa actagtttag  4740
tgagataaat tttgcgaaaa tttggaaaaa tactttgcaa agagatttta ttttgaaaat  4800
tgctcaatat ttgatttctt ttgaaaacta cactttctct ctagctaaat gactaattta  4860
tcctattaaa atgtatatac aacaagaaaa taaatttatt ttgttaaata ttatttaaat  4920
ttatttgaaa gtaacaaaac aagatataaa ataatcatcg ttgataacat aattttacgt  4980
gaagaaattt cagtcgttta aaacttgtca aattttgatc cagtgtcttt gtgtttcata  5040
aattatgcag tagagagaaa aaaatttgaa agttgctgtt tcagtgagat ggtgagtttt  5100
taacatgtaa agttttatat tatgtatcaa aattatcttt gttatgtaat attctctagt  5160
aaaaaggttt attattttta gaaagataaa cattgaaata ttataaatat ttatccaatt  5220
atatatttta aatcaatgta tttatcttaa taatttcgaa atttgaataa aaaccattaa  5280
aatataaaat ttaacttaaa cctggttaag acgtcttttt acatattgga aaagtgtaat  5340
ttttaaaata aaattgaatc aatgtatttt tcaaattaaa aaacataaat aggatatttt  5400
cctaattagc cgaaattcac taatcaattt caaagttcaa ctttatgtac gaggatgtct  5460
tttcaacata ataataatta gtgaccaaac ctaatccaaa ctcaaaagta actaaaccag  5520
agttctatca cctcaacaaa cacttgatgg gatttcacat atgatttttt atcattcata  5580
taattttatt tgattctgtt acttttataa tcaataaaac caaaaaagct aaaccgcagt  5640
cctttgtgtt tagtgaatgt atgccgattt atgtatttca acattgtatt ctactcttga  5700
atgatggaca aatatcaaga actgaagtgt cagaagtttc cgaaagaaca tgtcaacttg  5760
ttccatggac ttctttccca aattctttta agacttctgt ggatttccta aaccaaaaat  5820
aaagacatgg tttgtcattt ccgttttttt tttaataaaa gattcgattt atcttggatt  5880
aaacaaacta tagtaattta atgagtctca catatttata atgttggttt aattaatata  5940
atagggtttt tttctttaat tcggaaaaca agcatgtttg taatattatt agaatttcat  6000
aaatttccct ttggatatga tctgtaaatt ctcttcatac taccaacgca gcactagctg  6060
gcaacatttt cttttaaatt tgcattgaaa tttaccgttt tcttattggt tgatttaatt  6120
acttcaacaa aaggaaacaa atctagagtt atataaagta tatcttaaat tatgattgtt  6180
atctgctcta tccaatgatt ttctgaattg taaaatccat ttaaatacta gatattgtca  6240
ttcattgtat gtagaagcaa aatagaattt tgcatcttca attctccatt tatatggatg  6300
atttctaaca ctgttctaca gaaagaacac aaacactaca taacttcaaa aatttacgaa  6360
catgttaaaa attagtttca gcaaaactaa aaataagatt aataagaaaa attagattaa  6420
tatactaaga caaactaaaa cttaaaaata taacgataag tggtagctgt aattgcacaa  6480
ccgcaccaaa aa                                                     6492

SEQ ID NO: 61          moltype = DNA  length = 6962
FEATURE                Location/Qualifiers
source                 1..6962
                       mol_type = genomic DNA
                       organism = Brassica juncea
SEQUENCE: 61
tatcgaatga aacaaaagta caatcacagt tcatatagaa aggagataag attggatcaa  60
acaatacctt tgtttcaact ttggaggtgc gaaggagagc ttggaggtgc aaaggaaagc  120
caattgaaca aacaatacgt ttgtttcaac cttggaggtg cgtaggagag aacgacagcc  180
atcgtcgtct tgcgtcttgc ggagacaacg agggaagcgg cggagaagcc gagagaaacc  240
aaagaaaaga aaaagagaaa agaaaaatag aaaaatatat gctttgcctt tcgttagctg  300
acacgtggag gaaaaacccc tttagttatc gatcacaaaa atcctttctt aaggatcgat  360
aactcccctt ttatttagtt ttcatttaat taaataccca attaacttta aaaccccact  420
taaaatcccc cgttaaagat gctcttaggt cttatttaca aaattttccc aaatcgattc  480
aaaactacta cttgtaagaa ataaaacaat tgaaatgatt attgtgaaaa aatgaaatca  540
tatgtatatg tctcgataat ttttattttta ttgaatgaaa aataagagta ttacagtcta  600
tgttattgat aattcatggt gcatggatag tttttatttt attgaatgaa cattaagaga  660
attccatagt agttctcaaa aacaaaccaa aaagttattt aaactgaaac tattatttag  720
gtgatgattg tttacatggt ttttggattt tagtttttat tttttagatt tggtttttac  780
attttagttt ctgatttttg aattttgatt ttgctatata ttttaatttt tcaaaaaaac  840
ttgaatggtg attctagatt ttgctttttg gtttttaatt aattttttta aaatatattg  900
gaatctaaag tttgataact aattatttaa ttttaaagtt attttttatt tttaagaact  960
tcactcataa gttaattttc ttttaaacaa acttaaaatt actaaaataa atatcatttt  1020
aaataagtaa taccaataga actcttaaca aatatgcaaa atttacataa actaattaac  1080
caaattttaa atttatttta tccaaatgcc taaagcacag aaatttaata aaatgtttta  1140
```

-continued

```
ttcttgaaat aatacgaaca gtttatttta attcatgttt gaactttgaa aacatagctt  1200
tgtactgtca tagaagaatt ttttcaaaaa taatatctaa ttataaaaaa tatatataac  1260
taaagtttat gaattcttac ataagtgtta aactataggt taatacacaa gattcttgca  1320
tttcaaccct tccaatcata tctagaaacg ttaccaaaaa aagcaaaaaa tgttgttggt  1380
tttcgttttc gttttctttt gtctttcgga tactgtggtc tcatgtgata aagcatatat  1440
agagaggtca aaagaatcaa aacaaataag atatgctatg attgtttttt cttgataatg  1500
ttgattatta gcggtgatct catgaaaagt gtggccttgg atcagtgtta ctctagattt  1560
agcacttgat aatatttcga taaaagtctt caataacttt atggcgttat gacgacgctt  1620
tgaacattat ttactgcagc taatcttgat atataattcg tcttttctag ttcgcgcacg  1680
ccttccatat atacatgctg catcgcacca ctggtcgacg gatcaatttg aagatgtgac  1740
acaattcgtc ttccaagtcg tacgtcttcc aagtcgtacg tgttccaagt cgtacgtgtt  1800
cccgtaattt gaagatggaa cacaactatg tgctatgtaa caaaaaaaaa ttatttgcaa  1860
tagataatga aaaactaaaa agtggaagca aacaagaaat ttaagcaaaa tcggtgaaca  1920
ctgagctaaa gtaagtgaac ccacgggact catgatccca cctaaacctc cccaaaatgt  1980
cgagatacta agacaagaaa atgtatgtgt cactcttctt taggaagggc tatataaacc  2040
gtagatggac acaaggttcc atacaacaca acacatacat caacatatta actatgaagc  2100
ttcttgggct cgctttagtt tttctgttag cttctgcgag ttgcaaagct gacgaagaaa  2160
ttacttgtga agagaacaat ccattcacat gtagtaacac tgatatttta agcagtaaga  2220
acttcggaaa agacttcatc ttcggtgttg catcttctgc ttaccaggca tgtaacaaat  2280
gttgacatac catacttttt gacgtataga aaacactatt caaaaatgat aatatctaac  2340
tttgcatggt tgtttctttt catttcagat cgaaggaggg agaggtcgtg gtgttaacat  2400
ttgggatggc ttcagtcacc gatacccagg tatgtcgttt gcacggtgac atctatatat  2460
atatcatata tgacaggaat gttggttata agtactcata ttaatgtatt tgtaattact  2520
atcagagaaa tcagggtcag atttgaagaa tggagacact acttgtgagt catatacgag  2580
atggcaggtt aattcttcag tacatttgta gatactcatg actgaactat gtatacaaac  2640
tacgtgccga ttgagatgca atcaaaatat gaaactgcag aaagatgtag acgttatggg  2700
cgaactaaat gctactggct acagattttc ctttgcgtgg tcgagaatca ttccaagtac  2760
gtacagatta tcgatcagta catgtatata tatagttgga cgtgttttaa atgtacgatt  2820
tatatataca tgagcagaag gaaaggtgag taggggagtg aaccaaggag gtcttgatta  2880
ctaccacaaa ctcatagacg ccctcctcga aaagaatata actcctttcg ttaccctctt  2940
tcactgggac cttcctcaaa cactccaaga tgagtacgaa ggtttcttgg accgccagat  3000
catgtatgtt tatatttgtg acatgcttct tatattatta ataagagaag aaaaagatgg  3060
ttaattttag ttacatgcat tactgaaatg attctatatt aatatgcaca gacaagattt  3120
caaagattat gccgatctat gtttcaaaga atttggtgga aaggtaaagc actggatcac  3180
gatcaaccag ctatacacag tccctacgag aggctatgca gtcggaacag atgcacccgg  3240
tcgatgttct cctatggttg atactaagca caggtgttac ggcggaaatt cttcaacaga  3300
accctatatc gttgcacata accagcttct tgctcatgcc acggtcgtcg atctttacag  3360
gaccaaatat aaggtgaatg ctgtctccat atgtgaaaat taaggtggtg tctaacatat  3420
ctgattctaa tgtaaatatc acgtgaccaa cagttccaaa aagggaagat tggacctgtg  3480
atgataacaa gatggtttct tccatttgat gagtctgatc cggcctccat agaagcagct  3540
gagaggatga accaattctt ccatggatgg tatatatata tattaccaaa aatgtaacag  3600
tatctactgt atttgtatgt atgtataatg gaaaaatata catggatcag gtacatggag  3660
ccgctaacaa agggtagata cccagacatc atgaggcaga ttgtgggtag taggcttccc  3720
aactttaccg aggaagaagc ccaactcgtt gccggttcat atgattttct tggtctcaac  3780
tattacgtca ctcagtacgc ccagccgaaa cctaacccat atccttcaga gacacacact  3840
gccatgatgg acgctggtgt aaagctcaca tgtaagtacc acacaatatt actacttagt  3900
tacgaccttt ctatatattt tttttcttct ttttgttaac atactttgtg agagtatcaa  3960
ttatttcatc cttgtgttta cagatgataa ttcgcgtggt gaatttcttg gtccactggt  4020
atatatgaat gaaccacccc tatgatatct ctttcatttt ttattctatt tgcaatatat  4080
agaacaccac tgattatgtt ctcgtgattg atatgtatat ttgtttgctt cccttgctca  4140
gttcgttgaa gacaaagata acggaaacag ctattactat ccaaaaggaa tttattacgt  4200
gatggactac ttcaaaacca actacggcaa ccctttaatc tatgtcaccg agaacggtga  4260
gttctacata ctactactcc tctattttca tttataccac gcataatatt atgtaaccac  4320
aaaagtagac cgatattcaa tctaccgcag ggtgaatagt aatgaaaata attgtaaaag  4380
ttattttaca attattgtat tttcgaaatt ggtccaagaa actaacttac aaatattgtg  4440
taatattttt catgcaatgg cggcttaatt aggatttagt acgcccagtt cagaaaaccg  4500
tgagcaggct attgcggatt acaagcgaat tgattatctc tgcagtcatc tatgtttttct  4560
ccgtaaggtc atcaagtaag taatgctact atatggatgc ttttcttcca atgtttatca  4620
acttcttctc tttttggtaa tatatatata tatatatata tatatatata tatatatata  4680
tatatatata tgattgttct tgttttcagg gagaagggtg tcaacgtgag aggttatttt  4740
gcatgggctc ttggagacaa ttacgaattc tgtaaaggct ttaccgtcag atttggactc  4800
agttacgtta attgggacga tctcgatgat agaaacctca aagaatctgg caaatggtac  4860
cagagattca ttaacgggac agtcaagaac cttgccaaac aagatttcct ccgctcaagc  4920
ctctcttccc agagtcagaa gaagaggctg tctgatgcat gaaacacttc ccccccttca  4980
agatcatctc catgtctctc actctttata cttgctcaac cgataaagag cttcttctac  5040
ctatagtaat gtactaaata aatattctca ataaaaagat gatcagttac taatgaataa  5100
aaaatttatc taccactaca ttatgtcaag tcaagaagat cgagagaggg agacagaggg  5160
aaataacaca atttaaacca aaaacgtcac ccatacaaaa taaaaaaaaa aatacacggt  5220
ttatgcgaga aacttaagag caaccttatg gttgatacta aatttagata tctcaaacca  5280
aaaatattgt tagtttaatc tgtttttacc taaagttcaa ttttattttt tattttttaa  5340
gtcaatctaa ttggtgaaag acaatatgcg gccatatgag atttgttaaa aacttaaaat  5400
cgtgttaaaa gttctcgcat gcgaacctgc ttctcttctc tttcgtgttt tttgtatttt  5460
tgaatttttt taatctaaga tactctatct aaaacgtatc cattttgttt atcaatgtta  5520
tcaaggtctt atttttttcg agattccaca ttgatatgta agaccatcca ctacaagaaa  5580
acacgccgaa ttccgacgga gattccgacg gacgtcacag gcgtcggaca atttagacga  5640
aattctgacc gatttccgac gaaaacaaaa aatctgaagt cgtcggaatt ccgtcggcta  5700
attccgacga acttccgaga aaacaagggt cgtcggaata ttccgacgac ttttcgacga  5760
catccgataa acaatataac cgttgtagtc gtcgaaaagt cgtcggaata tccgacgatt  5820
ttggccatca gaatcccccct gttttcttgt agtgatctca actctatttt atttttcact  5880
```

-continued

```
tttttgcttc attttgaaag aactttttgtt ccaattctac ctcatttctt gcttcaacaa  5940
agcaataaac aatatatctt caaatttaaa aatatatcgt tcacgttttc aattttataa  6000
gataaaattt taactataaa ttgattctta atttttagtt atttttattt tgtcaccata  6060
aattatataa tattaattac ccaatcaatt tcaaaatttt tgactattgt tttcatctaa  6120
tattaattac ccaataaatt ttgactattt agcttgatta agaaaaatca aagataaata  6180
gtctcatatt tttatttcaa aacacttttg ttaactcata gaaaaatatt ttctttctaa  6240
aatatgatat tctttgtttg tttcttgtgt tatgtaataa ttttattaaa tgataatgtt  6300
taatatatat taaactctaa ttgtgataga ttattggtaa aataataatt gagtaacatt  6360
tataaatatg aaaaagtaca aatgtaatta ataactaata attattggag atagaatata  6420
gttagaatat tctttttaca gaaaataaaa aaaaaaccat tgaaataaat gttatttcat  6480
tttttttat aaaagtgaac tctgaaaaat aaaaatgaaa ccaatcttaa gagatgccct  6540
aaatccatga gtcttttttt aataagaaaa atatatttca tcaatatgtt ggaagctgaa  6600
gtaatataaa tagtatctcc taacgagaat tgaactcaaa tggtgatatg tctactagac  6660
agatttttac tgctaaacca acatatagtt ggttccatga atctcttcaa tcttattttc  6720
catatacaaa aagaaaataa ataattttaa aactaactca tgcacattcg tgaatgttta  6780
ttttacgata gatatataga tatttctaaa cacaacaatt tagtagttgc atttgtatta  6840
ctttagtgta tcgttgagac catatattgt attactggat catgtgatat atttttctta  6900
ttagatatgt gttggatgag ttatgtaatt ataaatatga ttagatctat gtattgatat  6960
gc                                                                 6962
```

MUSTARD GREEN PLANTS NAMED 'PWRG-1', 'PWRG-2,' AND 'PWSGC'

STATEMENT OF PRIORITY

This application is a continuation application of International Application Serial No. PCT/US2023/70367, filed on Jul. 18, 2023, which claims the benefit, under 35 U.S.C. § 119 (e), of U.S. Provisional Application No. 63/368,717 filed on Jul. 18, 2022, the entire contents of each of which is incorporated by reference herein.

STATEMENT REGARDING ELECTRONIC FILING OF A SEQUENCE LISTING

A Sequence Listing in XML format, entitled 1499-900WO_ST26.xml, 430,068 bytes in size, generated on Jul. 17, 2023 and filed herewith, is hereby incorporated by reference into the specification for its disclosure.

FIELD OF THE INVENTION

The present invention relates to *Brassica juncea* produced via CRISPR, in particular, to new *B. juncea* varieties designated 'PWRG-1', 'PWRG-2,' and 'PWSGC' having reduced myrosinase activity.

BACKGROUND OF THE INVENTION

Vegetables play an important role in food and nutritional security. Particularly, green leafy vegetables are considered an exceptional source for vitamins, minerals, and phenolic compounds. Mineral nutrients such as iron and calcium are higher in leafy vegetables than staple food grains. However, the Centers for Disease Control and Prevention (CDC) recently reported that just 1 in 10 adults meet the daily intake recommendations for fruits and vegetables. For consumers, multiple potential barriers exist for the consumption of fresh produce options, such as: cost, convenience, availability, and palatability/taste of the fresh produce. Among fresh produce, lettuce is commonly used as a major component for salads and provides additive options for sandwiches and burgers. Although lettuce is broadly available and commonly purchased by consumers, it lacks in nutrition value relative to other leafy green vegetables.

Leafy green vegetables such as kale have gained popularity as 'superfoods' and serve as a nutrient dense vegetable source for health-conscious consumers. In southern states, turnip and mustard greens, and collards are a common part of the diet. However, to minimize undesirable attributes associated with leafy greens, such as fibrous/tough leaves, bitterness, frilly textures and/or pungency, consumers often cook down the leafy greens to soften tissues and alter flavor/odor profiles with the incorporation of fats and other ingredients. Consequently, many of the nutrient-related benefits are reduced by the cooking process, and consumers are deprived of many of the direct benefits of consuming the fresh produce to begin with.

Among the most nutrient dense leafy green options available for consumers, mustard greens (*Brassica juncea*) are characterized by intraspecific diversity with variation of leaf traits such as color, size, texture, and heading morphology. If eaten fresh, mustard greens are pungent due to the reaction of myrosinase enzyme with its glucosinolate substrate. Consequently, mustard greens are either cooked to minimize pungency, or consumed fresh in smaller quantities, or as baby greens.

Therefore, there is a need in the art for reducing the reaction that results in pungency and to produce leafy greens with reduced pungency in flavor and/or odor, which would thereby encourage broader consumption of fresh healthy leafy greens. Furthermore, there is a need for manipulating similar chemical herbivory defense systems, found in other vegetables, to promote the consumption of additional fresh vegetables that are less pungent.

Accordingly, the present invention relates to new and distinct varieties of *B. juncea* having reduced pungency, which have been given the variety denominations of 'PWRG-1', 'PWRG-2,' and 'PWSGC.' 'PWRG-1', 'PWRG-2,' and 'PWSGC' intended for use to sell seed as well as baby and mature leaf products to consumers.

SUMMARY OF THE INVENTION

The present invention relates to new and distinctive *Brassica juncea* varieties designated 'PWRG-1', 'PWRG-2,' and 'PWSGC' having reduced pungent flavor and/or odor traits.

The new *B. juncea* varieties were produced via CRISPR from public domain *B. juncea* varieties. In each case, multiple copies of the myrosinase gene were modified as described in International Application No. PCT/US2020/046483, filed Aug. 14, 2020, which is hereby incorporated by reference herein. Additional selections were done after the editing. These selections were made in greenhouses in North Carolina as well as in the field in California.

In some aspects, the present invention provides seeds of the variety PWRG-1, PWRG-2, or PWSGC; plants of the variety PWRG-1, PWRG-2, or PWSGC and parts thereof, for example, leaves, pollen, embryos, cotyledons, hypocotyls, roots, root tips, anthers, pods, flowers, ovules, shoots, stems, stalks, pith and capsules, tissue culture comprising tissue, callus, cells or protoplasts of the variety PWRG-1, PWRG-2, or PWSGC; hybrids having a variety PWRG-1, PWRG-2, or PWSGC parent or ancestor; and PWRG-1-, PWRG-2-, or PWSGC-derived *Brassica juncea* plants, as well as genetically modified (e.g., by conventional breeding or genetic engineering techniques) forms of the foregoing plants and tissue culture, and cells of the foregoing varieties.

The present invention further provides methods of producing a *Brassica juncea* plant by crossing the PWRG-1, PWRG-2, or PWSGC variety with itself or a different *Brassica juncea* line. The invention further relates to methods for producing other *Brassica juncea* varieties or breeding lines derived from the variety PWRG-1, PWRG-2, or PWSGC by crossing the PWRG-1, PWRG-2, or PWSGC variety with a second *Brassica juncea* plant and growing the progeny seed to yield a PWRG-1-, PWRG-2-, or PWSGC-derived *Brassica juncea* plant. An additional aspect of the invention provides a method for a *Brassica juncea* plant that contains in its genetic material one or more transgenes, comprising crossing a PWRG-1, PWRG-2, or PWSGC variety containing one or more transgenes with either a second plant of another *Brassica juncea* variety, or a non-transformed PWRG-1, PWRG-2, or PWSGC *Brassica juncea* plant, wherein progeny are produced, so that the genetic material of the progeny that result from the cross comprise the transgene(s) optionally operably linked to one or more regulatory elements.

Another aspect of the invention provides methods for developing a *Brassica juncea* plant in a *Brassica juncea* plant breeding program using plant breeding techniques, which includes employing a PWRG-1, PWRG-2, or PWSGC *Brassica juncea* plant or a part thereof, or a PWRG-1-, PWRG-2-, or PWSGC-derived *Brassica juncea* plant, or a part thereof, as a source of plant breeding material.

Additional aspects of the invention provide a method of reducing pungency in a *B. juncea* plant or part thereof comprising editing one or more myrosinase alleles in the *B. juncea* plant or part thereof, wherein the edits result in a plant or part thereof comprising each of nucleotide sequences of SEQ ID NOs:1-15, or comprising each of the nucleotide sequences of SEQ ID NOs:1-3 and 8-19, or comprising each of the nucleotide sequences of SEQ ID NOs:20-27.

A further aspect provides a method of reducing pungency in a *B. juncea* plant or part thereof comprising crossing a *B. juncea* plant comprising each of nucleotide sequences of SEQ ID NOs:1-15 (e.g., PWRG-2) with a *B. juncea* plant that is not edited as described herein to produce progeny plants comprising one or more (e.g., 1, 2, 3, 4, 5, 6, 7, 8, 9, 10, 11, 12, 13, 14, or 15) of the nucleotide sequences of SEQ ID NOs:1-15 (e.g., one or more of SEQ ID NO:1, 2, 3, 4, 5, 6, 7, 8, 9, 10, 11, 12, 13, 14, or 15).

Additionally provided is a method of breeding a *B. juncea* plant or part thereof comprising crossing a *B. juncea* plant comprising each of nucleotide sequences of SEQ ID NOs: 1-15 (e.g., PWRG-2) with a *B. juncea* plant that is not edited as described herein to produce progeny plants comprising one or more (e.g., 1, 2, 3, 4, 5, 6, 7, 8, 9, 10, 11, 12, 13, 14, or 15) of the nucleotide sequences of SEQ ID NOs:1-15 (e.g., one or more of SEQ ID NO:1, 2, 3, 4, 5, 6, 7, 8, 9, 10, 11, 12, 13, 14, or 15).

Additional aspects of the invention provide a method of reducing pungency in a *B. juncea* plant or part thereof comprising crossing a *B. juncea* plant comprising each of nucleotide sequences of SEQ ID NOs:1-3 and 8-19 (e.g., PWRG-1) with a *B. juncea* plant that is not edited as described herein to produce progeny plants comprising one or more (e.g., 1, 2, 3, 4, 5, 6, 7, 8, 9, 10, 11, 12, 13, 14, or 15) of the nucleotide sequences of SEQ ID NOs:1-3 and 8-19 (e.g., one or more of SEQ ID NO:1, 2, 3, 8, 9, 10, 11, 12, 13, 14, 15, 16, 17, 18, or 19).

A further aspect provides a method of breeding a *B. juncea* plant or part thereof comprising crossing a *B. juncea* plant comprising each of nucleotide sequences of SEQ ID NOs:1-3 and 8-19 (e.g., PWRG-1) with a *B. juncea* plant that is not edited as described herein to produce progeny plants comprising one or more (e.g., 1, 2, 3, 4, 5, 6, 7, 8, 9, 10, 11, 12, 13, 14, or 15) of the nucleotide sequences of SEQ ID NOs:1-3 and 8-19 (e.g., one or more of SEQ ID NO:1, 2, 3, 8, 9, 10, 11, 12, 13, 14, 15, 16, 17, 18, or 19).

Additionally provided is a method of reducing pungency in a *B. juncea* plant or part thereof comprising crossing a *B. juncea* plant comprising each of nucleotide sequences of SEQ ID NOs:20-27 (e.g., PWSGC) with a *B. juncea* plant that is not edited as described herein to produce progeny plants comprising one or more (e.g., 1, 2, 3, 4, 5, 6, 7, or 8) of the nucleotide sequences of SEQ ID NOs:20-27 (e.g., one or more of SEQ ID NO:20, 21, 22, 23, 24, 25, 26, or 27).

In a further aspect a method of breeding a *B. juncea* plant or part thereof is provided comprising crossing a *B. juncea* plant comprising each of nucleotide sequences of SEQ ID NOs: 1-15 (e.g., PWSGC) with a *B. juncea* plant that is not edited as described herein to produce progeny plants comprising one or more (e.g., 1, 2, 3, 4, 5, 6, 7, or 8) of the nucleotide sequences of SEQ ID NOs:20-27 (e.g., one or more of SEQ ID NO:20, 21, 22, 23, 24, 25, 26, or 27).

A further aspect of the present invention provides a method of producing *Brassica juncea* seed by growing a plant of the present invention and harvesting the seed.

Additional aspects of the present invention provide products comprising *Brassica juncea* wherein the *Brassica juncea* further comprises *Brassica juncea* from the plants of the present invention, and parts thereof, for example, a leafy greens blend comprising a leaf of the variety PWRG-1, PWRG-2, and/or PWSGC.

These and other aspects of the invention are set forth in more detail in the description of the invention below.

DETAILED DESCRIPTION OF THE INVENTION

Figure 1:
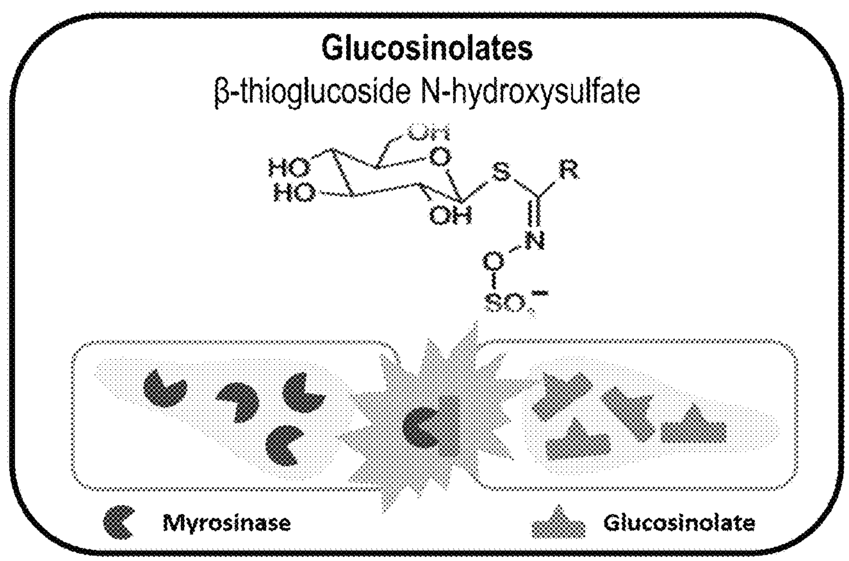
FIG. 1 illustrates glucosinolate metabolism by myrosinase and production of thioglucoside N-hydrosulfate.

The present invention now will be described hereinafter with reference to the accompanying examples, in which aspects of the invention are shown. This description is not intended to be a detailed catalog of all the different ways in which the invention may be implemented, or all the features that may be added to the instant invention. For example, features illustrated with respect to one aspect may be incorporated into other aspects, and features illustrated with respect to a particular aspect may be deleted from that aspect. Thus, the invention contemplates that in some aspects of the invention, any feature or combination of features set forth herein can be excluded or omitted. In addition, numerous variations and additions to the various aspects suggested herein will be apparent to those skilled in the art in light of the instant disclosure, which do not depart from the instant invention. Hence, the following descriptions are intended to illustrate some particular aspects of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular aspects only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some aspects of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

A "line" is a group of plants that displays very little overall variation among individuals sharing that designation. "Line" also refers to a homogeneous assemblage of plants carrying substantially the same genetic material that display little or no genetic variation between individuals for at least one trait, in particular the mutated myrosinase genes present in PWRG-1, PWRG-2, or PWSGC and the degradation of glucosinolates. "Variety" or "cultivar" may be used interchangeably with "line," but in general the former two terms refer to a line that is suitable for commercial production. "Genetically derived" as used for example in the phrase "genetically derived from the parent lines" means that the characteristic in question is dictated wholly or in part by an aspect of the genetic makeup of the plant in question.

As used herein, the term "plant" includes an immature or mature whole plant, including plant cells, plant protoplasts and plant tissue (e.g., in culture; tissue culture) from which *Brassica juncea* plants can be regenerated, plant calli, plant clumps, and plant cells that are intact in plants or parts of plants.

The term "plant part," as used herein, includes but is not limited to reproductive tissues (e.g., petals, sepals, stamens, pistils, receptacles, anthers, pollen, flowers, fruits, flower bud, ovules, seeds, embryos or pods); vegetative tissues (e.g., petioles, stems, roots, root hairs, root tips, pith, coleoptiles, stalks, shoots, branches, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts, and callus.

As used herein, a "baby" leaf refers to a leaf that having a length of 4.5 inches or less, optionally a length of about 2 inches to 4.5 inches (e.g., about 2, 2.25, 2.5, 2.75, 3, 3.25, 3.5, 3.75, 4, 4.25, or 4.5 inches) or any range or value therein, about 2 inches to about 4 inches (e.g., about 2, 2.25, 2.5, 2.75, 3, 3.25, 3.5, 3.75, or 4 inches) or any range or value therein. The length of the baby leaves in a leafy greens blend can be measured as an average. For example, over about 10 baby leaves, on average the length of the leaves is about 4.5 inches or less.

The length of baby leaves is measured from the tip of the leaf blade to the end of the petiole. A leaf may include a petiole or may not include a petiole. When no petiole is present the length of the leaf is measure from the tip to the bottom of the leaf blade, the bottom being where the petiole if present would be attached. In some aspects, a petiole, when present, may be about 0.1 to about 1 inch (e.g., about 0.1, 0.2, 0.3, 0.4, 0.5, 0.6, 0.7, 0.9, or 1 inch or any value or range therein) in length. In some aspects, a petiole may be less than or equal to 0.5 inches in length (e.g., about 0.1, 0.2, 0.3, 0.4, or 0.5 inches or any value or range therein).

As used herein, a "mature" leaf refers to a leaf that having a length of about 6 inches to about 14 inches (e.g., about 6, 6.5, 7, 7.5, 8, 8.5, 9, 9.5, 10, 10.5, 11, 11.5, 12, 12.5, 13, 13.5, or 14 inches) or any range or value therein. The length of mature leaves in a leafy greens blend can be measured as an average. Thus, in some aspects, over about 10 mature leaves, on average the length of the leaves is about 6 inches to about 14 inches. The length of a mature leaf is measured from the tip of the leaf blade to the bottom of the leaf blade. In a leafy greens mix, mature leaves are chopped into pieces, optionally the pieces are about 1-2 inches in size.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. A "protoplast" is an isolated plant cell without a cell wall or with only parts of the cell wall. Thus, in some aspects of the invention, a mustard plant cell comprising nucleic acids and/or nucleotide sequences of SEQ ID NOs:1-15 (e.g., PWRG-2), SEQ ID NOs:1-3 and 8-19 (e.g., PWRG-1) or SEQ ID NOs:20-27 (e.g., PWSGC) in a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes, and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "tissue culture" encompasses cultures of *Brassica juncea* tissue, cells, protoplasts and callus. Methods of culturing *Brassica juncea* tissue, cells, protoplasts and callus, as well as methods of regenerating plants from *Brassica juncea* tissue cultures are known in the art.

A plant having "(essentially) all the morphological and physiological characteristics" means a plant having essentially all or all the morphological and physiological characteristics when grown under the same environmental conditions of a plant described herein, e.g., the plant of PWRG-1, PWRG-2, or PWSGC, from which it was derived, e.g., the progenitor plant, the parent, the recurrent parent, the plant used for tissue- or cell culture, etc. For example, the plant may have all leaf and/or all flowering characteristics described. In some aspects, the plant having "all the morphological and physiological characteristics" are plants having all the morphological and physiological characteristics, except for certain characteristics, such as one, two or three, mentioned, e.g., the characteristic(s) derived from an introduced transgene or trait and/or except for the characteristics which differ in an essentially derived variety. So, the plant may have all leaf and/or flowering characteristics described, except for one, two or three characteristics described, in which the plant may thus differ.

The morphological and physiological characteristics mentioned above are commonly evaluated at significance levels of 1%, 5%, 8% or 10% significance level, when measured under the same environmental conditions. For example, a progeny plant of described herein, e.g., of PWRG-1, PWRG-2, or PWSGC may have one or more (or all, or all except one, two or three) of the essential morphological and/or physiological characteristics of the plants described herein, e.g., of PWRG-1, PWRG-2, or PWSGC, respectively, or one or more or all (or all except one, two or three) of the myrosinase activity and/or leaf characteristics, as determined at the 1% or 5% significance level when grown under the same environmental conditions.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the E1 generation. The term "BC1" refers to the second use of the recurrent parent, "BC2" refers to the third use of the recurrent parent, and so on.

As used herein, the term "selfing" refers to crossing a plant line with itself.

As used herein, the terms "cross" or "crossed" refer to the fusion of gametes via pollination to produce progeny (e.g., cells, seeds, or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "progeny" is, e.g., a first generation progeny, i.e., the progeny is directly derived from, obtained from, obtainable from or derivable from the parent plant by, e.g., traditional breeding methods (selfing and/or crossing) or regeneration. The term "progeny" also generally encompasses further generations such as second, third, fourth, fifth, sixth, seventh or more generations, i.e., generations of plants which are derived from, obtained from, obtainable from or derivable from the former generation by, e.g., traditional breeding methods, regeneration, or genetic transformation techniques. For example, a second generation progeny can be produced from a first generation progeny by any of the methods mentioned above. Progeny of a plant described herein, e.g., of a plant PWRG-1, PWRG-2, or PWSGC, may be essentially derived varieties or which retain all (or all except 1, 2 or 3) morphological and/or physiological characteristics of the plant described herein, e.g., of a plant PWRG-1, PWRG-2, or PWSGC, or which retain all (or all except 1, 2, or 3) of the myrosinase activity and/or leaf characteristics of the plant described herein, e.g., of a plant PWRG-1, PWRG-2, or PWSGC are encompassed herein. "$E_0$" refers to the first generation of CRISPR-edited plant material, "$E_1$" refers to the seed produced on $E_0$ plants, $E_1$ seed gives rise to $E_1$ plants that produce $E_2$ seed, etc., to subsequent $E_x$ progeny. As used herein, the terms "$E_1$ hybrid" refer to a first generation progeny plant produced by crossing an edited plant of variety PWRG-1, PWRG-2, or PWSGC with a different *Brassica juncea* plant.

The terms "transgene" or "transgenic" as used herein refer to at least one nucleic acid sequence that is taken from the genome of one organism, or produced synthetically, and which is then introduced into a host cell or organism or tissue of interest and which is subsequently integrated into the host's genome by means of "stable" transformation or transfection approaches.

The terms "transformation" or transfection" may be used interchangeably and as used herein refer to the introduction of a heterologous nucleic acid into a cell. Transformation of a cell may be stable or transient. Thus, in some aspects, a host cell or host organism (e.g., a plant) may be stably transformed with a polynucleotide/nucleic acid molecule of interest. In some aspects, a host cell or host organism may be transiently transformed with a polynucleotide/nucleic acid molecule of interest.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. Stable transformation as used herein can also refer to a transgene that is maintained extrachromasomally, for example, as a minichromosome or a plasmid.

"Genome" or "genomic" as used herein includes the nuclear and the plastid genome, and therefore includes integration of the nucleic acid into, for example, the chloroplast or mitochondrial genome.

A polynucleotide or nucleic acid construct may be operatively associated with a variety of promoters and/or other regulatory elements for expression in a plant and/or a cell of a plant. Thus, in some aspects, a polynucleotide or nucleic acid construct may further comprise one or more promoters, introns, enhancers, and/or terminators operably linked to one or more nucleotide sequences. In some aspects, a promoter may be operably associated with an intron (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some aspects, "percent sequence identity" can refer to the percentage of identical amino acids in an amino acid sequence as compared to a reference polypeptide.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some aspects, two nucleotide sequences considered to be substantially complementary hybridize to each other under highly stringent conditions.

A "locus" (loci plural) is a position on a chromosome where a gene or marker or allele is located. In some embodiments, a locus may encompass one or more nucleotides.

As used herein, "reduced pungency" refers to as the sensory perception of compounds released or produced by the hydrolysis of sinigrin (a glucosinylate). Myrosinase is the enzyme that hydrolyzes sinigrin. This can also be measured in the laboratory using a glucose release assay that is also aimed at measuring the activity of myrosinase. Thus, reduced pungency as used herein can mean reduced hydrolysis of glucosinolates and/or reduced amounts/production of alkenyl glucosinolates and/or aliphatic glucosinolates in a plant of the present invention as compared to a plant not comprising the edit and grown under the same conditions. In some embodiments, a plant of the present invention may exhibit a reduced pungency of about 95% to about 100% (e.g., about 95%, 96%, 96%, 97%, 98%, 99% or 100%).

Description of the Variety

The characteristics of the new varieties as described herein have been repeatedly observed and can be used to distinguish 'PWRG-1', 'PWRG-2,' 'PWSGC' as new and distinct varieties of *B. juncea* plant. Varieties 'PWRG-1' and 'PWRG-2' were derived from 'Red Giant' (not patented) and 'PWSGC' was derived from 'Southern Giant Curled' (not patented). Plants of the new varieties differ from plants of the starting material by at least the modification of the one or more copies of myrosinase which can reduce myrosinase activity enough to alter the flavor of the plants.

Within Brassicaceae, plants have evolved a specialized chemical reaction which is mediated by a spatially separated enzyme (myrosinase) and substrate pool (glucosinolates).

Upon tissue damage (i.e., herbivory), myrosinases come into contact with the glucosinolates and various degradation products can be produced; some of which are strongly pungent (e.g., allyl isothiocyanate (AITC)) (FIG. 1). Thus, this reaction has evolved as an anti-herbivory mechanism.

Identification of Myrosinases in *B. juncea*. The genome assembly version v1.5 and gene annotation of *Brassica juncea* was downloaded from *Brassica* Database (BRAD, brassica.db.org/brad/) and utilized for genomic analyses. In addition, *Arabidopsis thaliana* genome (assembly version TAIRA10) from Phytozome Database and the genomic progenitors of *B. juncea—Brassica rapa* and *Brassica nigra*—from BRAD were used for comparative analyses.

A BLAST search was conducted on the whole genome assembly with the myrosinase gene IDs from Table 1. Blast search results were filtered to retain sequence hits at least 70% query coverage and E value <1e-10. Phylogenetic analysis was then performed in GENEIOUS® (Version 2020.1.2) using Clustal Omega (Sievers & Higgins (2018) Clustal Omega for making accurate alignments of many protein sciences. *Protein Sci.* 27:135-145) for sequence alignment and neighbor joining methodology for tree inference. Orthologs of myrosinase were found by examining the tree topology and identification of gene clustering from multiple species for which the most common ancestor node is a speciation event. Manual annotation of the resulting genes was performed using visual examination of next generation sequencing short read and long read alignments to the genome assembly (NCBI datasets: SRP064721, SRP137085, SRP041526). Gene sequence polishing was done using visual examination of next generation sequencing short read alignments to the genome assembly (NCBI datasets: SRP058895).

TABLE 1

| Gene IDs used for queries | | | |
|---|---|---|---|
| Gene Name | *Arabidopsis* Gene ID | *Brassica rapa* gene ID | *Brassica nigra* gene ID |
| TGG1/Myrosinase | AT5G26000 | Bra020523, Bra020549, Bra032343 | BniB006711, BniB006713, BniB009758, BniB014275 |

Gene-Editing of Plants. Disarmed *Agrobacterium tumefaciens* was used to introduce a T-DNA cassette expressing a selectable marker and CRISPR Cas gene editing components targeted to create double-strand breaks in myrosinase gene coding sequences. The T-DNA further expressed crRNAs programmed to target *Brassica juncea* (L.) myrosinase coding genes. PCR and next generation sequencing were used to confirm that intended genetic changes were achieved. Genomic DNA was isolated from leaf tissue and used as a template in PCR reactions using primers specific to the genes targeted. The amplified products were subsequently sequenced and characterized to confirm the genetic changes. Events of interest were advanced and progeny selected from the segregating population. The nucleic acids of SEQ ID NOs:1-19 provide examples of mutations achieved in varieties PWRG-1 (SEQ ID NOs:1-3 and 8-19) and PWRG-2 (SEQ ID NOs:1-15) using CRISPR-mediated editing and SEQ ID NOs:20-27 provide examples of mutations achieved in variety PWGCS using CRISPR-mediated editing. Table 2 provides the parent cultivar, variety name, plant identification no (CEID) at stages $E_0$, $E_1$ and $E_2$ of the varieties of this invention. The plants provided in Table 2 are non-pungent or exhibit reduced pungency.

TABLE 2

| Edited Plants | | | |
|---|---|---|---|
| Parent Cultivar | Variety Name | Stage | CEID |
| Red Giant (not patented) | PWRG-1 | $E_0$ | CE15785 |
| | | $E_1$ | CE37306 |
| | | $E_2$ | CE60962 |
| Red Giant | PWRG-2 | $E_0$ | CE15785 |
| | | $E_1$ | CE37306 |
| | | $E_2$ | CE61087 |
| Southern Giant Curled (not patented) | PWGCS | $E_0$ | CE21573 |
| | | $E_1$ | CE46727 |
| | | $E_2$ | CE62251 |

The two Red Giant derived lines (i.e., PWRG-1 and PWRG-2) were selected from the same initial Red Giant population and were selfed to fix the traits. Thus, PWRG-1 and PWRG-2 have the same edited alleles of myrosinase (Table 3). PWRG-1 and PWRG-2 differ in other plant characteristics than the edited alleles of myrosinase. Likewise, the Southern Giant Curled derived line (PWGCS) was selected from the same initial Southern Giant Curled population and selfed to fix the traits.

TABLE 3

| Edited Alleles | | |
|---|---|---|
| Variety | Allele | SEQ ID NO: |
| PWRG-1 and PWRG-2 | edit_B04_cl1.3_left_and_B04_cl1.4_right_inversion_allele | 1 |
| | edit_B04_cl1.4_left_and_B04_cl1.5_right_inversion_allele | 2 |
| | edit_b_juncea_RG_v1-g7651_A03.1_rg | 3 |
| | edit_b_juncea_RG_v1-g80178_A02.1_rg | 8 |
| | edit_b_juncea_RG_v1-g80180_A02.2_rg | 9 |
| | edit_b_juncea_RG_v1-g80911_A01.1_rg | 10 |
| | edit_b_juncea_RG_v1-g88368_A09.1_rg | 11 |
| | edit_b_juncea_RG_v1-g96045_B04_cl2.1_rg | 12 |
| | edit_b_juncea_RG_v1-g96130_A02.4_rg | 13 |
| | edit_b_juncea_RG_v1-g101256_B07.1 | 14 |
| | edit_b_juncea_RG_v1-g80182_A02.3_rg | 15 |
| PWRG-1 | PWRG-1 edit_b_juncea_RG_v1-g51405_A09_cl2.1_rg | 16 |
| | PWRG-1-edit_b_juncea_RG_v1-g51407_A09_cl2.2_rg | 17 |
| | PWRG-1 edit_b_juncea_RG_v1-g51409_A09_cl2.3_rg | 18 |
| | PWRG-1 edit_b_juncea_RG_v1-g64202_B05 | 19 |
| PWRG-2 | edit_b_juncea_RG_v1-g51405_A09_cl2.1_rg | 4 |
| | edit_b_juncea_RG_v1-g51407_A09_cl2.2_rg | 5 |

TABLE 3-continued

| Edited Alleles | | |
|---|---|---|
| Variety | Allele | SEQ ID NO: |
| | PWRG-2 edit_b_juncea_RG_v1-g51409_A09_cl2.3_rg | 6 |
| | edit_b_juncea_RG_v1-g64202_B05 | 7 |
| PWSGC | edit_Southern_Giant_Curled--PW-D0853--b_juncea_RG_v1-g80178_A02.1_rg--A02.2_rg_inversion-allele-5prime extraction | 20 |
| | edit_Southern_Giant_Curled--PW-D0853--b_juncea_RG_v1-g80180_A02.2_rg--A02.1_rg_inversion_allele-3prime extraction | 21 |
| | edit_Southern_Giant_Curled--PW-D0853--b_juncea_RG_v1-g20529_B04_cl1.6rg--utg0000841_699955-709790 | 22 |
| | edit_Southern_Giant_Curled--PW-D0853--b_juncea_RG_v1-g20530_B04_cl1.1rg--utg0000841_712441-718888 | 23 |
| | edit_Southern_Giant_Curled--PW-D0853--b_juncea_RG_v1-g80182_A02.3_rg--utg0004541_64365-71109 | 24 |
| | edit_Southern_Giant_Curled--PW-D0853--b_juncea_RG_v1-g88368_A09.1_rg--utg0005391_989053-996014 | 25 |
| | edit_Southern_Giant_Curled--PW-D0853--b_juncea_RG_v1-g96045_B04_c12.1_rg--utg0006581_264170-270900 | 26 |
| | edit_Southern_Giant_Curled--PW-D0853--b_juncea_RG_v1-g96130_A02.4_rg--utg0006591_299567-306289 | 27 |

Table 4 provides the wild-type sequence for the targeted loci in the *Brassica juncea* varieties of Red Giant and Southern Giant Curled.

TABLE 4

| Wild-type Alleles | | |
|---|---|---|
| Variety | Allele | SEQ ID NO: |
| Red Giant | b_juncea_RG_v1-g7651_A03.1_rg | 28 |
| | b_juncea_RG_v1-g20528_B04_cl1.5rg | 29 |
| | b_juncea_RG_v1-g20529_B04_cl1.6rg | 30 |
| | b_juncea_RG_v1-g20530_B04_cl1.1rg | 31 |
| | b_juncea_RG_v1-g20532_B04_cl1.2rg | 32 |
| | b_juncea_RG_v1-g20534_B04_cl1.3rg | 33 |
| | b_juncea_RG_v1-g20564_B04_cl1.4rg | 34 |
| | b_juncea_RG_v1-g51405_A09_cl2.1_rg | 35 |
| | b_juncea_RG_v1-g51407_A09_cl2.2_rg | 36 |
| | b_juncea_RG_v1-g51409_A09_cl2.3_rg | 37 |
| | b_juncea_RG_v1-g64202_B05 | 38 |
| | b_juncea_RG_v1-g80178_A02.1_rg | 39 |
| | b_juncea_RG_v1-g80180_A02.2_rg | 40 |
| | b_juncea_RG_v1-g80182_A02.3_rg | 41 |
| | b_juncea_RG_v1-g80911_A01.1_rg | 42 |
| | b_juncea_RG_v1-g88368_A09.1_rg | 43 |
| | b_juncea_RG_v1-g96045_B04_cl2.1_rg | 44 |
| | b_juncea_RG_v1-g96130_A02.4_rg | 45 |
| | b_juncea_RG_v1-g101256_B07.1 | 46 |
| Southern Giant Curled | Southern_Giant_Curled--PW-D0853--b_juncea_RG_v1-g80911_A01.1_rg--utg0004611_128774-135457 | 47 |
| | Southern_Giant_Curled--PW-D0853--b_juncea_RG_v1-g101256_B07.1--utg0007741_235238-241971 | 48 |
| | Southern_Giant_Curled--PW-D0853--b_juncea_RG_v1-g96045_B04_cl2.1_rg--utg0006581_264170-270900 | 49 |
| | Southern_Giant_Curled--PW-D0853--b_juncea_RG_v1-g51409_A09_cl2.3_rg--utg0002511_961204-967841 | 50 |
| | Southern_Giant_Curled--PW-D0853--b_juncea_RG_v1-g51405_A09_cl2.1_rg--utg0002511_919371-926009 | 51 |
| | Southern_Giant_Curled--PW-D0853--b_juncea_RG_v1-g51407_A09_cl2.2_rg--utg0002511_939341-945968 | 52 |
| | Southern_Giant_Curled--PW-D0853--b_juncea_RG_v1-g20564_B04_cl1.4rg--utg0000841_832864-839391 | 53 |

TABLE 4-continued

| Wild-type Alleles | | |
|---|---|---|
| Variety | Allele | SEQ ID NO: |
| | Southern_Giant_Curled--PW-D0853--b_juncea_RG_v1-g20528_B04_cl1.5rg--utg0000841_690282-699408 | 54 |
| | Southern_Giant_Curled--PW-D0853--b_juncea_RG_v1-g20529_B04_cl1.6rg--utg0000841_699955-709790 | 55 |
| | Southern_Giant_Curled--PW-D0853--b_juncea_RG_v1-g64202_B05--utg0003351_119899-126710 | 56 |
| | Southern_Giant_Curled--PW-D0853--b_juncea_RG_v1-g20530_B04_cl1.1rg--utg0000841_712441-718888 | 57 |
| | Southern_Giant_Curled--PW-D0853--b_juncea_RG_v1-g20534_B04_cl1.3rg--utg0000841_727954-734722 | 58 |
| | Southern_Giant_Curled--PW-D0853--b_juncea_RG_v1-g7651_A03.1_rg--utg0000351_776699-783501 | 59 |
| | Southern_Giant_Curled--PW-D0853--b_juncea_RG_v1-g20532_B04_cl1.2rg--utg0000841_721815-728306 | 60 |
| | Southern_Giant_Curled--PW-D0853--b_juncea_RG_v1-g88368_A09.1_rg--utg0005391_989053-996014 | 61 |

Myrosinase Path. Lead $E_0$ candidate events were first identified by cross comparative taste evaluations to wild-type and other edited $E_0$ material. Lead $E_0$ candidates were characterized by a consensus non-pungent taste assessment call across a total of three researchers. These edited events were subsequently vegetatively propagated and evaluated with a quantitative myrosinase activity assay via the measurement of glucose release as a result of hydrolysis of exogenously supplied sinigrin to leaf extracts. Seeds were harvested from the lead $E_0$ events and a large $E_1$ progeny screening was deployed to assess the heritability of the trait and to aid in the association of underlying loci to the biochemical evaluation of the trait. $E_1$ progeny were sampled at multiple time points for cross-comparative assessments of glucose release activity to identify candidates to continue forward on a product development path.

Figure 2:
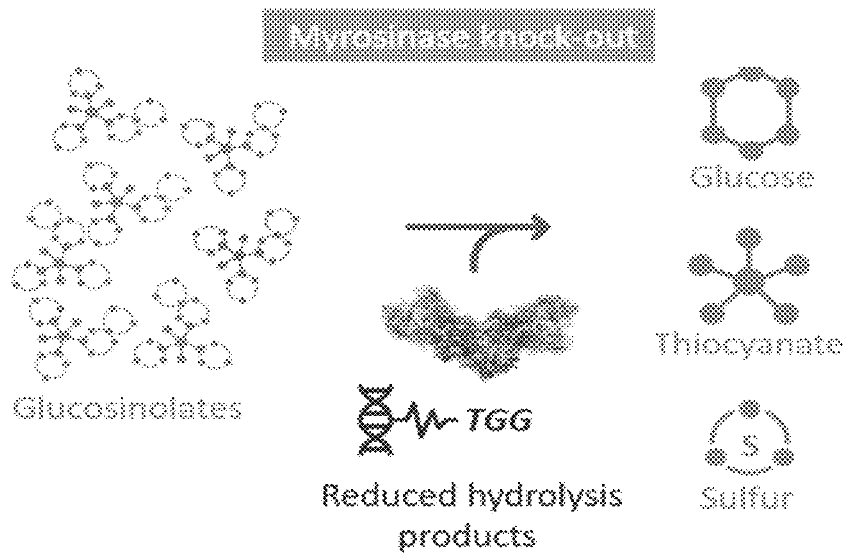
FIG. 2 provides a cartoon of an example strategy for reducing the pungency in a plant through myrosinase knockout. As shown, the end products may be used as a measure of the reduction in myrosinase activity and the reduction in pungency.
Figure 3:
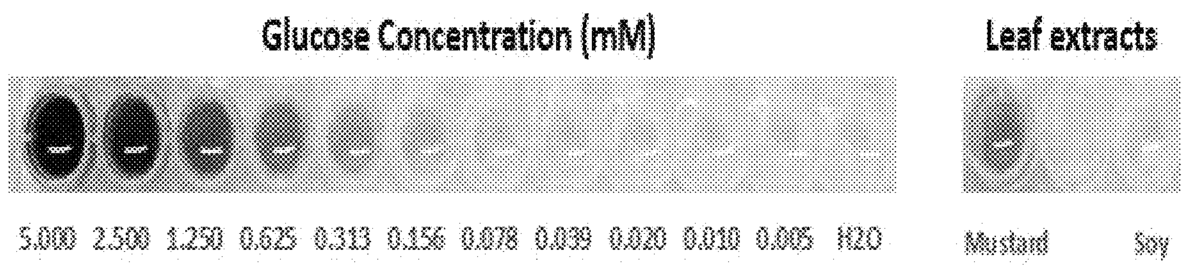
FIG. 3 illustrates colorimetric detection of myrosinase activity via detection of glucose. Range of glucose detection was prepared by evaluating a standard curve of various glucose concentrations. Leaf material (mustard) naturally containing myrosinase/glucosinolate reaction system (mustard) are compared with leaf material (soy) which lacks the reaction capabilities.

Functional Analysis of Edited Plants. Glucose is released as a product of the hydrolysis reaction of myrosinase with glucosinolate substrate. A relatively simple assay can be used to quantify the emittance of glucose as a rapid indicator of myrosinase activity as reported by Dosz et al., *J Agric Food Chem.* 62(32):8094-100 (2014)). As a control, myrosinase activity was tested via colorimetric detection of glucose as shown in FIG. 2 and FIG. 3. A range of glucose detection was prepared by evaluating a standard curve of various glucose concentrations. To demonstrate that released glucose was resultant from an endogenous myrosinase/glucosinolate reaction system, leaf material (mustard) naturally containing the enzymatic system were compared with leaf material (soy) which lacks the reaction capabilities.

Once the plant varieties were confirmed to comprise the intended disruption of myrosinases to reduce pungency in mustard greens, the colorimetric detection assay was used for cross-comparative analyses to measure, or semi-quantitate, the levels of detectable myrosinase activities (Table 5).

TABLE 5

Myrosinase activity for the edited plants

| CEID | Parental Cultivar | Generation | Days after planting | Glucose Release Assay |
|---|---|---|---|---|
| CE15785 | Red Giant | $E_0$ | 56 | NA |
| CE33147 (CE15785 clone) | Red Giant | $E_0$ | 18 | 0.07 |
| CE21573 | Southern Giant Curled | $E_0$ | 47 | 0.32 |
| Wild-type | Red Giant | | | |
| Wild-type | Southern Giant Curled | | | |

TABLE 6

Wild type GRA information:

| | | | | |
|---|---|---|---|---|
| CE42072 | Red Giant | WT | 19 | 1.51 |
| CE42072 | Red Giant | WT | 28 | 1.51 |
| CE42073 | Red Giant | WT | 19 | 2.17 |
| CE42073 | Red Giant | WT | 28 | 1.83 |
| CE42074 | Red Giant | WT | 19 | 1.92 |
| CE42074 | Red Giant | WT | 28 | 1.66 |
| CE42075 | Red Giant | WT | 19 | 1.82 |
| CE42077 | Red Giant | WT | 19 | 2.28 |
| CE42077 | Red Giant | WT | 28 | 1.76 |
| CE42078 | Red Giant | WT | 28 | 2.24 |
| CE42082 | Red Giant | WT | 36 | 2.04 |
| CE42082 | Red Giant | WT | 44 | 2.90 |
| CE42102 | Red Giant | WT | 36 | 2.61 |
| CE42102 | Red Giant | WT | 44 | 3.14 |
| CE42107 | Red Giant | WT | 36 | 2.62 |
| CE42107 | Red Giant | WT | 44 | 2.88 |
| CE42112 | Red Giant | WT | 36 | 2.29 |
| CE42112 | Red Giant | WT | 44 | 2.87 |
| CE42117 | Red Giant | WT | 36 | 2.49 |
| CE42117 | Red Giant | WT | 44 | 2.37 |
| CE42072 | Red Giant | WT | 19 | 1.51 |
| CE42072 | Red Giant | WT | 28 | 1.51 |
| CE42073 | Red Giant | WT | 19 | 2.17 |
| CE42073 | Red Giant | WT | 28 | 1.83 |
| CE42074 | Red Giant | WT | 19 | 1.92 |
| CE42074 | Red Giant | WT | 28 | 1.66 |
| CE42075 | Red Giant | WT | 19 | 1.82 |
| CE42077 | Red Giant | WT | 19 | 2.28 |
| CE42077 | Red Giant | WT | 28 | 1.76 |
| CE42078 | Red Giant | WT | 28 | 2.24 |
| CE42082 | Red Giant | WT | 36 | 2.04 |
| CE42082 | Red Giant | WT | 44 | 2.90 |

TABLE 6-continued

Wild type GRA information:

| | | | | |
|---|---|---|---|---|
| CE42102 | Red Giant | WT | 36 | 2.61 |
| CE42102 | Red Giant | WT | 44 | 3.14 |
| CE42107 | Red Giant | WT | 36 | 2.62 |
| CE42107 | Red Giant | WT | 44 | 2.88 |
| CE42112 | Red Giant | WT | 36 | 2.29 |
| CE42112 | Red Giant | WT | 44 | 2.87 |
| CE42117 | Red Giant | WT | 36 | 2.49 |
| CE42117 | Red Giant | WT | 44 | 2.37 |
| CE42024 | Southern Giant Curled | WT | 19 | 2.07 |
| CE42024 | Southern Giant Curled | WT | 28 | 2.63 |
| CE42025 | Southern Giant Curled | WT | 19 | 2.42 |
| CE42025 | Southern Giant Curled | WT | 28 | 2.08 |
| CE42026 | Southern Giant Curled | WT | 19 | 2.33 |
| CE42026 | Southern Giant Curled | WT | 28 | 2.01 |
| CE42027 | Southern Giant Curled | WT | 19 | 2.48 |
| CE42027 | Southern Giant Curled | WT | 28 | 2.66 |
| CE42028 | Southern Giant Curled | WT | 19 | 1.08 |
| CE42028 | Southern Giant Curled | WT | 28 | 2.33 |
| CE42048 | Southern Giant Curled | WT | 36 | 2.26 |
| CE42048 | Southern Giant Curled | WT | 44 | 3.55 |
| CE42052 | Southern Giant Curled | WT | 36 | 2.66 |
| CE42052 | Southern Giant Curled | WT | 44 | 2.97 |
| CE42062 | Southern Giant Curled | WT | 36 | 2.68 |
| CE42062 | Southern Giant Curled | WT | 44 | 3.06 |
| CE42066 | Southern Giant Curled | WT | 36 | 2.70 |
| CE42066 | Southern Giant Curled | WT | 44 | 3.10 |
| CE42071 | Southern Giant Curled | WT | 36 | 2.49 |
| CE42071 | Southern Giant Curled | WT | 44 | 2.89 |

The summarized call for each locus for an E0 plant was then paired with the associated quantitative glucose release assay absorbance value (GRA) measured on leaf sample collected from the same E0 plant. Lower GRA values are validated to be associated with lower myrosinase expression in the plant. Therefore, if a molecularly edited myrosinase locus is associated with lower GRA values, it can be inferred that the edited locus is also associated with less expression of myrosinase in the plant.

Field data were collected to characterize *Brassica juncea* varieties PWRG-1, PWRG-2, and PWSGC. Plants were at stage 42-45 days when the data were collected. Data were collected in June 2021 and February 2022 for PWRG-1 and PWRG-2 and February 2023 for PWSGC. Table 7 provides individual plant data for each variety.

TABLE 7

| Variety Description Information | | | | | |
|---|---|---|---|---|---|
| | PWRG-1 | | PWRG-2 | | PWSGC |
| Phenotype | June 2021 | February 2022 | June 2021 | February 2022 | February 2023 |
| Seed: Color[a] | Brown | Brown | Brown | Brown | Brown |
| Leaf: Shapea | Ovate | Ovate | Obovate | Ovate | Obovate |
| Leaf: Attitude[a] | Semi-Erect | Semi-Erect | Semi-Erect | Semi-Erect | Semi-Erect |
| Leaf: Length[b] | Long | Long | Long | Long | Long |
| Leaf: Width[b] | Medium | Medium | Broad | Broad | Broad |
| Leaf: Length of Petiole[a] | Medium | Medium | Medium | Medium | Long |
| Leaf: Width of Petiole[a] | Medium | Medium | Medium | Medium | Narrow |
| Leaf Blade: Size of Terminal Lobe[a] | NA | NA | NA | NA | Large |
| Leaf Blade: # of Lateral lobes[a] | NA | NA | NA | NA | Few |
| Leaf Blade: Pubescence on lower side[a] | Absent to Weak | Absent to Weak | Absent to Weak | Absent to Weak | Absent to Weak |
| Leaf Blade: Anthocyanin coloration[a] | Strong | Strong | Medium to Strong | Medium to Strong | NA |
| Leaf Blade: Intensity of Green Color[a] | NA | NA | NA | NA | Dark |
| Leaf Blade: Undulation of Margin[a] | Weak | Weak | Weak | Weak | Medium |
| Leaf Blade: Density of Incision of Margin[a] | Sparse to Medium | Sparse to Medium | Sparse to Medium | Sparse to Medium | Medium To Dense |
| Leaf Blade: Blistering[a] | Medium | Medium | Medium | Medium | Strong |
| Leaf Blade: Width of midrib at widest point[b] | Medium | Medium | Medium | Medium | Narrow |
| Stem: Type of main stem[a] | Oblong Type | Oblong Type | Oblong Type | Oblong Type | Oblong Type |
| Time to Beginning of Bolting[b] | Medium | Medium | Medium | Medium | Late |
| Time of Flowering[b] | Medium | Medium | Medium | Medium | Late |

[a]Visual observation;
[b]Visual observation based on measurements.

It is noted that PWRG-1 is different from PWRG-2 at several myrosinase loci (PWRG-1 (alleles SEQ ID NOs:1-3 and 8-19) and PWRG-2 (alleles SEQ ID NOs:1-15). Further, surface of the leaves of these two varieties differ in that PWRG-1 has a smoother leaf surface than PWRG-2, which has a more blistery leaf surface.

In addition to the varieties described herein, a breeder uses various methods to help determine which plants should be selected from segregating populations and ultimately which inbred lines will be used to develop hybrids for commercialization. In addition to knowledge of the germplasm and plant genetics, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest.

Accordingly, in some aspects, the present invention provides a *Brassica juncea* plant, or a part thereof, comprising in its genome a combination of edited myrosinase genes, the combination of myrosinase genes comprising each of SEQ ID NOs:1-15 (PWRG-2), or each of SEQ ID NOs:1-3 and 8-19 (PWRG-1), or each of SEQ ID NOs:20-27. In other aspects, the present invention provides a *Brassica juncea* variety designated PWRG-1 comprising in its genome a combination of edited myrosinase genes, the combination of myrosinase genes comprising each of the nucleic acid sequences of SEQ ID NOs:1-3 and 8-19; a *Brassica juncea* variety designated PWRG-2 comprising in its genome a combination of edited myrosinase genes, the combination of myrosinase genes comprising each of the nucleic acid sequences of SEQ ID NOs:1-3 and 8-19 (PWRG-1); or a *Brassica juncea* variety designated PWSGC comprising in its genome a combination of edited myrosinase genes, the combination of myrosinase genes comprising each of each of the nucleic acid sequences of SEQ ID NOs:20-27. In addition to comprising the combination of myrosinase genes comprising each of SEQ ID NOs:1-15, PWRG-2 further comprises a deletion of the myrosinase genes B04_c11.1 (SEQ ID NO:31), B04_c11.2 (SEQ ID NO:32) and B04_c11.6 (SEQ ID NO:30). Accordingly, in some embodiments, PWRG-2 is devoid of the myrosinase genes having the nucleic acid sequences of SEQ ID NOs:30-32. Further, in addition to comprising the combination of myrosinase genes comprising each of SEQ ID NOs:1-3 and 8-19, PWRG-1 further comprises a deletion of the myrosinase genes B04_c11.1 (SEQ ID NO:31), B04_c11.2 (SEQ ID NO:32) and B04_c11.6 (SEQ ID NO:30). Accordingly, in some embodiments, PWRG-1 is devoid of the myrosinase genes having the nucleic acid sequences of SEQ ID NOs: 30-32.

Another aspect of the present invention provides a *Brassica juncea* seed designated PWRG-1, PWRG-2, or PWSGC. A further aspect of the invention provides a *Brassica juncea* plant, or a part thereof, produced by the seed of the *Brassica juncea* variety PWRG-1, PWRG-2, or PWSGC. In yet a further aspect, the invention provides a leaf of a *Brassica juncea* plant produced by the seed of the *Brassica juncea* variety PWRG-1, PWRG-2, or PWSGC.

Another aspect of the invention provides pollen or an ovule of a *Brassica juncea* plant produced by the seed of PWRG-1, PWRG-2, or PWSGC. In some aspects, the present invention provides a *Brassica juncea* plant, or a part thereof, wherein at least one ancestor of said *Brassica juncea* plant is the *Brassica juncea* plant of the present invention. In addition, the present invention provides a *Brassica juncea* plant, or a part thereof, produced by the seed of PWRG-1, PWRG-2, or PWSGC or having at least one ancestor that is PWRG-1, PWRG-2, or PWSGC, optionally wherein the *Brassica juncea* plant further comprises a nucleic acid conferring male sterility.

The present invention additionally provides a *Brassica juncea* plant, or a part thereof, having all the morphological and physiological characteristics of *Brassica juncea* variety PWRG-1, PWRG-2, or PWSGC. In other aspects of the invention, the *Brassica juncea* plant, or a part thereof, having all the morphological and physiological characteristics of *Brassica juncea* variety PWRG-1, PWRG-2, or PWSGC, may further comprise a nucleic acid conferring male sterility.

Further provided is a tissue culture of regenerable cells of the plant, or part thereof, of the present invention, which culture regenerates *Brassica juncea* plants capable of expressing all the morphological and physiological characteristics of *Brassica juncea* variety PWRG-1, PWRG-2, or PWSGC. Regenerable cells of the invention may include but are not limited to cells from leaves, pollen, embryos, cotyledons, hypocotyls, roots, root tips, anthers, pods, flowers and a part thereof, ovules, shoots, stems, stalks, pith and capsules or callus or protoplasts derived therefrom. Thus, another aspect of this invention provides cells, which upon growth and differentiation produce *Brassica juncea* plants having the morphological and physiological characteristics of *Brassica juncea* variety PWRG-1, PWRG-2, or PWSGC. In some aspects, the *Brassica juncea* plant regenerated from the tissue culture may further comprises a nucleic acid conferring male sterility. In some aspects, the present invention provides cells of *Brassica juncea* variety PWRG-1, PWRG-2, or PWSGC. In some aspects, cells of variety PWRG-1, PWRG-2, or PWSGC may be transformed genetically, for example with one or more nucleic acids described herein, and transgenic plants of *Brassica juncea* variety PWRG-1, PWRG-2, or PWSGC are may be regenerated therefrom.

Additionally, a trait may be obtained by breeding a *Brassica juncea* comprising at least one transgene/POI with PWRG-1, PWRG-2, and/or PWSGC.

Such transgenes are expressed under control of regulatory sequences (e.g., promoters, enhancers, intervening sequences, terminators) well-known in the art and as described herein.

In some aspects, the present invention provides genomic DNA isolated from *Brassica juncea* variety PWRG-1, PWRG-2, or PWSGC. In some aspects, the genomic DNA isolated from *Brassica juncea* variety PWRG-1 may comprise a combination of edited myrosinase genes, the combination of edited myrosinase genes being SEQ ID NOs:1-3 and 8-19 (SEQ ID NOs:1, 2, 3, 4, 8, 9, 10, 11, 12, 13, 14, 15, 16, 17, 18, and 19). In some aspects, the genomic DNA isolated from *Brassica juncea* variety PWRG-2 may comprise a combination of edited myrosinase genes, the combination of edited myrosinase genes being SEQ ID NOs:1-15 (SEQ ID NOs:1, 2, 3, 4, 5, 6, 7, 8, 9, 10, 11, 12, 13, 14, and 15). In some aspects, the genomic DNA isolated from *Brassica juncea* variety PWSGC comprises in its genome a combination of edited myrosinase genes, the combination of edited myrosinase genes comprising each of SEQ ID NO:20-27 (SEQ ID NOs:20, 21, 22, 23, 24, 25, 26, and 27).

PWRG-1, PWRG-2, or PWSGC have each shown uniformity and stability within the limits of environmental influence for all the traits as described in the Variety Description Information (Table 6). A sufficient number of generations have been observed for each variety with careful attention paid to uniformity of plant type to ensure the homozygosity and phenotypic stability necessary for commercial production. No variant traits have been observed or are expected in PWRG-1, PWRG-2, or PWSGC.

Other Aspects of the Invention

The present invention also encompasses hybrid plants produced from *Brassica juncea* variety PWRG-1, PWRG-2, or PWSGC; *Brassica juncea* plants derived from PWRG-1, PWRG-2, or PWSGC; and PWRG-1, PWRG-2, or PWSGC plants comprising a nucleic acid that has been introduced therein by traditional breeding or genetic engineering techniques; and seeds, plant parts, and tissue cultures of the foregoing plants, as well as methods of producing the plants of the invention.

Accordingly, methods for crossing the *Brassica juncea* plants of the present invention are provided. Such methods may comprise crossing the plant of the present invention, PWRG-1, PWRG-2, or PWSGC, with itself or a second *Brassica juncea* plant. The present invention further encompasses a method for producing hybrid *Brassica juncea* seed, the method comprising crossing two *Brassica juncea* plants and harvesting the resultant hybrid *Brassica juncea* seed, wherein at least one *Brassica juncea* plant is the *Brassica juncea* plant of the present invention, PWRG-1, PWRG-2, or PWSGC. In some aspects, a method for producing a first generation ($E_1$) hybrid *Brassica juncea* seed is provided comprising crossing the plant of the present invention with a different *Brassica juncea* plant and harvesting the resultant first generation ($E_1$) hybrid *Brassica juncea* seed. Further provided by the present invention are seeds produced by these methods and plants or parts thereof grown from the seeds.

Additionally provided, is a method for producing a PWRG-1-, PWRG-2-, or PWSGC-derived *Brassica juncea* plant comprising: (a) crossing *Brassica juncea* variety PWRG-1, PWRG-2, or PWSGC with a second *Brassica juncea* plant to yield progeny *Brassica juncea* seed; (b) growing said progeny *Brassica juncea* seed, under plant growth conditions, to yield said PWRG-1-, PWRG-2-, or PWSGC-derived *Brassica juncea* plant. The method may still further comprise: a) crossing said PWRG-1-, PWRG-2-, or PWSGC-derived *Brassica juncea* plant with itself or another *Brassica juncea* plant to yield additional PWRG-1, PWRG-2, or PWSGC-derived progeny seed; (b) growing said progeny seed of step (a) under plant growth conditions, to yield additional PWRG-1, PWRG-2, or PWSGC-derived *Brassica juncea* plants; and (c) repeating the crossing and growing steps of (a) and (b) multiple times, e.g., 0 to 7 times, to generate further PWRG-1, PWRG-2, or PWSGC-derived *Brassica juncea* plants. In some aspects, the crossing and growing steps of (a) and (b) in step (c) are repeated from 0 to 2 times, from 0 to 3 times, from 0 to 4 times, 0 to times, from 0 to 6 times, from 0 to 7 times, from 0 to 8 times, from 0 to 9 times or from 0 to times, in order to generate further PWRG-1, PWRG-2, or PWSGC-derived *Brassica juncea* plants. In other aspects, the crossing and growing steps of (a) and (b) in step (c) are repeated from 0 to n times in order to generate further PWRG-1, PWRG-2, or PWSGC-derived

*Brassica juncea* plants. The invention further provides plants produced by these methods. Accordingly, the invention encompasses progeny plants and parts thereof with at least one ancestor that is a hybrid *Brassica juncea* PWRG-1, PWRG-2, or PWSGC plant and more specifically where the pedigree of this progeny includes 1, 2, 3, 4, 5, 6, and/or 7 cross pollinations to a *Brassica juncea* PWRG-1, PWRG-2, or PWSGC plant or a plant that has PWRG-1, PWRG-2, or PWSGC as a progenitor.

Other aspects of the present invention provide a method for producing a *Brassica juncea* plant that contains in its genetic material one or more transgenes, comprising crossing the *Brassica juncea* plant of the present invention with either a second plant of another *Brassica juncea* line, or a non-transformed *Brassica juncea* plant of the present invention, wherein progeny are produced, so that the genetic material of the progeny that result from the cross comprises the transgene(s) operably linked to one or more regulatory elements. In one aspect of the invention, the one or more transgenes include but are not limited to a nucleic acid conferring herbicide resistance, insect resistance, disease resistance (e.g., bacterial, fungal or viral resistance) and/or male sterility. Further provided by the present invention are plants produced by this method. As used herein, the term "resistance" and the term "tolerance" refer to the ability of a plant to withstand exposure to an insect, a disease or pathogen, an herbicide or other agent or condition (abiotic or biotic). A resistant or tolerant plant variety will have a level of resistance or tolerance, respectively, that is higher than a comparable wild-type variety grown under the same environmental conditions, optionally at least about 10% to about 99% (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or any range or value therein) or higher (or increased over) than a comparable wild-type variety grown under the same environmental conditions.

Also provided is a method for producing *Brassica juncea* seed by growing the *Brassica juncea* variety PWRG-1, PWRG-2, or PWSGC to produce seed and harvesting said seed. In some aspects, the PWRG-1, PWRG-2, or PWSGC plant is grown in a greenhouse, tent, in an open field or environmental chamber, such as, for example, a controlled environmental chamber.

Further provided is a method for developing a *Brassica juncea* plant in a *Brassica juncea* plant breeding program using plant breeding techniques, which include employing a *Brassica juncea* plant of the present invention, or a part thereof, as the source of plant breeding material. Plant breeding techniques that can be used in the method include, but are not limited to, recurrent selection, backcrossing, pedigree breeding, restriction fragment length polymorphism enhanced selection, genetic marker enhanced selection, double haploid breeding, single seed descent, multiple seed descent, and/or transformation. Further provided are plants produced by this method.

The present invention also provides a method for obtaining a *Brassica juncea* inbred line by planting a collection of seed comprising seed of a hybrid, one of whose parent is the *Brassica juncea* variety PWRG-1, PWRG-2, or PWSGC, said collection also comprising seed of said inbred line; growing *Brassica juncea* plants from said collection of seeds; identifying an inbred plant from said inbred line; selecting said inbred plant; and controlling pollination in a manner which preserves the homozygosity of said inbred plant. In some aspects, one parent of the inbred plant has all the physiological and morphological characteristics of *Brassica juncea* variety PWRG-1, PWRG-2, or PWSGC.

At least one aspect provides a method of producing a double haploid variety (a) isolating a flower bud of the $E_1$ plant of as provided herein, (b) dissecting out a haploid microspore; (c) placing the haploid microspore in culture; (d) inducing the microspore to differentiate into an embryo and subsequently into a plantlet; (e) identifying, whether the plantlet contains a diploid chromosome number, wherein the diploid chromosome number occurred through chromosome doubling; and continuing to grow the plantlet if it contains a diploid chromosome number.

Also provided herein is a method of reducing pungency in a *B. juncea* plant or part thereof comprising editing one or more myrosinase alleles in the *B. juncea* plant or part thereof, wherein the edits result in a plant or part thereof comprising each of nucleotide sequences of SEQ ID NOs: 1-15, or comprising each of the nucleotide sequences of SEQ ID NOs:1-3 and 8-19, or comprising each of the nucleotide sequences of SEQ ID NOs:20-27.

Further provided is a method of reducing pungency in a *B. juncea* plant or part thereof comprising crossing a *B. juncea* plant comprising each of nucleotide sequences of SEQ ID NOs:1-15 (e.g., PWRG-2) with a *B. juncea* plant that is not edited as described herein to produce progeny plants comprising one or more (e.g., 1, 2, 3, 4, 5, 6, 7, 8, 9, 10, 11, 12, 13, 14, or 15) of the nucleotide sequences of SEQ ID NOs:1-15 (e.g., one or more of SEQ ID NO:1, 2, 3, 4, 5, 6, 7, 8, 9, 10, 11, 12, 13, 14, or 15).

Additionally provided is a method of breeding a *B. juncea* plant or part thereof comprising crossing a *B. juncea* plant comprising each of nucleotide sequences of SEQ ID NOs: 1-15 (e.g., PWRG-2) with a *B. juncea* plant that is not edited as described herein to produce progeny plants comprising one or more (e.g., 1, 2, 3, 4, 5, 6, 7, 8, 9, 10, 11, 12, 13, 14, or 15) of the nucleotide sequences of SEQ ID NOs:1-15 (e.g., one or more of SEQ ID NO:1, 2, 3, 4, 5, 6, 7, 8, 9, 10, 11, 12, 13, 14, or 15).

Also provided herein is a method of reducing pungency in a *B. juncea* plant or part thereof comprising crossing a *B. juncea* plant comprising each of nucleotide sequences of SEQ ID NOs:1-3 and 8-19 (e.g., PWRG-1) with a *B. juncea* plant that is not edited as described herein to produce progeny plants comprising one or more (e.g., 1, 2, 3, 4, 5, 6, 7, 8, 9, 10, 11, 12, 13, 14, or 15) of the nucleotide sequences of SEQ ID NOs:1-3 and 8-19 (e.g., one or more of SEQ ID NO:1, 2, 3, 8, 9, 10, 11, 12, 13, 14, 15, 16, 17, 18, or 19).

Further provided is a method of breeding a *B. juncea* plant or part thereof comprising crossing a *B. juncea* plant comprising each of nucleotide sequences of SEQ ID NOs:1-3 and 8-19 (e.g., PWRG-1) with a *B. juncea* plant that is not edited as described herein to produce progeny plants comprising one or more (e.g., 1, 2, 3, 4, 5, 6, 7, 8, 9, 10, 11, 12, 13, 14, or 15) of the nucleotide sequences of SEQ ID NOs:1-3 and 8-19 (e.g., one or more of SEQ ID NO:1, 2, 3, 8, 9, 10, 11, 12, 13, 14, 15, 16, 17, 18, or 19).

Additionally provided is a method of reducing pungency in a *B. juncea* plant or part thereof comprising crossing a *B. juncea* plant comprising each of nucleotide sequences of SEQ ID NOs:20-27 (e.g., PWSGC) with a *B. juncea* plant that is not edited as described herein to produce progeny plants comprising one or more (e.g., 1, 2, 3, 4, 5, 6, 7, or 8) of the nucleotide sequences of SEQ ID NOs:20-27 (e.g., one or more of SEQ ID NO:20, 21, 22, 23, 24, 25, 26, or 27).

Further provided is a method of breeding a *B. juncea* plant or part thereof comprising crossing a *B. juncea* plant comprising each of nucleotide sequences of SEQ ID NOs:1-15 (e.g., PWSGC) with a *B. juncea* plant that is not edited as described herein to produce progeny plants comprising one or more (e.g., 1, 2, 3, 4, 5, 6, 7, or 8) of the nucleotide sequences of SEQ ID NOs:20-27 (e.g., one or more of SEQ ID NO:20, 21, 22, 23, 24, 25, 26, or 27).

Accordingly, any methods using the variety PWRG-1, PWRG-2, or PWSGC are part of this invention: selfing, backcrosses, hybrid production, crosses to populations, and the like. All plants produced using the variety PWRG-1, PWRG-2, or PWSGC as a parent are within the scope of this invention including plants derived from the variety PWRG-1, PWRG-2, or PWSGC. Advantageously, PWRG-1, PWRG-2, or PWSGC cultures used in crosses with other *Brassica juncea* varieties can be used to produce a first generation ($E_1$) *Brassica juncea* hybrid seed and plants with superior characteristics, e.g., reduced pungency.

I. Evaluation of Plants for Homozygosity and Phenotypic Stability

It is desirable and advantageous for a *Brassica juncea* variety to be highly homogeneous, homozygous and phenotypically uniform and stable for use as a commercial cultivar. In the case of inbreds or other lines, there are many analytical methods available to determine the homozygotic and phenotypic stability of the variety.

The oldest and most traditional method of analysis is the observation of phenotypic traits. The data are usually collected in field experiments over the life of the *Brassica juncea* plants to be examined. Phenotypic characteristics most often observed are for traits associated with seed color, seed yield, time to flowering, time to beginning of bolting, disease resistance, maturity, plant height, stem type, internode distance, flower color, leaf color, leaf yield, leaf size and shape, leaf angle, lamina-midrib ratio, and concentration of chemical components such as allyl isothiocyanate.

In addition to phenotypic observations, the genotype of a plant can also be examined. There are many laboratory-based techniques available for the analysis, comparison and characterization of plant genotypes; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The presence or absence of a marker in the plant genotype may be determined by any method known in the art. For example, the marker sequence (or its complement) may be used as a hybridization probe, e.g., for Southern or in situ analysis of genomic DNA. Typically, however, due to greater ease and sensitivity, an amplification method, such as PCR will be used to detect the presence or absence of the marker in the plant genotype.

Molecular markers can be used in any method of nucleic acid amplification known in the art. Such methods include but are not limited to Polymerase Chain Reaction (PCR; described in U.S. Pat. Nos. 4,683,195; 4,683,202; 4,800,159; 4,965,188), Strand Displacement Amplification (SDA; described by G. Walker et al., *Proc. Nat. Acad. Sci. USA* 89: 392 (1992); G. Walker et al., *Nucl. Acids Res.* 20: 1691 (1992); U.S. Pat. No. 5,270,184), thermophilic Strand Displacement Amplification (tSDA; EP 0 684 315 to Frasier et al.), Self-Sustained Sequence Replication (3SR; J. C. Guatelli et al., *Proc Natl. Acad. Sci. USA* 87: 1874-78 (1990)), Nucleic Acid Sequence-Based Amplification (NASBA; U.S. Pat. No. 5,130,238 to Cangene), the Qβ replicase system (P. Lizardi et al., *BioTechnology* 6: 1197 (1988)), or transcription based amplification (D. Y. Kwoh et al., *Proc. Natl. Acad. Sci. USA* 86: 1173-77 (1989)).

II. Transfer of Traits into *Brassica juncea* Variety PWRG-1, PWRG-2, or PWSGC Genetic variants of PWRG-1, PWRG-2, or PWSGC that are naturally-occurring or created through traditional breeding methods using variety PWRG-1, PWRG-2, or PWSGC are also intended to be within the scope of this invention. In particular aspects, the invention encompasses plants of variety PWRG-1, PWRG-2, or PWSGC, and parts thereof, further comprising one or more additional traits, in particular, specific, single gene transferred traits. Examples of traits that may be transferred include, but are not limited to, herbicide resistance, disease resistance (e.g., bacterial fungal or viral disease), nematode resistance, tolerance to abiotic stresses (e.g., drought, temperature, salinity), yield enhancement, improved nutritional quality (e.g., oil starch and protein content or quality), altered chemical composition (e.g., nicotine, secondary alkaloids, total alkaloids, reducing sugars), improved leaf characteristics (color, shape, size, number, angle), altered reproductive capability (e.g., male sterility) or other agronomically important traits.

Such traits may be introgressed into variety PWRG-1, PWRG-2, or PWSGC from another *Brassica juncea* variety or may be directly transformed into variety PWRG-1, PWRG-2, or PWSGC (discussed below). One or more new traits may be transferred to variety PWRG-1, PWRG-2, or PWSGC, or, alternatively, one or more traits of variety PWRG-1, PWRG-2, or PWSGC may be altered or substituted. The introgression of a trait(s) into variety PWRG-1, PWRG-2, or PWSGC may be achieved by any method of plant breeding known in the art, for example, pedigree breeding, backcrossing, doubled-haploid breeding, and the like.

The laboratory-based techniques described above, in particular RFLP and SSR, can be used in such backcrosses to identify the progenies having the highest degree of genetic identity with the recurrent parent. This permits one to accelerate the production of *Brassica juncea* varieties having at least 90% genetic identity, optionally having at least 95%, or at least 99% genetic identity, with the recurrent parent, and further comprising the trait(s) introgressed from the donor parent. Such determination of genetic identity can be based on molecular markers used in the laboratory-based techniques described above.

The last backcross generation can be selfed to give pure breeding progeny for the nucleic acid(s) being transferred. The resulting plants generally have essentially all of the morphological and physiological characteristics of variety PWRG-1, PWRG-2, or PWSGC, in addition to the transferred trait(s) (e.g., one or more single gene traits). The exact backcrossing protocol will depend on the trait being altered to determine an appropriate testing protocol.

Those skilled in the art will appreciate that the *Brassica juncea* nucleic acids described below in connection with *Brassica juncea* plants produced by genetic engineering techniques may also be introduced into variety PWRG-1, PWRG-2, or PWSGC by conventional breeding methods.

III. Transformation of *Brassica juncea*

With the advent of molecular biological techniques that have allowed the isolation and characterization of nucleic acids that encode specific protein products, scientists in the field of plant biology developed a strong interest in engineering the genome of plants to contain and express foreign nucleic acids, or additional, or modified versions of native or endogenous nucleic acids (perhaps driven by different promoters) in order to alter the traits of a plant in a specific manner. Such foreign, additional and/or modified nucleic acids are referred to herein collectively as "transgenes." The term "transgene," as used herein, is not necessarily intended to indicate that the foreign nucleic acid is from a different plant species. For example, the transgene may be a particular allele derived from another *Brassica juncea* line or may be an additional copy of an endogenous gene. Over the last twenty to twenty-five years several methods for producing transgenic plants have been developed. Therefore, in particular aspects, the present invention also encompasses transformed versions of the *Brassica juncea* variety PWRG-1, PWRG-2, or PWSGC.

In general, methods to transform, modify, edit or alter plant endogenous genomic DNA include altering the plant native DNA sequence or introducing a pre-existing transgenic sequence including regulatory elements, coding and non-coding sequences. Genetic transformation methods include introduction of foreign or heterologous sequences and genome editing techniques which modify the native sequence. Transformation methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes (see, e.g., WO 2009/114321; Gao et al., *Plant Journal* 1:176-187 (2010)). Another site-directed engineering method is through the use of zinc finger domain recognition coupled with the restriction properties of restriction enzyme. See, e.g., Urnov et al., *Nat. Rev. Genet.* 11(9):636-46 (2010); Shukla et al., *Nature* 459 (7245):437-41 (2009). A transcription activator-like (TAL) effector-DNA modifying enzyme (TALE or TALENT is also used to engineer changes in plant genome. See, e.g., US 2011/0145940, Cermak et al., *Nucleic Acids Res.* 39(12):e82 (2011) and Boch et al., *Science* 326(5959):1509-12 (2009). Site-specific modification of plant genomes can also be performed using the bacterial type II CRISPR (clustered regularly interspaced short palindromic repeats)/Cas (CRISPR-associated) system. See, e.g., Belhaj et al., *Plant Methods* 9:39 (2013); the Cas9/guide RNA-based system allows targeted cleavage of genomic DNA guided by a customizable small noncoding RNA in plants (see, e.g., WO 2015/026883A1).

In some aspects, plant transformation involves the construction of an expression vector that will function in plant cells. Such a vector comprises DNA or RNA comprising a nucleic acid under control of, or operatively linked to, a regulatory element (for example, a promoter). The expression vector may contain one or more such operably linked nucleic acid/regulatory element combinations. The vector(s) may be in the form of, for example, a plasmid or a virus, and can be used, alone or in combination with other vectors, to provide transformed *Brassica juncea* plants, using transformation methods as described below to incorporate transgenes into the genetic material of the *Brassica juncea* plant(s).

Any transgene(s) known in the art may be introduced into a *Brassica juncea* plant, tissue, cell or protoplast according to the present invention, e.g., to improve commercial or agronomic traits, herbicide resistance, disease resistance (e.g., to a bacterial, fungal, or viral disease), insect resistance, nematode resistance, yield enhancement, nutritional quality (e.g., oil starch and protein content or quality), leaf characteristics (color, shape, size, number, angle), and altered reproductive capability (e.g., male sterility) or chemical composition (e.g., nicotine, total alkaloids, reducing sugars). Alternatively, a transgene may be introduced for the production of recombinant proteins (e.g., enzymes) or metabolites.

In particular aspects of the invention, a transgene conferring herbicide resistance, insect resistance, bacterial disease resistance, fungal disease resistance, or viral disease resistance is introduced into the *Brassica juncea* plant. Alternatively, a transgene conferring male sterility is introduced.

A. Expression Vectors for *Brassica juncea* Transformation

1. Genetic Markers

Expression vectors typically include at least one genetic marker, operably linked to a regulatory element (a promoter, for example) that allows transformed cells containing the marker to be either recovered by negative selection, i.e., inhibiting growth of cells that do not contain the selectable marker, or by positive selection, i.e., screening for the product encoded by the genetic marker. Many commonly used selectable marker for plant transformation are well known in the transformation art, and include, for example, nucleic acids that code for enzymes that metabolically detoxify a selective chemical agent which may be an antibiotic or a herbicide, or nucleic acids that encode an altered target which is insensitive to the inhibitor. A few positive selection methods are also known in the art.

One commonly used selectable marker for plant transformation is neomycin phosphotransferase II (npfII), isolated from transposon Tn5, which when placed under the control of plant regulatory signals confers resistance to kanamycin (Fraley et al., *Proc. Natl. Acad. Sci. U.S.A.* 80: 4803 (1983)). Another commonly used selectable marker is hygromycin phosphotransferase, which confers resistance to the antibiotic hygromycin (Vanden Elzen et al., *Plant Mol. Biol.* 5:299 (1985)).

Additional selectable markers of bacterial origin that confer resistance to antibiotics include gentamycin acetyl transferase, streptomycin phosphotransferase, aminoglycoside-3'-adenyl transferase, the bleomycin resistance determinant (Hayford et al., *Plant Physiol.* 86:1216 (1988); Jones et al., *Mol. Gen. Genet.,* 210:86 (1987); Svab et al., *Plant Mol. Biol.* 14:197 (1990); Hille et al., *Plant Mol. Biol.* 7:176 (1986)). Other selectable markers confer resistance to herbicides such as glyphosate, glufosinate or bromoxynil (Comai et al., *Nature* 317:741 (1985); Gordon-Kamm et al., *Plant Cell* 2:603 (1990); and Stalker et al., *Science* 242:419 (1988)).

Selectable markers for plant transformation that are not of bacterial origin include, for example, mouse dihydrofolate reductase, plant 5-eno/pyruvylshikimate-3-phosphate synthase and plant acetolactate synthase (Eichholtz et al.,

*Somatic Cell Mol. Genet.* 13:67 (1987); Shah et al., *Science* 233:478 (1986); Charest et al., *Plant Cell Rep.* 8:643 (1990)).

Another class of markers for plant transformation requires screening of presumptively transformed plant cells rather than direct genetic selection of transformed cells for resistance to a toxic substance such as an antibiotic. These markers are particularly useful to quantify or visualize the spatial pattern of expression in specific tissues and are frequently referred to as reporters because they can be fused to a nucleic acid or regulatory sequence for the investigation of nucleic acid expression. Commonly used reporters for screening presumptively transformed cells include β-glucuronidase (GUS), β-galactosidase, luciferase and chloramphenicol acetyltransferase (Jefferson, R. A., *Plant Mol. Biol. Rep.* 5:387 (1987); Teeri et al., *EMBO J* 8:343 (1989); Koncz et al., *Proc. Natl. Acad. Sci. U.S.A.* 84:131 (1987); De Block et al., *EMBO J.* 3:1681 (1984)).

In vivo methods for visualizing GUS activity that do not require destruction of plant tissue are also available (Molecular Probes Publication 2908, IMAGENE GREEN™, p. 1-4 (1993) and Naleway et al., *J. Cell Biol.* 115:15 (1991)). However, these in vivo methods for visualizing GUS activity have not proven useful for recovery of transformed cells because of low sensitivity, high fluorescent backgrounds, and limitations associated with the use of luciferase as a selectable marker.

In addition, a nucleic acid encoding Green Fluorescent Protein (GFP) has been utilized as a marker for nucleic acid expression in prokaryotic and eukaryotic cells (Chalfie et al., *Science* 263:802 (1994)). GFP and mutants of GFP may be used as screenable markers.

2. Promoters

Nucleic acids included in expression vectors are typically driven by a nucleotide sequence comprising a regulatory element, for example, a promoter. Several types of promoters are now well known in the transformation art, as are other regulatory elements that can be used alone or in combination with promoters.

As used herein, the term "promoter" refers to a region of a nucleotide sequence that incorporates the necessary signals for the efficient expression of a coding sequence. This may include sequences to which an RNA polymerase binds but is not limited to such sequences and can include regions to which other regulatory proteins bind together with regions involved in the control of protein translation and can also include coding sequences. A "plant promoter" is a promoter capable of initiating transcription in plant cells. Such promoters include those that drive expression of a nucleotide sequence constitutively, those that drive expression when induced, and those that drive expression in a tissue- or developmentally specific manner, as these various types of promoters are known in the art.

Constitutive Promoters. Thus, for example, in some aspects of the invention, a constitutive promoter can be used to drive the expression of a transgene in a plant cell. A constitutive promoter is an unregulated promoter that allows for continual transcription of its associated coding sequence. Thus, constitutive promoters are generally active under most environmental conditions, in most or all cell types and in most or all states of development or cell differentiation.

Any constitutive promoter functional in a plant can be utilized in the instant invention. Exemplary constitutive promoters include, but are not limited to, the promoters from plant viruses including, but not limited to, the 35S promoter from CaMV (Odell et al., *Nature* 313:810 (1985)); figwort mosaic virus (FMV) 35S promoter (P-FMV35S, U.S. Pat. Nos. 6,051,753 and 6,018,100); the enhanced CaMV35S promoter (e35S); the 1'- or 2'-promoter derived from T-DNA of *Agrobacterium tumefaciens*; the nopaline synthase (NOS) and/or octopine synthase (OCS) promoters, which are carried on tumor-inducing plasmids of *Agrobacterium tumefaciens* (Ebert et al., *Proc. Natl. Acad. Sci. U.S.A.,* 84:5745 5749 (1987); actin promoters including, but not limited to, rice actin (McElroy et al., *Plant Cell* 2:163 (1990); U.S. Pat. No. 5,641,876); histone promoters; tubulin promoters; ubiquitin and polyubiquitin promoters (Sun & Callis, *Plant J.,* 11(5):1017-1027 (1997)); Christensen et al., *Plant Mol. Biol* 12:619 (1989) and Christensen et al., *Plant Mol. Biol.* 18:675 (1992)); pEMU (Last et al., *Theor. Appl. Genet.* 81:581 (1991)); the mannopine synthase promoter (MAS) (Velten et al., *EMBO J.* 3:2723 (1984)); maize H3 histone (Lepelit et al., *Mol. Gen. Genet.* 231:276 (1992) and Atanassova et al., *Plant Journal* 2: 291 (1992)); the ALS promoter, a XbaI/NcoI fragment 5' to the *Brassica napus* ALS3 structural gene (or a nucleotide sequence that has substantial sequence similarity to said XbaI/NcoI fragment); ACT11 from *Arabidopsis* (Huang et al., *Plant Mol. Biol.* 33:125-139 (1996)); Cat3 from *Arabidopsis* (GENBANK Accession No. U43147, Zhong et al., *Mol. Gen. Genet.* 251:196-203 (1996)); GPc1 from maize (GENBANK Accession No. X15596, Martinez et al., *J. Mol. Biol.* 208: 551-565 (1989)); and Gpc2 from maize (GENBANK Accession No. U45855, Manjunath et al., *Plant Mol. Biol.* 33:97-112 (1997)).

Inducible Promoters. In some aspects of the present invention, an inducible promoter can be used to drive the expression of a transgene. Inducible promoters activate or initiate expression only after exposure to, or contact with, an inducing agent. Inducing agents include, but are not limited to, various environmental conditions (e.g., pH, temperature), proteins and chemicals. Examples of environmental conditions that can affect transcription by inducible promoters include pathogen attack, anaerobic conditions, extreme temperature and/or the presence of light. Examples of chemical inducing agents include, but are not limited to, herbicides, antibiotics, ethanol, plant hormones and steroids. Any inducible promoter that is functional in a plant can be used in the instant invention (see, Ward et al., *Plant Mol. Biol.* 22: 361 (1993)). Exemplary inducible promoters include, but are not limited to, that from the ACEI system, which responds to copper (Melt et al., *PNAS* 90:4567 (1993)); the ln2 nucleic acid from maize, which responds to benzenesulfonamide herbicide safeners (Hershey et al., (1991) *Mol. Gen. Genetics* 227:229 (1991) and Gatz et al., *Mol. Gen. Genetics* 243:32 (1994)); a heat shock promoter, including, but not limited to, the soybean heat shock promoters Gmhsp 17.5-E, Gmhsp 17.2-E and Gmhsp 17.6-L and those described in U.S. Pat. No. 5,447,858; the Tet repressor from Tn10 (Gatz et al., *Mol. Gen. Genet.* 227:229 (1991)) and the light-inducible promoter from the small subunit of ribulose bisphosphate carboxylase (ssRUBISCO). Other examples of inducible promoters include, but are not limited to, those described by Moore et al. (*Plant J.* 45:651-683 (2006)). Additionally, some inducible promoters respond to an inducing agent to which plants do not normally respond. An example of such an inducible promoter is the inducible promoter from a steroid hormone gene, the transcriptional activity of which is induced by a glucocorticosteroid hormone (Schena et al., *Proc. Natl. Acad. Sci. U.S.A.* 88: 421 (1991)).

Tissue-Specific or Tissue-Preferred Promoters. In further aspects of the present invention, a tissue-specific promoter can be used to drive the expression of a transgene in a particular tissue in the transgenic plant. Tissue-specific promoters drive expression of a nucleic acid only in certain tissues or cell types, e.g., in the case of plants, in the leaves, stems, flowers and their various parts, roots, fruits and/or seeds, etc. Thus, plants transformed with a nucleic acid of interest operably linked to a tissue-specific promoter produce the product encoded by the transgene exclusively, or preferentially, in a specific tissue or cell type.

Any plant tissue-specific promoter can be utilized in the instant invention. Exemplary tissue-specific promoters include, but are not limited to, a root-specific promoter, such as that from the phaseolin gene (Murai et al., *Science* 23:476 (1983) and Sengupta-Gopalan et al., *Proc. Natl. Acad. Sci. USA* 82:3320 (1985)); a leaf-specific and light-induced promoter such as that from cab or rubisco (Simpson et al. *EMBO J.* 4:2723 (1985) and Timko et al., *Nature* 318:579 (1985)); the fruit-specific E8 promoter from tomato (Lincoln et al., *Proc. Nat'l. Acad. Sci. USA* 84:2793-2797 (1988); Deikman et al. *EMBO J.* 7:3315-3320 (1988); Deikman et al., *Plant Physiol.* 100:2013-2017 (1992); seed-specific promoters of, for example, *Arabidopsis thaliana* (Krebbers et al., *Plant Physiol.* 87:859 (1988)); an anther-specific promoter such as that from LAT52 (Twell et al., *Mol. Gen. Genet.* 217:240 (1989)) or European Patent Application No 344029, and those described by Xu et al. (*Plant Cell Rep.* 25:231-240 (2006)) and Gomez et al. (*Planta* 219:967-981 (2004)); a pollen-specific promoter such as that from Zm13 (Guerrero et al., *Mol. Gen. Genet.* 224:161 (1993)), and those described by Yamaji et al. (*Plant Cell Rep.* 25:749-57 (2006)) and Okada et al. (*Plant Cell Physiol.* 46:749-802 (2005)); a pith-specific promoter, such as the promoter isolated from a plant TrpA gene as described in International PCT Publication No. WO 93/07278; and a microspore-specific promoter such as that from apg (Twell et al., *Sex. Plant Reprod.* 6: 217 (1993)). Exemplary green tissue-specific promoters include the maize phosphoenol pyruvate carboxylase (PEPC) promoter, small subunit ribulose bis-carboxylase promoters (ssRUBISCO) and the chlorophyll a/b binding protein promoters.

3. Signal Sequences for Targeting Proteins to Subcellular Compartments

Transport of proteins produced by transgenes to a subcellular compartment such as the chloroplast, vacuole, peroxisome, glyoxysome, cell wall or mitochondrion, or for secretion into the apoplast, may be accomplished by means of operably linking a nucleotide sequence encoding a signal sequence typically at the 5' and/or 3' region of a sequence encoding the protein of interest. Association of targeting sequences with the coding sequence may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art (see, for example, Becker et al., *Plant Mol. Biol.* 20:49 (1992); Close, P. S., Master's Thesis, Iowa State University (1993); Knox, et al., *Plant Mol. Biol.* 9:3 (1987); Lerner et al., *Plant Physiol.* 91:124 (1989); Fontes et al., *Plant Cell* 3:483 (1991); Matsuoka et al., *Proc. Natl. Acad. Sci.* 88:834 (1991); Gould et al., *J. Cell Biol* 108:1657 (1989); Creissen et al., *Plant J.* 2:129 (1991); Kalderon et al., *Cell* 39:499 (1984); Stiefel et al., *Plant Cell* 2:785 (1990)).

B. Foreign Nucleic Acids That May Be Introduced into *Brassica juncea* Plants With transgenic plants according to the present invention, nucleic acids of agronomic importance can be expressed in transformed plants. More particularly, plants can be genetically engineered to express various phenotypes of agronomic interest. Exemplary nucleic acids implicated in this regard include, but are not limited to, those described below.

As an example, a nucleic acid conferring male sterility may be transformed into variety PWRG-1, PWRG-2, or PWSGC. There are several methods of conferring genetic male sterility available, such as multiple mutant nucleic acids at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. Examples include: (A) Introduction of a deacetylase nucleic acid under the control of a tapetum-specific promoter and with the application of the chemical N-Ac-PPT (WO 01/29237). (B) Introduction of various stamen-specific promoters (WO 92/13956, WO 92/13957). (C) Introduction of the barnase and the barstar nucleic acids (Paul et al. *Plant Mol. Biol.* 19:611-622 (1992)). For additional examples of nuclear male and female sterility systems and nucleic acids, see also, Nikova et al., *Plant Cell, Tissue and Organ Culture* 27:289-295 (1991); Nikova et al., *Euphytica* 94:375-378 (1997); Atanassov et al., *Theoretical and Applied Genetics* 97:982-985 (1998); Berbec, A. *Bull. Spec. Coresta*, Lisbon Congress, p. 79, abstract AP30, (2000); U.S. Pat. Nos. 5,859,341; 6,297,426; 5,478,369; 5,824,524; 5,850,014; and 6,265,640; all of which are hereby incorporated by reference.

In an additional aspect, a transgene whose expression results or contributes to a desired trait to be transferred to variety PWRG-1, PWRG-2, or PWSGC comprises a nucleic acid encoding an insecticidal protein, such as, for example, a crystal protein of *Bacillus thuringiensis* or a vegetative insecticidal protein from *Bacillus cereus*, such as VIP3 (see, for example, Estruch et al., *Nat. Biotechnol.* 15:137 (1997)).

In a further aspect, a transgene introduced into variety PWRG-1, PWRG-2, or PWSGC comprises a nucleic acid conferring herbicide tolerance whose expression renders plants of variety PWRG-1, PWRG-2, or PWSGC tolerant to the herbicide. For example, expression of an altered acetohydroxyacid synthase (AHAS) enzyme confers upon plants tolerance to various imidazolinone or sulfonamide herbicides (U.S. Pat. No. 4,761,373). In a still further aspect, a nucleic acid conferring tolerance to imidazolinones or sulfonylurea herbicides is transferred into variety PWRG-1, PWRG-2, or PWSGC. Expression of a mutant acetolactate synthase (ALS) will render the plants resistant to inhibition by sulfonylurea herbicides (U.S. Pat. No. 5,013,659).

U.S. Pat. No. 4,975,374 describes plant cells and plants containing a nucleic acid encoding a mutant glutamine synthetase (GS) which confers resistance to herbicides that are known to inhibit GS, e.g., phosphinothricin and methionine sulfoximine. In addition, expression of a Streptomyces bar nucleic acid encoding a phosphinothricin acetyl transferase results in tolerance to the herbicide phosphinothricin or glufosinate (U.S. Pat. No. 5,489,520). U.S. Pat. No. 5,162,602 discloses plants tolerant to inhibition by cyclohexanedione and aryloxyphenoxypropanoic acid herbicides. The tolerance is conferred by an altered acetyl coenzyme A carboxylase (ACCase). U.S. Pat. No. 5,554,798 discloses transgenic glyphosate tolerant plants, which tolerance is conferred by an altered 5-enolpyruvyl-3-phosphoshikimate (EPSP) synthase nucleic acid. In another particular aspect, tolerance to a protoporphyrinogen oxidase inhibitor is achieved by expression of a tolerant protoporphyrinogen oxidase enzyme in plants (U.S. Pat. No. 5,767,373). In another particular aspect, a nucleic acid transferred into variety PWRG-1, PWRG-2, or PWSGC comprises a transgene conferring tolerance to a herbicide and at least one other transgene conferring another trait, such as for example, insect resistance or tolerance to another herbicide.

Other illustrative transgenes are set forth below.

1. Transgenes that Confer Resistance to Pests or Disease and that Encode (A) Plant disease resistance. Plant defenses are often activated by specific interaction between the product of a nucleic acid coding for disease resistance gene (R) in the plant and the product of a corresponding nucleic acid coding for avirulence (Avr) in the pathogen. A plant variety can be transformed with a cloned nucleic acid conferring resistance in order to engineer plants that are resistant to specific pathogens (see, for example, Jones et al., *Science* 266:789 (1994), cloning of the tomato Cf-9 gene for resistance to *Cladosporium fulvum*; Martin et al., *Science* 262:1432 (1993), tomato Pto gene for resistance to *Pseudomonas syringae* pv.; Mindrinos et al., *Cell* 78:1089 (1994), *Arabidopsis* RSP2 nucleic acid encoding resistance to *Pseudomonas syringae*).

(B) A *Bacillus thuringiensis* protein, a derivative thereof or a synthetic polypeptide modeled thereon (see, for example, Geiser et al., *Gene* 48: 109 (1986), disclosing the cloning and nucleotide sequence of Bt δ-endotoxin). Moreover, DNA molecules encoding δ-endotoxin can be purchased from American Type Culture Collection (Rockville, MD), for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 91/14778; WO 99/31248; WO 01/12731; WO 99/24581; WO 97/40162 and U.S. application Ser. Nos. 10/032,717; 10/414,637; and 10/606,320.

(C) A lectin (see, for example, the disclosure by Van Damme et al., *Plant Mol. Biol.* 24:25 (1994)), which discloses the nucleotide sequences of several *Clivia miniata* mannose-binding lectins.

(D) A vitamin-binding protein such as avidin (see WO 93/06487). This publication teaches the use of avidin and avidin homologues as larvicides against insect pests.

(E) An enzyme inhibitor, for example, a protease inhibitor or an amylase inhibitor (see, for example, Abe et al., *J. Biol. Chem.* 262:16793 (1987), nucleotide sequence of rice cysteine proteinase inhibitor; Huub et al., *Plant Mol. Biol.* 21:985 (1993); nucleotide sequence of cDNA encoding tobacco proteinase inhibitor 1; and Sumitani et al., *Biosci. Biotech. Biochem.* 57:1243 (1993), nucleotide sequence of *Streptomyces nitrosporeus* amylase inhibitor).

(F) An insect-specific hormone or pheromone such as an ecdysteroid or juvenile hormone, a variant thereof, a mimetic based thereon, or an antagonist or agonist thereof (see, for example, the disclosure of Hammock et al., *Nature* 344:458 (1990), of baculovirus expression of cloned juvenile hormone esterase, an inactivator of juvenile hormone).

(G) An insect-specific peptide or neuropeptide which, upon expression, disrupts the physiology of the affected pest (for example, see the disclosures of Regan, *J. Biol. Chem.* 269:9 (1994), expression cloning yields DNA coding for insect diuretic hormone receptor; Pratt et al., *Biochem. Biophys. Res. Comm.* 163:1243 (1989), an allostatin is identified in *Diploptera puntata*); Chattopadhyay et al. *Crit. Rev. Microbiol.* 30(1):33 54 2004 (2004); Zjawiony, *J. Nat. Prod.* 67 (2):300-310 (2004); Carlini & Grossi-de-Sa, *Toxicon,* 40(11):1515 1539 (2002); Ussuf et al., *Curr. Sci.* 80 (7):847 853 (2001); and Vasconcelos & Oliveira, *Toxicon* 44 (4):385-403 (2004). See also U.S. Pat. No. 5,266,317 to Tomalski et al., which discloses nucleic acids encoding insect-specific, paralytic neurotoxins.

(H) An insect-specific venom produced in nature by a snake, a wasp, or the like (see, e.g., Pang et al., *Gene* 116:165 (1992), for disclosure of heterologous expression in plants of a nucleic acid encoding a scorpion insectotoxic peptide).

(I) An enzyme responsible for an hyperaccumulation of a monterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic (see WO 93/02197 in the name of Scott et al., which discloses the nucleotide sequence of a callase). DNA molecules which contain chitinase-encoding sequences can be obtained, for example, from the ATCC under Accession Nos. 39637 and 67152 (see also Kramer et al., *Insect Biochem. Mol. Biol.* 23:691 (1993), which describes the nucleotide sequence of a cDNA encoding tobacco hookworm chitinase, and Kawalleck et al., *Plant Mol. Biol.* 21:673 (1993), which provides the nucleotide sequence of parsley ubi4-2 polyubiquitin).

(K) A molecule that stimulates signal transduction. For example, see the disclosure by Botella et al., *Plant Mol. Biol.* 24:757 (1994), of nucleotide sequences for mung bean calmodulin cDNA clones, and Griess et al., *Plant Physio.* 104:1467 (1994), which provides the nucleotide sequence of a maize calmodulin cDNA clone.

(L) A hydrophobic moment peptide (see WO 95/16776 which discloses peptide derivatives of Tachyplesin which inhibit fungal plant pathogens, and WO 95/18855 which teaches synthetic antimicrobial peptides that confer disease resistance).

(M) A membrane permease, a channel former or a channel blocker. For example, see the disclosure by Jaynes et al., *Plant Sci.* 89:43 (1993)), of heterologous expression of a cecropin-β lytic peptide analog to render transgenic tobacco plants resistant to *Pseudomonas solanacearum.*

(N) A viral-invasive protein or a complex toxin derived therefrom. For example, the accumulation of viral coat proteins in transformed plant cells imparts resistance to viral infection and/or disease development effected by the virus from which the nucleic acid encoding the coat protein is derived, as well as by related viruses (see Beachy et al., *Ann. Rev. Phytopathol.* 28:451 (1990)). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus (Id.).

(O) An insect-specific antibody or an immunotoxin derived therefrom. Thus, an antibody targeted to a critical metabolic function in the insect gut would inactivate an affected enzyme, killing the insect (Cf. Taylor et al., Abstract #497, SEVENTH INT'L SYMPOSIUM ON MOLECULAR PLANT-MICROBE INTERACTIONS (Edinburgh, Scotland (1994)); enzymatic inactivation in transgenic tobacco via production of single-chain antibody fragments).

(P) A virus-specific antibody (see, for example, Taviadoraki et al., *Nature* 366:469 (1993); showing that transgenic plants expressing recombinant antibody are protected from virus attack).

(Q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase (see Lamb et al., *Bio/Technology* 10: 1436 (1992)). The cloning and characterization of a nucleic acid which encodes a bean endopolygalacturonase-inhibiting protein is described by Toubart et al., *Plant J.* 2:367 (1992).

(R) A developmental-arrestive protein produced in nature by a plant. For example, Logemann et al., *Bio/Technology* 10:305 (1992), have shown that transgenic plants expressing the barley ribosome-inactivating nucleic acid have an increased resistance to fungal disease.

(S) Nucleic acids involved in the Systemic Acquired Resistance (SAR) Response and/or the pathogenesis related nucleic acids. Briggs, *Current Biology,* 5(2) (1995), Pieterse & Van Loon *Curr. Opin. Plant Bio.* 7(4):456 64 (2004) and Somssich *Cell* 113(7):815-6 (2003).

(T) Nucleic acids encoding resistance to fungi (Cornelissen & Melchers, *Pl. Physiol.* 101:709-712, (1993) and Parijs et al., *Planta* 183:258-264 (1991) and Bushnell et al., *Can. J. Plant Pathol.* 20(2):137-149 (1998). Also see U.S. application Ser. No. 09/950,933.

2. Transgenes that Confer Resistance to a Herbicide, for Example (A) An herbicide that inhibits the growing point or meristem, such as an imidazalinone or a sulfonylurea. Exemplary transgenes or nucleic acids in this category code for mutant ALS or AHAS enzyme as described, for example, by Lee et al., *EMBO J.* 7:1241 (1988), and Miki et al., *Theor. Appl. Genet.* 80:449 (1990), respectively.

(B) Glyphosate (resistance imparted by mutant 5-enolpyruvl-3-phosphikimate synthase (EPSP) and aroA nucleic acids) and other phosphono compounds such as glufosinate (phosphinothricin acetyl transferase (PAT) and *Streptomyces hygroscopicus* phosphinothricin acetyl transferase (bar) nucleic acids), and pyridinoxy or phenoxy proprionic acids and cycloshexones (ACCase inhibitor-encoding nucleic acids). See, for example, U.S. Pat. No. 4,940,835 to Shah et al., which discloses the nucleotide sequence of a form of EPSP which can confer glyphosate resistance. A DNA molecule encoding a mutant aroA can be obtained under ATCC accession No. 39256, and the mutant nucleotide sequence is disclosed in U.S. Pat. No. 4,769,061 to Comai. European patent application No. 0 333 033 to Kumada et al. and U.S. Pat. No. 4,975,374 to Goodman et al. discloses nucleotide sequences encoding glutamine synthetase which confers resistance to herbicides such as L-phosphinothricin. The nucleotide sequence encoding a phosphinothricin-acetyl-transferase is provided in European application No. 0 242 246 to Leemans et al. De Greef et al., *Bio/Technology* 7:61 (1989), describes the production of transgenic plants that express chimeric bar coding for phosphinothricin acetyl transferase activity. Exemplary nucleic acids conferring resistance to phenoxy proprionic acids and cycloshexones, such as sethoxydim and haloxyfop, are the Acc1-S1, Acc1-S2 and Acc1-S3 nucleic acids described by Marshall et al., *Theor. Appl. Genet.* 83:435.

(C) An herbicide that inhibits photosynthesis, such as a triazine (psbA and gs+) and a benzonitrile (nitrilase). Przibilla et al., *Plant Cell* 3:169 (1991), describe the transformation of Chlamydomonas with plasmids encoding mutant psbA. Nucleic acids encoding nitrilase are disclosed in U.S. Pat. No. 4,810,648 to Stalker, and these nucleic acids are available under ATCC Accession Nos. 53435, 67441 and 67442. Cloning and expression of DNA coding for a glutathione S-transferase is described by Hayes et al., *Biochem. J.* 285:173 (1992).

3. Transgenes that Confer or Contribute to a Value-Added Trait, Such as (A) Decreased phytate content: Introduction of a phytase-encoding nucleic acid would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase.

(B) Modified carbohydrate composition effected, for example, by transforming plants with a nucleic acid encoding an enzyme that alters the branching pattern of starch (see Shiroza et al., *J. Bacteriol.* 170:810 (1998), nucleotide sequence of *Streptococcus mutans* fructosyltransferase; Steinmetz et al., *Mol. Gen. Genet.* 200:220 (1985), nucleotide sequence of *Bacillus subtilis* levansucrase; Pen et al., *Bio/Technology* 10:292 (1992), production of transgenic plants that express *Bacillus licheniformis* α-amylase; Elliot et al., *Plant Mol. Biol.* 21:515 (1993), nucleotide sequences of tomato invertase; Søgaard et al., *J. Biol. Chem.* 268:22480 (1993), site-directed mutagenesis of barley α-amylase nucleic acid; and Fisher et al., *Plant Physiol.* 102:1045 (1993), maize endosperm starch branching enzyme II).

Those skilled in the art will appreciate that the transgenes described above may also be transferred into *Brassica juncea* plants using conventional breeding techniques as known in the art and as described herein.

As a further alternative, the transgene can encode an antisense RNA molecule or any other non-translated RNA as known in the art. In a further alternative aspect, the transgene effects gene suppression in the host plant.

C. Methods for *Brassica juncea* Transformation

Plants can be transformed according to the present invention using any suitable method known in the art. Intact plants, plant tissue, explants, meristematic tissue, protoplasts, callus tissue, cultured cells, and the like may be used for transformation depending on the plant species and the method employed. Procedures for transforming a wide variety of plant species are well known and routine in the art and described throughout the literature. Such methods include, but are not limited to, transformation via bacterial-mediated nucleic acid delivery, viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

Bacterial-mediated nucleic acid delivery includes but is not limited to DNA delivery by *Agrobacterium* spp. and is described, for example, in Horsch et al. (*Science* 227:1229 (1985); Ishida et al. (*Nature Biotechnol.* 14:745 750 (1996); and Fraley et al. (*Proc. Natl. Acad. Sci.* 80: 4803 (1983)). Transformation by various other bacterial species is described, for example, in Broothaerts et al. (*Nature* 433: 629-633 (2005)).

Physical delivery of nucleotide sequences via microparticle bombardment is also well known and is described, for example, in Sanford et al. (*Methods in Enzymology* 217: 483-509 (1993)) and McCabe et al. (*Plant Cell Tiss. Org. Cult.* 33:227-236 (1993)).

Another method for physical delivery of nucleic acid to plants is sonication of target cells. This method is described, for example, in Zhang et al. (*Bio/Technology* 9:996 (1991)). Nanoparticle-mediated transformation is another method for delivery of nucleic acids into plant cells (Radu et al., *J. Am. Chem. Soc.* 126: 13216-13217 (2004); Torney, et al. *Society for In Vitro Biology*, Minneapolis, MN (2006)). Alternatively, liposome or spheroplast fusion can be used to introduce nucleotide sequences into plants. Examples of the use of liposome or spheroplast fusion are provided, for example, in Deshayes et al. (*EMBO J.,* 4:2731 (1985), and Christou et al. (*Proc Natl. Acad. Sci. U.S.A.* 84:3962 (1987)). Direct uptake of nucleic acid into protoplasts using $CaCl_2$ precipitation, polyvinyl alcohol or poly-L-ornithine is described, for example, in Hain et al. (*Mol. Gen. Genet.* 199:161 (1985)) and Draper et al. (*Plant Cell Physiol.* 23:451 (1982)). Electroporation of protoplasts and whole cells and tissues is described, for example, in Donn et al. (In Abstracts of VII$^{th}$ International Congress on Plant Cell and Tissue Culture IAPTC, A2-38, p 53 (1990); D'Halluin et al. (*Plant Cell* 4:1495-1505 (1992)); Spencer et al. (*Plant Mol. Biol.* 24:51-61 (1994)) and Fromm et al. (*Proc. Natl. Acad. Sci.* 82: 5824 (1985)). Polyethylene glycol (PEG) precipitation is described, for example, in Paszkowski et al. (*EMBO J.* 3:2717 2722 (1984)). Microinjection of plant cell protoplasts or embryogenic callus is described, for example, in Crossway (*Mol. Gen. Genetics* 202:179-185 (1985)). Silicon carbide whisker methodology is described, for example, in Dunwell et al. (*Methods Mol. Biol.* 111:375-382 (1999)); Frame et al. (*Plant J.* 6:941-948 (1994)); and Kaeppler et al. (*Plant Cell Rep.* 9:415-418 (1990)).

Plant cells, which have been transformed by any method known in the art, can also be regenerated to produce intact plants using known techniques.

Plant regeneration from cultured protoplasts is described in Evans et al., *Handbook of Plant Cell Cultures*, Vol. 1: (MacMilan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues.

Means for regeneration vary from plants species to plant species. In some embodiments, a suspension of transformed protoplasts or a petri plate containing transformed explants may be provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. A large number of plants have been shown capable of regeneration from transformed individual cells to obtain transgenic whole plants.

The regenerated plants are transferred to standard soil conditions and cultivated in a conventional manner. The plants are grown and harvested using conventional procedures.

The foregoing methods for transformation may be used for producing transgenic inbred lines. Transgenic inbred lines can then be crossed, with another (non-transformed or transformed) inbred line, in order to produce a transgenic hybrid *Brassica juncea* plant. Alternatively, a genetic trait that has been engineered into a particular *Brassica juncea* line using the foregoing transformation techniques can be moved into another line using traditional backcrossing techniques that are well known in the plant breeding arts. For example, a backcrossing approach can be used to move an engineered trait from a non-elite line into an elite *Brassica juncea* line, or from a hybrid *Brassica juncea* plant containing a foreign nucleic acid in its genome into a line or lines, which do not contain that nucleic acid. As used above, "crossing" can refer to a simple X by Y cross, or the process of backcrossing, depending on the context.

V. Products

*Brassica juncea* plants, or parts thereof, of the present invention may be utilized in any product containing *Brassica juncea* including without limitation food or feed products, including dietary supplements, and/or pharmaceuticals; and may be in any form including leaf *Brassica juncea*, shredded *Brassica juncea*, cut *Brassica juncea*, or *Brassica juncea* extract. Accordingly, some aspects of the invention provide *Brassica juncea* products produced from the plants of the present invention, or parts thereof.

In some aspects, leaves of the *Brassica juncea* variety PWRG-1, PWRG-2, and/or PWSGC may be used in a leafy greens blend. A leafy greens blend may comprise leaves from any one of the *Brassica juncea* varieties PWRG-1, PWRG-2, and/or PWSGC. A leafy greens blend may comprise leaves from any one of the *Brassica juncea* varieties PWRG-1, PWRG-2, and/or PWSGC in combination with at least one (e.g., 2, 3, 4, 5, 6, 7, 8, 9, 10, or more) different varieties, cultivars, and/or species of *Brassica*, or any combination thereof. In some aspects, the at least one (e.g., 2, 3, 4, or 5) different variety, cultivar, or species of *Brassica* may comprise, consist essentially of, or consist of a different cultivar or variety of *Brassica juncea*, and/or a different variety, cultivar, or species of *Brassica rapa, Brassica carinata, Brassica napus* and/or *Brassica oleracea*, in any combination. In some aspects, a leafy greens blend may comprise at least two (e.g., 2, 3, 4, 5, 6, 7, 8, 9, or 10 or more) different varieties, cultivars and/or species of *Brassica juncea, Brassica rapa, Brassica napus, Brassica carinata* and/or *Brassica oleracea*, in any combination.

In some aspects, a *Brassica juncea* useful in a leafy greens blend comprising the varieties of the invention may be a frill mustard. In some aspects, a *Brassica juncea* cultivar useful with the varieties of the invention may be one or more of Central Red (frill mustard), Red Giant, Southern Giant Curled, Green Wave, Spicy Green, Florida Broadleaf, Carolina Broadleaf, and/or Osaka Purple.

In some aspects, a *Brassica rapa* useful in a leafy greens blend comprising the varieties of the invention may be Chinese cabbage (e.g., *Brassica rapa* subspecies pekinensis, and/or *Brassica rapa* subspecies chinensis; e.g., napa cabbage, bok choy), mustard greens (e.g., mustard greens that are grown for the leaves), yu choi, pak choi, spinach mustard (e.g., *Brassica rapa* var. *perviridis*; komatsuna), and/or Asian Brassica (e.g., mizuna, mibuna, and optionally, komatsuna greens; e.g., Japanese mustard, potherb mustard, Japanese greens, and California peppergrass). In some aspects, a *Brassica rapa* cultivar may comprise Beka Santoh (Chinese cabbage), Hiroshimana (Chinese cabbage), Komatsuna, Late green, Osaka Shirona (Chinese cabbage), Purple Gem (pak choi), Red Tatsoi (pak choi), Tall White Stem (pak choi), Tendergreen (spinach mustard), Tokyo Bekana (Asian brasicca) and/or Vitamina (Chinese cabbage).

In some aspects, a *Brassica napus* useful in a leafy greens blend comprising the varieties of the invention may be kale. In some aspects, a *Brassica napus* cultivar useful in a leafy greens blend comprising the varieties of the invention may be Red Russian kale.

In some aspects, a *Brassica carinata* useful in a leafy greens blend comprising the varieties of the invention may be kale. In some aspects, a *Brassica carinata* cultivar useful in a leafy greens blend comprising the varieties of the invention may be Ethiopian Kale (Ethiopian mustard).

In some aspects, a *Brassica oleracea* useful in a leafy greens blend comprising the varieties of the invention may be cabbage, for example, loose leaf cabbage and/or kale. In some aspects, a *Brassica oleracea* cultivar useful in a leafy greens blend comprising the varieties of the invention may be Red Acre (loose leaf cabbage) and/or Morris Heading (loose leaf cabbage).

The amount of leaves from any particular species, cultivar or variety in a leafy greens blend is a percentage by weight of the total amount of leaves in the blend. In some aspects, a leafy greens blend may comprise, consist of, or consist essentially of leaves from at least one (e.g., 1, 2, 3, 4, 5, 6, 7, 8 or more) of the *Brassica juncea* varieties PWRG-1, PWRG-2, and/or PWSGC in the amount of about 10%-100% by weight of total amount of leaves in the leafy greens blend (e.g., about 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range or value therein), optionally about 20% to about 90%, or about 15, 20, 25, 30, 35, 40, 45, 50, 55, 60, 65, 70, 75, 80, 85, 90, 95, or 100% by weight of the total amount of leaves in the leafy greens blend).

In some aspects, the leaves of the leafy greens blend may comprise baby leaves. In some aspects, the leaves of the leafy greens blend may comprise mature leaves. In some aspects, the leaves of the leafy greens blend may include both mature leaves and baby leaves. In some aspects, when a leafy greens blend comprises both baby leaves and mature leaves it may comprise about 5% to about 95% by weight of baby leaves (about 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range or value therein) and about 5% to about 95% by weight of mature leaves (about 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range or value therein). In some aspects, a leafy greens blend of the invention does not include mature leaves from *Brassica carinata* and/or *Brassica oleracea* and/or from the *Brassica rapa* groupings of yu choi, pak choi and/or Chinese cabbage.

In some embodiments, a kit is provided comprising the leafy greens blends as described herein. In some embodiments, the kit may further comprise other vegetables and greens, including but not limited to lettuce, spinach, celery, broccoli, carrots, cauliflower, radish, cucumber, tomato, cherry tomato, grape tomato, arugula, and/or endive (curly, flat leaf (escarole)).

VI. Industrial Applicability

This invention is also directed to methods for producing a *Brassica juncea* plant by crossing a first parent *Brassica juncea* plant with a second parent *Brassica juncea* plant wherein either the first or second parent *Brassica juncea* plant is a *Brassica juncea* plant of variety PWRG-1, PWRG-2, or PWSGC or a *Brassica juncea* plant of variety PWRG-1, PWRG-2, or PWSGC further comprising one or more additional traits (e.g., single gene traits). Further, both first and second parent *Brassica juncea* plants can come from variety PWRG-1, PWRG-2, or PWSGC or a *Brassica juncea* plant of variety PWRG-1, PWRG-2, or PWSGC further comprising one or more traits (e.g., single gene traits). Thus, any such methods using the *Brassica juncea* variety PWRG-1, PWRG-2, or PWSGC or a *Brassica juncea* plant of PWRG-1, PWRG-2, or PWSGC further comprising one or more additional traits (e.g., one or more single gene traits) are part of this invention: selfing, backcrosses, doubled-haploid production, hybrid production, crosses to populations, and the like. All plants produced using *Brassica juncea* variety PWRG-1, PWRG-2, or PWSGC, or modified variety PWRG-1, PWRG-2, or PWSGC further comprising one or more additional traits (e.g., one or more single gene traits) as a parent are within the scope of this invention. Advantageously, *Brassica juncea* variety PWRG-1, PWRG-2, or PWSGC or modified variety PWRG-1, PWRG-2, or PWSGC further comprising one or more additional traits (e.g., one or more single gene traits) are used in crosses with other, different, *Brassica juncea* inbreds to produce first generation ($E_1$) *Brassica juncea* hybrid seeds and plants with superior characteristics.

VIII. Deposits

A deposit of at least 625 seeds of *Brassica juncea* variety PWRG-1 has been made with the American Type Culture Collection (ATCC), Manassas, VA 20110 USA on Jul. 18, 2023. The deposit has been assigned ATCC Accession Number PTA-127617.

A deposit of at least 625 seeds of *Brassica juncea* variety PWRG-2 has been made with the ATCC, Manassas, VA 20110 USA on Jul. 18, 2023. The deposit has been assigned ATCC Accession Number PTA-127618.

A deposit of at least 625 seeds of *Brassica juncea* variety PWSGC has been made with the ATCC, Manassas, VA 20110 USA on Jul. 18, 2023. The deposit has been assigned ATCC Accession Number PTA-127619.

These deposits of the *Brassica juncea* varieties PWRG-1, PWRG-2, and PWSGC will be maintained in the ATCC depository, which is a public depository, for a period of 30 years, or 5 years after the most recent request, or for the effective life of the patent, whichever is longer, and will be replaced if it becomes nonviable during that period. Applicants do not waive any infringement of their rights granted under this patent or under the Plant Variety Protection Act (7 U.S.C. 2321 et seq.)

What is claimed is:

1. A *Brassica juncea* seed, the *Brassica juncea* seed designated as

PWRG-1, representative seed of said variety having been deposited under ATCC Accession No. PTA-127617;

PWRG-2, representative seed of said variety having been deposited under ATCC Accession No. PTA-127618; or PWSGC, representative seed of said variety having been deposited under ATCC Accession No. PTA-127619.

2. A *Brassica juncea* plant, or a part thereof, produced by the seed of claim 1.

3. The plant part of claim 2, wherein said part is a leaf or a portion thereof, a pollen, or an ovule.

4. A *Brassica juncea* plant, or a part thereof, having all the physiological and morphological characteristics of PWRG-1, the *Brassica juncea* variety PWRG-1 having been deposited under ATCC Accession No. PTA-127617;

PWRG-2, the *Brassica juncea* variety PWRG-2 having been deposited under ATCC Accession No. PTA-127618; or PWSGC, the *Brassica juncea* variety PWSGC having been deposited under ATCC Accession No. PTA-127619.

5. A tissue culture of regenerable cells of the plant, or part thereof, of claim 4, optionally wherein the regenerable cells are from plant parts selected from the group consisting of leaves, pollen, embryos, cotyledons, hypocotyls, roots, root tips, anthers, pods, flowers and a part thereof, ovules, shoots, stems, stalks, pith and capsules or wherein the regenerable cells are callus or protoplasts derived therefrom.

6. A *Brassica juncea* plant regenerated from the tissue culture of claim 5 expressing all the morphological and physiological characteristics of

*Brassica juncea* variety PWRG-1, the *Brassica juncea* variety PWRG-1 having been deposited under ATCC Accession No. PTA-127617;

*Brassica juncea* variety PWRG-2, the *Brassica juncea* variety PWRG-2 having been deposited under ATCC Accession No. PTA-127618; or

*Brassica juncea* variety PWSGC, the *Brassica juncea* variety PWSGC having been deposited under ATCC Accession No. PTA-127619.

7. A method for producing a first generation ($E_1$) hybrid *Brassica juncea* seed comprising crossing the plant of claim 2 with a different *Brassica juncea* plant and harvesting the resultant first generation ($E_1$) hybrid *Brassica juncea* seed.

8. A method for producing a first generation ($E_1$) hybrid *Brassica juncea* seed comprising crossing the plant of claim 4 with a different *Brassica juncea* plant and harvesting the resultant first generation ($E_1$) hybrid *Brassica juncea* seed.

9. An $E_1$ hybrid *Brassica juncea* seed produced by the method of claim 7.

10. An $E_1$ hybrid *Brassica juncea* seed produced by the method of claim 8.

11. An $E_1$ hybrid *Brassica juncea* plant, or a part thereof, grown from the seed of claim 9.

12. An $E_1$ hybrid *Brassica juncea* plant, or a part thereof, grown from the seed of claim 10.

13. A method for producing hybrid *Brassica juncea* seed comprising crossing two *Brassica juncea* plants and harvesting the resultant hybrid *Brassica juncea* seed, wherein at least one *Brassica juncea* plant is the *Brassica juncea* plant of claim 2.

14. A method for producing hybrid *Brassica juncea* seed comprising crossing two *Brassica juncea* plants and harvesting the resultant hybrid *Brassica juncea* seed, wherein at least one *Brassica juncea* plant is the *Brassica juncea* plant of claim 4.

15. A method for producing a PWRG-1-, PWRG-2-, or PWSGC-derived *Brassica juncea* plant comprising:

(a) crossing *Brassica juncea* variety PWRG-1, PWRG-2, or PWSGC with a second *Brassica juncea* plant to yield progeny *Brassica juncea* seed, representative seed of said *Brassica juncea* PWRG-1 variety having been deposited under ATCC Accession No. PTA-127617;

representative seed of said *Brassica juncea* PWRG-2 variety having been deposited under ATCC Accession No. PTA-127618; or representative seed of said *Brassica juncea* PWSGC variety having been deposited under ATCC Accession No. PTA-127617; and (b) growing said progeny *Brassica juncea* seed, under plant growth conditions, to yield said PWRG-1-, PWRG-2-, or PWSGC-derived *Brassica juncea* plant.

16. The method of claim 15, further comprising:

(a) crossing said PWRG-1-, PWRG-2-, or PWSGC-derived *Brassica juncea* plant with itself or another *Brassica juncea* plant to yield additional progeny *Brassica juncea* seed;

(b) growing said progeny *Brassica juncea* seed of step (a) under plant growth conditions, to yield additional PWRG-1-, PWRG-2-, or PWSGC-derived *Brassica juncea* plants; and (c) repeating the crossing and growing steps of (a) and (b) to generate further PWRG-1-, PWRG-2-, or PWSGC-derived *Brassica juncea* plants.

17. The *Brassica juncea* plant, or a part thereof, of claim 2, wherein the plant or a part thereof has been transformed so that its genetic material comprises one or more transgenes operably linked to one or more regulatory elements.

18. A method for producing a *Brassica juncea* plant that contains in its genetic material one or more transgenes, comprising crossing the *Brassica juncea* plant of claim 17 with either a second plant of another *Brassica juncea* line, or a non-transformed

*Brassica juncea* variety PWRG-1, the *Brassica juncea* variety PWRG-1 having been deposited under ATCC Accession No. PTA-127617;

*Brassica juncea* variety PWRG-2, the *Brassica juncea* variety PWRG-2 having been deposited under ATCC Accession No. PTA-127618;

or *Brassica juncea* variety PWSGC, the *Brassica juncea* variety PWSGC having been deposited under ATCC Accession No. PTA-127619, wherein progeny are produced, so that the genetic material of the progeny that result from the cross comprises the transgene(s) operably linked to one or more regulatory elements.

19. A method for developing a *Brassica juncea* plant in a *Brassica juncea* plant breeding program using plant breeding techniques, comprising: using the *Brassica juncea* plant, or a part thereof, of claim 2 as a source of said breeding material.

20. A method of producing *Brassica juncea* seed, comprising growing the plant of claim 2 to produce seed and harvesting said seed.

21. A *Brassica juncea* plant, seed, or plant part comprising in its genome a combination of edited myrosinase genes, the combination of edited myrosinase genes (a) comprising the nucleotide sequences of SEQ ID NOs: 1-3 and 8-19;

(b) comprising the nucleotide sequences of SEQ ID NOs: 1-15; or (c) comprising the nucleotide sequences of SEQ ID NOs: 20-27.

22. A *Brassica juncea* product produced from the *Brassica juncea* plant or plant part of claim 2.

23. The *Brassica juncea* product of claim 22, wherein the product is a leafy greens blend.

* * * * *